(12) United States Patent
Spencer et al.

(10) Patent No.: US 8,691,210 B2
(45) Date of Patent: Apr. 8, 2014

(54) METHODS AND COMPOSITIONS FOR GENERATING AN IMMUNE RESPONSE BY INDUCING CD40 AND PATTERN RECOGNITION RECEPTORS AND ADAPTORS THEREOF

(76) Inventors: David M Spencer, Houston, TX (US); Natalia Lapteva, Houston, TX (US)

( * ) Notice: Subject to any disclaimer, the term of this patent is extended or adjusted under 35 U.S.C. 154(b) by 736 days.

(21) Appl. No.: 12/445,939

(22) PCT Filed: Oct. 19, 2007

(86) PCT No.: PCT/US2007/081963
§ 371 (c)(1),
(2), (4) Date: Oct. 26, 2010

(87) PCT Pub. No.: WO2008/049113
PCT Pub. Date: Apr. 24, 2008

(65) Prior Publication Data
US 2011/0033383 A1   Feb. 10, 2011

Related U.S. Application Data

(60) Provisional application No. 60/862,211, filed on Oct. 19, 2006, provisional application No. 60/895,088, filed on Mar. 15, 2007.

(51) Int. Cl.
*C12N 15/85* (2006.01)

(52) U.S. Cl.
USPC ...... 424/93.21; 435/69.1; 435/69.7; 435/377; 435/455; 536/23.4

(58) Field of Classification Search
USPC .............. 424/93.21; 536/23.4; 435/69.7, 377, 435/455
See application file for complete search history.

(56) References Cited

U.S. PATENT DOCUMENTS

| | | | |
|---|---|---|---|
| 4,514,506 A | 4/1985 | Braatz et al. | |
| 5,348,253 A | 9/1994 | Gratzer | |
| 5,538,880 A | 7/1996 | Lundquist et al. | |
| 5,550,214 A | 8/1996 | Eberlein et al. | |
| 5,550,318 A | 8/1996 | Adams et al. | |
| 5,589,343 A | 12/1996 | Marchand et al. | |
| 5,610,042 A | 3/1997 | Chang et al. | |
| 5,645,992 A | 7/1997 | Lott et al. | |
| 5,648,226 A | 7/1997 | Van den Eynde et al. | |
| 5,709,995 A | 1/1998 | Chisari et al. | |
| 5,719,054 A | 2/1998 | Boursnell et al. | |
| 5,741,899 A | 4/1998 | Capon et al. | |
| 5,750,395 A | 5/1998 | Fikes et al. | |
| 5,780,036 A | 7/1998 | Chisari | |
| 5,830,462 A | 11/1998 | Crabtree et al. | |
| 5,834,266 A | 11/1998 | Crabtree et al. | |
| 5,840,839 A | 11/1998 | Wang et al. | |
| 5,869,337 A | 2/1999 | Crabtree et al. | |
| 5,869,608 A | 2/1999 | Caldwell et al. | |
| 5,871,753 A | 2/1999 | Crabtree et al. | |
| 5,925,565 A | 7/1999 | Berlioz et al. | |
| 5,935,819 A | 8/1999 | Eichner et al. | |
| 5,955,596 A | 9/1999 | Zagursky et al. | |
| 5,965,242 A | 10/1999 | Patton et al. | |
| 5,994,313 A | 11/1999 | Crabtree et al. | |
| 6,011,018 A | 1/2000 | Crabtree et al. | |
| 6,043,082 A | 3/2000 | Crabtree et al. | |
| 6,046,047 A | 4/2000 | Crabtree et al. | |
| 6,046,158 A | 4/2000 | Ariizumi et al. | |
| 6,054,436 A | 4/2000 | Crabtree et al. | |
| 6,497,876 B1 | 12/2002 | Maraskovsky et al. | |
| 6,558,951 B1 | 5/2003 | Tomai et al. | |
| 6,670,186 B1 | 12/2003 | Nair et al. | |
| 6,943,245 B2 | 9/2005 | Killary et al. | |
| 7,404,950 B2 | 7/2008 | Spencer | |
| 2003/0082163 A1 | 5/2003 | Shu | |
| 2003/0091593 A1 | 5/2003 | Bachmann et al. | |
| 2003/0092132 A1 | 5/2003 | Rodgers | |
| 2003/0108527 A1 | 6/2003 | Seya et al. | |
| 2003/0153518 A1 | 8/2003 | Foxwell et al. | |
| 2003/0206917 A1 | 11/2003 | Tykocinski et al. | |
| 2003/0232055 A1 | 12/2003 | Medzhitov | |
| 2004/0019195 A1 | 1/2004 | Scholm et al. | |
| 2004/0209836 A1 | 10/2004 | Spencer et al. | |
| 2005/0215472 A1 | 9/2005 | Schulke et al. | |
| 2007/0081963 A1 | 4/2007 | Oh et al. | |
| 2008/0274140 A1 | 11/2008 | Weiner et al. | |
| 2009/0175880 A1 | 7/2009 | Keler et al. | |

(Continued)

FOREIGN PATENT DOCUMENTS

| EP | 0273085 | 7/1984 |
|---|---|---|
| EP | 0510691 | 10/1992 |

(Continued)

OTHER PUBLICATIONS

Hanks et al, Nature Medicine 11(2):130-137, 2005.*
Lee et al, J. Biol. Chem. 279(11):10564-10574, 2004.*
Nishiya et al, J. Biol. Chem. 279(18):19008-19017, 2004.*
Krug et al, Eur. J. Immunol. 31:3026-3037, 2001.*
Medzhitov et al, Molecular Cell 2:253-258, 1998.*
Aliprantis et al, EMBO J. 19(13):3325-3336, 2000.*
Jonuleit et al, Eur. J. Immunol. 27:3135-3142, 1997.*
"Sipuleucel-T:APC 8015, APC-8015, prostate cancer vaccine—Dendreon." Drugs R D. 2006;7(3):197-201.
Adam et al., "Cross-linking of the p55 Tumor Necrosis Factor Receptor Cytoplasmic Domain by a Dimeric Ligand Induces nuclear Factor-kB and Mediates Cell Death," The Journal of Biological Chemistry vol. 270, No. 29, Jul. 21, 1995, pp. 17482-17487.

(Continued)

Primary Examiner — Kevin Hill
(74) Attorney, Agent, or Firm — Grant Anderson LLP

(57) ABSTRACT

Provided are methods for activating an antigen-presenting cell and eliciting an immune response by inducing pattern recognition receptor activity, and CD40 activity. Also provided are methods for activating an antigen-presenting cell and eliciting an immune response by inducing CD40 activity without prostaglandin E2. Also provided are methods for activating an antigen-presenting cell and eliciting an immune response by inducing an inducible chimeric molecule comprising a region of a pattern recognition receptor or an adaptor thereof.

14 Claims, 38 Drawing Sheets

(56) References Cited

U.S. PATENT DOCUMENTS

| | | | |
|---|---|---|---|
| 2009/0311183 A1 | 12/2009 | Devy et al. |
| 2010/0196336 A1 | 8/2010 | Park et al. |
| 2010/0203067 A1 | 8/2010 | Spencer et al. |
| 2011/0033383 A1 | 2/2011 | Spencer et al. |
| 2011/0287038 A1 | 11/2011 | Slawin et al. |

FOREIGN PATENT DOCUMENTS

| | | |
|---|---|---|
| WO | WO 94/09699 | 5/1990 |
| WO | WO 96/12796 | 5/1996 |
| WO | WO 01/83551 | 11/2001 |
| WO | WO 02/36769 | 5/2002 |
| WO | WO 2008/049113 | 4/2004 |
| WO | WO 2004/073641 | 9/2004 |
| WO | WO 2010/033949 | 3/2006 |
| WO | WO 2011/130566 | 10/2011 |

OTHER PUBLICATIONS

Adema et al., "A dendritic-cell-deprived C-C chemokine that preferentially attracts naïve T cells." Nature. Jun. 12, 1997;387(6634):713-717.
Adema et al., "Migration of dendritic cell based cancer vaccines: in vivo veritas?" Curr Opin Immunol. Apr. 2005;17(2):170-174.
Albert et al., "Dendritic cell maturation is required for the cross-tolerization of CD8+ T cells." Nat Immunol. Nov. 2001;2(11):1010-1017.
Amara et al, "A versatile synthetic dimerizer for the regulation of protein-protein interactions." PNAS 1997;94:10618-10623.
Anderson et al., "A homologue of the TNF receptor and its ligand enhance T-cell growth and dendritic-cell function." Nature. Nov. 13, 1997;390(6656)1 75-179.
Arcone et al., "Identification of sequences responsible for acute-phase induction of human C-reactive protein." Nucleic Acids Res. Apr. 25, 1988;16(8):3195-3207.
Ardeshna et al., "The PI3 kinase, p38 SAP kinase, and NF-kappaB signal transduction pathways are involved in the survival and maturation of lipopolysaccharide-stimulated human monocyte-derived dendritic cells." Blood. Aug. 1, 2000;96(3):1039-1046.
Banchereau et al., "Dendritic cells and the control of immunity." Nature. Mar. 19, 1998;392(6673):245-252.
Banchereau et al., "Dendritic cells as therapeutic vaccines against cancer." Nat Rev Immunol. Apr. 2005;5(4):296-306.
Banchereau et al., "Dendritic cells: controllers of the immune system and a new promise for immunotherapy." Ann NY Acad Sci. Apr. 2003;987:180-187.
Banchereau et al., "Immunobiology of dendritic cells." Annu Rev Immunol. 2000; 18:767-811.
Bander et al., "Phase I trial of 177Iutetium-labeled J591, a monoclonal antibody to prostate-specific membrane antigen, in patients with androgen-independent prostate cancer." J Clin Oncol. Jul. 20, 2005;23(21):4591-601.
Belshaw et al. (Sep. 1996). "Controlling programmed cell death with a cyclophilin-cyclosporin-based chemical inducer of dimerization." Chemistry & Biology. 3(9): pp. 731-738.
Bennett et al., "Apoptosis of rat vascular smooth muscle cells is regulated by p53-dependent and -independent pathways." Circ Res. Aug. 1995;77(2):266-273.
Bennett et al., "Help for cytotoxic-T-cell response is mediated by CD40 signalling." Nature. Jun. 4, 1998;393(6684):478-480.
Bernard et al., "HIV-specific cytotoxic T-lymphocyte activity in immunologically normal HIV-infected persons." AIDS. Nov. 12, 1998;12(16):2125-2139.
Beutler B., "Inferences, questions and possibilities in Toll-like receptor signalling." Nature. Jul. 8, 2004;430(6996):257-263.
Bianco FJ, et al., "Natural History of Biochemically-Recurrent Castrate-Resistant Disease in Men treated with maximal androgen blockage for a Rising PSA after Radical Prostatectomy," Cancer Symposium: Abstract 278, 2005.
Bisping et al., "Targeting receptor kinases by a novel indolinone derivative in multiple myeloma: abrogation of stroma-derived interleukin-6 secretion and induction of apoptosis in cytogenetically defined subgroups." Blood. Mar. 1, 2006;107(5):2079-2089.
Blau et al., "A proliferation switch for genetically modified cells." Proc Natl Acad Sci USA. Apr. 1, 1997;94(7):3076-3081.
Bojak et al., "Muscle specific versus ubiquitous expression of Gag based HIV-1 DNA vaccines: a comparative analysis." Vaccine. May 6, 2002;20(15)1975-1979.
Boldin et al., "Involvement of MACH, a Novel MORT1/FADD-Interacting Protease, in Fas/APO-1- and TNF Receptor—Induced Cell Death," Cell vol. 85, 803-815, Jun. 14, 1996.
Bonnert et al., GeneBank: AAC50954.1; GI: 1814020; Feb. 2, 1997.
Bowie et al, "Deciphering the message in protein sequences: tolerance to amino acid substitutions." Science Mar. 1990; 247:1306-1310.
Carter et al., "Prostate-specific membrane antigen is a hydrolase with substrate and pharmacologic characteristics of a neuropeptidase." Proc Natl Acad Sci U S A. Jan. 23, 1996;93(2):749-53.
Caux et al., "CD34+ hematopoietic progenitors from human cord blood differentiate along two independent dendritic cell pathways in response to GM-CSF+TNF alpha." Adv Exp Med Biol. 1997;417:21-25.
Caux et al., "In vitro regulation of development and function of dendritic cells." Hematol Cell Ther. Oct. 1996;38(5):463.
Cazeaux et al., "Comparative study of immune responses induced after immunization with plasmids encoding the HIV-1 Nef protein under the control of the CMV-IE or the muscle-specific desmin promoter." Vaccine. Sep. 10, 2002;20(27-28):3322-31.
Chan et al., "A Domain in TNF Receptors that mediates ligand-independent receptor assembly and signaling," Science 288, 2351-2354, (2001).
Chan, Francis Ka-Ming, "Three is Better Than One: Pre-Ligand Receptor Assembly in the Regulation of TNF Receptor Signaling," Cytokine, Feb. 2007;37(2) 101-107.
Chang et al., "Metastatic renal cell carcinoma neovasculature expresses prostate-specific membrane antigen." Urology. Apr. 2001;57(4):801-5.
Chang et al., "Prostate-specific membrane antigen is produced in tumor-associated neovasculature." Clin Cancer Res. Oct. 1999;5(10):2674-81.
Chatterjee et al., "Strategies for efficient gene transfer into hematopoietic cells. The use of adeno-associated virus vectors in gene therapy." Ann NY Acad Sci. Dec. 29, 1995;770:79-90.
Chen C, Okayama H., "High-efficiency transformation of mammalian cells by plasmid DNA." Mol Cell Biol. Aug. 1987;7(8):2745-2752.
Chen et al., "A testicular antigen aberrantly expressed in human cancers detected by autologous antibody screening." Proc Natl Acad Sci USA. Mar. 4, 1997;94(5)1 914-1918.
Cheung et al., "Plasmid encoding papillomavirus Type 16 (HPV16) DNA construced with codon optimization improved the immunogenicity against HPV infection." Vaccine. Dec. 16, 2004;23(5):629-638.
Chiodoni et ai, "Dendritic Cells Infiltrating Tumors Cotransduced with Granulocyte/Macrophage Colony-Stimulating factor (GM-CSF) and CD40 Ligand Genes Take Up and Present Endo- genous Tumor-Associated Antigens, and Prime Naive Mice for a Cytotoxic T Lymphocyte Response," J. Exp. Med. vol. 190, No. 1, Jul. 5, 1999. pp. 125-133.
Choe et al., "Crystal structure of human toll-like receptor 3 (TLR3) ectodomain." Science. Jul. 22, 2005;309(5734):581-585.
Christiansen et al., "N-glycosylation and microtubule integrity are involved in apical targeting of prostate-specific membrane antigen: implications for immunotherapy." Mol Cancer Ther. May 2005;4(5):704-14.
Cisco et al., "Induction of human dendritic cell maturation using transfection with RNA encoding a dominant positive toll-like receptor 4." J Immunol. Jun. 1, 2004;172(11):7162-7168.
Clackson et al., "Redesigning an FKBP-ligand interface to generate chemical dimerizers with novel specificity." Proc Natl Acad Sci USA. Sep. 1, 1998;95(18):10437-10442.
Clackson T., "Dissecting the functions of proteins and pathways using chemically induced dimerization." Chem Biol Drug Des. Jun. 2006;67(6):440-442.

(56) References Cited

OTHER PUBLICATIONS

Clarke et al., "Randomized phase II trial of chemoradiotherapy followed by either dose-dense or metronomic temozolomide for newly diagnosed glioblastoma." J Clin Oncol. Aug. 10, 2009;27(23):3861-7.

Clarke Sr., "The critical role of CD40/CD4OL in the CD4-dependent generation of CD8+ T cell immunity." J Leukoc Biol. May 2000;67(5):607-614.

Clarke, S.J., et al., "A phase I, pharmacokinetic (PK), and preliminary efficacy assessment of ALD518, a humanized anti-IL-6 antibody, in patients with advanced cancer ," 2009, J. Clin. Oncol. 27:15s (suppl.; abstr. 3025).

Coffin "Molecular Mechanisms of Nucleic Acid Integration," Journal of Mecical Virology, 31:43-19 (1990).

Cohen et al., "Nucleotide sequence of the cDNA encoding human tyrosinase-related protein." Nucleic Acids Res. May 11, 1990;18(9):2807-2808.

Contin et al., "Membrane-anchored CD40 is processed by the tumor necrosis factor-alpha-converting enzyme. Implications for CD40 signaling." J Biol Chem. Aug. 29, 2003;278(35):32801-32809.

Coupar et al., "A general methods for the construction of recombinant vaccinia viruses expressing multiple foreign genes." Gene. Aug. 15, 1988;68(1)1-10.

Cranmer et al., "Clinical applications of dendritic cell vaccination in the treatment of cancer." Cancer Immunol Immunother. Apr. 2004;54(4):275-306.

Crawford et al., "A controlled trial of leuprolide with and without flutamide in prostatic carcinoma." N Engl J Med. Aug. 17, 1989;321(7):419-424, w/, erratum N. Engl J Med Nov. 16, 1989;321(20):1420.

Cremer et al., "Long-lived immature dendritic cells mediated by TRANCE-RANK interaction." Blood. Nov. 15, 2002;100(10):3646-3655.

Cristofanilli et al., "Circulating tumor cells, disease progression, and survival in metastatic breast cancer." N Engl J Med. Aug. 19, 2004;351(8):781-91.

Cyster JG., "Chemokines and cell migration in secondary lymphoid organs." Science. Dec. 10, 1999;286(5447):2098-2102.

Dallal RM, Lotze MT., "The dendritic cell and human cancer vaccines." Curr Opin Immunol. Oct. 2000;12(5):583-588.

Davis et al., "Crystal structure of prostate-specific membrane antigen, a tumor marker and peptidase." Proc Natl Acad Sci USA. Apr. 26, 2005;102(17):5981-5986.

De Becker et al., "The adjuvant monophosphoryl lipid A increases the function of antigen-presenting cells." Int Immunol. Jun. 2000;12(6):807-815.

de Gruijl et al, "Prolonged Maturation and Enhanced Transduction of Dendritic Cells Migrated from Human Skin Explants After in Situ Delivery of CD40-Targeted Adenoviral Vectors," The Journal of Immunology vol. 169,2002 PQS 5322-5331.

de la Thille et al., "Detection of prostate-specific membrane antigen expressing cells in blood obtained from renal cancer patients: a potential biomarker of vascular invasion." Cancer Detect Prev. 2000;24(6):579-88.

De Vries et al., "Effective migration of antigen-pulsed dendritic cells to lymph nodes in melanoma patients is determined by their maturation state." Cancer Res. Jan. 1, 2003;63(1):12-17.

Deml et al. "Multiple effects of codon usage optimization on expression and immunogenicity of DNA candidate vaccines encoding the human immunodeficiency virus type 1 Gag protein," 2001. J. Virol. 75:10991-11001.

Deonarain, "Ligand-targeted receptor-mediated vectors for gene delivery," 1998, Expert Opin. Ther. Pat., vol. 8, pp. 53-69.

Diehl et al., "CD40 activation in vivo overcomes peptide-induced peripheral cytotoxic T-lymphocyte tolerance and augments anti-tumor vaccine efficacy." Nat Med. Jul. 1999;5(7):774-779.

Donnelly et al., "DNA vaccines." Annu Rev Immunol. 1997;15:617-48.

Dudley et al., "Adoptive cell transfer therapy following non-myeloablative but lymphodepleting chemotherapy for the treatment of patients with refractory metastic melanoma." J Clin Oncol. Apr. 1, 2005;23(10):2346-2357.

Elgueta et al., "Molecular mechanism and function of CD40/CD40L engagement in the immune system," Immunological Reviews, 229, (2009) 152-172.

Evel-Kabler et al., "SOCS1 restricts dendritic cells' ability to break self tolerance and induce antitumor immunity by regulating IL-12 production and signaling." J Clin Invest. Jan. 2006;116(1):90-100.

Fan et al., "Improved artificial death switches based on caspases and FADD." Hum Gene Ther. Sep. 20, 1999;10(14):2273-2285.

Farrar et al., "Activation of the Raf-1 kinase cascade by coumermycin-induced dimerization," Nature Sep. 12, 1996;383(6596)1 78-181.

Fearon et al., "The instructive role of innate immunity in the acquired immune response," Science, Apr. 5, 1996;272(5258):50-53.

Fechheimer et al., "Transfection of mammalian cells with plasmid DNA by scrape loading and sonication loading." Proc Natl Acad Sci USA. Dec. 1987;84(23):8463-8467.

Fernandez et al., "Dendritic cells directly trigger NK cell functions: cross-talk relevant in innate anti-tumor immune responses in vivo." Nat Med. Apr. 1999;5(4):405-411.

Ferrari et al., "Second-strand synthesis is a rate-limiting step for efficient transduction by recombinant adeno-associated virus vectors." J Virol. May 1996;70(5):3227-3234.

Fisher et al., "Transduction with recombinant adeno-associated virus for gene therapy is limited by leading-strand synthesis." J Virol. Jan. 1996;70(1):520-532.

Flotte et al., "Stable in vivo expression of the cystic fibrosis transmembrane conductance regulator with an adeno-associated virus vector." Proc Natl Acad Sci USA. Nov. 15, 1993;90(22):10613-10617.

Flotte TR, Carter BJ. "Adeno-associated virus vectors for gene therapy." Gene Ther. Aug. 1995;2(6):357-362.

Flotte, "Prospects for Virus-Based Gene Therapy for Cystic Fibrosis," Journal of Bioenergetics and Bioinformatics, vol. 25, No. 1, 1993.

Freeman et al., "The role of (111)in Capromab Pendetide (Prosta-ScintR) immunoscintigraphy in the management of prostate cancer." Q J Nucl Med. Jun. 2002;46(2):131-7.

Fujio Y, Walsh K., "Akt mediates cytoprotection of endothelial cells by vascular endothelial growth factor in an anchorage-dependent manner." J Biol Chem. Jun. 4, 1999;274(23)16349-16354.

Galbiati et al., "N-terminal fatty acylation of the alpha-subunit of the G-protein Gi1 : only the myristoylated protein is a substrate for palmitoylation." Biochem J. Nov. 1, 1994;303(Pt 3):697-700.

Gauthier-Campbell et al., "Regulation of dendritic branching and pilopodia formation in hippocampal neurons by specific acylated protein motifs." Mol Biol Cell. May 2004;15(5):2205-2217.

Gefter et al., "A simple method for polyethylene glycol-promoted hybridization of mouse myeloma cells." Somatic Cell Genet. Mar. 1977;3(2):231-236.

Gestwicki JE, Marinec PS., Chemical control over protein-protein interactions: beyond inhibitors. Comb Chem High Throughput Screen. Sep. 2007;10(8):667-675.

Gilboa E, Vieweg J., "Cancer immunotherapy with mRNA-transfected dendritic cells." Immunol Rev. Jun. 2004;199:251-263.

Gilboa E., "The promise of cancer vaccines." Nat Rev Cancer. May 2004;4(5):401-411.

Gittes RF., "Carcinoma of the prostate." N Engl J Med. Jan. 24, 1991;324(4):236-245.

Goodman et al., "Recombinant adeno-associated virus-mediated gene transfer into hematopoietic progenitor cells." Blood. Sep. 1, 1994;84(5)1 492-1500.

Goodwin et al., "Suppression of human T-cell mitogenesis by prostaglandin. Existence of a prostaglandin-producing suppressor cell." J Exp Med. Dec. 1, 1977;146(6):1719-1734.

Goodwin JS., "Immunomodulation by eicosanoids and anti-anflammatory drugs." Curr Opin Immunol. Dec. 1989;2(2):264-268.

Gopal TV., "Gene transfer method for transient gene expression, stable transformation, and cotransformation of suspension cell cultures." Mol Cell Biol. May 1985;5(5):1188-1190.

(56) References Cited

OTHER PUBLICATIONS

Gossen et al., "Transcriptional activation by tetracyclines in mammalian cells." Science. Jun. 23, 1995;268(5218)1 766-1769.
Gossen M, Bujard H., "Tight control of gene expression in mammalian cells by tetracycline-responsive promoters." Proc Natil Acad Sci USA. Jun. 15, 1992;89(12):5547-5551.
Graham FL, van der Eb AJ., "A new technique for the assay of infectivity of human adenovirus 5 DNA." Virology. Apr. 1973;52(2):456-467.
Granucci et al., "Eerly events in dendritic cell maturation induced by LPS." Microbes Infect. Nov. 1999;1(13):1079-1084.
Granucci et al., "Inducible IL-2 production by dendritic cells revealed by global gene expression analysis." Nat Immunol. Sep. 2001;2(9):882-888.
Granucci et al., "Modulation of cytokine expression in mouse dendritic cell clones." Eur J Immunol. Oct. 1994;24(10):2522-2526.
Grewal IS, Flavell RA., "CD40 and CD154 in cell-mediated immunity." Annu Rev Immunol. 1998;16:111-135.
Hammad et al., "Monocyte-derived dendritic cells induce a house dust mite-specific Th2 allergic inflammation in the lung of humanized SCID mice:involvement of CCR7." J Immunol. Aug. 1, 2002;169(3):1524-1534.
Hanks B.A., et al.. "Re-engIneered CD40 receptor enables potent pharmacological activation of dendritic-cell cancer vaccines in vivo" Nature Medicine, vol. 11, No. 2. 2005 pp. 130-137.
Harbury et al., "Crystal structure of an isoleucine-zipper trimer," Nature, vol. 371, Sep. 1, 1994, 80-83.
Hauer et al., "TNF receptor (TNFR)-associated factor (TRAF) 3 serves as an Inhibitor of TRAF2 5-medIated activation of the noncanonical NF-B pathway by TRAF-binding TNFRs." PNAS, vol. 102, No. 8, Feb. 22, 2005; pp. 2874-2879.
Hay et al., "Replication of Adenovirus Mini-Chromasomes," J. Mol. Biol. (1984) 175, 493-510.
He et al., "A simplified system for generating recombinant adenoviruses." Proc Natl Acad Sci USA. Mar. 3, 1998;95(5):2509-2514.
Hearing et al., "Identification of a repeated sequence element required for efficient encapsidation of the adenovirus type 5 chromosome." J Virol. Aug. 1987;61(8):2555-2558.
Hearing P, Shenk T., "Functional analysis of the nucleotide sequence surrounding the cap site for adenovirus type 5 region E1A messenger RNAs." J Mol Biol. Jul. 15, 1983;167(4):809-822.
Hermans et al., "CD8+ T cell-dependent elimination of dendritic cells in vivo limits the induction of antitumor immunity." J Immunol. Mar. 15, 2000;164(6):3095-3101.
Ho et al., "Dimeric ligands define a role for transcriptional activation domains in reinitiation." Nature. Aug. 29, 1996;382(6594):822-826.
Hodge et al., "Vector-based delivery of tumor-associated antigens and T-cell co-stimulatory molecules in the induction of immune responses and anti-tumor immunity," Cancer Detect Prevent 2002; 26;275-291.
Holler et al., "Development of improved soluble inhibitors of FasL and CD40L based on oligomerized receptors," Journal of Immunologial Methods 237(2000) 159-173.
Hollstein et al., "Database of p53 gene somatic mutations in human tumors and cell lines." Nucleic Acids Ress. Sep. 1994;22(17):3551-3555.
Holsinger et al., "Signal transduction in T lymphocytes using a conditional allele of Sos." Proc Natl Acad Sci USA. Oct. 10, 1995;92(21):9810-9814.
Hoshino et al., "Cutting edge:Toll-like receptor 4(TLR4)-deficient mice are hyporesponsive to lipopolysaccharide: evidence for TLR4 as the Lps gene product." J Immunol. Apr. 1, 1999;162(7):3749-3752.
Hou WS, Van Parijs L., "A Bcl-2-dependent molecular timer regulates the lifespan and immunogenicity of dendritic cells." Nat Immunol. Jun. 2004;5(6):583-589.
Ismaili et al., "Monophosphoryl lipid A activates both human dendritic cells and T cells." J Immunol. Jan. 15, 2002;168(2):926-932.
Israeli et al., "Expression of the prostate-specific membrane antigen." Cancer Res. Apr. 1, 1994;54(7):1807-11.
Israeli et al., "Sensitive nested reverse transcription polymerase chain reaction detection of circulating prostatic tumor cells: comparison of prostate-specific membrane antigen and prostate-specific antigen-based assays." Cancer Res. Dec. 15, 1994;54(24):6306-10.
Israeli et al., Molecular cloning of a complementary DNA encoding a prostate-specific membrane antigen. Cancer Res. Jan. 15, 1993;53(2):227-230.
Iuliucci et al., "Intravenous safety and pharmacokinetics of a novel dimerizer drug, AP1903, in healthy volunteers." J Clin Pharmacol. Aug. 2001;41(8):870-9.
Jackson et al., "A second tyrosinase-related protein, TRP-2, maps to and is mutated at the mouse slaty locus." EMBO J. Feb. 1992;11(2):527-535.
Jacquot et al, "CD154/CD40 and CD70/CD27 interactions have different and sequential functions in T cell-dependent B cell responses: enhancement of plasma cell differentiation by CD27 signaling," J Immunol 1997; 159: 2652-2657.
Janeway et al., "Approaching the asymptote? Evolution and revolution in immunology." Cold Spring Harb Symp Quant Biol. 1989;54 Pt 1:1-13.
Jemal et al., "Cancer statastics, 2008." CA Cancer J Clin. Mar.-Apr. 2008;58(2):71-96.
Josien et al., "TRANCE, a tumor necrosis factor family member, enhances the longevity and adjuvant properties of dendritic cells in vivo." J Exp Med. Feb. 7, 2000;191(3):495-502.
Kadowaki N. et al., "Subsets of human dendritic cell precursors express different toll-like receptors and respond to different microbial antigens," J Exp Med. 2001, vol. 194, pp. 863-869.
Kagan JC, Medzhitov R., "Phosphoinositide-mediated adaptor recruitment controls Toll-like receptor signaling." Cell. Jun. 2, 2006;125(5):943-955.
Kageyama et al., "Differing utilization of homologous transcription initiation sites of rat K and T kininogen genes under inflammation condition." J Biol Chem. Feb. 15, 1987;262(5):2345-2351.
Kalams et al., "The critical need for CD4 help in maintaining effective cytotoxic T lymphocyte responses." J Exp Med. Dec. 21, 1998;188(12):2199-2204.
Kalinski et al., "Dendritic cells, obtained from peripheral blood precursors in the presence of PGE2, promote Th2 responses." Adv Exp Med Biol. 1997;417:363-367.
Kalinski et al., "Prostaglandin E(2) is a selective inducer of interleukin-12 p40 (IL-12p40) production and an inhibitor of bioactive IL-12p70 heterodimer." Blood. Jun. 1, 2001;97(11):3466-3469.
Kandel ES, Hay N., "The regulation and activities of the multifunctional serine/threonine kinase Akt/PKB." Exp Cell Res. Nov. 25, 1999;253(1):210-229.
Kanto et al., "Ceramide mediates tumor-induced dendritic cell apoptosis." J Immunol. Oct. 1, 2001;167(7):3773-3784.
Kantoff et al., "Overall survival analysis of a phase II randomized controlled trial of a Poxviral-based PSA-targeted immunotherapy in metastatic castration-resistant prostate cancer." J Clin Oncol. Mar. 1, 2010;28(7)1099-105.
Kantoff et al., "Sipuleucel-T immunotherapy for castration-resistant prostate cancer." N Engl J Med. Jul. 29, 2010;363(5):411-22.
Kaplitt et al., "Long-term gene expression and phenotypic correction using adeno-associated virus vectors in the mammalian brain." Nat Genet. Oct. 1994;8(2):148-154.
Kaplitt et al., "Long-term gene transfer in porcine myocardium after coronary infusion of an adeno-associated virus vector." Ann Thorac Surg. Dec. 1996;62(6):1669-76.
Kawakami et al., "Identification of a human melanoma antigen recognized by tumor-infiltrating lymphocytes associated with in vivo tumor rejection." Proc Natl Acad Sci USA. Jul. 5, 1994;91(14):6458-6462.
Kawakami et al., "Identification of the immunodominant peptides of the MART-1 human melanoma antigen recognized by the majority of HLA-A2-restricted tumor infiltrating lymphocytes." J Exp Med. Jul. 1, 1994;180(1):347-352.
Kehry, Marilyn R., "CD40-Mediated Signaling in B Cells, Balancing Cell Survival, Growth and Death," The American Association of Immunologists, 1996, 2345-2348.

(56) References Cited

OTHER PUBLICATIONS

Kelly WK, Slovin SF., "Chemotherapy for androgen-independent prostate cancer: myth or reality." Curr Oncol Rep. Sep. 2000;2(5):394-401.
Kempf et al, "Improved stimulation of human dendritic cells by receptor engagement with surface-modified microparticles," J Drug Target vol. 11 No. 1, Jan. 2003 pp. 11-18.
Kessler et al., "Gene delivery to skeletal muscle results in sustained expression and systemic delivery of a therapeutic protein." Proc Natl Acad Sci USA. Nov. 26, 1996;93(24)14082-14087.
Kikuchi et al., "Dendritic cells genetically modified to express CD40 ligand and pulsed with antigen can initiate antigen-specific humoral immunity independent of CD4+ T cells." Nat Med. Oct. 2000;6(10):1154-1159.
Klein et al., "High-velocity microprojectiles for delivering nucleic acids into living cells," (1987) Nature, 327,70-73.
Kobayashi et al., "IRAK-M is a negative regulator of Toll-like receptor signaling." Cell. Jul. 26, 2002;1 10(2):191-202.
Koeberl et al., "Persistent expression of human clotting factor IX from mouse liver after intravenous injection of adeno-associated virus vectors." Proc Natl Acad Sci USA. Feb. 18, 1997;94(4):1426-1431.
Kohler G, Milstein C., "Continuous cultures of fused cells secreting antibody of predefined specificity." Nature. Aug. 7, 1975;256(5517):495-497.
Kohler G, Milstein C., "Derivation of specific antibody-producing tissue culture and tumor lines by cell fusion." Eur J Immunol. Jul. 1976;6(7):511-519.
Kopytek et al., "Chemically induced dimerization of dihydrofolate reductase by a homobifunctional dimer of methotrexate." Chem Biol. May 2000;7(5):313-321.
Korst et al., "Effect of adenovirus gene transfer vectors on the immunologic functions of mouse dendritic cells." Mol Ther. Mar. 2002;5(3):307-315.
Kraaij et al., "Prostate specific membrane antigen (PSMA) is a tissue-specific target for adenoviral transduction of prostate cancer in vitro." Prostate. Feb. 15, 2005;62(3):253-9.
Kumar et al., "Immunogenicity testing of a novel engineered Hiv-1 envelope gp140 DNA vaccine construct." DNA Cell Biol. Jul. 2006;25(7):383-392.
Kutzler et al., "Coimmunization with an optimized IL-15 plasmid results in enhanced function and longevity of CD8 T cells that are partially independent of CD4 T cell help." J Immunol. Jul. 1, 2005;175(1):112-123.
Kutzler MA, Weiner DB., "DNA vaccines: ready for prime time?" Nat Rev Genet. Oct. 2008;9(10):776-788.
Kwon et al., "Isolation and sequence of a cDNA clone for human tyrosinase that maps at the mouse c-albino locus." Proc Natl Acad Sci USA. Nov. 1987;84(21):7473-7477.
Labeur et al., "Generation of tumor immunity by bone marrow-derived dendritic cells correlates with dendritic cell maturation stage." J Immunol. Jan. 1, 1999;162(1):168-175.
Laddy et al., "Heterosubtypic protection against pathogenic human and avian influenza viruses via in vivo electroporation of synthetic consensus DNA antigens." PLoS One. Jun. 25, 2008;3(6):e2517.
Langenkamp et al., "Kinetics of dendritic cell activation: impact on priming of TH1, TH1 and nonpolarized T cells." Nat Immunol. Oct. 2000;1(4):311-316.
Lanzavecchia A, Sallusto F., "Dynamics of T lymphocyte responses: intermediates, effectors, and memory cells." Science. Oct. 6, 2000;290(5489):92-97.
Lanzavecchia A, Sallusto F., "Regulation of T cell immunity by dendritic cells." Cell. Aug. 10, 2001;106(3):263-266.
Lapointe et al., "Human dendritic cells require multiple activation signals for the efficient generation of tumor antigen-specific T lymphocytes." Eur J Immunol. Nov. 2000;30(11):3291-3298.
Lapteva et al., "Development of Novel CD4-Independent iCD4O-Dendritic Cell Vaccine for HIV-1 Immunotherapy," vol. 17, No. Suppl 1, May 2009, 12th Annual Meeting of the American Society of Gene Therapy: San Diego, CA, May 27-30, 2009.

Lapteva et al., "Enhance Activation of Human Dendritic Cells by inducible CD40 and Toll-like Receptor-4 Ligation," Cancer Research 2007, 67; (21) Nov. 1, 2007, pp. 10528-10537.
Lee et al., "A clinical grade cocktail of cytokines and PGE2 results in uniform maturation of human monocyte-derived dendritic cells: implications for immunotherapy." Vaccine. Dec. 19, 2002;20 Suppl 4:A8-A22.
Lee et al., "Cytoplasmic domain-mediated dimerizations of toll-like receptor 4 observed by beta-lactamase enzyme fragment complementation." J Biol Chem. Mar. 12, 2004;279(11):10564-10574.
Leo et al., "Partition coefficients and their uses." Chem Rev. Dec. 1971;71(6):525-616.
Levrero et al., "Defective and nondefective adenovirus vectors for expressing foreign genes in vitro and in vivo." Gene. May 30, 1991;101(2):195-202.
Li et al., "A novel conditional Akt 'survival+A185 switch' reversibly protects cells from apoptosis." Gene Ther. Feb. 2002;9(4):233-244.
Li et al., "The HIV-1 Env protein signal sequence retards its cleavage and down-regulates the glycoprotein folding." Virology. Jul. 5, 2000;272(2):417-428.
Liu et al., "Constitutive and antibody-induced internalization of prostate-specific membrane antigen." Cancer Res. Sep. 15, 1998;58(18):4055-60.
Liu et al., "Differential regulation of interleukin (IL)-12 p35 and p40 gene expression and interferon (IFN)-gamma-primed IL-12 production by IFN regulatory factor 1." J Exp Med. Oct. 2003;198(8):1265-1276.
Liu et al., "Monoclonal antibodies to the extracellular domain of prostate-specific membrane antigen also react with tumor vascular endothelium." Cancer Res. Sep. 1, 1997;57(17):3629-34.
Livak et al., "Analysis of relative gene expression data using real-time quantitative PCR and the 2(-Delta Delta C(T)) Method." Methods. Dec. 2001;25(4):402-408.
Lodge et al., Dendridic Cell-based Immunotherapy of Prostate Cancer: Immune Monitoring of a Phase II Clincal Trial, Cancer Res. 60:829-833, 2000.
Loiarro et al., "Peptide-mediated interference of TIR domain dimerization in MyD88 inhibits interleukin-1-dependent activation of NF-{kappa}B." J Biol. Chem. Apr. 22, 2005;280(16)15809-15814.
Luft et al., "Functionally distinct dendritic cell (DC) populations induced by physiologic stimuli: prostaglandin E(2) regulates the migratory capacity of specific DC subsets." Blood. Aug. 15, 2002;100(4):1362-1372.
Luo et al., "Oligomerization activates c-RAF-1 through a Ras-dependent mechanism." Nature. Sep. 12, 1996;383(6596):181-185.
MacCorkle et al., "Synthetic activation of caspases: artificial death switches." Proc Natl Acad Sci USA. Mar. 31, 1998;95(7):3655-3660.
Macejak DG, Sarnow P., "Internal initiation of translation mediated by the 5' leader of a cellular mRNA." Nature. Sep. 5, 1991;353(6339):90-94.
Machiels et al., "Prospective randomized study comparing docetaxel, estramustine, and prednisone with docetaxel and prednisone in metastatic hormone-refractory prostate cancer." J Clin Oncol. Nov. 10, 2008;26(32):5261-8.
Malin et al., "Vaccinia expression of *Mycobacterium tuberculosis*-secreted proteins: tissue plasminogen activator signal sequence enhances expression and immunogenicity of *M. tuberculosis* Ag85." Microbes Infect. Nov. 2000;2(14):1677-1685.
Malissen B, Ewbank JJ., "'TaiLoRing' the response of dendritic cells to pathogens." Nat Immunol. Aug. 2005;6(8):750-769.
Mann et al., "Construction of a retrovirus packaging mutant and its use to produce helper-free defective retrovirus." Cell. May 1983;33(1):153-159.
Marsland et al., "CCL19 and CCL21 induce a potent proinflammatory differentiation program in licensed dendritic cells." Immunity. Apr. 2005;22(4):493-505.
Martln-Fontecha et al., "Regulation of dendritic cell migration to the draining lymph node: impact on T lymphocyte traffic and priming." J Exp Med. Aug. 18, 2003;198(4):615-621.

(56) References Cited

OTHER PUBLICATIONS

Mazouz et al., "CD40 triggering increases the efficiency of dendritic cells for antitumoral immunization." Cancer Immun. Mar. 27, 2002;2:2.
McCown et al., "Differential and persistent expression patterns of CNS gene transfer by an adeno-associated virus (AAV) vector." Brain Res. Mar. 25, 1996;713(1-2):99-107.
McIlroy et al., "Histamine and prostaglandin E up-regulate the production of Th2-attracting chemokines (CCL17 and CCL22) and down-regulate IFN-gamma-induced CXCL10 production by immature human dendritic cells." Immunology. Apr. 2006;117(4):507-516.
McWhirter et al., "Crystallographic analysis of CD40 recognition and signaling by human TRAF2." Proc Natl Acad Sci USA. Jul. 20, 1999;96(15):8408-8413.
Medema et al., "Expression of the serpin serine protease inhibitor 6 protects dendritic cells from cytotoxic T lymphocyte-induced apoptosis: differential modulation by T helper type 1 and type 2 cells." J Exp Med. Sep. 3, 2001;194(5):657-667.
Medzhitov et al., "A human homologue of the *Drosophila* Toll protein signals activation of adaptive immunity." Nature. Jul. 24, 1997;388(6640):394-397.
Megiovanni et al., "Double-stranded RNA stimulation of CD40 ligation of monocyte-derived dendritic cells as models to study their activation and maturation process." Eur Cytokine Netw. Apr.-Jun. 2004;15(2):126-134.
Melief et al., "Effective therapeutic anticancer vaccines based on preCision guiding of cytolytic T lymphocytes" Immunol Rev. vol. 188, Oct. 2002, pp. 177-182.
Meyer et al., "Cutting edge: cyclooxygenase-2 activation suppresses Th1 polarization in response to *Helicobacter pylori*." J Immunol. Oct. 15, 2003;171(8):3913-3917.
Meylan et al., "Intracellular pattern recognition receptors in the host response." Nature. Jul. 6, 2006;442(7098):39-44.
Miga et al., "Dendritic cell longevity and T cell persistence is controlled by CD154-CD40 interactions." Eur J Immunol. Mar. 2001;31(3):959-965.
Mizukami et al., "Adeno-associated virus type 2 binds to a 150-kilodalton cell membrane glycoprotein." Virology. Mar. 1, 1996;217(1):124-130.
Mochizuki et al., "Akt protein kinase inhibits non-apoptotic programmed cell death induced by ceramide." J Biol Chem. Jan. 25, 2002;277(4):2790-2797.
Montgomery et al., "Heterologous and homologous protection against influenza A by DNA vaccination: optimization of DNA vectors." DNA Cell Biol. Nov. 1993;12(9):777-783.
Morgan et al., "Cancer regression in patients after transfer of genetically engineered lymphocytes." Science. Oct. 6, 2006;314(5796)126-129.
Morse et al., "Migration of human dendritic cells after injection in patients with metastic malignancies." Cancer Res. Jan. 1, 1999;5((1):56-58.
Mukherjee et al., "Lipid-dependent recruitment of neuronal Src to lipid rafts in the brain." J Biol Chem. Oct. 17, 2003;278(42):40806-40814.
Nabel et al., "Recombinant gene expression in vivo within endothelial cells of the arterial wall." Science. Jun. 16, 1989;244(4910):1342-1344.
Nakagami et al., "Safety and efficacy of docetaxel, estramustine phosphate and hydrocortisone in hormone-refractory prostate cancer patients." Int J Urol. Jul. 2010;17(7):629-34.
Napolitanl et al., "Selected Toll-like receptor agonist combinations synergistically trigger a T helper type 1-polarizing program in dendrinic cells," Nat Immunol. Aug. 2005; vol. 6. No. 8, pp. 769-776.
Narayanan et al. A composite MyD88/CD40 switch synergistically activates mouse and human dendritic cells for enhanced antitumor efficacy. J Clin Invest. 2011, vol. 121(4), p. 1524-1529.

Narum et al., "Codon optimization of gene fragments encoding *Plasmodium falciparum* merzoite proteins enhances DNA vaccine protein expression and immunogenicity in mice." Infect Immun. Dec. 2001;69(12):7250-7253.
Nestle et al., "Dendritic cells: On the move from bench to bedside." Nat Med. Jul. 2001;7(7):761-765.
Ni et al., "Molecular basis for CD40 signaling mediated by TRAF3." Proc Natl Acad Sci USA. Sep. 12, 2000;97(19):10395-10399.
Nicolau et al., "Liposomes as carriers for in vivo gene transfer and expression." Methods Enzymol. 1987;149:157-176.
Nociari et al., "A novel one-step, highly sensitive fluorometric assay to evaluate cell-mediated cytotoxicity." J Immunol Methods. Apr. 15, 1998;213(2)157-167.
Nopora A, Brocker T., "Bcl-2 controls dendritic cell longevity in vivo." J Immunol. Sep. 15, 2002;169(6):3006-3014.
Oehm et al., "Purification and Molecular Cloning of the APO-1 Cell Surface Antigen, a Member of the Tumor Necrosis Factorperve Growth Factor Receptor Superfamily, Sequence Identity With the Fas Antigen*," The Journal of Biological Chemistry, vol. 267, No. 15, May 25, 1992 10709-10715.
Ohshima et al., "Expression and function of OX40 ligand on human dendritic cells." J Immunol. Oct. 15, 1997;159(8):3838-3848.
Oliviero et al., "The human haptoglobin gene: transcriptional regulation during development and acute phase induction." EMBO J. Jul. 1987;6(7):1905-1912.
O'Neill et al., "Manipulating dendritic cell biology for the active immunotherapy of cancer." Blood. Oct. 15, 2004;104(8):2235-2246.
O'Sullivan B, Thomas R., "CD40 and dendritic cell function." Crit Rev Immunol. 2003;23(1-2):83-107.
Ozinsky et al., "The repertoire for pattern recognition of pathogens by the innate immune system is defined by cooperation between toll-like receptors." Proc Natl Acad Sci USA. Dec. 5, 2000;97(25):13766-13771.
Page et al., "A nonisotopic method for the measurement of cell membrane integrity." Anticancer Res. Jul.-Aug. 1998;18(4A):2313-2316.
Palecek et al., "Integrin-ligand binding properties govern cell migration speed through cell-substratum adhesiveness." Nature. Feb. 6, 1997;385(6616):537-540.
Park et al., "Cutting Edge: CpG DNA inhibits dendritic cell apoptosis by up-regulating cellular inhibitor of apoptosis proteins through the phosphatidylinositide-3'-OH kinase pathway." J Immunol. Jan. 1, 2002;168(1):5-8.
Pasare C, Medzhitov R., "Toll pathway-dependent blockade of CD4+CD25+ T cell-mediated suppression by dendritic cells." Science. Feb. 14, 2003;299(5609)1033-1036.
Paskind et al., "Dependence of Moloney murine leukemia virus production on cell growth." Virology. Sep. 1975;67(1):242-248.
Pelletier J, Sonenberg N., "Internal initiation of translation of eukaryotic mRNA directed by a sequence derived from poliovirus RNA." Nature. Jul. 28, 1988;334(6180):320-325.
Perales et al., "Gene transfer in vivo: sustained expression and regulation of genes introduced into the liver by receptor-targeted uptake." Proc Natl Acad Sci USA. Apr. 26, 1994;91(9):4086-4090.
Ping et al., "Altered beta-adrenergic receptor signaling in heart failure, in vivo gene transfer via adeno and adeno-associated virus." Microcirculation. Jun. 1996;3(2):225-228.
Pinto et al., "Prostate-specific membrane antigen: a novel folate hydrolase in human prostatic carcinoma cells." Clin Cancer Res. Sep. 1996;2(9):1445-51.
Poli V, Cortese R., "Interleukin 6 induces a liver-specific nuclear protein that binds to the promoter of acute-phase genes." Proc Natl Acad Sci USA. Nov. 1989;86(21):8202-8206.
Potter et al., "Enhancer-dependent expression of human kappa immunoglobulin genes introduced into mouse pre-B lymphocytes by electroporation." Proc Natl Acad Sci USA. Nov. 1984;81(22):7161-7165.
Prins et al., "The TLR-7 agonist, imiquimod, enhances dendritic cell survival and promotes tumor antigen-specific T cell priming: relation to central nervous system antitumor immunity." J Immunol. Jan. 1, 2006;176(1):157-164.

(56) References Cited

OTHER PUBLICATIONS

Prowse KR, Baumann H., "Hepatocyte-stimulating factor, beta 2 interferon, and interleukin-1 enhance expresson of the rat alpha 1-acid glycoprotein gene via a distal upstream regulatory region." Mol Cell Biol. Jan. 1988;8(1):42-51.

Pruschy et al., "Mechanistic Sutdies of a Signaling Pathway Activated by the Organic Dimerizer FK1012," Chemistry and biology 1994 vol. 1, No. 3, 164-172.

Puccetti et al., "Effects of IL-12 and IL-23 on antigen-presenting cells at the interface between innate and adaptive immunity." Crit Rev Immunol. 2002;22(56):373-390.

Pullen et al., "CD40 signaling through tumor necrosis factor receptor-associated factors (TRAFs). Binding site specificity and activation of downstream pathways by distinct TRAFs." J Biol Chem. May 14, 1999;274(20)14246-14254.

Ramos et al., "An Inducible Caspase 9 Suicide Gene to Improve the Safety of Mesenchymal Stromal Cell Therapies," Stem Cells, Translational and Clinical Research, Apr. 15, 2010, pp. 1-16.

Re F, Strominger JL., "Toll-Ike receptor 2(TLR2) and TLR4 differentially activate human dendritic cells." J Biol Chem. Oct. 5, 2001;276(40):37692-37699.

Reis e Sousa C., "Dendritic cells as sensors of infection." Immunity. May 2001;14(5):495-498.

Renan MJ., "Cancer genes: current status, future prospects, and applications in radiotherapy/oncology." Radiother Oncol. Nov. 1990;19(3):197-218.

Rescigno et al., "Dendritic cell survival and maturation are regulated by different signaling pathways." J Exp Med. Dec. 7, 1998;188(11):2175-2180.

Richard et al, "Expansion of Genetically modified Primary Human HemopOietic cells Using Chemical Inducers of Dimerization," Blood vol. 95, 2000 pp. 430-436.

Ridge et al., "A conditioned dendritic cell can be a temporal bridge between a CD4+ T-helper and a T-Killer cell." Nature. Jun. 4, 1998;393(6684):474-478.

Ridgway D., "The first 1000 dendritic cell vaccinees." Cancer Invest. 2003;21(6):873-886.

Riol-Blanco et al., "The chemokine receptor CCR7 activates in dendritic cells two signaling modules that independently regulate chemotaxis and migratory speed." J Immunol. Apr. 1, 2005;174(7):4070-4080.

Rippe et al., "DNA-mediated gene transfer into adult rat hepatocytes in primary culture." Mol Cell Biol. Feb. 1990;10(2):689-695.

Rivera et al., "A humanized system for pharmacologic control of gene expression." Nat Med. Sep. 1996;2(9):1028-1032.

Rivera, V.M., "Controlling Gene Expression USing SynthetiC Ligands," Methods: A companion to Methods in Enzymology vol. 14, 1998 pp. 421-429.

Ron et al., "Angiotensinogen gene-nducible enhancer-binding protein 1, a member of a new family of large nuclear proteins that recognize nuclear factor kappa B-binding sites through a zinc finger motif." Mol Cell Biol. May 1991;11(5):2887-2895.

Rosenberg SA., "A new era for cancer immunotherapy based on the genes that encode cancer antigens." Immunity. Mar. 1999;10(3):281-287.

Roux et al., "A versatile and potentially general approach to the targeting of specific cell types by retrovirus: application to the infection of human cells by means of major histocompatibility complex class I and class II antigens by mouse ecotropic murine leukemia virus-derived viruses." Proc Natl Acad Sci USA. Dec. 1989;86(23):9079-9083.

Salkowski et al., "Lipopolysaccharide and monophosphoryl lipid A differentially regulate interleukin-12, gamma interferon, and interleukin-10 mRNA production in murine macrophages." Infect Immun. Aug. 1997;65(8):3239-3247.

Sallusto et al., "Rapid and coordinated switch in chemokine receptor expression during dendritic cell maturation." Eur J Immunol. Sep. 1998;28(9):2760-2769.

Samulski et al., "A recombinant plasmid from which an infectious adeno-associated virus genome can be excised in vitro and its use to study viral replication." J Virol. Oct. 1987;61(10):3096-3101.

Sanchez-Sanchez et al., "The multiple personalities of the chemokine receptor CCR7 in dendritic cells." J Immunol. May 1, 2006;176(9):5153-5159.

Sato et al., "Combination of monocyte-derived dendrinic cells and activated T cells which express CD40 ligand" an new approach to cancer Immunotherapy, Cancer Imminol Immunther, vol. 53, No. 1, Jan. 2004, pp. 53-61.

Scandella et al., "CCL19/CCL21-triggered signal transduction and migration of dendritic cells requires prostaglandin E2." Blood. Mar. 1, 2004;103(5):1595-1601.

Scandella et al., "Prostaglandin E2 is a key factor for CCR7 surface expression and migration of monocyte-derved dendritic cells." Blood. Aug. 15, 2002;100(4):1354-1361.

Schellhammer et al., "Prostate specific antigen decreases after withdrawal of antiandrogen therapy with bicalutamide or flutamide in patients receiving combined androgen blockade." J Urol. May 1997;157(5):1731-1735.

Scher et al., "Clinical trials in relapsed prostate cancer: defining the target." J Natl Cancer Inst. Nov. 20, 1996;88(22):1623-1634.

Scher et al., "Design and end points of clinical trials for patients with progressive prostate cancer and castrate levels of testosterone: recommendations of the Prostate Cancer Clinical Trials Working Group." J Clin Oncol. Mar. 1, 2008;26(7):1148-59.

Scher Hi, Kelly WK., "Flutamide withdrawal syndrome: its impact on clinical trials in hormone-refractory prostate cancer." J Clin Oncol. Aug. 1993;11(8):1566-1572.

Schneider et al., "Inactivation of the human immunodeficiency virus type 1 inhibitory elements allows Rev-independent expression of Gag and Gag/protease and particle formation." J Virol. Jul. 1997;71(7):4892-4903.

Schoenberger et al., "T-cell help for cytotoxic T lymphocytes is mediated by CD40-CD40L interactions." Nature. Jun. 4, 1998;393(6684):480-483.

Schuler et al., "The use of dendritic cells in cancer immunotherapy." Curr Opin Immunol. Apr. 2003; 15(2):138-147.

Schuster, et al., "ALD518, a humanized anti-IL-6 antibody, treats anemia in patients with advanced non-small cell lung cancer (NSCLC): Results of a phase II, randomized, double-blind, placebo-controlled trial," 2010, J. Clin. Oncol. 28-7s (suppl.; abstr. 7631).

Schweitzer BA, Kool ET., "Aromatic Nonpolar Nucleosides as Hydrophobic Isosteres of Pyrimidine and Purine Nucleosides." J Org Chem. Dec. 1, 1994;59(24):7238-7242.

Shaffer et al., "Circulating tumor cell analysis in patients with progressive castration-resistant prostate cancer." Clin Cancer Res. Apr. 1, 2007;13(7):2023-9.

Shen et al., "Silencing of SOCS1 enhances antigen presentation by dendritic cells and antigen-specific anti-tumor immunity." Nat Biotechnol. Dec. 2004;22(12):1546-1553.

Silver et al., "Prostate-specific membrane antigen expression in normal and malignant human tissues." Clin Cancer Res. Jan. 1997;3(1):81-5.

Simpson et al., "Consequences of Fas-ligand and perforin expression by colon T cells in a mouse model of inflammatory bowel disease." Gastroenterology. Oct. 1998; 115(4):849-855.

Small EJ, Srinivas S., "The antiandrogen withdrawal syndrome. Experience in a large cohort of unselected patients with advanced prostate cancer." Cancer. Oct. 15, 1995;76(8):1428-1434.

Small EJ, Vogelzang NJ., "Second-line hormonal therapy for advanced prostate cancer: a shifting paradigm." J Clin Oncol. Jan. 1997;15(1):382-388.

Smith et al., "Cognate CD4(+) T cell licensing of dendritic cells in CD8(+) T cell immunity." Nat Immunol. Nov. 2004;5(11):1142-1148.

Smith et al., "DNA/MVA vaccine for HIV type 1:effects of codon-optimization and the expression of aggregates or virus-like particles on the immunogenicity of the DNA prime." AIDS Res Hum Retroviruses. Dec. 2004;20(12):1335-1347.

Snyder et al., "Prostaglandins modulate macrophage la expression." Nature. Sep. 9, 1982;299(5879)163-165.

(56) References Cited

OTHER PUBLICATIONS

Sorensen et al., "Endostatin reduces cascularization, blood flow, and growth in a rat gliosarcoma." Neuro Oncol. Jan. 2002;4(1):1-8.
Spencer et al., "A general strategy for producing conditional alleles of Src-like tyrosine kinases." Proc Natl Acad Sci USA Oct. 10, 1995;92(21):9805-9809.
Spencer et al., "Controlling signal transduction with synthetic ligands." Science. Nov. 12, 1993;262(5136)1 019-1024.
Spencer et al., "Functional analysis of Fas signaling in vivo using synthetic inducers of dimerization." Curr Biol. Jul. 1, 1996;6(7):839-847.
Sporri R, Reis e Sousa C., "Inflammatory mediators are insufficient for full dendritic cell activation and promote expansion of CD4+ T cell populations lacking helper function." Nat Immunol. Feb. 2005;6(2):1 63-170.
Steinman et al., "Tolerogenic dendritic cells." Annu Rev Immunol. 2003;21:685-711.
Steinman RM, Pope M., "Exploiting dendritic cells to improve vaccine efficacy." J Clin Invest. Jun. 2002;109(12):1519-1526.
Strasser et al., "Integrin Activation by Regulated Dimerization and Oligomerization of Platelet Endothelial Cell Adhesion Molecule (PECAM)-1 from Within the Cell," Immunity Review 30, Feb. 20, 2009, 180-192.
Strober et al., "Signalling pathways and molecular interactions of NOD1 and NOD2." Nat Rev Immunol. Jan. 2006;6(1):9-20.
Su et al., "Alternatively spliced variants of prostate-specific membrane antigen RNA: ratio of expression as a potential measurement of progression." Cancer Res. Apr. 1, 1995;55(7):1441-1443.
Su et al., "Telomerase mRNA-transfected dendritic cells stimulate antigen-specific CD8+ and CD4+ T cell responses in patients with metastatic prostate cancer." J Immunol. Mar. 15, 2005;174(6):3798-3807.
Suarez-Alvarez et al, Epigenetic Mechanisms Regulate MHC and Antigen Processing Moleculers in Human Embryonic and Induced Pluripotent Stem Cells. PLoS One (April) 5(4):e10192, 2010, pp. 1-12.
Suda et al., "Molecular Cloning and Expression of the Fas Ligand, a Novel Member of the Tumor Necrosis Factor Family," Cell vol. 75, 1169-1176 Dec. 17, 1993.
Tai et al., "Mechanisms by which SGN-40, a Humanized Anti-CD40 Antibody, Induces Cytotoxicity in Human Multiple Myeloma Celis: ClinicalImplications," Cancer Research, Apr. 15, 2004, vol. 64, pp. 2846-2852.
ten Klooster JP, Hordijk PL., "Targeting and localized signalling by small GTPases." Biol Cell. Jan. 2007;99(1):1-12.
Tepler et al., "The gene for the rat mast cell high affinity IgE receptor alpha chain. Structure and alternative mRNA splicing patterns." J Biol Chem. Apr. 5, 1989;264(10):5912-5915.
Termeer et al., "Oligosaccharides of hyaluronan are potent activators of dendritic cells." J Immunol. Aug. 15, 2000;165(4):1863-1870.
Thompson et al., "The low-toxicity versions of LPS, MPL adjuvant and RC529, are efficient adjuvants for CD4+ T Cells." J Leukoc Biol. Dec. 2005;78(6):1273-1280.
Tibbetts C., "Viral DNA sequence from incomplete particles of human adenovirus type 7." Cell. Sep. 1977;12(1):243-249.
Tone M . et al., "Regulation of CD40 function by its isoforms generated through alternative splicing," PNAS. Feb. 13, 2001, vol. 98, No. 4, pp. 1751-1756.
Tong et al, "Prospects for CD40-directed Experimental Therapy of Human Cancer," Cancer Gene Therapy vol. 10, 2003,pp. 1-13.
Troyer et al., "Detection and characterization of the prostate-specific membrane antigen (PSMA) in tissue extracts and body fluids." Int J Cancer. Sep. 4, 1995;62(5):552-8.
Tur-Kaspa et al., "Use of electroporation to introduce biologically active foreign genes into primary rat hepatocytes." Mol Cell Biol. Feb. 1986;6(2):716-718.
van der Pouw Krann T.C., et al., "Prostaglandin E2 is a potent inhibitor of human interleukin12 production," J Exp Med., 1995, vol. 181, pp. 775-779.

Vassiliou et al., "Prostaglandin E2 promotes the survival of bone marrow-derived dendritic cells." J Immunol. Dec. 1, 2004;173(11):6955-6964.
Vidalain et al., "CD40 signaling in human dendritic cells is initiated within membrane rafts." EMBO J. 2000; 19:3304-3313.
Vieweg J, Jackson A., "Modulation of antitumor responses by dendritic cells." Springer Semin Immunopathol. Jan. 2005;26(3):329-341.
Vincent et al., "Targeting of proteins to membranes through hedgehog auto-processing." Nat Biotechnol. Aug. 2003;21(8):936-940.
Vonderheide et al., "CD40 activation of carcinoma cells increases expression of adhesion and major histocompatibility molecules but fails to induce either CD80/CD86 expression or T cell alloreactivity." Int J Oncol. Oct. 2001;19(4):791-798.
Wagner et al., "Transferrin-polycation conjugates as carriers for DNA uptake into cells." Proc Natl Acad Sci USA. May 1990;87(9):3410-3414.
Wang et al., "Relative contributions of codon usage, promoter efficiency and leader sequence to the antigen expression and immunogenicity of HIV-1 Env DNA vaccine." Vaccine. May 22, 2006;24(21):4531-4540.
Werneburg et al., "Molecular Characterization of CD40 Signaling Intermediates," The Journal of Biological Chemistry, vol. 276, Nov. 16, 2001, 43334-43342.
Werts et al., "TIR, CARD and PYRIN: three domains for an antimicrobial triad." Cell Death Differ. May 2006;14(5):798-815.
Wesemann et al., "Suppressor of cytokine signaling 1 inhibits cytokine induction of CD40 expression in macrophages." J Immunol. Sep. 1, 2002;169(5):2354-2360.
Wilson et al., "A 58-base-par region of the human C3 gene confers synergistic inducibility by interleukin-1 and interleukin-6." Mol Cell Biol. Dec. 1990;10(12):6181-6191.
Wilson et al., "Implantation of vascular grafts lined with genetically modified endothelial cells." Science. JuN. 16, 1989;244(4910):1344-1346.
Woltman et al., "Rapamycin specifically interferes with GM-CSF signaling in human dendritic cells, leading to apoptosis via increased p27KIP1 expression." Blood. Feb. 15, 2003;101(4):1439-1445.
Wong et al., "Fos Antigen and p55 TNF Receptor Signal Apoptosis Through Distinct Pathways," Journal of Immunology, 1994, 152: pp. 1751-1755.
Wong P, Famer EG., "Feedback regulation of pathogen-specific T cell priming." Immunity. Apr. 2003;18(4):499-511.
Wright et al., "Upregulation of prostate-specific membrane antigen after androgen-deprivation therapy." Urology. Aug. 1996;48(2):326-34.
Wu and Wu, "Liver-directed gene delivery," Adv Drug Delivery Rev, 1993;12:159-167.
Wu et al., "Codon optimization reveals critical factors for high level expression of two rare codon genes in *Escherichia coli*: RNA stability and secondary structure but not tRNA abundance." Biochem Biophys Res Commun. Jan. 2, 2004;313(1):8996.
Wu Gy, Wu CH., "Receptor-mediated in vitro gene transformation by a soluble DNA carrier system." J Biol Chem. Apr. 5, 1987;262(10):4429-32.
Xiao et al., "Efficient long-term gene transfer into muscle tissue of immunocompetent mice by adeno-associated virus vector." J Virol. Nov. 1996;70(11):8098-8108.
Xiao et al., "Establishment of a Cell Model Based on FKBP12 Dimerization for Screening of FK506-like Neurotrophic small Molecular Compounds." J Biomol Screen. Apr. 2006;11(3):225-235.
Xie et al., "Adenovirus-mediated tissue-targeted expression of a caspase-9-based artificial death switch for the treatment of prostate cancer." Cancer Res. Sep. 15, 2001;61(18):6795-6804.
Xu et al., "Optimization of transcriptional regulatory elements for constructing plasmid vectors." Gene. Jul. 11, 2001;272(1-2):149-156.
Yadava A, Ockenhouse CF., "Effect of codon optimization on expression levels of a functionally folded malaria vaccine candidate in prokaryotic and eukaryotic expression systems." Infect Immun. Sep. 2003;71(9):4961-4969.

(56) References Cited

OTHER PUBLICATIONS

Yan et al., "Enhanced cellular immune responses elicited by an engineered Hiv-1 subtype B consensus-based envelope DNA vaccine." Mol Ther. Feb. 2007;15(2):411-421.
Yanagawa Y, Onoe K., "CCL19 induces rapid dendritic extension of murine dendritic cells." Blood. Sep. 15, 2002;100(6):1948-1956.
Yang et al., "In vivo and in vitro gene transfer to mammalian somatic cells by particle bombardment." Proc Natl Acad Sci USA. Dec. 1990;87(24):9568-9572.
Yang et al., "Induction of inflammation by West Nile virus capsid through the caspase-9 apoptotic pathway." Emerg Infect Dis. Dec. 2002;8(12)1379-1384.
Zechner et al., "Recombinant human cachectin/tumor necrosis factor by not interleukin-1 alpha downregulates lipoprotein lipase gene expression at the transcriptional level in mouse 3T3-L1 adipocytes." Mol Cell Biol. Jun. 1988;8(6):2394-2401.
Zhang et al., "Integrin-nucleated Toll-like receptor (TLR) dimerization reveals subcellular targeting of TLRs and distinct mechanisms of TLR4 activation and signaling." FEBS Lett. Dec. 4, 2002;532(1-2)1 71-176.
Zhang et al., "mRNA secondary structure at start AUG codon is a key limiting factor for human protein expression in *Escherichia coli*." Biochem Biophys Res Commun. Oct. 13, 2006;349(1):69-78.
Zhao et al., "Integrin Activation by Regulated Dimerization and Oligomerization of Platelet Endothelial Cell Adhesion Molecule (PECAM)-1 from Within the Cell," Jan. 8, 2001, The Journal of Cell Biology, vol. 152, 65-73.
Zhou et al., "Multiple RNA splicing and the presence of cryptic RNA splice donor and acceptor sites may contribute to low expression levels and poor immunogenicity of potential DNA vaccines containing the env gene of equine infectious anemia virus (EIAV)." Vet Microbiol. Aug. 25, 2002;88(2):127-151.
Zitvogel et al., "Therapy of murine tumors with tumor peptide-pulsed dendritic cells: dependence on T cells, B7 costimulation, and T helper cell 1-associated cytokines." J Exp Med. Jan. 1, 1996;183(1):87-97.
Zlatkine et al., "Retargeting of cytosolic proteins to the plasma membrane by the Lck protein tyrosine kinase dual acylation motif." J Cell Sci. Mar. 1997;110(Pt5):673-679.
zur Medege et al., "Expression and immunogenicity of sequence-modified human immunodeficiency virus type 1 subtype B pol and gagpol DNA vaccines." J Virol. Jun. 2003;77(11):6197-6207.
Supplementary European Search Report dated Oct. 4, 2006 in European Application EP04712328, filed on Feb. 18, 2004.
Extended European Search Report dated Aug. 9, 2012 in European Application No. EP 09815355 filed on: Sep. 21, 2009 based on International Application No. PCT/US 2009/057738.
International Preliminary Report on Patentability mailed on: Sep. 29, 2005 in International Patent Application: PCT/US2004/04757 filed on: Feb. 18, 2004 and published as WO 2004/073641 on: Sep. 2, 2004.
International Search Report mailed on: Jan. 13, 2005 in International Patent Application: PCT/US2004/04757 filed on: Feb. 18, 2004 and published as WO 2004/073641 on: Sep. 2, 2004.
International Search Report and Written Opinion dated: Nov. 17, 2008 in International Application No. PCT/US07/81963 filed Oct. 19, 2007 and published as: WO/2008/049113 on Apr. 24, 2008.
International Preliminary Report on Patentability dated: Apr. 22, 2009 in International Application No. PCT/US07/81963 filed Oct. 19, 2007 and published as: WO/2008/049113 on Apr. 24, 2008.
International Preliminary Report on Patentability mailed: Mar. 31, 2011, for International Application No. PCT/US2009/057738, filed Sep. 21, 2009 and published as WO2010033949 on Mar. 25, 2010.
International Search Report and Written Opinion mailed: Feb. 2, 2010, for International Application No. PCT/US2009/057738, filed Sep. 21, 2009 and published as WO2010033949 on Mar. 25, 2010.
International Search Report and Written Opinion dated: Oct. 21, 2011 in International Application No. PCT/US11/032572 filed Apr. 14, 2011 and published as: WO/2011/130566 on Oct. 20, 2011.
Office Action Dated: Mar. 21, 2008 in U.S. Appl. No. 10/781,384 filed: Feb. 18, 2004 and issued as: 7,404,950 on: Jul. 29, 2008.
Office Action Dated: Jun. 27, 2007 in U.S. Appl. No. 10/781,384 filed: Feb. 18, 2004 and issued as: 7,404,950 on: Jul. 29, 2008.
Office Action Dated: Dec. 27, 2006 in U.S. Appl. No. 10/781,384 filed: Feb. 18, 2004 and issued as: 7,404,950 on: Jul. 29, 2008.
Office Action Dated: May 5, 2006 in U.S. Appl. No. 10/781,384 filed: Feb. 18, 2004 and issued as: 7,404,950 on: Jul. 29, 2008.
Office Action Dated: May 20, 2011 in U.S. Appl. No. 12/165,360 filed: Jun. 30, 2008 and Published as: 2008/0269160 on: Oct. 30, 2008.
Office Action Dated: Oct. 22, 2010 in U.S. Appl. No. 12/165,360 filed: Jun. 30, 2008 and Published as: 2008/0269160 on: Oct. 30, 2008.
Office Action Dated: Aug. 17, 2012 in U.S. Appl. No. 12/563,991 filed: Sep. 21, 2009 and Published as: 2010/0203067 on: Aug. 12, 2010.
Office Action Dated: Feb. 7, 2012 in U.S. Appl. No. 12/563,991 filed: Sep. 21, 2009 and Published as: 2010/0203067 on: Aug. 12, 2010.
Office Action Dated: Mar. 13, 2013 in U.S. Appl. No. 13/087,329 filed: Apr. 14, 2011 and Published as: 2011/0287038 on: Nov. 24, 2011 (Examiner: Phillip Gamble).
Extended European Search Report dated: Sep. 5, 2012 in European Patent Application No. EP 11193762, filed: Oct. 19, 2007.
Extended European Search Report dated: Sep. 12, 2012 in European Patent Application No. EP 11193768 filed: Oct. 19, 2007.
Kelleher et al., "Lipopolysaccharide Modulation of Dendritic Cells is Insufficient to Mature Dendritic Cells to Generate CTLs from Native Polyclonal CD8+ T Cells In Vitro, Whereas CD40 Ligation is Essential," The Journal of Immunology, The American Society of Immunologists, vol. 167, No. 11, Jan. 1, 2001, pp., 6247-6255.
Park et al, "An essential role for Akt1 in dendritic cell function and tumor immunotherapy," Nature Biology, vol. 24, No. 12, Dec. 2006, pp. 1581-1590.
Ronni et al., "Common interaction surfaces of the toll-like receptor 4 cytoplasmic domain stimulate multiple nuclear targets," Molecular and Cellular Biology, Apr. 2003, vol. 23, No. 7, pp., 2543-2555.
Schultz et al., "CD40 triggering of heterodimeric IL-12 p70 production by dendritic cells in vivo requires a microbial priming signal," Immunity, vol. 13, No. 4, Oct. 2000. pp. 453-462.
Aliprantis et al., "The apoptotic signaling pathway activated by Toll-like receptor-2," EMBO J. 19(13):3325-3336, (2000).
Burns et al., Inhibition of Interleukin 1 Receptor/Toll-like Receptor Signaling through the Alternatively Spliced, Short Form of MyD88 Is Due to Its Failure to Recruit IRAK-4, J. Exp. Med 197(2):263-268, Jan. 20, 2003.
GenBank Accession No. M29540, Human carcinoembryonic antigen mRNA (CEA), complete cds, Nov. 1, 1994.
Horng et al., "*Drosophila* MyD88 is an adapter in the Toll signaling pathway," PNAS 98(22):12654-12658, Oct. 23, 2001.
Hostager et al., "Different: CD40-mediated Signaling Events Require Distinct CD40 Structural features," J. Immunol. 157:1047-1053, Aug. 1, 1996.
Jonuleit et al., "Pro-inflammatory cytokines and prostaglandins induce maturation of potent immunostimulatory dendritic cells under fetal calf serum-free conditions," Eur. J. Immunol 27:3135-3142, Dec. 1997.
Medzhitov et al.,"MyD88 is an adaptor protein in the hToll/IL-1 receptor family signaling pathways," Molecular Cell, 2:253-258, Aug. 1998.
Rudinger, "Characteristics in the amino acids as components of a peptide hormone sequence" Chapter 1 in Peptide Hormones, Biological Council, The Co-ordinating Committee for Symposia on Drug Action, Edited by J.A. Parsons, University Park Press, Baltimore, London, Tokyo, Jun. 1976; pp. 1-7.

* cited by examiner

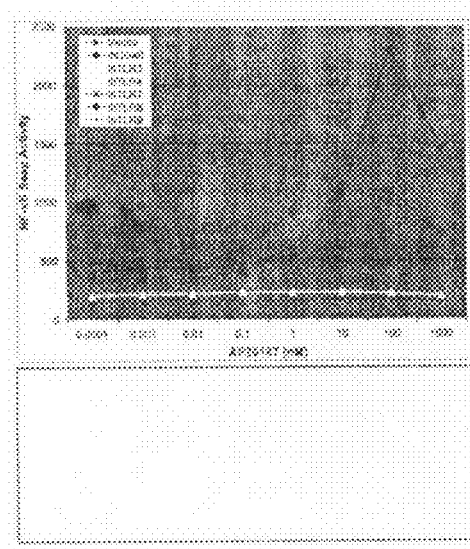

In an embodiment of an inducible PRR, 2-3 FKBP12(V36) domains are attached to the amino or carboxy termini of the conserved cytoplasmic signaling domains (TIR) of the representative TLR. The chimeric protein is attached to the plasma membrane with a myristoylation-signaling domain or the transmembrane domain of the representative TLR.

METHODS AND COMPOSITIONS FOR GENERATING AN IMMUNE RESPONSE BY INDUCING CD40 AND PATTERN RECOGNITION RECEPTORS AND ADAPTORS THEREOF

PRIORITY

Priority is claimed to international patent application number PCT/US2007/081963, filed on Oct. 19, 2007, entitled Methods and Compositions for Generating an Immune Response by Inducing CD40 and Pattern Recognition Receptors and Adaptors Thereof, which claims the benefit of U.S. Provisional Application Ser. No. U.S. 60/862,211, filed Oct. 19, 2006, and entitled Methods and Compositions for Generating an Immune Response by Inducing CD40 and a Toll-Like Receptor; and U.S. Provisional Application Ser. No. U.S. 60/895,088, filed Mar. 15, 2007, and entitled Methods and Compositions for Generating an Immune Response via Inducible Pattern Recognition Receptor and Adaptors Thereof, which are each referred to and incorporated herein by reference in their entirety.

FIELD OF THE INVENTION

The invention relates generally to the field of immunology, and in particular, methods and compositions for activating antigen-presenting cells and for inducing immune responses.

SEQUENCE LISTING DISCLOSURE

In accordance with 37 C.F.R. §1.52(e)(5), the material in the text file containing the sequence listing is hereby incorporated by reference in its entirety. The text file containing the sequence listing is named "BEL-2002-PC.txt," is 21 kilobytes in size and was created on Mar. 25, 2009.

BACKGROUND

Due to their unique method of processing and presenting antigens and the potential for high-level expression of costimulatory and cytokine molecules, dendritic cells (DC) are effective antigen-presenting cells (APCs) for priming and activating naïve T cells[1]. This property has led to their widespread use as a cellular platform for vaccination in a number of clinical trials with encouraging results[2,3]. However, the clinical efficacy of DC vaccines in cancer patients has been unsatisfactory, probably due to a number of key deficiencies, including suboptimal activation, limited migration to draining lymph nodes, and an insufficient life span for optimal T cell activation in the lymph node environment.

A parameter in the optimization of DC-based cancer vaccines is the interaction of DCs with immune effector cells, such as CD4+, CD8+ T cells and T regulatory (Treg) cells. In these interactions, the maturation state of the DCs is a key factor in determining the resulting effector functions[4]. To maximize CD4+ and CD8+ T cell priming while minimizing Treg expansion, DCs need to be fully mature, expressing high levels of co-stimulatory molecules, (like CD40, CD80, and CD86), and pro-inflammatory cytokines, like IL-12p70 and IL-6. Equally important, the DCs must be able to migrate efficiently from the site of vaccination to draining lymph nodes to initiate T cell interactions[5].

For the ex vivo maturation of monocyte-derived immature DCs, the majority of DC-based trials have used a standard maturation cytokine cocktail (MC), comprised of TNF-alpha, IL-1beta, IL-6, and $PGE_2$. The principal function of prostaglandin E2 ($PGE_2$) in the standard maturation cocktail is to sensitize the CC chemokine receptor 7 (CCR7) to its ligands, CC chemokine ligand 19 (CCL19) and CCL21 and thereby enhance the migratory capacity of DCs to the draining lymph nodes[6,7]. However, $PGE_2$ has also been reported to have numerous properties that are potentially deleterious to the stimulation of an immune response, including suppression of T-cell proliferation,[8,9] inhibition of pro-inflammatory cytokine production (e.g., IL-12p70 and TNF-alpha[10,11]), and down-regulation of major histocompatibility complex (MHC) II surface expression[12]. Therefore, maturation protocols that can avoid $PGE_2$ while promoting migration are likely to improve the therapeutic efficacy of DC-based vaccines.

A DC activation system based on targeted temporal control of the CD40 signaling pathway has been developed to extend the pro-stimulatory state of DCs within lymphoid tissues. DC functionality was improved by increasing both the amplitude and the duration of CD40 signaling[13]. To accomplish this, the CD40 receptor was re-engineered so that the cytoplasmic domain of CD40 was fused to synthetic ligand-binding domains along with a membrane-targeting sequence. Administration of a lipid-permeable, dimerizing drug, AP20187 (AP), called a chemical inducer of dimerization (CID)[14], led to the in vivo induction of CD40-dependent signaling cascades in murine DCs. This induction strategy significantly enhanced the immunogenicity against both defined antigens and tumors in vivo beyond that achieved with other activation modalities[13]. The robust potency of this chimeric ligand-inducible CD40 (named iCD40) in mice suggested that this method might enhance the potency of human DC vaccines, as well.

Pattern recognition receptor (PRR) signaling, an example of which is Toll-like receptor (TLR) signaling also plays a critical role in the induction of DC maturation and activation, and human DCs express, multiple distinct TLRs[15]. The eleven mammalian TLRs respond to various pathogen-derived macromolecules, contributing to the activation of innate immune responses along with initiation of adaptive immunity. Lipopolysaccharide (LPS) and a clinically relevant derivative, monophosphoryl lipid A (MPL), bind to cell surface TLR-4 complexes[16], leading to various signaling pathways that culminate in the induction of transcription factors, such as NF-kappaB and IRF3, along with mitogen-activated protein kinases (MAPK) p38 and c-Jun kinase (JNK)[17,18]. During this process DCs mature, and partially upregulate pro-inflammatory cytokines, like IL-6, IL-12, and Type I interferons[19]. LPS-induced maturation has been shown to enhance the ability of DCs to stimulate antigen-specific T cell responses in vitro and in vivo[20].

SUMMARY

An inducible CD40 (iCD40) system has been applied to human dendritic cells (DCs) and it has been demonstrated that combining iCD40 signaling with Pattern recognition receptor (PRR) ligation causes persistent and robust activation of human DCs. These activated DCs not only possess high migratory capacity in vitro and in vivo, but also produce high levels of IL-12 and potently activate antigen-specific helper (TH1) and cytotoxic T lymphocytes. These studies demonstrate potent DC activation and migratory capacity can be achieved in the absence of maturation cocktails that contain $PGE_2$. These features form the basis of cancer immuno-therapies for treating such cancers as advanced, hormone-refractory prostate cancer, for example. Accordingly, it has been discovered that the combination of inducing CD40 and a PRR synergistically activates antigen-presenting cells and induces an immune response against an antigen. It also has been discovered that antigen-presenting cells can be activated and immune responses can be generated against an antigen by inducing CD40.

Thus, provided herein is a method for activating an antigen-presenting cell, which comprises: (a) transducing an antigen-presenting cell with a nucleic acid having a nucleotide sequence that encodes a chimeric protein, wherein the chimeric protein comprises a membrane targeting region, a ligand-binding region and a CD40 cytoplasmic polypeptide region lacking the CD40 extracellular domain; (b) contacting the antigen-presenting cell with a non-protein multimeric ligand that binds to the ligand-binding region; and (c) contacting the antigen-presenting cell with a PRR ligand, for example, a TLR ligand whereby the antigen-presenting cell is activated. In certain embodiments, antigen-presenting cell is not contacted with prostaglandin $E_2$ ($PGE_2$) when contacted with the multimeric ligand, and in particular embodiments, the antigen-presenting cell is not contacted with a composition comprising prostaglandin $E_2$ ($PGE_2$) and one or more components selected from the group consisting of IL-1beta, IL-6 and TNF alpha.

Also provided is a method for activating an antigen-presenting cell, which comprises: (a) transducing an antigen-presenting cell with a nucleic acid having a nucleotide sequence that encodes a chimeric protein, wherein the chimeric protein comprises a membrane targeting region, a ligand-binding region and a CD40 cytoplasmic polypeptide region lacking the CD40 extracellular domain; and (b) contacting the antigen-presenting cell with a non-protein multimeric ligand that binds to the ligand-binding region, wherein the antigen-presenting cell is not contacted with prostaglandin E2 ($PGE_2$) when contacted with the multimeric ligand, whereby the antigen-presenting cell is activated. In some embodiments, the method further comprises contacting the antigen-presenting cell with a PRR ligand, for example, a Toll-like receptor (TLR) ligand.

Further, provided is a method for inducing a cytotoxic T lymphocyte (CTL) immune response against an antigen, which comprises: contacting an antigen-presenting cell sensitized with an antigen with: (a) a multimeric ligand that binds to a chimeric protein in the cell, wherein the chimeric protein comprises a membrane targeting region, a ligand-binding region and a CD40 cytoplasmic polypeptide region lacking the CD40 extracellular domain, and (b) a PRR ligand, for example, a Toll-like receptor (TLR) ligand; whereby a CTL immune response is induced against the antigen. In certain embodiments, antigen-presenting cell is not contacted with prostaglandin $E_2$ ($PGE_2$) when contacted with the multimeric ligand, and in particular embodiments, the antigen-presenting cell is not contacted with a composition comprising prostaglandin $E_2$ ($PGE_2$) and one or more components selected from the group consisting of IL-1beta, IL-6 and TNF alpha.

Also provided is a method for inducing an immune response against an antigen, which comprises: contacting an antigen-presenting cell sensitized with an antigen with a multmeric ligand that binds to a chimeric protein in the cell, wherein: (a) the chimeric protein comprises a membrane targeting region, a ligand-binding region and a CD40 cytoplasmic polypeptide region lacking the CD40 extracellular domain, and (b) the antigen-presenting cell is not contacted with prostaglandin $E_2$ ($PGE_2$) when contacted with the multimeric ligand; whereby an immune response against the antigen is induced. The method can further comprise contacting the antigen-presenting cell with a PRR ligand, for example, a TLR ligand.

Provided also is a method for inducing a cytotoxic T lymphocyte (CTL) immune response against an antigen, which comprises: contacting a human antigen-presenting cell sensitized with an antigen with: (a) a multimeric molecule having two or more regions that bind to and multimerize native CD40, and (b) a PRR ligand, for example, a TLR ligand ligand; whereby a CTL immune response is induced against the antigen. In such methods, the multimeric molecule can be an antibody that binds to an epitope in the CD40 extracellular domain (e.g., humanized anti-CD40 antibody; Tai et al., *Cancer Research* 64, 2846-2852 (2004)), can be a CD40 ligand (e.g., U.S. Pat. No. 6,497,876 (Maraskovsky et al.)) or may be another co-stimulatory molecule (e.g., B7/CD28).

In the methods for inducing an immune response presented herein, the antigen-presenting cell can be transduced ex vivo or in vivo with a nucleic acid that encodes the chimeric protein. The antigen-presenting cell may be sensitized to the antigen at the same time the antigen-presenting cell is contacted with the multimeric ligand, or the antigen-presenting cell can be pre-sensitized to the antigen before the antigen-presenting cell is contacted with the multimerization ligand. In some embodiments, the antigen-presenting cell is contacted with the antigen ex vivo. In certain embodiments the antigen-presenting cell is transduced with the nucleic acid ex vivo and administered to the subject by intradermal administration, and sometimes the antigen-presenting cell is transduced with the nucleic acid ex vivo and administered to the subject by subcutaneous administration. The antigen may be a tumor antigen, and the CTL immune response can induced by migration of the antigen-presenting cell to a draining lymph node.

Also provided herein is a composition comprising an antigen-presenting cell and a PRR ligand, for example, a TLR ligand, wherein: the antigen-presenting cell is transduced with a nucleic acid having a nucleotide sequence that encodes a chimeric protein, and the chimeric protein comprises a membrane targeting region, a ligand-binding region and a CD40 cytoplasmic polypeptide region lacking the CD40 extracellular domain. The composition may further comprise a non-protein multimeric ligand that binds to the ligand-binding region.

In the methods and compositions presented herein, the membrane targeting region can be a myristoylation targeting region. In some embodiments, the CD40 cytoplasmic polypeptide region is encoded by a polynucleotide sequence in SEQ ID NO: 1. The multimeric ligand often is a small molecule and it sometimes is dimeric, such as a dimeric FK506 or a dimeric FK506 analog (e.g., AP1903). Any suitable PRR ligand, for example, any suitable TLR ligand can be utilized, and can be selected by the person of ordinary skill in the art (e.g., Napolitani et al., *Nature Immunology*, Advanced Online Publication doi:10.1038/ni1223 (2005)). The TLR ligand in certain embodiments is selected from the group consisting of lipopolysaccharide (LPS), monophosphoryl lipid A (MPL), FSL-1, Pam3, CSK4, poly(I:C), synthetic imidazoquinoline resiquimod (R848; U.S. Pat. No. 6,558,951 to Tomai et al.) and CpG, and the TLR ligand sometimes is a TLR4 ligand such as LPS or MPL. The nucleic acid can be contained within a viral vector, such as an adenoviral vector, for example. In certain embodiments, the antigen-presenting cell is transduced with the nucleic acid ex vivo or in vivo, and sometimes the antigen-presenting cell is a dendritic cell, such as a human dendritic cell, for example.

Also provided herein is a method for assessing migration of an antigen-presenting cell to a lymph node, which comprises: (a) injecting into a subject an antigen-presenting cell that produces a detectable protein, and (b) determining the amount of the detectable protein in the lymph node of the animal, whereby migration of the antigen-presenting cell to the lymph node is assessed from the amount of the detectable protein in the lymph node. In such methods the animal can be a rodent, such as a rat or a mouse (e.g., irradiated mouse). In some embodiments, the detectable protein is a luciferase protein, such as a chick beetle (e.g., Pyrophorus plagiophalamus) red-shifted luciferase protein. In certain embodiments, the antigen-presenting cell has been transduced with a nucleic acid having a polynucleotide sequence that encodes the detectable protein. In certain embodiments, the lymph node is the popliteal lymph node or inguinal lymph node. The antigen-presenting cell can be a dendritic cell, such as a human dendritic cell. In certain embodiments, the lymph node is removed from the animal before the amount of detectable protein is determined, and sometimes the D-Luciferin is administered to the removed lymph node. The amount of the detectable protein may be qualitative (e.g., relative amounts compared across different samples) and can be quantitative (e.g., a concentration). The amount of the detectable protein may be determined by directly detecting the protein. For example, the protein may be fluorescent (e.g., green fluorescent protein or a red-shifted or blue-shifted version) or can be bound to a fluorescent label (e.g., an antibody linked to a fluorophore). Alternatively, the amount of the detectable protein can determined indirectly by administering a substrate to the animal that is converted into a detectable product by the protein and detecting the detectable product. For example, the amount of a luciferase protein can be determined by administering D-Luciferin to the animal and detecting the D-Luciferin product generated by the luciferase produced in the antigen-presenting cell.

Provided also in the present invention are methods for activating an antigen-presenting cell, which comprise: transducing (or transfecting) an antigen-presenting cell with a nucleic acid having a nucleotide sequence that encodes a chimeric protein, wherein the chimeric protein comprises (i) a membrane-targeting region, (ii) a ligand-binding region and (iii-a) a signaling region and/or cytoplasmic region of a pattern recognition receptor (PRR) or (iii-b) an adapter of a PRR; and contacting the antigen-presenting cell with a non-protein multimeric ligand that binds to the ligand-binding region; whereby the antigen-presenting cell is activated. In certain embodiments the chimeric protein comprises a CD40 cytoplasmic polypeptide region lacking the CD40 extracellular domain. The CD40 cytoplasmic polypeptide region in certain embodiments is encoded by a polynucleotide sequence in SEQ ID NO: 1

In some embodiments the chimeric protein comprises a signaling region and/or cytoplasmic region of a PRR. Sometimes the PRR is a NOD-like PRR, such as a NOD1 PRR or a NOD2 PRR, for example. In certain embodiments the PRR is not a NOD-like PRR, and is not a NOD1 PRR or a NOD2 PRR, for example. The PRR in some embodiments is a RIG-like helicase (RLH), such as a RIG-I PRR or an Mda-5 PRR, for example. The PRR sometimes is a Toll-like receptor (TLR) PRR, such as a TLR3, TLR4, TLR7, TLR8 and TLR9, and in certain embodiments the chimeric protein comprises a cytoplasmic region, or a TIR (Toll/IL-1R) region, from a TLR PRR. In certain embodiments the chimeric protein comprises an adapter that binds to a PRR of any one of embodiments described herein. The adaptor may be selected from the group consisting of MyD88, TRIF/TICAM-1, TIRAM/ICAM-2, MAL/TIRAP, or protein-protein interaction domains from said adaptors, such as TIR, CARD or pyrin domains (PYD) in certain non-limiting embodiments. Nucleic acid sequences and protein sequences of such molecules, and signaling regions and cytoplasmic regions therein, are known to the person of ordinary skill in the art (e.g., World Wide Web address ncbi.nlm.nih.gov/entrez/query.fcgi?db=gene).

In certain embodiments, the membrane targeting region is a myristoylation-targeting region, although the membrane-targeting region can be selected from other types of transmembrane-targeting regions, such as regions described hereafter. In some embodiments the ligand is a small molecule, and sometimes the molecule is dimeric. Examples of dimeric molecules are dimeric FK506 and dimeric FK506 analogs. In certain embodiments the ligand is AP1903 or AP20187. In some embodiments, the chimeric protein includes one or more ligand-binding regions, such as two or three ligand-binding regions, for example. The ligand-binding regions often are tandem.

The nucleic acid in certain embodiments is contained within a viral vector, such as an adenoviral vector for example. The antigen-presenting cell in some embodiments is contacted with an antigen, sometimes ex vivo. In certain embodiments the antigen-presenting cell is in a subject and an immune response is generated against the antigen, such as a cytotoxic T-lymphocyte (CTL) immune response. In certain embodiments, an immune response is generated against a tumor antigen (e.g., PSMA). In some embodiments, the nucleic acid is prepared ex vivo and administered to the subject by intradermal administration or by subcutaneous administration, for example. Sometimes the antigen-presenting cell is transduced or transfected with the nucleic acid ex vivo or in vivo. In some embodiments, the nucleic acid comprises a promoter sequence operably linked to the polynucleotide sequence. Alternatively, the nucleic acid comprises an ex vivo-transcribed RNA, containing the protein-coding region of the chimeric protein.

Also provided herein is a composition which comprises a nucleic acid having a polynucleotide sequence that encodes a chimeric protein, wherein the chimeric protein comprises (i) a membrane targeting region, (ii) a ligand-binding region that binds to a multimeric non-protein ligand, and (iii-a) a signaling region and/or cytoplasmic region of a pattern recognition receptor (PRR) or (iii-b) an adapter of a PRR. Embodiments pertaining to methods described above also are applicable to compositions herein.

Figure 3:
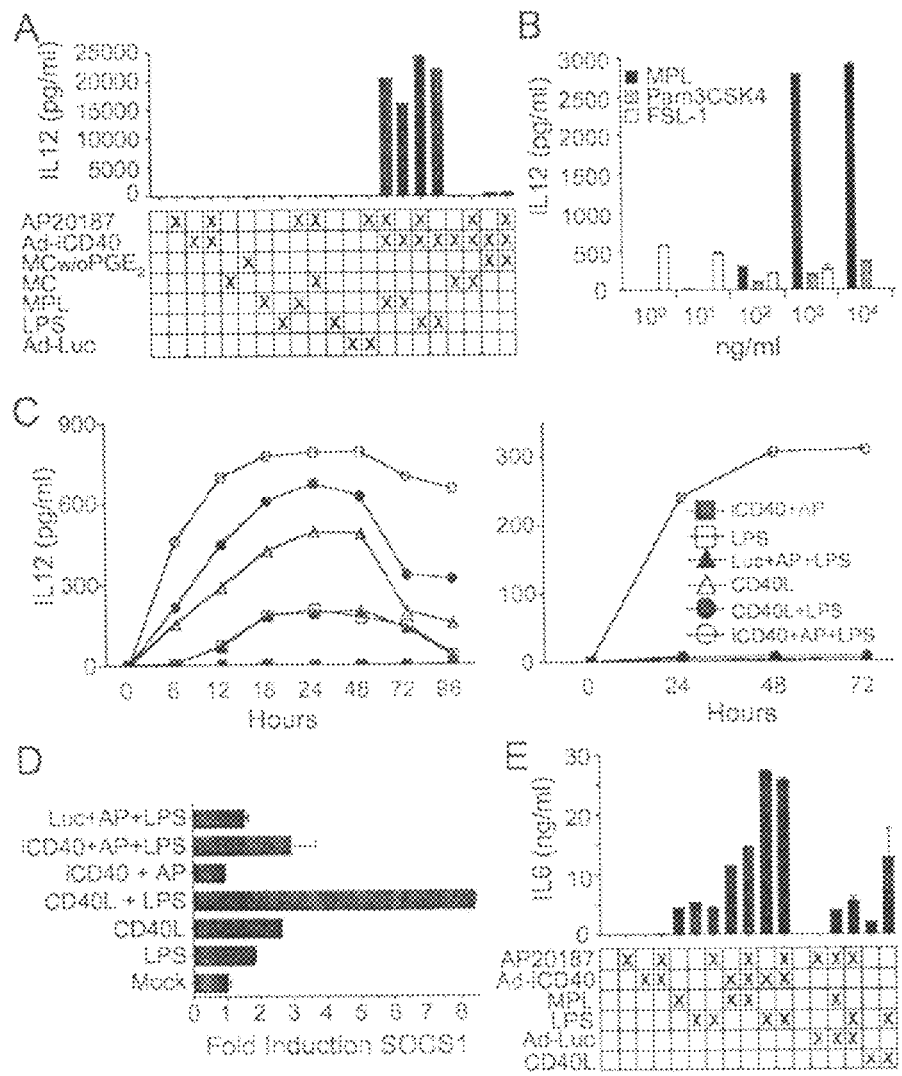

FIG. 3. Synergism of iCD40 and TLR-4 for IL-12p70 and IL-6 production. A. Immature human DCs ($5 \times 10^5$) were transduced with Ad5/f35-iCD40 or Ad5/f35-Luciferase (Luc) and stimulated with 1 microgram/ml of LPS or MPL for 48 hours in the presence of 100 nM AP20187 (AP) dimerizer drug. Alternatively, DCs were stimulated with standard maturation cocktail (MC), or with MC lacking $PGE_2$ (MC w/o $PGE_2$). The supernatants were assayed by ELISA (in duplicate) for IL-12p70 level 48 hours following various treatments. B. DCs were transduced with Ad5/f35-iCD40 and stimulated with FSL-1, Pam3CSK4 or MPL for 48 hours. The supernatants were assayed by ELISA 48 hours post-stimulation. C. DCs were transduced with Ad5/f35-iCD40 and stimulated with 1 microgram/ml LPS or CD40L (Alexis Biochemicals). IL-12p70 production was monitored at 6 h, 12 h, 18 h, 24 h, 48 h, 72 h and 96 h post-stimulation (left panel). In parallel, cells of the same donor were washed 3 times 24 h post-stimulation and cultured in medium without stimulatory factors. The expression of IL-12p70 was monitored for 3 more days, every 24 hours (right panel). D. Expression of human SOCS1 gene was measured in DCs transduced and stimulated (as described above) for 24 hours. The expression levels were measured in duplicates and normalized by 18S ribosomal RNA housekeeping gene expression. The fold increase above mock expression is shown. E. DCs were transduced with Ad5/f35-iCD40 or Ad5/f35-Luc and stimulated with LPS, MPL and CD40L for 48 hours with or without 100 nM of AP20187 dimerizer drug. The supernatants were assayed by ELISA (in duplicates) for IL-6 48 h following various treatments. All the experiments were performed with DCs from at least three different donors. The IL-12p70 and IL-6 expression levels were measured from at least 5 different donors.

Figure 4:
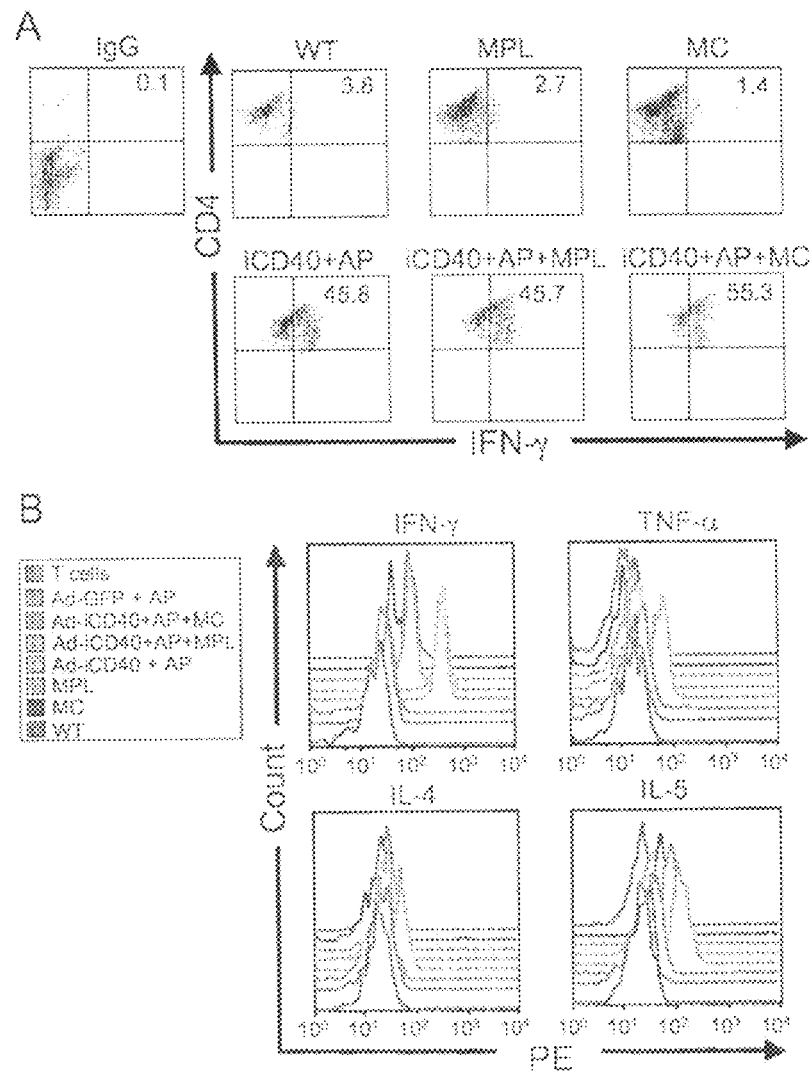

FIG. 4. iCD40-DCs significantly induce antigen-specific TH1 polarized CD4+ T cells. A. DCs from HLA DR11.5 donor were pulsed with tetanus toxoid and transduced with the described agents. Autologous CD4+CD45RA+ T cells were co-cultured with DCs (at DC:T cell ratio 1:10) for 7 days and restimulated at day 8 with DCs pulsed with TTp30 peptide (FNNFTVSFWLRVPKVSASHLE) (SEQ ID NO: 5). T cells were double stained with anti-interferon-gamma-FITC and anti-CD4-PE antibodies. The percentage of CD4+/IFN-gamma+ T cells is indicated. B. Supernatants were harvested and analyzed by BD Cytometric Bead Array Flex Set for expression of IFN-gamma, TNF-alpha, IL-4, and IL-5. Results of one experiment out of three are shown.

Figure 5:
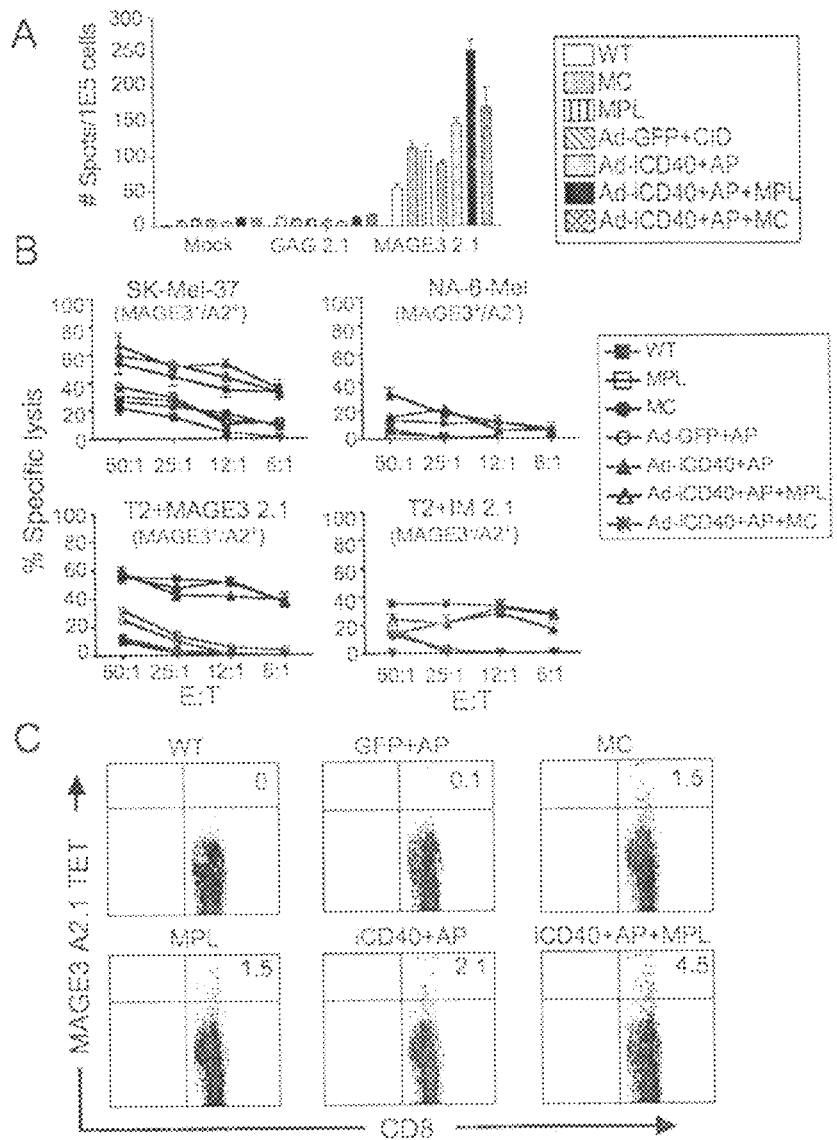

FIG. 5. Enhanced induction of MAGE-3 antigen-specific CTL by iCD40-DCs. DCs derived from HLA-A2 positive donors were transduced with indicated reagents and pulsed with 25 micrograms/ml of MAGE3 protein. DCs were cultured with autologous T-cells (1:3 DC:T cell ratio) for 7 days in complete RPMI supplemented with 20 IU/ml of hIL-2. T cells were restimulated with DCs at day 7. A. Frequency of MAGE3 2.1 peptide-specific T cells were determined by IFN-gamma ELISPOT analysis. 100,000 T cells/well were stimulated with MAGE3 2.1 or GAG 2.1 (negative control)/irrelevant peptide) or cultured without stimulation (mock). B. DCs from HLA-A2 positive donor were co-cultured with autologous T cells. After three serial stimulations with DCs, T cells were evaluated for antigen-specific lytic activity using a $^{51}Cr$ release assay. The assays were performed in triplicate. IM, influenza matrix peptide. C. The effector T cell populations generated after serial stimulation with DCs were stained with MAGE3 A2.1 peptide-loaded HLA-A2 tetramer. MAGE3 peptide-specific CD8+ T cells were identified using flow cytometry. The percentages indicate the fraction of tetramer-positive cells within the entire populations of CD8+ T cells. Representative results of one experiment out of three (independent donors) performed are shown.

Figure 6:
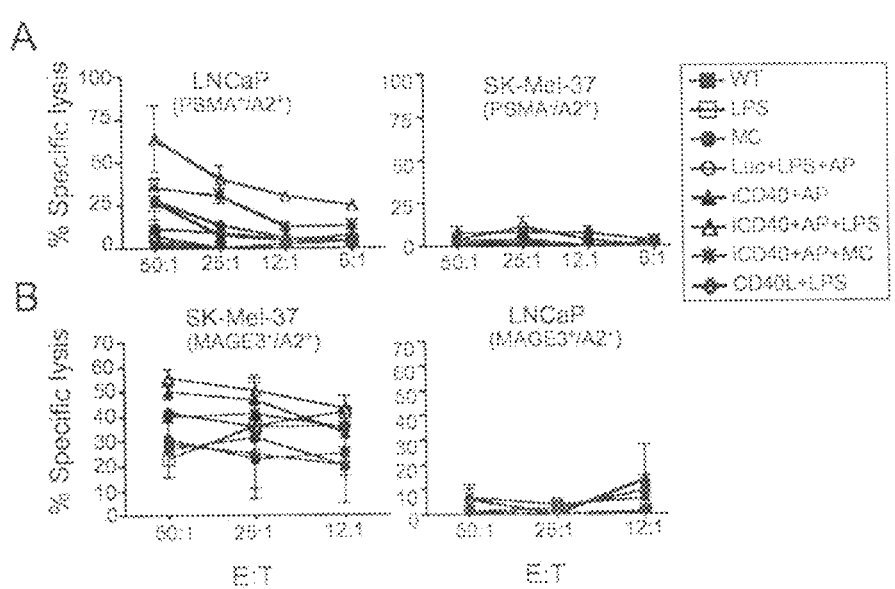

FIG. 6. Enhanced cytolytic function of PSMA-specific CTL induced by iCD40-DCs. A. DCs generated from HLA-A2+ male volunteers were pulsed with 50 micrograms/ml PSMA protein, transduced with Ad-iCD40 or Ad-Luc and cultured with LPS (1 micrograms/ml) or MC. Antigen-specific CTL activity was assessed by chromium-release assay. B. DCs of the same HLA-A2+ male donor were pulsed with MAGE-3 2.1 peptide. MAGE-3-specific CTL cytolytic activity was measured in chromium-release assay.

Figure 7:
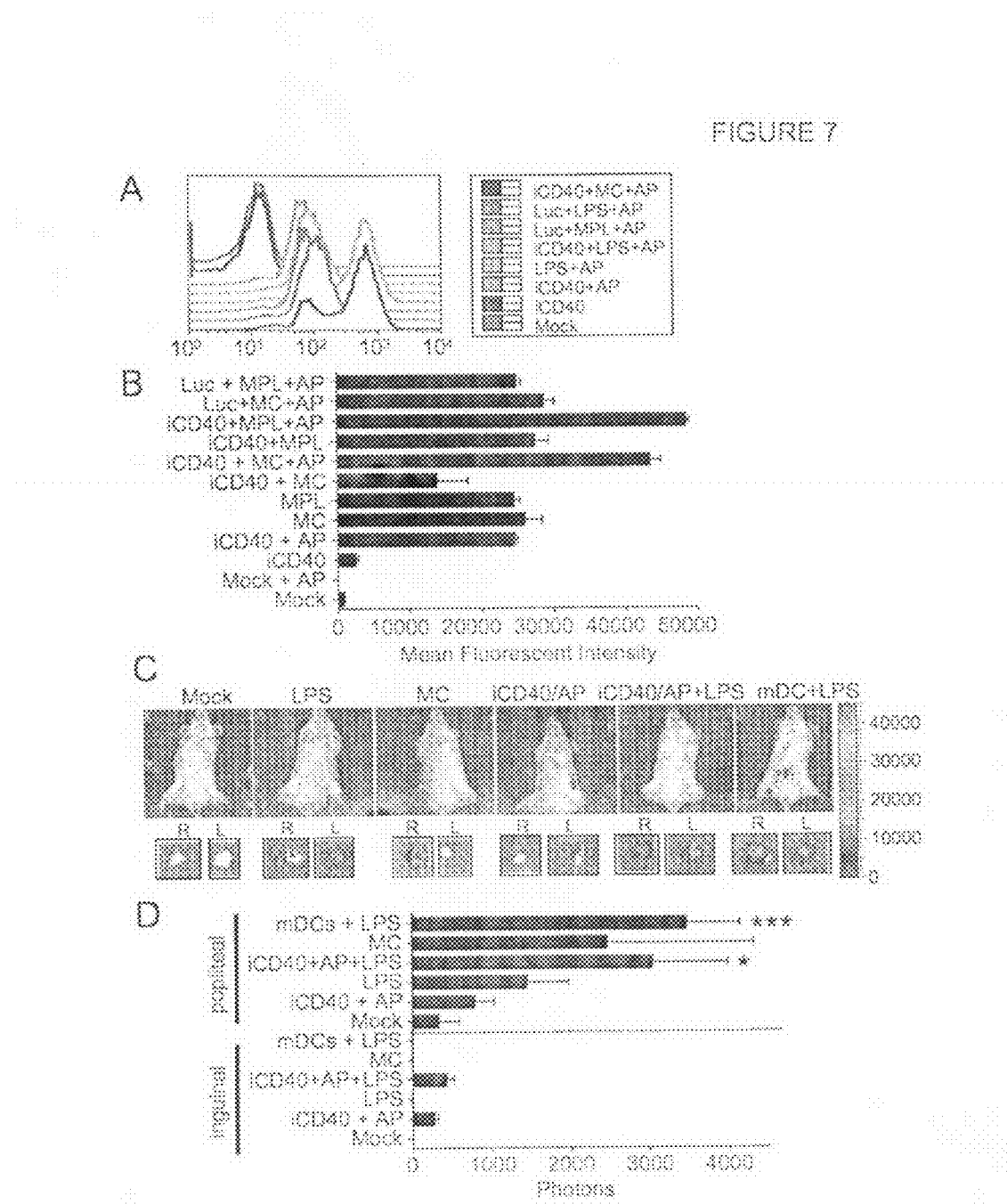

FIG. 7. Up-regulation of CCR7 expression and enhanced migratory capacities of iCD40-DCs. A. Human DCs were transduced with Ad-iCD40 (iCD40) or Ad-Luc (Luc) and cultured for 48 h with 100 nM AP20187 (AP), MC and 1 micrograms/ml LPS or MPL. CCR7 expression was measured using PE-conjugated anti-human CCR7 mAb. The percentage of CCR7-positive cells is indicated. Similar results were obtained for at least five different donors. B. Human DCs were transduced with 10,000 VP/cell of Ad5f35-iCD40 (iCD40) or Ad-Luciferase (Luc) and incubated for 48 hours with 1 micrograms/ml MPL or MC and 100 nM AP20187. DCs were labeled with Green-CMFDA cell tracker and added to the upper chamber. Fluorescence of cells migrated through the microporous membrane was measured. Each experiment (including the control spontaneous migration to the medium) was performed in triplicate for at least four different donors. C. Human DCs were transduced with Ad-CBR-Luc or iCD40 and stimulated as indicated. Mouse DCs (mDCs) were transduced with Ad-CBR-Luc and stimulated with LPS. $2 \times 10^6$ DCs were injected into both hind footpads of three mice/group (n=6). Mice were imaged at day 2 after inoculation (upper panel), and popliteal lymph nodes (lower panel) were removed at day 2 post-DC inoculation. D. Mean luminescent signal from the removed popliteal and inguinal LNs was measured and normalized by background subtraction (* $p<0.05$, *** $p<0.001$ compared to mock DCs).

Figure 1:
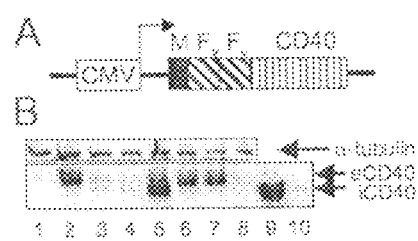
FIG. 1. Schematic diagram of iCD40 and expression in human DCs. A. The human CD40 cytoplasmic domain can be subcloned downstream of a myristoylation-targeting domain (M) and two tandem domains (Fv)[22]. The expression of M-Fv-Fv-CD40 chimeric protein, referred to here as inducible CD40 (iCD40) can be under cytomegalovirus (CMV) promoter control. B. The expression of endogenous (eCD40) and recombinant inducible (iCD40) forms of CD40 assessed by Western blot. Lane 1, wild type DCs (endogenous CD40 control); lane 2, DCs stimulated with 1 microgram/ml of LPS; lanes 3 and 4, DCs transduced with 10,000 VP/cell (MOI~160) of Ad5/f35-iCD40 (iCD40-DCs) with and without AP20187 dimerizer drug respectively; lane 5, iCD40-DCs stimulated with LPS and AP20187; lane 6, DCs stimulated with CD40L and LPS; lane 7, DCs transduced with Ad5/f35-GFP (GFP-DCs) at MOI 160 and stimulated with AP20187 and LPS; lane 8, GFP-DCs stimulated with AP20187; lane 9, 293 T cells transduced with Ad5/f35-iCD40 (positive control for inducible form of CD40). The expression levels of alpha-tubulin served as internal control.
Figure 8:
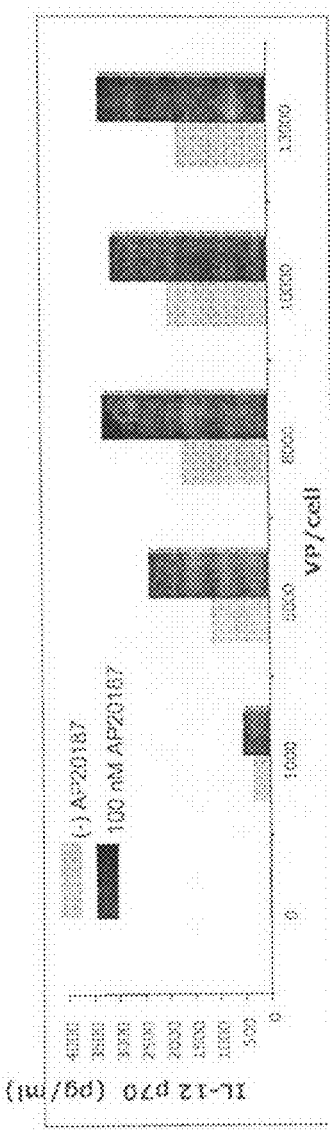
Figure 9:
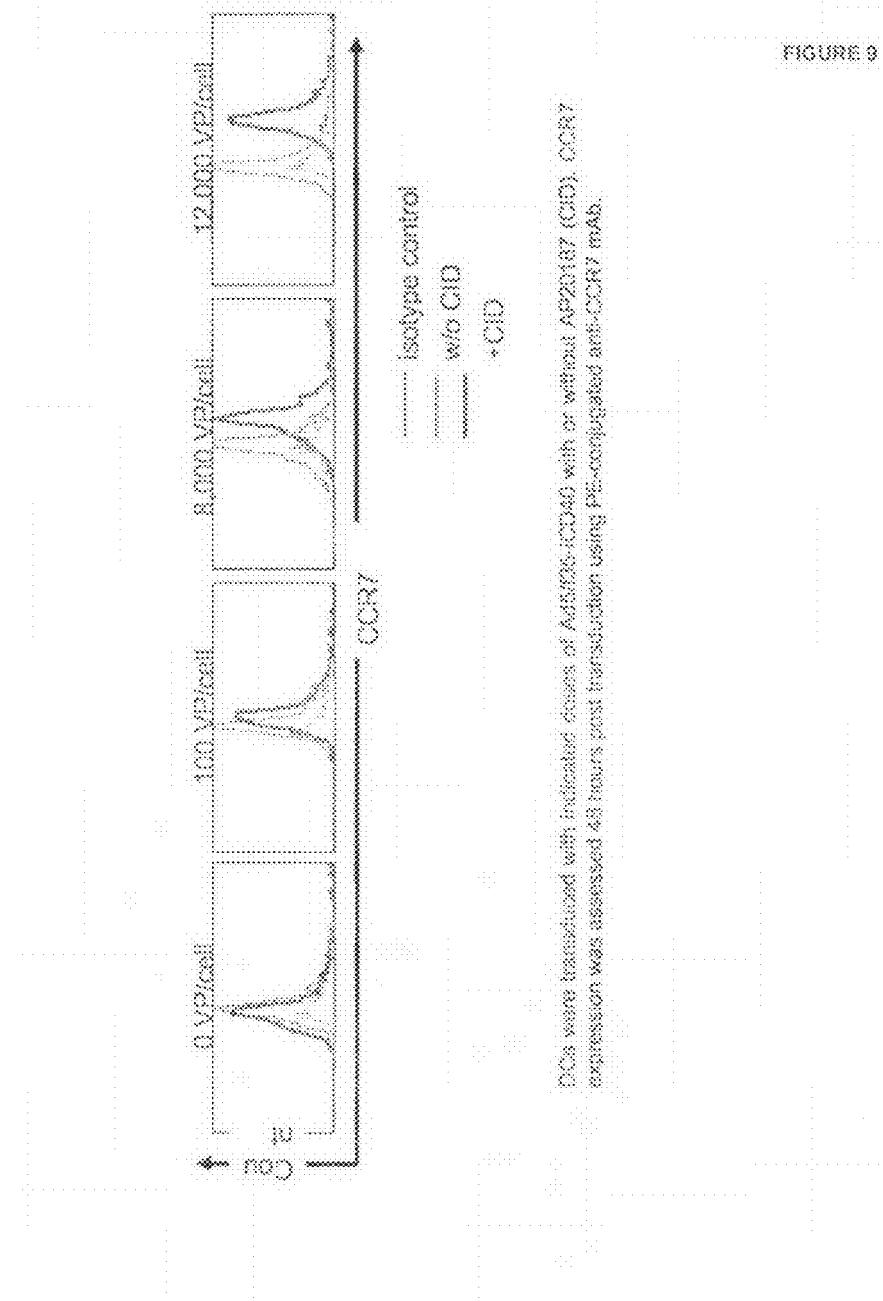
Figure 10:
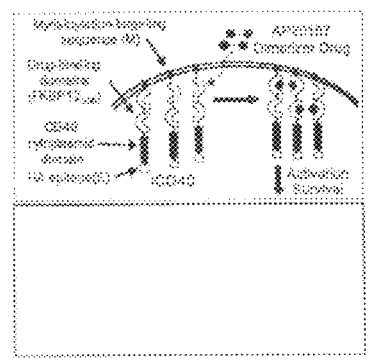

FIG. 8 is a supplementary figure to FIG. 1.
FIG. 9 is a supplementary figure to FIG. 2.
FIG. 10. Schematic of iCD40. Administration of the lipid-permeable dimerizing drug, AP20187/AP1903[1], leads to oligomerization of the cytoplasmic domain of CD40, modified to contain AP20187-binding domains and a myristoylation-targeting sequence.

Figure 11:
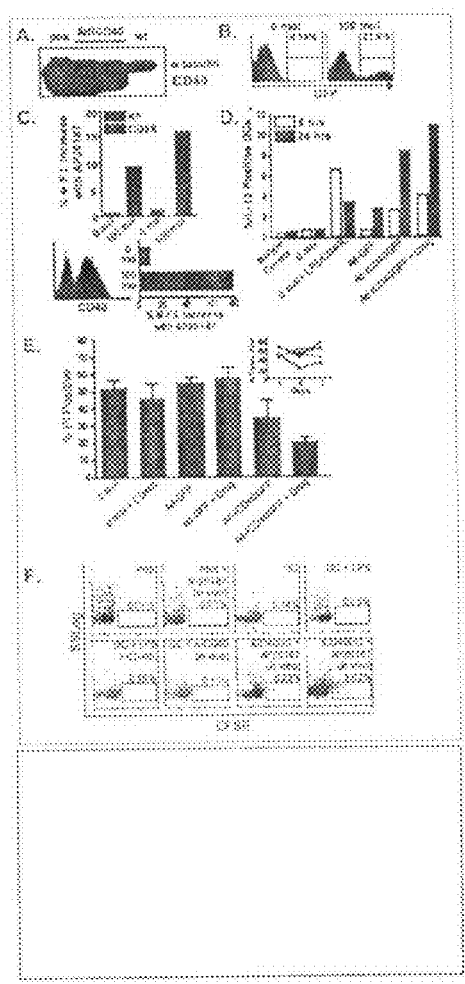

FIG. 11. iCD40 activates primary DCs and prolongs their longevity. A. Western blot (-HA) of primary DCs infected with AD-iCD40-GFP. B. Flow cytometry analysis of transduced DCs. C. Flow cytometry of $K^b$, B7.2 and endogenous CD40 on iCD40-stimulated DCs. D. Kinetics of IL-12 induction (ELISA) by iCD40 and LPS. E. Survival kinetics of DCs following CD40L or iCD40 stimulation. F. Survival kinetic of DCs in vivo. Draining popliteal lymph nodes were collected 42 h after DC injection, and propidium iodide-negative populations were analyzed by flow cytometry.

Figure 12:
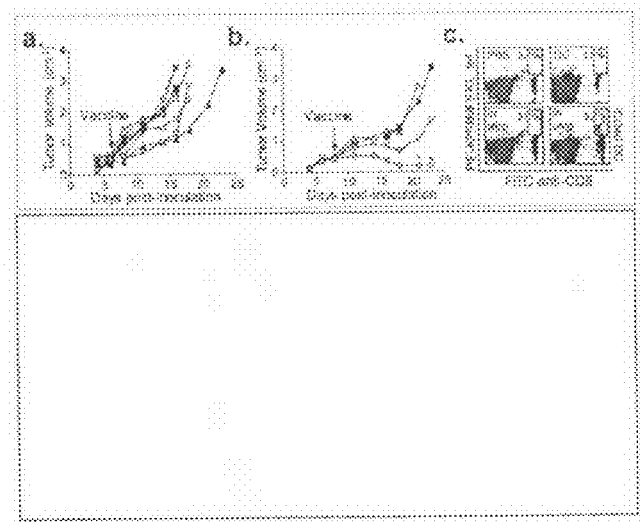

FIG. 12. iCD40 enhances the efficacy of DC-based tumor vaccines and the potency of DC-mediated tumor immunosurveillance. (a) Activation of SIINFEKL-pulsed (SEQ ID NO: 6) iCD40 BMDCs with LPS or CD40L or both in vitro, or with CD40-specific mAb in vivo, show no efficacy towards large (greater than 0.5 cm$^3$) EG.7-OVA tumors. Open square, PBS.exp.1; filled triangle, PBS.exp.2; open inverted triangle, DC; open diamond, DC+LPS; open circle, DC+LPS/CD40L; filled square, DC+rat IgG; open triangle, CD40-specific mAb in vivo. (b) In vivo drug-mediated activation of iCD40-expressing DCs eliminates established EG.7-OVA tumors after a single vaccination. Filled square, PBS; open triangle, iCD40 DC; open inverted triangle, iCD40 DC+AP20187 in vitro; open diamond, iCD40.

Figure 13:
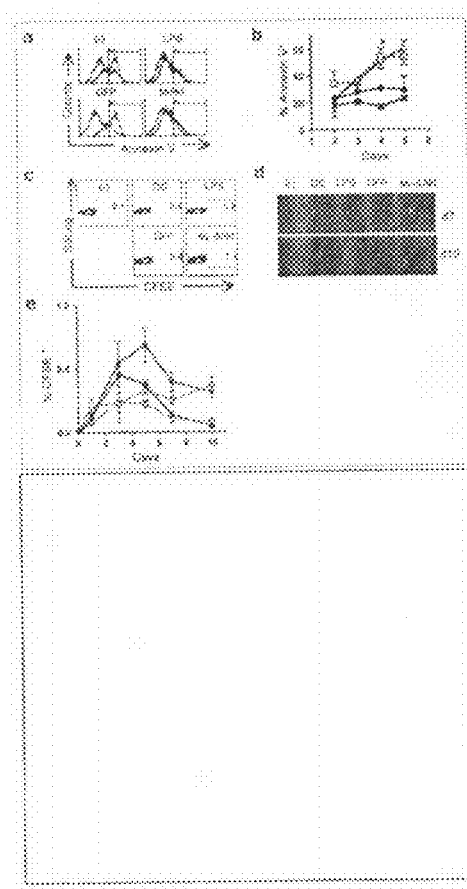

FIG. 13. $M_F$-ΔAkt and M-Akt induce BMDC longevity in vitro and in vivo. (a, b) BMDCs were left untreated (□), or treated with LPS (■), Ad-EGFP (○) or Ad-M-Akt (●) at 100 m.o.i. and further incubated for 2 to 5 d without GM-CSF. In vitro DC apoptosis examined by Annexin V-PE staining. Histograms of d5 (black line) were compared to that of d2 (red line) (a), Error bars=mean+std. of results pooled from three independent experiments. *, P<0.05 between Ad-EGFP and Ad-M-Akt (b). (c, d, e) Effect of Ad-$M_F$-ΔAkt on BMDC longevity, in vivo. CFSE-stained BMDCs were untreated (□), or treated with LPS (■), Ad-EGFP (○) or Ad-$M_F$-ΔAkt (●) for 2 hr before injection into hind legs of syngeneic mice (n=2-4 per time point). (c) After indicated times, draining popliteal LN cells were stained with PI. PF/CFSE cells were analyzed by flow cytometry. Background CFSE$^+$ from PBS control (−) was subtracted for each value. (d) Boxed numbers indicate d 5 CFSE$^+$ percent. (e) Representative LNs isolated from indicated mice on days 7 and 10.

Figure 14:
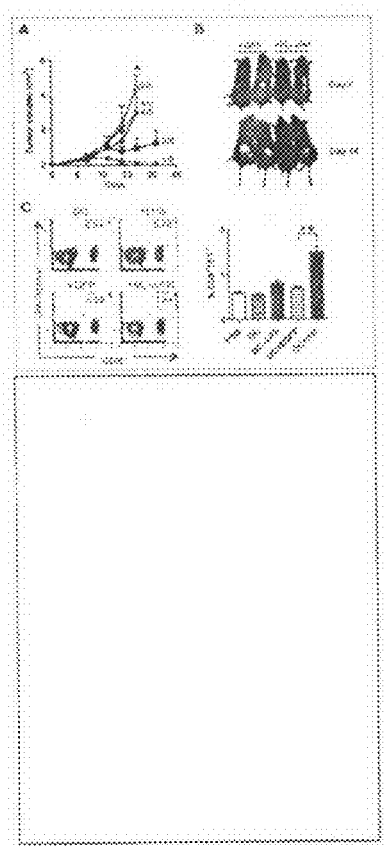

FIG. 14. $M_F$-ΔAkt expression enhances the efficacy of DC-based tumor vaccines. (a) Syngeneic BL/6 mice (n=5) challenged with EG.7-ova cells (2×10$^6$) at d0 were treated with PBS (○) or 2×10$^6$ BMDCs (■) pulsed with SIINFEKL (SEQ ID NO: 6) peptide (10 μg/ml) and LPS (1 μg/ml) (■), 100 m.o.i. of Ad-EGFP (●) or Ad-$M_F$-ΔAkt (▲) at d7, and tumor sizes were recorded biweekly. Numbers indicate fraction of mice bearing tumors (>0.1 cm$^3$). *, P<0.05 (b) Representative examples of EG7-OVA tumor-bearing mice vaccinated with Ad-EGFP or Ad-$M_F$-ΔAkt BMDCs. Tumors were compared on d7 and d14 after vaccination. (c) Left, PBMCs from indicated group at d21 were isolated and stained with PE-K$^b$SIINFEKL (SEQ ID NO: 6) tetramer and FITC-conjugated CD8. Right, mean percentage of CD8$^+$ and K$^b$SIINFEKL (SEQ ID NO: 6) tetramer positive population in PBMCs from two to three mice per group. Error bars represent mean±S.E.M. *, p<0.05, **, P<0.005.

Figure 15:
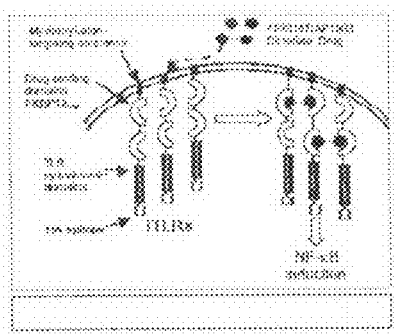

FIG. 15 is a schematic of CID-inducible TLRs.

FIG. 16. Inducible TLR7 and 8 signal in Jurkat T cells. Jurkat TAg cells were co-transiently transfected with NF-kappaB-SEAP reporter plasmid along with various iTLRs, positive control ihCD40, or negative control vector. After 24 h cells were treated with dilutions of CID for an additional 20 hrs. Average of 2 wells shown. Representative of 3 experiments. All constructs verified by sequence and protein analysis.

Figure 17:
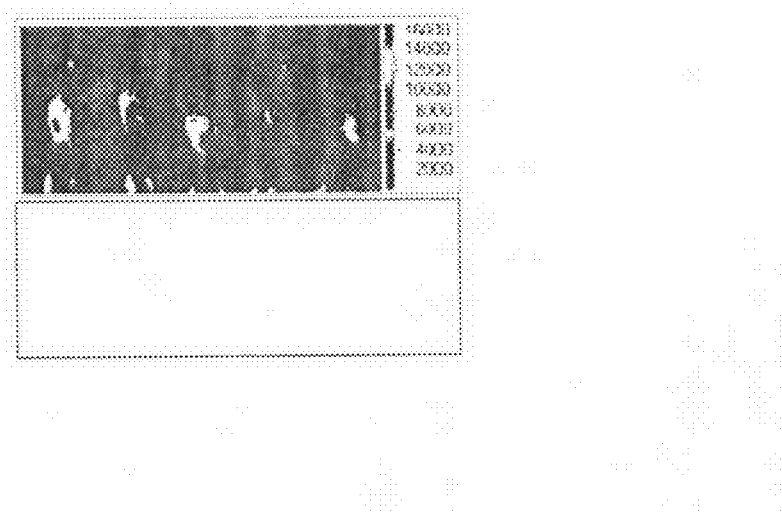

FIG. 17. Detection of chemiluminescent B16 tumors in syngeneic C57BL/6 mice. B16 melanoma cells were stably transfected with expression plasmid, pEF1-CBR-IRES-Neo. 10E5 cells were injected subQ and imaged using an IVIS™ imaging system 5 days later following i.p. D-Luciferin (~1 mg) injection. Note: even non-palpable tumors detected.

Figure 18:
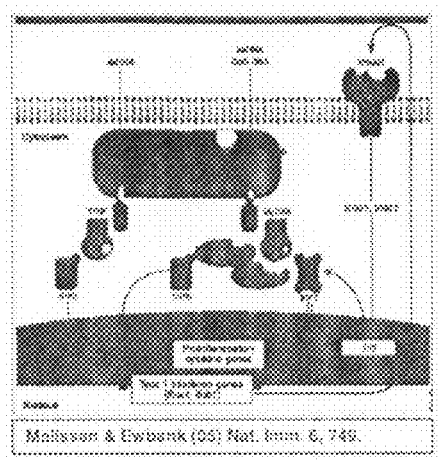

FIG. 18 is a schematic from Malissen & Ewbank (05) Nat. 1 mm. 6, 749.

Figure 19:
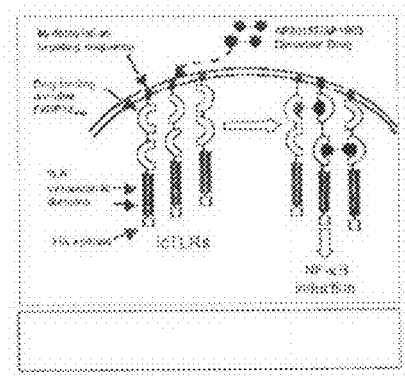

FIG. 19 is a schematic of CID-inducible composite Toll-like receptors (icTLRs).

Figure 20:
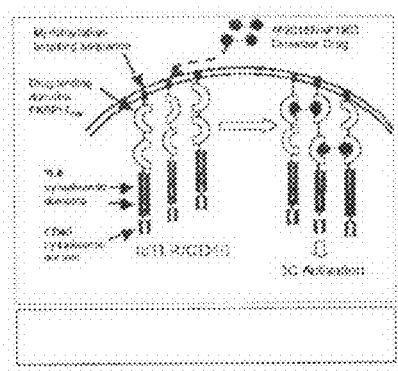

FIG. 20 is a schematic of CID-inducible composite TLR (icTLRs)/CD40.

Figure 21:
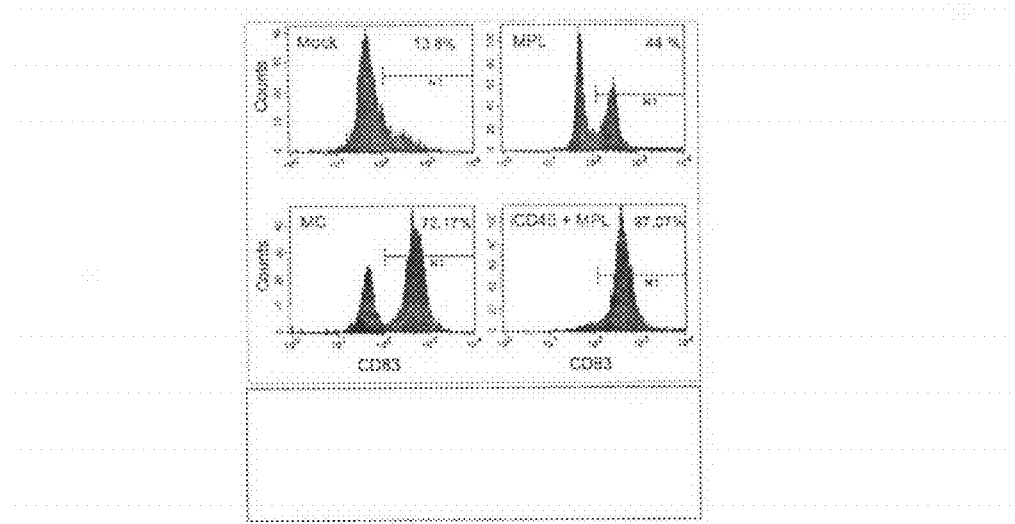

FIG. 21 Synergism of TLR4 and iCD40 signaling. MoDCs were stained for CD83 expression 48 h following MPL (1 mg/ml), MC (IL 1b (150 ng/ml), IL6 (150 ng/ml), TNFa (10 ng/ml), PGE$_2$ (1 mg/ml)), iCD40 (10 k vp/cell)/AP20187 (100 nM)+MPL, or mock stimulation. Percentage CD83 cells shown.

Figure 22:
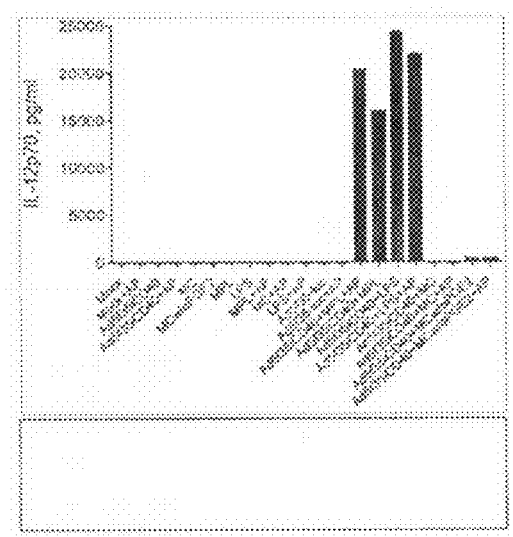

FIG. 22. Synergism of TLR4 and iCD40 signaling for IL12p70 production. Supernatants were assayed by ELISA for IL12p70 levels following various treatments (48 hrs) of MoDCs. In this experiment only iCD40+TLR4 ligation (with MPL or LPS) led to high-level IL12 production.

Figure 23:
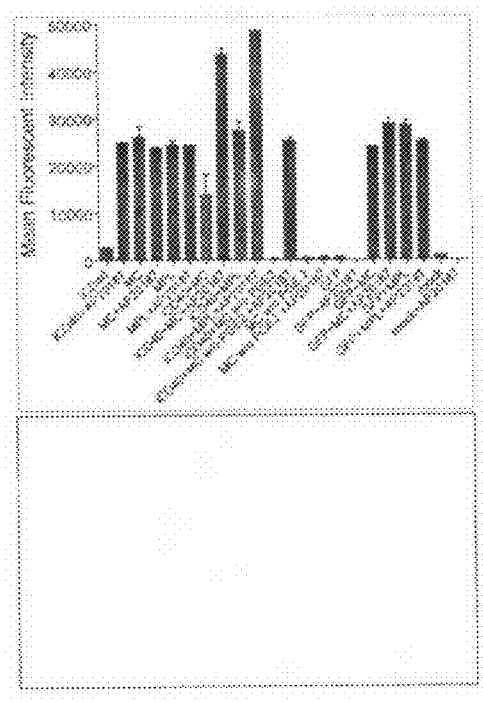

FIG. 23 Inducible CD40 triggers migration as well as standard maturation cocktail (MC). MoDCs were transduced with 10 k vp/cell Ad5/f35-ihCD40 (iCD40) or Ad5/f35-GFP (GFP), treated (48 h) with AP20187 (CID), MC (±PGE$_2$), MPL or nothing and were labeled with membrane-impermeant fluorescent dye, Green-CMFDA. 5000 cells were placed in the top chamber of a 96-well HTS Fluoroblok plates (BD Falcon) and specific migration (in 30') across an 8 m filter to the lower chamber containing CCL19 (100 ng/ml) was measured by a FLUOstar OPTIMA reader (BMG Labtech, Inc.) at 485/520 nm and subtracted from background migration. Representative of at least 5 exps performed in triplicate.

Figure 24:
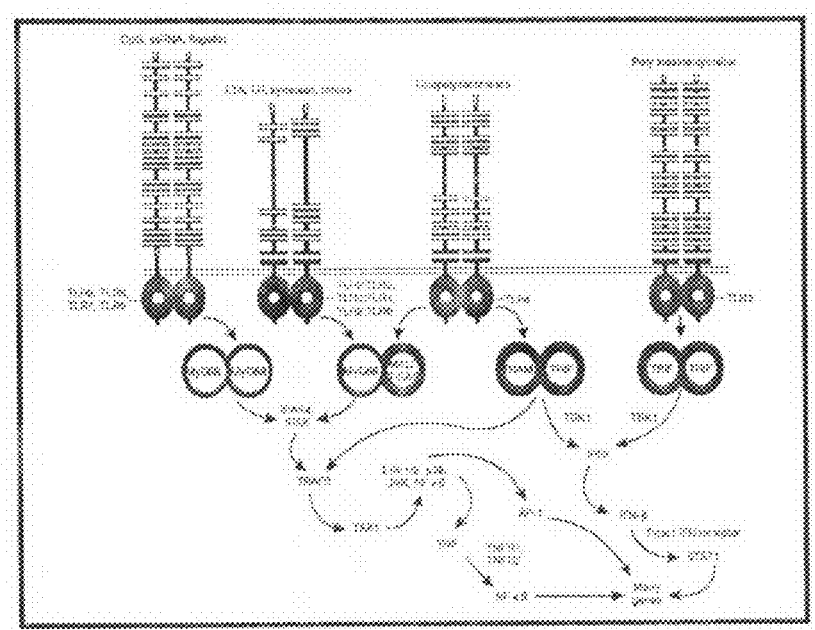

FIG. 24: The principal relationships between the Toll-like receptors (TLRs), their adaptors, protein kinases that are linked to them, and downstream signaling effects. Nature 430, 257-263(8 Jul. 2004).

Figure 25A:
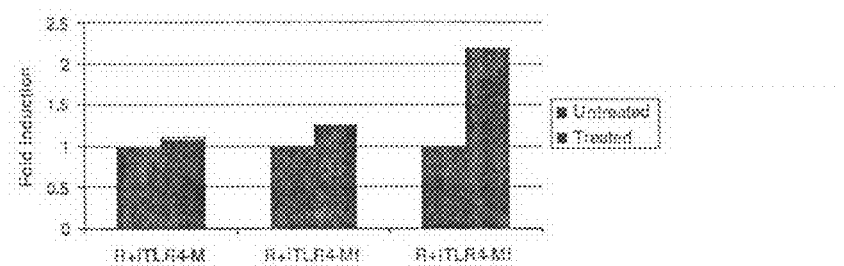

FIG. 25A. Chimeric iTLR4s in RAW 264.7 cells
RAW 264.7 cells were cotransfected transiently with 3 microgram expression plasmids for chimeric iTLR4s and 1 microgram NFkappaB-dependent SEAP reporter plasmid (indicated as R in Figure).

Figure 25B:
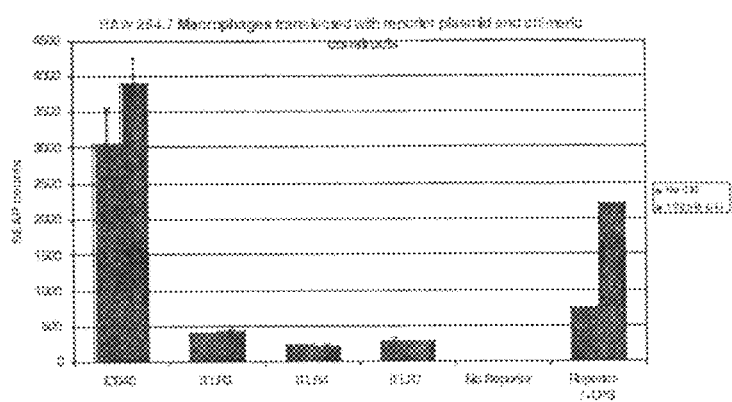

FIG. 25B. Chimeric iTLRs in RAW 264.7 cells
RAW 264.7 cells were cotransfected transiently with 3 microgram expression plasmids for chimeric iTLRs and 1 microgram SEAP reporter plasmid. iTLR4, iTLR7 and iCD40 activity were tested using a NF-kappaB-dependent reporter while iTLR3 activity was tested using an IFNgamma-dependent reporter plasmid. iCD40 was used as the positive control. 1 microgram/ml LPS was used as a positive control for reporter activity.

Figure 26:
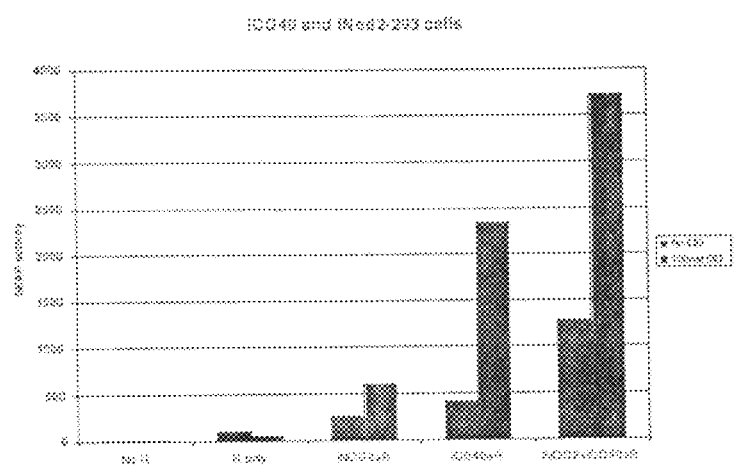

FIG. 26. iNod2 and iCD40 in 293 cells
293 cells were cotransfected transiently at the rate of 1 million cells/well (of a 6-well plate) with 3 microgram expression plasmids for chimeric iNod-2 and 1 microgram NFkappaB-dependent SEAP reporter plasmid (indicated as R in Figure). iCD40 was used as the positive control.

Figure 27:
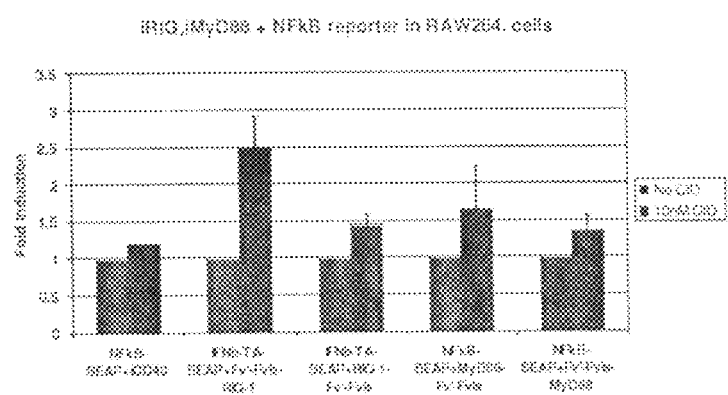

FIG. 27. iRIG-1 and iMyD88 in RAW264.7 cells
RAW 264.7 cells were cotransfected transiently with 3 micrograms expression plasmids for iRIG-1 and 1 micrograms IFNgamma-dependent SEAP reporter plasmid; and 3 micrograms iMyD88 with 1 micrograms NF-kappaB-dependent SEAP reporter plasmid.

Figure 28:
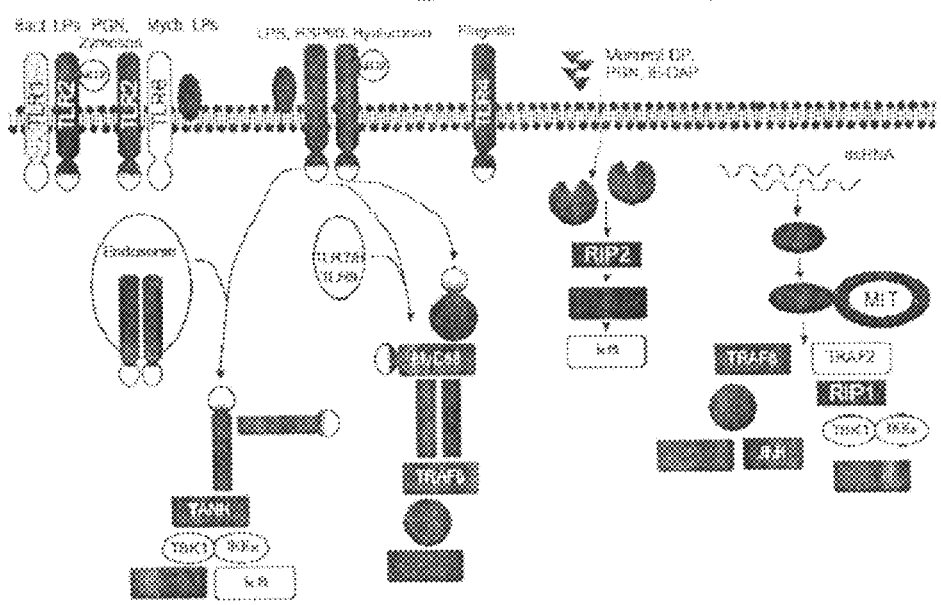

FIG. 28. Schematic of Pattern recognition receptors

Figure 29:
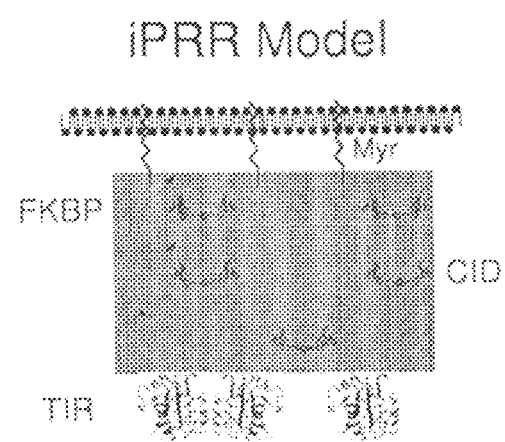

FIG. 29 presents an embodiment of an inducible PRR, where 2-3 FKBP12 (V36) domains are attached to the amino or carboxy termini of the conserved cytoplasmic signaling domains (TIR) of the representative TLR. The chimeric protein is attached to the plasma membrane with a myristoylation signaling domain or the transmembrane domain of the representative TLR.

Figure 30A:
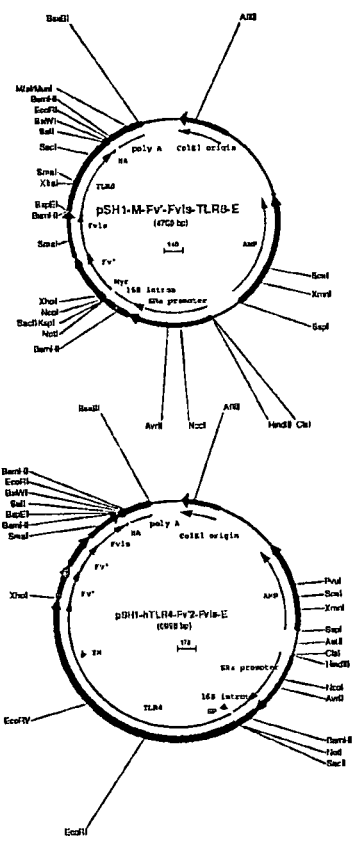

FIG. 30A. iPRR plasmid embodiments.

Figure 30B:
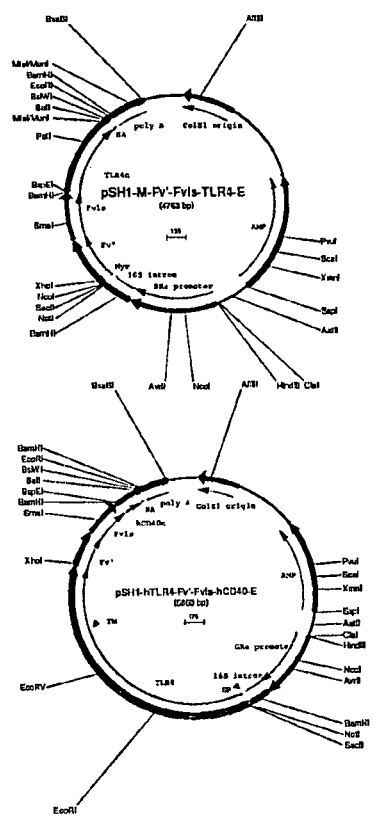

FIG. 30B. iPRR plasmid embodiments.

Figure 30C:
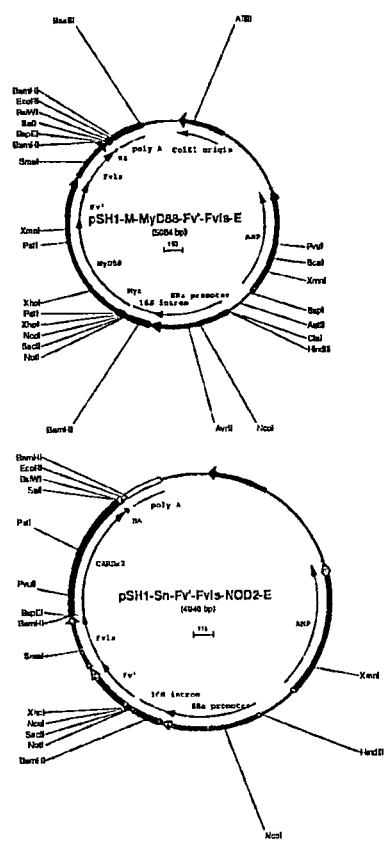

FIG. 30C. iPRR plasmid embodiment.

Figure 31:
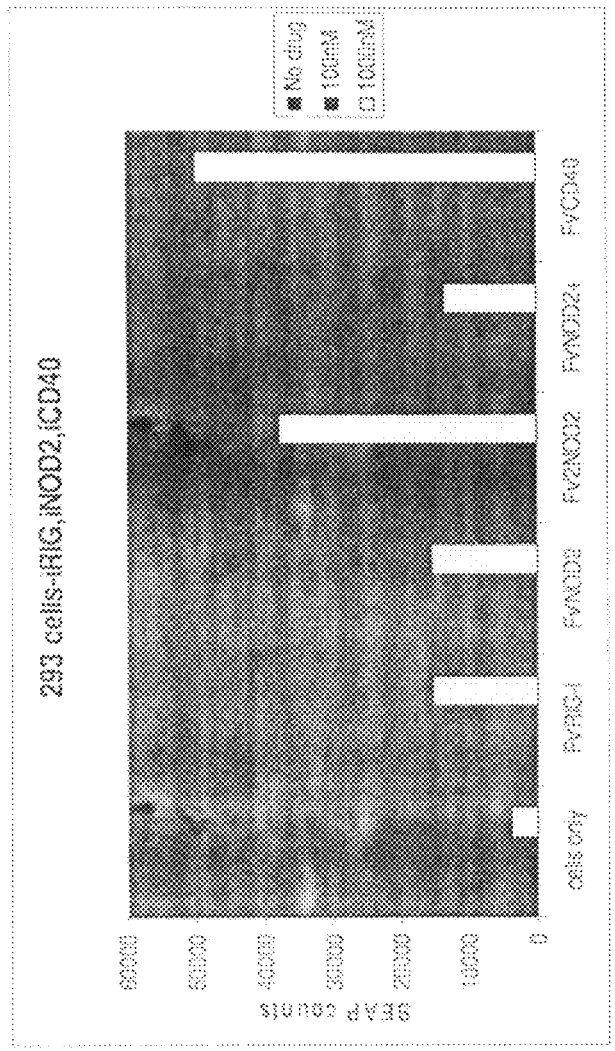

FIG. 31 is a graph of induction of NF-kappa B SEAP reporter in iRIG, iNOD2, and iCD40-transfected 293 cells.

Figure 32:
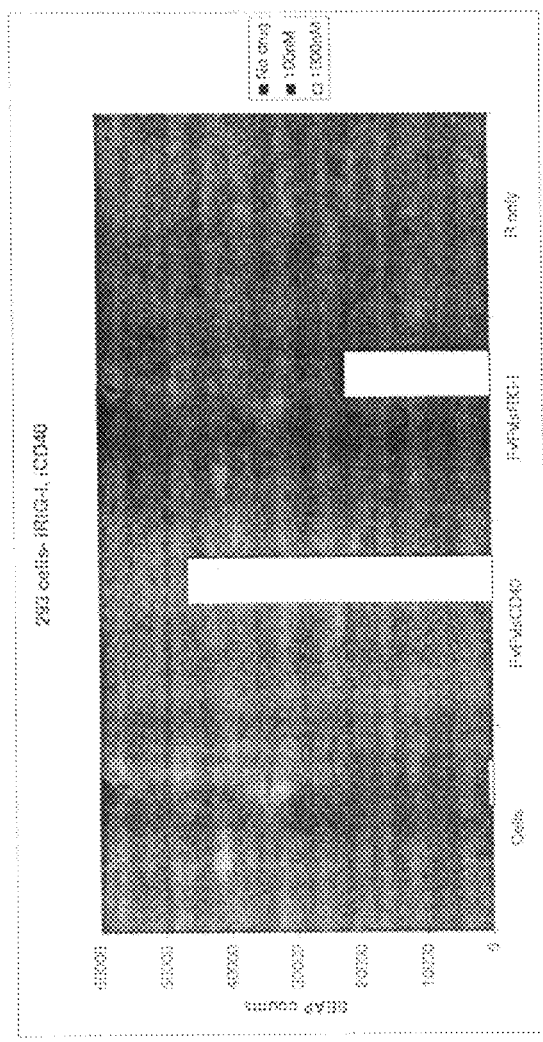

FIG. 32 is a graph of induction of NF-kappa B SEAP reporter in iRIG-I and iCD40 transfected 293 cells.

Figure 33:
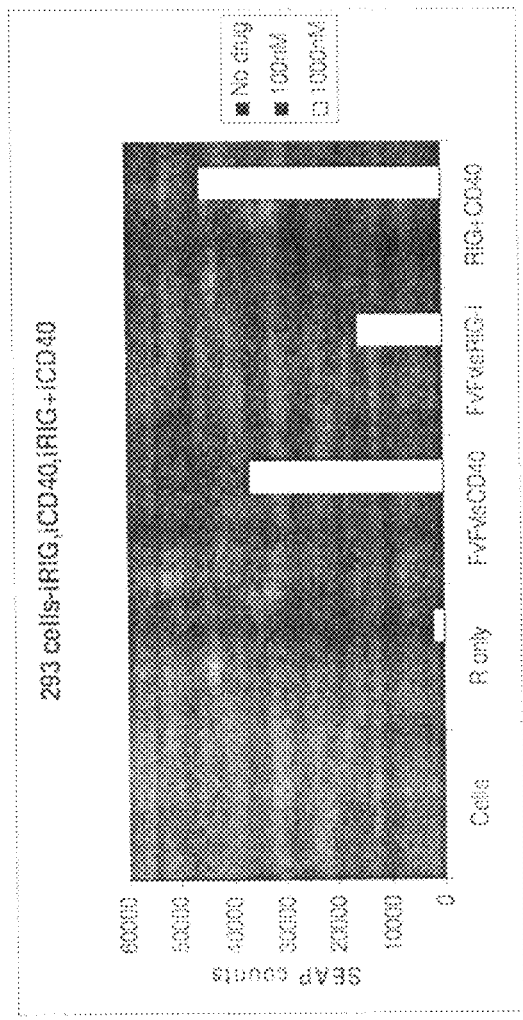

FIG. 33 is a graph of induction of NF-kappa B SEAP reporter in iRIG, iCD40), and iRIG+CD40 transfected 293 cells.

Figure 34:
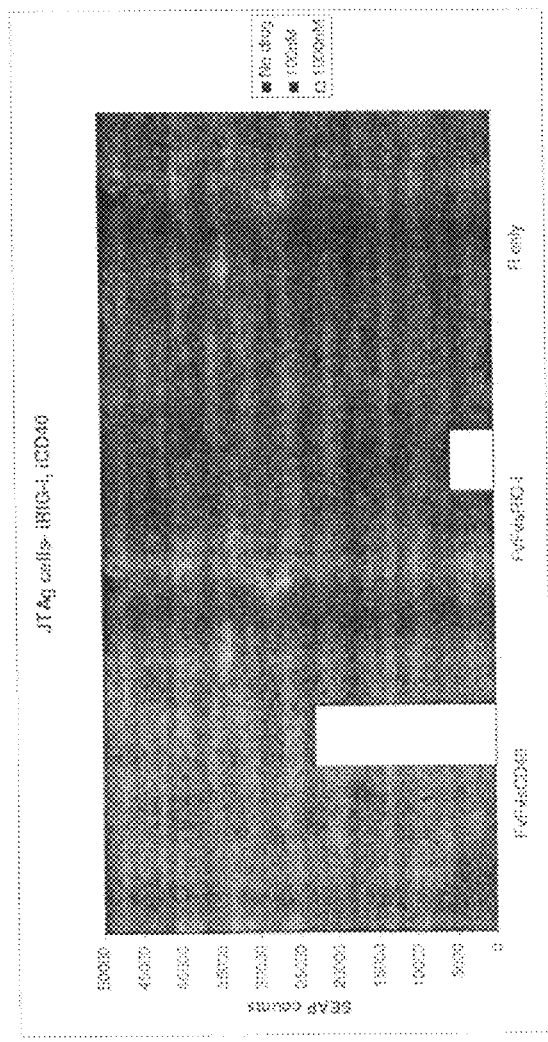

FIG. 34 is a graph of induction of NF-kappa B SEAP reporter in iRIG-I and iCD40 transfected Jurkat Tag cells.

Figure 35:
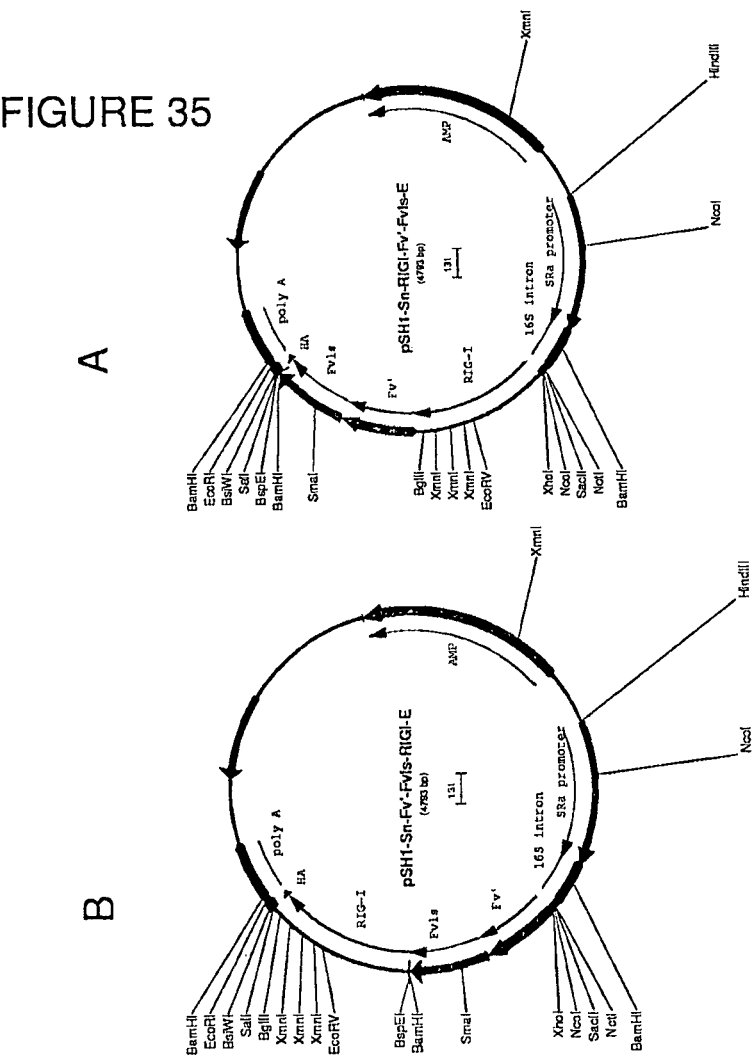

FIGS. 35A and 35B provide plasmid maps for pSH1-Sn-RIGI-Fv'-Fvls-E and pSH1-Sn-Fv'-Fvls-RIGI-E, respectively. The term "Sn" represents "S" with a NcoI site, added for cloning purposes. The term "S" represents the term non-targeted.

DETAILED DESCRIPTION

I. Definitions

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

The term "allogeneic" as used herein, refers to cell types or tissues that are antigenically distinct. Thus, cells or tissue transferred from the same species can be antigenically distinct.

The term "antigen" as used herein is defined as a molecule that provokes an immune response. This immune response may involve either antibody production, or the activation of specific immunologically competent cells, or both. An antigen can be derived from organisms, subunits of proteins/antigens, killed or inactivated whole cells or lysates. Exemplary organisms include but are not limited to, *Helicobacters, Campylobacters, Clostridia, Corynebacterium diphtheriae, Bordetella pertussis*, influenza virus, parainfluenza viruses, respiratory syncytial virus, *Borrelia burgdorfei, Plasmodium*, herpes simplex viruses, human immunodeficiency virus, papillomavirus, *Vibrio cholera, E. coli*, measles virus, rotavirus, *shigella, Salmonella typhi, Neisseria gonorrhea*. Therefore, a skilled artisan realizes that any macromolecule, including virtually all proteins or peptides, can serve as antigens. Furthermore, antigens can be derived from recombinant or genomic DNA. A skilled artisan realizes that any DNA, which contains nucleotide sequences or partial nucleotide sequences of a pathogenic genome or a gene or a fragment of a gene for a protein that elicits an immune response results in synthesis of an antigen. Furthermore, one skilled in the art realizes that the present invention is not limited to the use of the entire nucleic acid sequence of a gene or genome. It is readily inherent that the present invention includes, but is not limited to, the use of partial nucleic acid sequences of more than one gene or genome and that these nucleic acid sequences are arranged in various combinations to elicit the desired immune response.

The term "antigen-presenting cell" is any of a variety of cells capable of displaying, acquiring, or presenting at least one antigen or antigenic fragment on (or at) its cell surface. In general, the term "antigen-presenting cell" can be any cell that accomplishes the goal of the invention by aiding the enhancement of an immune response (i.e., from the T-cell or -B-cell arms of the immune system) against an antigen or antigenic composition. Such cells can be defined by those of skill in the art, using methods disclosed herein and in the art. As is understood by one of ordinary skill in the art (see, for example Kuby, 2000, incorporated herein by reference), and used herein certain embodiments, a cell that displays or presents an antigen normally or preferentially with a class II major histocompatibility molecule or complex to an immune cell is an "antigen-presenting cell." In certain aspects, a cell (e.g., an APC cell) may be fused with another cell, such as a recombinant cell or a tumor cell that expresses the desired antigen. Methods for preparing a fusion of two or more cells is well known in the art, such as for example, the methods disclosed in Goding, pp. 65-66, 71-74 1986; Campbell, pp. 75-83, 1984; Kohler and Milstein, 1975; Kohler and Milstein, 1976, Gefter et al., 1977, each incorporated herein by reference. In some cases, the immune cell to which an antigen-presenting cell displays or presents an antigen to is a CD4+ TH cell. Additional molecules expressed on the APC or other immune cells may aid or improve the enhancement of an immune response. Secreted or soluble molecules, such as for example, cytokines and adjuvants, may also aid or enhance the immune response against an antigen. Such molecules are well known to one of skill in the art, and various examples are described herein.

The term "cancer" as used herein is defined as a hyperproliferation of cells whose unique trait—loss of normal controls—results in unregulated growth, lack of differentiation, local tissue invasion, and metastasis. Examples include but are not limited to, melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder.

The terms "cell," "cell line," and "cell culture" as used herein may be used interchangeably. All of these terms also include their progeny, which are any and all subsequent generations. It is understood that all progeny may not be identical due to deliberate or inadvertent mutations.

As used herein, the term "iCD40 molecule" is defined as an inducible CD40. This iCD40 can bypass mechanisms that extinguish endogenous CD40 signaling. The term "iCD40" embraces "iCD40 nucleic acids", "iCD40 polypeptides" and/or iCD40 expression vectors. Yet further, it is understood the activity of iCD40 as used herein is driven by CID.

As used herein, the term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There are times when the full or partial genomic sequence is preferred, such as where the non-coding regions are required for optimal expression or where non-coding regions such as introns are to be targeted in an antisense strategy.

The term ""dendritic cell" (DC) is an antigen-presenting cell existing in vivo, in vitro, ex vivo, or in a host or subject, or which can be derived from a hematopoietic stem cell or a monocyte. Dendritic cells and their precursors can be isolated from a variety of lymphoid organs, e.g., spleen, lymph nodes, as well as from bone marrow and peripheral blood. The DC has a characteristic morphology with thin sheets (lamellipodia) extending in multiple directions away from the dendritic cell body. Typically, dendritic cells express high levels of MHC and costimulatory (e.g., B7-1 and B7-2) molecules. Dendritic cells can induce antigen specific differentiation of T cells in vitro, and are able to initiate primary T cell responses in vitro and in vivo.

As used herein, the term "expression construct" or "transgene" is defined as any type of genetic construct containing a nucleic acid coding for gene products in which part or all of the nucleic acid encoding sequence is capable of being transcribed can be inserted into the vector. The transcript is translated into a protein, but it need not be. In certain embodiments, expression includes both transcription of a gene and translation of mRNA into a gene product. In other embodiments, expression only includes transcription of the nucleic acid encoding genes of interest. In the present invention, the term "therapeutic construct" may also be used to refer to the expression construct or transgene. One skilled in the art realizes that the present invention utilizes the expression construct or transgene as a therapy to treat hyperproliferative diseases or disorders, such as cancer, thus the expression construct or transgene is a therapeutic construct or a prophylactic construct.

As used herein, the term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are described infra.

As used herein, the term "ex vivo" refers to "outside" the body. One of skill in the art is aware that ex vivo and in vitro can be used interchangeably.

As used herein, the term "functionally equivalent", as used herein, refers to a CD40 nucleic acid fragment, variant, or analog, refers to a nucleic acid that codes for a CD40 polypeptide, or a CD40 polypeptide, that stimulates an immune response to destroy tumors or hyperproliferative disease. Preferably "functionally equivalent" refers to a CD40 polypeptide that is lacking the extracellular domain, but is capable of amplifying the T cell-mediated tumor killing response by upregulating dendritic cell expression of antigen presentation molecules.

The term "hyperproliferative disease" is defined as a disease that results from a hyperproliferation of cells. Exemplary hyperproliferative diseases include, but are not limited to cancer or autoimmune diseases. Other hyperproliferative diseases may include vascular occulsion, restenosis, atherosclerosis, or inflammatory bowel disease.

As used herein, the term "gene" is defined as a functional protein, polypeptide, or peptide-encoding unit. As will be understood by those in the art, this functional term includes genomic sequences, cDNA sequences, and smaller engineered gene segments that express, or is adapted to express, proteins, polypeptides, domains, peptides, fusion proteins, and mutants.

The term "immunogenic composition" or "immunogen" refers to a substance that is capable of provoking an immune response. Examples of immunogens include, e.g., antigens, autoantigens that play a role in induction of autoimmune diseases, and tumor-associated antigens expressed on cancer cells.

The term "immunocompromised" as used herein is defined as a subject that has reduced or weakened immune system. The immunocompromised condition may be due to a defect or dysfunction of the immune system or to other factors that heighten susceptibility to infection and/or disease. Although such a categorization allows a conceptual basis for evaluation, immunocompromised individuals often do not fit completely into one group or the other. More than one defect in the body's defense mechanisms may be affected. For example, individuals with a specific T-lymphocyte defect caused by HIV may also have neutropenia caused by drugs used for antiviral therapy or be immunocompromised because of a breach of the integrity of the skin and mucous membranes. An immunocompromised state can result from indwelling central lines or other types of impairment due to intravenous drug abuse; or be caused by secondary malignancy, malnutrition, or having been infected with other infectious agents such as tuberculosis or sexually transmitted diseases, e.g., syphilis or hepatitis.

As used herein, the term "pharmaceutically or pharmacologically acceptable" refers to molecular entities and compositions that do not produce adverse, allergic, or other untoward reactions when administered to an animal or a human.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

As used herein, the term "polynucleotide" is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. Furthermore, one skilled in the art is cognizant that polynucleotides include mutations of the polynucleotides, include but are not limited to, mutation of the nucleotides, or nucleosides by methods well known in the art.

As used herein, the term "polypeptide" is defined as a chain of amino acid residues, usually having a defined sequence. As used herein the term polypeptide is interchangeable with the terms "peptides" and "proteins".

As used herein, the term "promoter" is defined as a DNA sequence recognized by the synthetic machinery of the cell, or introduced synthetic machinery, required to initiate the specific transcription of a gene.

As used herein, the term "regulate an immune response" or "modulate an immune response" refers to the ability to modify the immune response. For example, the composition of the present invention is capable of enhancing and/or activating the immune response. Still further, the composition of the present invention is also capable of inhibiting the immune response. The form of regulation is determined by the ligand that is used with the composition of the present invention. For example, a dimeric analog of the chemical results in dimerization of the co-stimulatory polypeptide leading to activation of the DCs, however, a monomeric analog of the chemical does not result in dimerization of the co-stimulatory polypeptide, which would not activate the DCs.

The term "transfection" and "transduction" are interchangeable and refer to the process by which an exogenous DNA sequence is introduced into a eukaryotic host cell. Transfection (or transduction) can be achieved by any one of a number of means including electroporation, microinjection, gene gun delivery, retroviral infection, lipofection, superfection and the like.

As used herein, the term "syngeneic" refers to cells, tissues or animals that have genotypes. For example, identical twins or animals of the same inbred strain. Syngeneic and isogeneic can be used interchangeable.

The term "subject" as used herein includes, but is not limited to, an organism or animal; a mammal, including, e.g., a human, non-human primate (e.g., monkey), mouse, pig, cow, goat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate.

As used herein, the term "under transcriptional control" or "operatively linked" is defined as the promoter is in the correct location and orientation in relation to the nucleic acid to control RNA polymerase initiation and expression of the gene.

As used herein, the terms "treatment", "treat", "treated", or "treating" refer to prophylaxis and/or therapy. When used with respect to an infectious disease, for example, the term refers to a prophylactic treatment which increases the resistance of a subject to infection with a pathogen or, in other words, decreases the likelihood that the subject will become infected with the pathogen or will show signs of illness attributable to the infection, as well as a treatment after the subject has become infected in order to fight the infection, e.g., reduce or eliminate the infection or prevent it from becoming worse.

As used herein, the term "vaccine" refers to a formulation which contains the composition of the present invention and which is in a form that is capable of being administered to an animal. Typically, the vaccine comprises a conventional saline or buffered aqueous solution medium in which the composition of the present invention is suspended or dissolved. In this form, the composition of the present invention can be used conveniently to prevent, ameliorate, or otherwise treat a condition. Upon introduction into a subject, the vaccine is able to provoke an immune response including, but not limited to, the production of antibodies, cytokines and/or other cellular responses.

II. Dendritic Cells

The innate immune system uses a set of germline-encoded receptors for the recognition of conserved molecular patterns present in microorganisms. These molecular patterns occur in certain constituents of microorganisms including: lipopolysaccharides, peptidoglycans, lipoteichoic acids, phosphatidyl cholines, bacteria-specific proteins, including lipoproteins, bacterial DNAs, viral single and double-stranded RNAs, unmethylated CpG-DNAs, mannans and a variety of other bacterial and fungal cell wall components. Such molecular patterns can also occur in other molecules such as plant alkaloids. These targets of innate immune recognition are called Pathogen Associated Molecular Patterns (PAMPs) since they are produced by microorganisms and not by the infected host organism (Janeway et al., 1989; Medzhitov et al., 1997).

The receptors of the innate immune system that recognize PAMPs are called Pattern Recognition Receptors (PRRs) (Janeway et al., 1989; Medzhitov et al., 1997). These receptors vary in structure and belong to several different protein families. Some of these receptors recognize PAMPs directly (e.g., CD14, DEC205, collectins), while others (e.g., complement receptors) recognize the products generated by PAMP recognition. Members of these receptor families can, generally, be divided into three types: 1) humoral receptors circulating in the plasma; 2) endocytic receptors expressed on immune-cell surfaces, and 3) signaling receptors that can be expressed either on the cell surface or intracellularly (Medzhitov et al., 1997; Fearon et al., 1996).

Cellular PRRs are expressed on effector cells of the innate immune system, including cells that function as professional antigen-presenting cells (APC) in adaptive immunity. Such effector cells include, but are not limited to, macrophages, dendritic cells, B lymphocytes and surface epithelia. This expression profile allows PRRs to directly induce innate effector mechanisms, and also to alert the host organism to the presence of infectious agents by inducing the expression of a set of endogenous signals, such as inflammatory cytokines and chemokines, as discussed below. This latter function allows efficient mobilization of effector forces to combat the invaders.

The primary function of dendritic cells (DCs) is to acquire antigen in the peripheral tissues, travel to secondary lymphoid tissue, and present antigen to effector T cells of the immune system (Banchereau, et al., 2000; Banchereau, et al., 1998). As DCs carry out their crucial role in the immune response, they undergo maturational changes allowing them to perform the appropriate function for each environment (Termeer, C. C. et al., 2000). During DC maturation, antigen uptake potential is lost, the surface density of major histocompatibility complex (MHC) class I and class II molecules increases by 10-100 fold, and CD40, costimulatory and adhesion molecule expression also greatly increases (Lanzavecchia, A. et al., 2000). In addition, other genetic alterations permit the DCs to home to the T cell-rich paracortex of draining lymph nodes and to express T-cell chemokines that attract naïve and memory T cells and prime antigen-specific naïve TH0 cells (Adema, G. J. et al., 1997). During this stage, mature DCs present antigen via their MHC II molecules to CD4+ T helper cells, inducing the upregulation of T cell CD40 ligand (CD40L) that, in turn, engages the DC CD40 receptor. This DC:T cell interaction induces rapid expression of additional DC molecules that are crucial for the initiation of a potent CD8+ cytotoxic T lymphocyte (CTL) response, including further upregulation of MHC I and II molecules, adhesion molecules, costimulatory molecules (e.g., B7.1, B7.2), cytokines (e.g., IL-12) and anti-apoptotic proteins (e.g., Bcl-2) (Anderson, D. M., et al., 1997; Caux, C., et al., 1997; Ohshima, Y., et al., 1997; Sallusto, F., et al., 1998). CD8+ T cells exit lymph nodes, reenter circulation and home to the original site of inflammation to destroy pathogens or malignant cells.

One key parameter influencing the function of DCs is the CD40 receptor, serving as the "on switch" for DCs (Bennett, S. R. et al., 1998; Clark, S. R. et al., 2000; Fernandez, N. C., et al., 1999; Ridge, J. P. et al., 1998; Schoenberger, S. P., et al., 1998). CD40 is a 48-kDa transmembrane member of the TNF receptor superfamily (McWhirter, S. M., et al., 1999). CD40-CD40L interaction induces CD40 trimerization, necessary for initiating signaling cascades involving TNF receptor associated factors (TRAFs) (Ni, C. Z., et al., 2000; Pullen, S. S. et al., 1999). CD40 uses these signaling molecules to activate several transcription factors in DCs, including NF-kappa B, AP-1, STAT3, and p38MAPK (McWhirter, S. M., et al., 1999).

The present invention contemplates a novel DC activation system based on recruiting signaling molecules or co-stimulatory polypeptides to the plasmid membrane of the DCs resulting in prolonged/increased activation and/or survival in the DCs. Co-stimulatory polypeptides include any molecule or polypeptide that activates the NFkappaB pathway, Akt pathway, and/or p38 pathway. The DC activation system is based upon utilizing a recombinant signaling molecule fused to a ligand-binding domains (i.e., a small molecule binding domain) in which the co-stimulatory polypeptide is activated and/or regulated with a ligand resulting in oligomerization (i.e., a lipid-permeable, organic, dimerizing drug). Other systems that may be used to crosslink or oligomerization of co-stimulatory polypeptides include antibodies, natural ligands, and/or artificial cross-reacting or synthetic ligands. Yet further, other dimerization systems contemplated include the coumermycin/DNA gyrase B system.

Co-stimulatory polypeptides that can be used in the present invention include those that activate NFkappaB and other variable signaling cascades for example the p38 pathway and/or Akt pathway. Such co-stimulatory polypeptides include, but are not limited to Pattern Recognition Receptors, C-reactive protein receptors (i.e., Nod1, Nod2, PtX3-R), TNF receptors (i.e., CD40, RANK/TRANCE-R, OX40, 4-1BB), and HSP receptors (Lox-1 and CD-91). Pattern Recognition Receptors include, but are not limited to endocytic pattern-recognition receptors (i.e., mannose receptors, scavenger receptors (i.e., Mac-1, LRP, peptidoglycan, techoic acids, toxins, CD11c/CR4)); external signal pattern-recognition receptors (Toll-like receptors (TLR1, TLR2, TLR3, TLR4, TLR5, TLR6, TLR7, TLR8, TLR9, TLR10), peptidoglycan recognition protein, (PGRPs bind bacterial peptidoglycan, and CD14); internal signal pattern-recognition receptors (i.e., NOD-receptors 1 & 2), RIG1, and PRRs shown in FIG. 28. Those of ordinary skill in the art are also aware of other Pattern Recognition Receptors suitable for the present invention, including those discussed in, for example, Werts C., et al., Cell Death and Differentiation (2006) 13:798-815; Meylan, E., et al., Nature (2006) 442:39-44; and Strober, W., et al., Nature Reviews (2006) 6:9-20.

III. Engineering Expression Constructs

The present invention involves an expression construct encoding a co-stimulatory polypeptide and a ligand-binding domain, all operatively linked. More particularly, more than one ligand-binding domain is used in the expression construct. Yet further, the expression construct contains a membrane-targeting sequence. One with skill in the art realizes that appropriate expression constructs may include a co-stimulatory polypeptide element on either side of the above FKBP ligand-binding elements. The expression construct of the present invention may be inserted into a vector, for example a viral vector or plasmid.

A. Co-Stimulatory Polypeptides

In the present invention, co-stimulatory polypeptide molecules are capable of amplifying the T-cell-mediated response by upregulating dendritic cell expression of antigen presentation molecules. Co-stimulatory proteins that are contemplated in the present invention include, for example, but are not limited to the members of tumor necrosis factor (TNF) family (i.e., CD40, RANK/TRANCE-R, OX40, 4-1B), Toll-like receptors, C-reactive protein receptors, Pattern Recognition Receptors, and HSP receptors. Typically, the cytoplasmic domains from these co-stimulatory polypeptides are used in the expression vector. The cytoplasmic domain from one of the various co-stimulatory polypeptides, including mutants thereof, where the recognition sequence involved in initiating transcription associated with the cytoplasmic domain is known or a gene responsive to such sequence is known.

In specific embodiments of the present invention, the co-stimulatory polypeptide molecule is CD40. The CD40 molecule comprises a nucleic acid molecule which: (1) hybridizes under stringent conditions to a nucleic acid having the sequence of a known CD40 gene and (2) codes for a CD40 polypeptide. Preferably the CD40 polypeptide is lacking the extracellular domain. Exemplary polynucleotide sequences that encode CD40 polypeptides include, but are not limited to SEQ.ID.NO: 1 and CD40 isoforms from other species. It is contemplated that other normal or mutant variants of CD40 can be used in the present invention. Thus, a CD40 region can have an amino acid sequence that differs from the native sequence by one or more amino acid substitutions, deletions and/or insertions. For example, one or more TNF receptor associated factor (TRAF) binding regions may be eliminated or effectively eliminated (e.g., a CD40 amino acid sequence is deleted or altered such that a TRAF protein does not bind or binds with lower affinity than it binds to the native CD40 sequence). In particular embodiments, a TRAF 3 binding region is deleted or altered such that it is eliminated or effectively eliminated (e.g., amino acids 250-254 may be altered or deleted; Hauer et al., PNAS102(8): 2874-2879 (2005)).

In certain embodiments, the present invention involves the manipulation of genetic material to produce expression constructs that encode an inducible form of CD40 (iCD40). Such methods involve the generation of expression constructs containing, for example, a heterologous nucleic acid sequence encoding CD40 cytoplasmic domain and a means for its expression, replicating the vector in an appropriate helper cell, obtaining viral particles produced therefrom, and infecting cells with the recombinant virus particles.

Thus, the preferable CD40 molecule of the present invention lacks the extracellular domain. In specific embodiments, the extracellular domain is truncated or removed. It is also contemplated that the extracellular domain can be mutated using standard mutagenesis, insertions, deletions, or substitutions to produce an CD40 molecule that does not have a functional extracellular domain. A CD40 nucleic acid may have the nucleic acid sequence of SEQ.ID.NO: 1. The CD40 nucleic acids of the invention also include homologs and alleles of a nucleic acid having the sequence of SEQ.ID.NO: 1, as well as, functionally equivalent fragments, variants, and analogs of the foregoing nucleic acids.

In the context of gene therapy, the gene will be a heterologous polynucleotide sequence derived from a source other than the viral genome, which provides the backbone of the vector. The gene is derived from a prokaryotic or eukaryotic source such as a bacterium, a virus, yeast, a parasite, a plant, or even an animal The heterologous DNA also is derived from more than one source, i.e., a multigene construct or a fusion protein. The heterologous DNA also may include a regulatory sequence, which is derived from one source and the gene from a different source.

B. Ligand-Binding Regions

The ligand-binding ("dimerization") domain of the expression construct of this invention can be any convenient domain that will allow for induction using a natural or unnatural ligand, preferably an unnatural synthetic ligand. The ligand-binding domain can be internal or external to the cellular membrane, depending upon the nature of the construct and the choice of ligand. A wide variety of ligand-binding proteins, including receptors, are known, including ligand-binding proteins associated with the cytoplasmic regions indicated above. As used herein the term "ligand-binding domain can be interchangeable with the term "receptor". Of particular interest are ligand-binding proteins for which ligands (preferably small organic ligands) are known or may be readily produced. These ligand-binding domains or receptors include the FKBPs and cyclophilin receptors, the steroid receptors, the tetracycline receptor, the other receptors indicated above, and the like, as well as "unnatural" receptors, which can be obtained from antibodies, particularly the heavy or light chain subunit, mutated sequences thereof, random amino acid sequences obtained by stochastic procedures, combinatorial syntheses, and the like.

For the most part, the ligand-binding domains or receptor domains will be at least about 50 amino acids, and fewer than about 350 amino acids, usually fewer than 200 amino acids, either as the natural domain or truncated active portion thereof. Preferably the binding domain will be small (<25 kDa, to allow efficient transfection in viral vectors), monomeric (this rules out the avidin-biotin system), nonimmunogenic, and should have synthetically accessible, cell permeable, nontoxic ligands that can be configured for dimerization.

The receptor domain can be intracellular or extracellular depending upon the design of the expression construct and the availability of an appropriate ligand. For hydrophobic ligands, the binding domain can be on either side of the membrane, but for hydrophilic ligands, particularly protein ligands, the binding domain will usually be external to the cell membrane, unless there is a transport system for internalizing the ligand in a form in which it is available for binding. For an intracellular receptor, the construct can encode a signal peptide and transmembrane domain 5' or 3' of the receptor domain sequence or by having a lipid attachment signal sequence 5' of the receptor domain sequence. Where the receptor domain is between the signal peptide and the transmembrane domain, the receptor domain will be extracellular.

The portion of the expression construct encoding the receptor can be subjected to mutagenesis for a variety of reasons. The mutagenized protein can provide for higher binding affinity, allow for discrimination by the ligand of the naturally occurring receptor and the mutagenized receptor, provide opportunities to design a receptor-ligand pair, or the like. The change in the receptor can involve changes in amino acids known to be at the binding site, random mutagenesis using combinatorial techniques, where the codons for the amino acids associated with the binding site or other amino acids associated with conformational changes can be subject to mutagenesis by changing the codon(s) for the particular amino acid, either with known changes or randomly, expressing the resulting proteins in an appropriate prokaryotic host and then screening the resulting proteins for binding.

Antibodies and antibody subunits, e.g., heavy or light chain, particularly fragments, more particularly all or part of the variable region, or fusions of heavy and light chain to create high-affinity binding, can be used as the binding domain. Antibodies that are contemplated in the present invention include ones that are an ectopically expressed human product, such as an extracellular domain that would not trigger an immune response and generally not expressed in the periphery (i.e., outside the CNS/brain area). Such examples, include, but are not limited to low affinity nerve growth factor receptor (LNGFR), and embryonic surface proteins (i.e., carcinoembryonic antigen).

Yet further, antibodies can be prepared against haptenic molecules, which are physiologically acceptable, and the individual antibody subunits screened for binding affinity. The cDNA encoding the subunits can be isolated and modified by deletion of the constant region, portions of the variable region, mutagenesis of the variable region, or the like, to obtain a binding protein domain that has the appropriate affinity for the ligand. In this way, almost any physiologically acceptable haptenic compound can be employed as the ligand or to provide an epitope for the ligand. Instead of antibody units, natural receptors can be employed, where the binding domain is known and there is a useful ligand for binding.

C. Oligomerization

The transduced signal will normally result from ligand-mediated oligomerization of the chimeric protein molecules, i.e., as a result of oligomerization following ligand-binding, although other binding events, for example allosteric activation, can be employed to initiate a signal. The construct of the chimeric protein will vary as to the order of the various domains and the number of repeats of an individual domain.

For multimerizing the receptor, the ligand for the ligand-binding domains/receptor domains of the chimeric surface membrane proteins will usually be multimeric in the sense that it will have at least two binding sites, with each of the binding sites capable of binding to the receptor domain. Desirably, the subject ligands will be a dimer or higher order oligomer, usually not greater than about tetrameric, of small synthetic organic molecules, the individual molecules typically being at least about 150 D and fewer than about 5 kDa, usually fewer than about 3 kDa. A variety of pairs of synthetic ligands and receptors can be employed. For example, in embodiments involving natural receptors, dimeric FK506 can be used with an FKBP receptor, dimerized cyclosporin A can be used with the cyclophilin receptor, dimerized estrogen with an estrogen receptor, dimerized glucocorticoids with a glucocorticoid receptor, dimerized tetracycline with the tetracycline receptor, dimerized vitamin D with the vitamin D receptor, and the like. Alternatively higher orders of the ligands, e.g., trimeric can be used.

For embodiments involving unnatural receptors, e.g., antibody subunits, modified antibody subunits or modified receptors and the like, any of a large variety of compounds can be used. A significant characteristic of these ligand units is that they bind the receptor with high affinity and are able to be dimerized chemically.

In certain embodiments, the present invention utilizes the technique of chemically induced dimerization (CID) to produce a conditionally controlled protein or polypeptide. In addition to this technique being inducible, it also is reversible, due to the degradation of the labile dimerizing agent or administration of a monomeric competitive inhibitor.

CID system uses synthetic bivalent ligands to rapidly crosslink signaling molecules that are fused to ligand-binding domains CID. This system has been used to trigger the oligomerization and activation of cell surface (Spencer et al., 1993; Spencer et al., 1996; Blau et al., 1997), or cytosolic proteins (Luo et al., 1996; MacCorkle et al., 1998), the recruitment of transcription factors to DNA elements to modulate transcription (Ho et al., 1996; Rivera et al., 1996) or the recruitment of signaling molecules to the plasma membrane to stimulate signaling (Spencer et al., 1995; Holsinger et al., 1995).

The CID system is based upon the notion that surface receptor aggregation effectively activates downstream signaling cascades. In the simplest embodiment, the CID system uses a dimeric analog of the lipid permeable immunosuppressant drug, FK506, which loses its normal bioactivity while gaining the ability to crosslink molecules genetically fused to the FK506-binding protein, FKBP12. By fusing one or more FKBPs and a myristoylation sequence to the cytoplasmic signaling domain of a target receptor, one can stimulate signaling in a dimerizer drug-dependent, but ligand and ectodomain-independent manner. This provides the system with temporal control, reversibility using monomeric drug analogs, and enhanced specificity. The high affinity of third-generation AP20187/AP1903 CIDs for their binding domain, FKBP12 permits specific activation of the recombinant receptor in vivo without the induction of non-specific side effects through endogenous FKBP12. In addition, the synthetic ligands are resistant to protease degradation, making them more efficient at activating receptors in vivo than most delivered protein agents.

The ligands used in the present invention are capable of binding to two or more of the ligand-binding domains. One skilled in the art realizes that the chimeric proteins may be able to bind to more than one ligand when they contain more than one ligand-binding domain. The ligand is typically a non-protein or a chemical. Exemplary ligands include, but are not limited to dimeric FK506 (e.g., FK1012).

Since the mechanism of CD40 activation is fundamentally based on trimerization, this receptor is particularly amenable to the CID system. CID regulation provides the system with 1) temporal control, 2) reversibility by addition of a non-active monomer upon signs of an autoimmune reaction, and 3) limited potential for non-specific side effects. In addition, inducible in vivo DC CD40 activation would circumvent the requirement of a second "danger" signal normally required for complete induction of CD40 signaling and would potentially promote DC survival in situ allowing for enhanced T cell priming. Thus, engineering DC vaccines to express iCD40 amplifies the T cell-mediated killing response by upregulating DC expression of antigen presentation molecules, adhesion molecules, TH1 promoting cytokines, and pro-survival factors.

Other dimerization systems contemplated include the coumermycin/DNA gyrase B system. Coumermycin-induced dimerization activates a modified Raf protein and stimulates the MAP kinase cascade. See Farrar et al., 1996.

D. Membrane-Targeting

A membrane-targeting sequence provides for transport of the chimeric protein to the cell surface membrane, where the same or other sequences can encode binding of the chimeric protein to the cell surface membrane. Molecules in association with cell membranes contain certain regions that facilitate the membrane association, and such regions can be incorporated into a chimeric protein molecule to generate membrane-targeted molecules. For example, some proteins contain sequences at the N-terminus or C-terminus that are acylated, and these acyl moieties facilitate membrane association. Such sequences are recognized by acyltransferases and often conform to a particular sequence motif Certain acylation motifs are capable of being modified with a single acyl moiety and others are capable of being modified with multiple acyl moieties. For example the N-terminal sequence of the protein kinase Src can comprise a single myristoyl moiety. Dual acylation regions are located within the N-terminal regions of certain protein kinases (e.g., Yes, Fyn, Lck) and G-protein alpha subunits. Such dual acylation regions often are located within the first eighteen amino acids of such proteins, and conform to the sequence motif Met-Gly-Cys-Xaa-Cys (SEQ ID NO: 7), where the Met is cleaved, the Gly is N-acylated and one of the Cys residues is S-acylated. The Gly often is myristoylated and a Cys can be palmitoylated. Acylation regions conforming to the sequence motif Cys-Ala-Ala-Xaa (so called "CAAX boxes"), which can be modified with C15 or C10 isoprenyl moieties, from the C-terminus of G-protein gamma subunits and other proteins (e.g., World Wide Web address ebi.ac.uk/interpro/DisplayIproEntry?ac=IPR001230) also can be utilized. These and other acylation motifs are known to the person of ordinary skill in the art (e.g., Gauthier-Campbell et al., Molecular Biology of the Cell 15: 2205-2217 (2004); Glabati et al., Biochem. J. 303: 697-700 (1994) and Zlakine et al., J. Cell Science 110: 673-679 (1997)), and can be incorporated in chimeric molecules to induce membrane localization. In certain embodiments, a native sequence from a protein containing an acylation motif is incorporated into a chimeric protein. For example, in some embodiments, an N-terminal portion of Lck, Fyn or Yes or a G-protein alpha subunit, such as the first twenty-five N-terminal amino acids or fewer from such proteins (e.g., about 5 to about 20 amino acids, about 10 to about 19 amino acids, or about 15 to about 19 amino acids of the native sequence with optional mutations), may be incorporated within the N-terminus of a chimeric protein. In certain embodiments, a C-terminal sequence of about 25 amino acids or less from a G-protein gamma subunit containing a CAAX box motif sequence (e.g., about 5 to about 20 amino acids, about 10 to about 18 amino acids, or about 15 to about 18 amino acids of the native sequence with optional mutations) can be linked to the C-terminus of a chimeric protein.

In some embodiments, an acyl moiety has a log p value of +1 to +6, and sometimes has a log p value of +3 to +4.5. Log p values are a measure of hydrophobicity and often are derived from octanol/water partitioning studies, in which molecules with higher hydrophobicity partition into octanol with higher frequency and are characterized as having a higher log p value. Log p values are published for a number of lipophilic molecules and log p values can be calculated using known partitioning processes (e.g., Chemical Reviews, Vol. 71, Issue 6, page 599, where entry 4493 shows lauric acid having a log p value of 4.2). Any acyl moiety can be linked to a peptide composition described above and tested for antimicrobial activity using known methods and those described hereafter. The acyl moiety sometimes is a C1-C20 alkyl, C2-C20 alkenyl, C2-C20 alkynyl, C3-C6 cycloalkyl, C1-C4 haloalkyl, C4-C12 cyclalkylalkyl, aryl, substituted aryl, or aryl (C1-C4) alkyl, for example. Any acyl-containing moiety sometimes is a fatty acid, and examples of fatty acid moieties are propyl (C3), butyl (C4), pentyl (C5), hexyl (C6), heptyl (C7), octyl (C8), nonyl (C9), decyl (d10), undecyl (C11), lauryl (C12), myristyl (C14), palmityl (C16), stearyl (C18), arachidyl (C20), behenyl (C22) and lignoceryl moieties (C24), and each moiety can contain 0, 1, 2, 3, 4, 5, 6, 7 or 8 unsaturations (i.e., double bonds). An acyl moiety sometimes is a lipid molecule, such as a phosphatidyl lipid (e.g., phosphatidyl serine, phosphatidyl inositol, phosphatidyl ethanolamine, phosphatidyl choline), sphingolipid (e.g., shingomyelin, sphigosine, ceramide, ganglioside, cerebroside), or modified versions thereof. In certain embodiments, one, two, three, four or five or more acyl moieties are linked to a membrane association region.

A chimeric protein herein also may include a single-pass or multiple pass transmembrane sequence (e.g., at the N-terminus or C-terminus of the chimeric protein). Single pass transmembrane regions are found in certain CD molecules, tyrosine kinase receptors, serine/threonine kinase receptors, TGFbeta, BMP, activin and phosphatases. Single pass transmembrane regions often include a signal peptide region and a transmembrane region of about 20 to about 25 amino acids, many of which are hydrophobic amino acids and can form an alpha helix. A short track of positively charged amino acids often follows the transmembrane span. Multiple pass proteins include ion pumps, ion channels, and transporters, and include two or more helices that span the membrane multiple times. All or substantially all of a multiple pass protein sometimes is incorporated in a chimeric protein. Sequences for single pass and multiple pass transmembrane regions are known and can be selected for incorporation into a chimeric protein molecule by the person of ordinary skill in the art.

Any membrane-targeting sequence can be employed that is functional in the host and may, or may not, be associated with one of the other domains of the chimeric protein. In some embodiments of the invention, such sequences include, but are not limited to myristoylation-targeting sequence, palmitoylation targeting sequence, prenylation sequences (i.e., farnesylation, geranyl-geranylation, CAAX Box) or transmembrane sequences (utilizing signal peptides) from receptors.

E. Selectable Markers

In certain embodiments of the invention, the expression constructs of the present invention contain nucleic acid constructs whose expression is identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as herpes simplex virus thymidine kinase (tk) are employed. Immunologic markers also can be employed. The selectable marker employed is not believed to be important, so long as it is capable of being expressed simultaneously with the nucleic acid encoding a gene product. Further examples of selectable markers are well known to one of skill in the art and include reporters such as EGFP, beta-gal or chloramphenicol acetyltransferase (CAT).

F. Control Regions

1. Promoters

The particular promoter employed to control the expression of a polynucleotide sequence of interest is not believed to be important, so long as it is capable of directing the expression of the polynucleotide in the targeted cell. Thus, where a human cell is targeted, it is preferable to position the polynucleotide sequence-coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, B-actin, rat insulin promoter and glyceraldehyde-3-phosphate dehydrogenase can be used to obtain high-level expression of the coding sequence of interest. The use of other viral or mammalian cellular or bacterial phage promoters which are well known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it is desirable to prohibit or reduce expression of one or more of the transgenes. Examples of transgenes that are toxic to the producer cell line are pro-apoptotic and cytokine genes. Several inducible promoter systems are available for production of viral vectors where the transgene products are toxic (add in more inducible promoters).

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of Drosophila, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter, which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of E. coli. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system would be preferable so that the producer cells could be grown in the presence of tetracycline or doxycycline and prevent expression of a potentially toxic transgene, but when the vector is introduced to the patient, the gene expression would be constitutively on.

In some circumstances, it is desirable to regulate expression of a transgene in a gene therapy vector. For example, different viral promoters with varying strengths of activity are utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoietic cells is desired, retroviral promoters such as the LTRs from MLV or MMTV are often used. Other viral promoters that are used depending on the desired effect include SV40, RSV LTR, HIV-1 and HIV-2 LTR, adenovirus promoters such as from the E1A, E2A, or MLP region, AAV LTR, HSV-TK, and avian sarcoma virus.

Similarly tissue specific promoters are used to effect transcription in specific tissues or cells so as to reduce potential toxicity or undesirable effects to non-targeted tissues. For example, promoters such as the PSA associated promoter or prostate-specific glandular kallikrein.

In certain indications, it is desirable to activate transcription at specific times after administration of the gene therapy vector. This is done with such promoters as those that are hormone or cytokine regulatable. Cytokine and inflammatory protein responsive promoters that can be used include K and T kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitrypsin, lipoprotein lipase (Zechner et al., 1988), angiotensinogen (Ron et al., 1991), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 anti-chymotrypsin.

It is envisioned that any of the above promoters alone or in combination with another can be useful according to the present invention depending on the action desired. In addition, this list of promoters should not be construed to be exhaustive or limiting, those of skill in the art will know of other promoters that are used in conjunction with the promoters and methods disclosed herein.

2. Enhancers

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Any promoter/enhancer combination (as per the Eukaryotic Promoter Data Base EPDB) can be used to drive expression of the gene. Eukaryotic cells can support cytoplasmic transcription from certain bacterial promoters if the appropriate bacterial polymerase is provided, either as part of the delivery complex or as an additional genetic expression construct.

3. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the invention, and any such sequence is employed such as human or bovine growth hormone and SV40 polyadenylation signals. Also contemplated as an element of the expression cassette is a terminator. These elements can serve to enhance message levels and to minimize read through from the cassette into other sequences.

4. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be in-frame with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements is used to create multigene, or polycistronic messages. IRES elements are able to bypass the ribosome-scanning model of 5' methylated cap-dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

IV. Methods of Gene Transfer

In order to mediate the effect of the transgene expression in a cell, it will be necessary to transfer the expression constructs of the present invention into a cell. Such transfer may employ viral or non-viral methods of gene transfer. This section provides a discussion of methods and compositions of gene transfer.

A transformed cell comprising an expression vector is generated by introducing into the cell the expression vector. Suitable methods for polynucleotide delivery for transformation of an organelle, a cell, a tissue or an organism for use with the current invention include virtually any method by which a polynucleotide (e.g., DNA) can be introduced into an organelle, a cell, a tissue or an organism, as described herein or as would be known to one of ordinary skill in the art.

A host cell can, and has been, used as a recipient for vectors. Host cells may be derived from prokaryotes or eukaryotes, depending upon whether the desired result is replication of the vector or expression of part or all of the vector-encoded polynucleotide sequences. Numerous cell lines and cultures are available for use as a host cell, and they can be obtained through the American Type Culture Collection (ATCC), which is an organization that serves as an archive for living cultures and genetic materials. In specific embodiments, the host cell is a dendritic cell, which is an antigen-presenting cell.

It is well within the knowledge and skill of a skilled artisan to determine an appropriate host. Generally this is based on the vector backbone and the desired result. A plasmid or cosmid, for example, can be introduced into a prokaryote host cell for replication of many vectors. Bacterial cells used as host cells for vector replication and/or expression include DH5alpha, JM109, and KC8, as well as a number of commercially available bacterial hosts such as SURE® Competent Cells and SOLOPACK Gold Cells (STRATAGENE®, La Jolla, Calif.). Alternatively, bacterial cells such as E. coli LE392 could be used as host cells for phage viruses. Eukaryotic cells that can be used as host cells include, but are not limited to yeast, insects and mammals. Examples of mammalian eukaryotic host cells for replication and/or expression of a vector include, but are not limited to, HeLa, NIH3T3, Jurkat, 293, COS, CHO, Saos, and PC12. Examples of yeast strains include, but are not limited to, YPH499, YPH500 and YPH501.

A. Non-Viral Transfer

1. Ex Vivo Transformation

Methods for transfecting vascular cells and tissues removed from an organism in an ex vivo setting are known to those of skill in the art. For example, canine endothelial cells have been genetically altered by retroviral gene transfer in vitro and transplanted into a canine (Wilson et al., 1989). In another example, Yucatan minipig endothelial cells were transfected by retrovirus in vitro and transplanted into an artery using a double-balloon catheter (Nabel et al., 1989). Thus, it is contemplated that cells or tissues may be removed and transfected ex vivo using the polynucleotides of the present invention. In particular aspects, the transplanted cells or tissues may be placed into an organism. Thus, it is well within the knowledge of one skilled in the art to isolate dendritic cells from an animal, transfect the cells with the expression vector and then administer the transfected or transformed cells back to the animal.

2. Injection

In certain embodiments, a polynucleotide may be delivered to an organelle, a cell, a tissue or an organism via one or more injections (i.e., a needle injection), such as, for example, subcutaneously, intradermally, intramuscularly, intravenously, intraperitoneally, etc. Methods of injection of vaccines are well known to those of ordinary skill in the art (e.g., injection of a composition comprising a saline solution). Further embodiments of the present invention include the introduction of a polynucleotide by direct microinjection. The amount of the expression vector used may vary upon the nature of the antigen as well as the organelle, cell, tissue or organism used.

Intradermal, intranodal, or intralymphatic injections are some of the more commonly used methods of DC administration. Intradermal injection is characterized by a low rate of absorption into the bloodstream but rapid uptake into the lymphatic system. The presence of large numbers of Langerhans dendritic cells in the dermis will transport intact as well as processed antigen to draining lymph nodes. Proper site preparation is necessary to perform this correctly (i.e., hair must be clipped in order to observe proper needle placement). Intranodal injection allows for direct delivery of antigen to lymphoid tissues. Intralymphatic injection allows direct administration of DCs.

3. Electroporation

In certain embodiments of the present invention, a polynucleotide is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference).

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

4. Calcium Phosphate

In other embodiments of the present invention, a polynucleotide is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

5. DEAE-Dextran

In another embodiment, a polynucleotide is delivered into a cell using DEAE-dextran followed by polyethylene glycol. In this manner, reporter plasmids were introduced into mouse myeloma and erythroleukemia cells (Gopal, 1985).

6. Sonication Loading

Additional embodiments of the present invention include the introduction of a polynucleotide by direct sonic loading. LTK—fibroblasts have been transfected with the thymidine kinase gene by sonication loading (Fechheimer et al., 1987).

7. Liposome-Mediated Transfection

In a further embodiment of the invention, a polynucleotide may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a polynucleotide complexed with Lipofectamine (Gibco BRL) or Superfect (Qiagen).

8. Receptor Mediated Transfection

Still further, a polynucleotide may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a polynucleotide-binding agent. Others comprise a cell receptor-specific ligand to which the polynucleotide to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand is chosen to correspond to a receptor specifically expressed on the target cell population.

In other embodiments, a polynucleotide delivery vehicle component of a cell-specific polynucleotide-targeting vehicle may comprise a specific binding ligand in combination with a liposome. The polynucleotide(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a polynucleotide to cells that exhibit upregulation of the EGF receptor.

In still further embodiments, the polynucleotide delivery vehicle component of a targeted delivery vehicle may be a liposome itself, which will preferably comprise one or more lipids or glycoproteins that direct cell-specific binding. For example, lactosyl-ceramide, a galactose-terminal asialoganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

9. Microprojectile Bombardment

Microprojectile bombardment techniques can be used to introduce a polynucleotide into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one polynucleotide and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

B. Viral Vector-Mediated Transfer

In certain embodiments, transgene is incorporated into a viral particle to mediate gene transfer to a cell. Typically, the virus simply will be exposed to the appropriate host cell under physiologic conditions, permitting uptake of the virus. The present methods are advantageously employed using a variety of viral vectors, as discussed below.

1. Adenovirus

Adenovirus is particularly suitable for use as a gene transfer vector because of its mid-sized DNA genome, ease of manipulation, high titer, wide target-cell range, and high infectivity. The roughly 36 kb viral genome is bounded by 100-200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5 tripartite leader (TL) sequence, which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present invention, it is possible achieve both these goals while retaining the ability to manipulate the therapeutic constructs with relative ease.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsulation is localized between 194-385 bp (0.5-1.1 map units) at the left end of the viral genome (Hearing et al., 1987). This signal mimics the protein recognition site in bacteriophage lambda DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194-358 bp) region of the genome grew poorly even in a cell line that complemented the early (E1A) function (Hearing and Shenk, 1983). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals is packaged selectively when compared to the helpers. If the preference is great enough, stocks approaching homogeneity should be achieved.

2. Retrovirus

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed psi, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and psi components is constructed (Mann et al., 1983). When a recombinant plasmid containing a human cDNA, together with the retroviral LTR and psi sequences is introduced into this cell line (by calcium phosphate precipitation for example), the psi sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., 1975).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

3. Adeno-Associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low-level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al., 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, 1995; Chatterjee et al., 1995; Ferrari et al., 1996; Fisher et al., 1996; Flotte et al., 1993; Goodman et al., 1994; Kaplitt et al., 1994; 1996, Kessler et al., 1996; Koeberl et al., 1997; Mizukami et al., 1996).

AAV-mediated efficient gene transfer and expression in the lung has led to clinical trials for the treatment of cystic fibrosis (Carter and Flotte, 1995; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al., 1996).

4. Other Viral Vectors

Other viral vectors are employed as expression constructs in the present invention. Vectors derived from viruses such as vaccinia virus (Ridgeway, 1988; Baichwal and Sugden, 1986; Coupar et al., 1988) canary pox virus, and herpes viruses are employed. These viruses offer several features for use in gene transfer into various mammalian cells.

Once the construct has been delivered into the cell, the nucleic acid encoding the transgene are positioned and expressed at different sites. In certain embodiments, the nucleic acid encoding the transgene is stably integrated into the genome of the cell. This integration is in the cognate location and orientation via homologous recombination (gene replacement) or it is integrated in a random, non-specific location (gene augmentation). In yet further embodiments, the nucleic acid is stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

V. Enhancement of an Immune Response

In certain embodiments, the present invention contemplates a novel DC activation strategy that incorporates the manipulation of signaling co-stimulatory polypeptides that activate NF B pathways, Akt pathways, and/or p38 pathways. This DC activation system can be used in conjunction with or without standard vaccines to enhance the immune response since it replaces the requirement for CD4+ T cell help during APC activation (Bennett S. R. et al., 1998; Ridge, J. P. et al., 1998; Schoenberger, S. P., et al., 1998). Thus, the DC activation system of the present invention enhances immune responses by circumventing the need for the generation of MHC class II-specific peptides.

In specific embodiments, the DC activation is via CD40 activation. Thus, DC activation via endogenous CD40/CD40L interactions may be subject to downregulation due to negative feedback, leading rapidly to the "IL-12 burn-out effect". Within 7 to 10 hours after CD40 activation, an alternatively spliced isoform of CD40 (type II) is produced as a secretable factor (Tone, M., et al., 2001). Type II CD40 may act as a dominant negative receptor, downregulating signaling through CD40L and potentially limiting the potency of the immune response generated. Therefore, the present invention co-opts the natural regulation of CD40 by creating an inducible form of CD40 (iCD40), lacking the extracellular domain and activated instead by synthetic dimerizing ligands (Spencer, D. M. et al., 1993) through a technology termed chemically induced dimerization (CID).

The present invention comprises a method of enhancing the immune response in an subject comprising the step of administering either the expression vector, expression construct or transduced antigen-presenting cells of the present invention to the subject. The expression vector of the present invention encodes a co-stimulatory polypeptide, such as iCD40.

In certain embodiments the antigen-presenting cells are comprised in an animal, such as human, non-human primate, cow, horse, pig, sheep, goat, dog, cat, or rodent. The subject is a human, more preferably, a patient suffering from an infectious disease, and/or a subject that is immunocompromised, or is suffering from a hyperproliferative disease.

In further embodiments of the present invention, the expression construct and/or expression vector can be utilized as a composition or substance that activates antigen-presenting cells. Such a composition that "activates antigen-presenting cells" or "enhances the activity antigen-presenting cells" refers to the ability to stimulate one or more activities associated with antigen-presenting cells. Such activities are well known by those of skill in the art. For example, a composition, such as the expression construct or vector of the present invention, can stimulate upregulation of co-stimulatory molecules on antigen-presenting cells, induce nuclear translocation of NF-κB in antigen-presenting cells, activate toll-like receptors in antigen-presenting cells, or other activities involving cytokines or chemokines.

An amount of a composition that activates antigen-presenting cells which "enhances" an immune response refers to an amount in which an immune response is observed that is greater or intensified or deviated in any way with the addition of the composition when compared to the same immune response measured without the addition of the composition. For example, the lytic activity of cytotoxic T cells can be measured, e.g., using a 51Cr release assay, with and without the composition. The amount of the substance at which the CTL lytic activity is enhanced as compared to the CTL lytic activity without the composition is said to be an amount sufficient to enhance the immune response of the animal to the antigen. In a preferred embodiment, the immune response in enhanced by a factor of at least about 2, more preferably by a factor of about 3 or more. The amount of cytokines secreted may also be altered.

The enhanced immune response may be an active or a passive immune response. Alternatively, the response may be part of an adaptive immunotherapy approach in which antigen-presenting cells are obtained with from a subject (e.g., a patient), then transduced with a composition comprising the expression vector or construct of the present invention. The antigen-presenting cells may be obtained from the blood of the subject or bone marrow of the subject. In certain preferred embodiments, the antigen-presenting cells are isolated from the bone marrow. In a preferred embodiment, the antigen-presenting cells are administered to the same or different animal (e.g., same or different donors). In a preferred embodiment, the subject (e.g., a patient) has or is suspected of having a cancer, such as for example, prostate cancer, or has or is suspected of having an infectious disease. In other embodiments the method of enhancing the immune response is practiced in conjunction with a known cancer therapy or any known therapy to treat the infectious disease.

The expression construct, expression vector and/or transduced antigen-presenting cells can enhance or contribute to the effectiveness of a vaccine by, for example, enhancing the immunogenicity of weaker antigens such as highly purified or recombinant antigens, reducing the amount of antigen required for an immune response, reducing the frequency of immunization required to provide protective immunity, improve the efficacy of vaccines in subjects with reduced or weakened immune responses, such as newborns, the aged, and immunocompromised individuals, and enhance the immunity at a target tissue, such as mucosal immunity, or promote cell-mediated or humoral immunity by eliciting a particular cytokine profile.

Yet further, an immunocompromised individual or subject is a subject that has a reduced or weakened immune response. Such individuals may also include a subject that has undergone chemotherapy or any other therapy resulting in a weakened immune system, a transplant recipient, a subject currently taking immunosuppressants, an aging individual, or any individual that has a reduced and/or impaired CD4 T helper cells. It is contemplated that the present invention can be utilize to enhance the amount and/or activity of CD4 T helper cells in an immunocompromised subject.

In specific embodiments, prior to administering the transduced antigen-presenting cell, the cells are challenged with antigens (also referred herein as "target antigens"). After challenge, the transduced, loaded antigen-presenting cells are administered to the subject parenterally, intradermally, intranodally, or intralymphatically. Additional parenteral routes include, but are not limited to subcutaneous, intramuscular, intraperitoneal, intravenous, intraarterial, intramyocardial, transendocardial, transepicardial, intrathecal, and infusion techniques.

The target antigen, as used herein, is an antigen or immunological epitope on the antigen, which is crucial in immune recognition and ultimate elimination or control of the disease-causing agent or disease state in a mammal. The immune recognition may be cellular and/or humoral. In the case of intracellular pathogens and cancer, immune recognition is preferably a T lymphocyte response.

The target antigen may be derived or isolated from a pathogenic microorganism such as viruses including HIV, (Korber et al, 1977) influenza, Herpes simplex, human papilloma virus (U.S. Pat. No. 5,719,054), Hepatitis B (U.S. Pat. No. 5,780,036), Hepatitis C (U.S. Pat. No. 5,709,995), EBV, Cytomegalovirus (CMV) and the like. Target antigen may be derived or isolated from pathogenic bacteria such as from *Chlamydia* (U.S. Pat. No. 5,869,608), *Mycobacteria, Legionella, Meningiococcus*, Group A *Streptococcus, Salmonella, Listeria, Hemophilus influenzae* (U.S. Pat. No. 5,955, 596) and the like.

Target antigen may be derived or isolated from pathogenic yeast including *Aspergillus*, invasive *Candida* (U.S. Pat. No. 5,645,992), *Nocardia, Histoplasmosis, Cryptosporidia and the like*.

Target antigen may be derived or isolated from a pathogenic protozoan and pathogenic parasites including but not limited to *Pneumocystis carinii, Trypanosoma, Leishmania* (U.S. Pat. No. 5,965,242), *Plasmodium* (U.S. Pat. No. 5,589, 343) and *Toxoplasma gondii*.

Target antigen includes an antigen associated with a pre-neoplastic or hyperplastic state. Target antigen may also be associated with, or causative of cancer. Such target antigen may be tumor specific antigen, tumor associated antigen (TAA) or tissue specific antigen, epitope thereof, and epitope agonist thereof. Such target antigens include but are not limited to carcinoembryonic antigen (CEA) and epitopes thereof such as CAP-1, CAP-1-6D (46) and the like (GenBank Accession No. M29540), MART-1 (Kawakami et al, 1994), MAGE-1 (U.S. Pat. No. 5,750,395), MAGE-3, GAGE (U.S. Pat. No. 5,648,226), GP-100 (Kawakami et al., 1992), MUC-1, MUC-2, point mutated ras oncogene, normal and point mutated p53 oncogenes (Hollstein et al., 1994), PSMA (Israeli et al., 1993), tyrosinase (Kwon et al. 1987) TRP-1 (gp75) (Cohen et al., 1990; U.S. Pat. No. 5,840,839), NY-ESO-1 (Chen et al., PNAS 1997), TRP-2 (Jackson et al., 1992), TAG72, KSA, CA-125, PSA, HER-2/neu/c-erb/B2, (U.S. Pat. No. 5,550,214), BRC-I, BRC-II, bcr-abl, pax3-fkhr, ews-fli-1, modifications of TAAs and tissue specific antigen, splice variants of TAAs, epitope agonists, and the like. Other TAAs may be identified, isolated and cloned by methods known in the art such as those disclosed in U.S. Pat. No. 4,514,506. Target antigen may also include one or more growth factors and splice variants of each.

An antigen may be expressed more frequently in cancer cells than in non-cancer cells. The antigen may result from contacting the modified dendritic cell with prostate specific membrane antigen (PSMA) or fragment thereof. In certain embodiments, the modified dendritic cell is contacted with a PSMA fragment having the amino acid sequence of SEQ ID NO: 4 (e.g., encoded by the nucleotide sequence of SEQ ID NO: 3).

For organisms that contain a DNA genome, a gene encoding a target antigen or immunological epitope thereof of interest is isolated from the genomic DNA. For organisms with RNA genomes, the desired gene may be isolated from cDNA copies of the genome. If restriction maps of the genome are available, the DNA fragment that contains the gene of interest is cleaved by restriction endonuclease digestion by methods routine in the art. In instances where the desired gene has been previously cloned, the genes may be readily obtained from the available clones. Alternatively, if the DNA sequence of the gene is known, the gene can be synthesized by any of the conventional techniques for synthesis of deoxyribonucleic acids.

Genes encoding an antigen of interest can be amplified by cloning the gene into a bacterial host. For this purpose, various prokaryotic cloning vectors can be used. Examples are plasmids pBR322, pUC and pEMBL.

The genes encoding at least one target antigen or immunological epitope thereof can be prepared for insertion into the plasmid vectors designed for recombination with a virus by standard techniques. In general, the cloned genes can be excised from the prokaryotic cloning vector by restriction enzyme digestion. In most cases, the excised fragment will contain the entire coding region of the gene. The DNA fragment carrying the cloned gene can be modified as needed, for example, to make the ends of the fragment compatible with the insertion sites of the DNA vectors used for recombination with a virus, then purified prior to insertion into the vectors at restriction endonuclease cleavage sites (cloning sites).

Antigen loading of dendritic cells with antigens may be achieved by incubating dendritic cells or progenitor cells with the polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide. Antigens from cells or MHC molecules may be obtained by acid-elution or other methods known in the art (see Zitvogel et al., 1996).

One skilled in the art is fully aware that activation of the co-stimulatory molecule of the present invention relies upon oligomerization of ligand-binding domains, for example CID, to induce its activity. In specific embodiments, the ligand is a non-protein. More specifically, the ligand is a dimeric FK506 or dimeric FK506 analogs, which result in enhancement or positive regulation of the immune response. The use of monomeric FK506 or monomeric FK506 analogs results in inhibition or reduction in the immune response negatively.

T-lymphocytes are activated by contact with the antigen-presenting cell that comprises the expression vector of the present invention and has been challenged, transfected, pulsed, or electrofused with an antigen.

Electrofusing in the present invention is a method of generating hybrid cells. There are several advantages in producing cell hybrids by electrofusion. For example, fusion parameters can be easily and accurately electronically controlled to conditions depending on the cells to be fused. Further, electrofusion of cells has shown to the ability to increase fusion efficiency over that of fusion by chemical means or via biological fusogens. Electrofusion is performed by applying electric pulses to cells in suspension. By exposing cells to an alternating electric field, cells are brought close to each other in forming pearl chains in a process termed dielectrophoresis alignment. Subsequent higher voltage pulses cause cells to come into closer contact, reversible electropores are formed in reversibly permeabilizing and mechanically breaking down cell membranes, resulting in fusion.

T cells express a unique antigen binding receptor on their membrane (T-cell receptor), which can only recognize antigen in association with major histocompatibility complex (MHC) molecules on the surface of other cells. There are several populations of T cells, such as T helper cells and T cytotoxic cells. T helper cells and T cytotoxic cells are primarily distinguished by their display of the membrane bound glycoproteins CD4 and CD8, respectively. T helper cells secret various lymphokines, that are crucial for the activation of B cells, T cytotoxic cells, macrophages and other cells of the immune system. In contrast, a naïve CD8 T cell that recognizes an antigen-MHC complex proliferates and differentiates into an effector cell called a cytotoxic CD8 T lymphocyte (CTL). CTLs eliminate cells of the body displaying antigen, such as virus-infected cells and tumor cells, by producing substances that result in cell lysis.

CTL activity can be assessed by methods described herein or as would be known to one of skill in the art. For example, CTLs may be assessed in freshly isolated peripheral blood mononuclear cells (PBMC), in a phytohaemaglutinin-stimulated IL-2 expanded cell line established from PBMC (Bernard et al., 1998) or by T cells isolated from a previously immunized subject and restimulated for 6 days with DC infected with an adenovirus vector containing antigen using standard 4 h 51Cr release microtoxicity assays. One type of assay uses cloned T-cells. Cloned T-cells have been tested for their ability to mediate both perforin and Fas ligand-dependent killing in redirected cytotoxicity assays (Simpson et al., 1998). The cloned cytotoxic T lymphocytes displayed both Fas- and perforin-dependent killing. Recently, an in vitro dehydrogenase release assay has been developed that takes advantage of a new fluorescent amplification system (Page et al., 1998). This approach is sensitive, rapid, and reproducible and may be used advantageously for mixed lymphocyte reaction (MLR). It may easily be further automated for large-scale cytotoxicity testing using cell membrane integrity, and is thus considered in the present invention. In another fluorometric assay developed for detecting cell-mediated cytotoxicity, the fluorophore used is the non-toxic molecule AlamarBlue (Nociari et al., 1998). The AlamarBlue is fluorescently quenched (i.e., low quantum yield) until mitochondrial reduction occurs, which then results in a dramatic increase in the AlamarBlue fluorescence intensity (i.e., increase in the quantum yield). This assay is reported to be extremely sensitive, specific and requires a significantly lower number of effector cells than the standard $^{51}$Cr release assay.

Other immune cells that are induced by the present invention include natural killer cells (NK). NKs are lymphoid cells that lack antigen-specific receptors and are part of the innate immune system. Typically, infected cells are usually destroyed by T cells alerted by foreign particles bound the cell surface MHC. However, virus-infected cells signal infection by expressing viral proteins that are recognized by antibodies. These cells can be killed by NKs. In tumor cells, if the tumor cells lose expression of MHC 1 molecules, then it may be susceptible to NKs.

In further embodiments, the transduced antigen-presenting cell is transfected with tumor cell mRNA. The transduced transfected antigen-presenting cell is administered to an animal to effect cytotoxic T lymphocytes and natural killer cell anti-tumor antigen immune response and regulated using dimeric FK506 and dimeric FK506 analogs. The tumor cell mRNA is mRNA from a prostate tumor cell.

Yet further, the transduced antigen-presenting cell is pulsed with tumor cell lysates. The pulsed transduced antigen-presenting cells are administered to an animal to effect cytotoxic T lymphocytes and natural killer cell anti-tumor antigen immune response and regulated using dimeric FK506 and dimeric FK506 analogs. The tumor cell lysates is a prostate tumor cell lysate.

The following references, to the extent that they provide exemplary procedural or other details supplementary to those set forth herein, are specifically incorporated herein by reference: Gossen and Bujard, Proc. Natl. Acad. Sci. USA, 89:5547-5551, 1992; Gossen et al., Science, 268:1766-1769, 1995; Pelletier and Sonenberg, Nature, 334:320-325, 1988; Macejak and Sarnow, Nature, 353:90-94, 1991; Kageyama et al., (1987) J. Biol. Chem., 262, 2345-2351; Arcone, et al., (1988) Nucl. Acids Res., 16(8), 3195-3207; Oliviero et al., (1987) EMBO J., 6, 1905-1912; Poli and Cortese, (1989) Proc. Nat'l Acad. Sci. USA, 86, 8202-8206; Wilson et al., (1990) Mol. Cell. Biol., 6181-6191; Prowse and Baumann, (1988) Mol Cell Biol, 8, 42-51; Ron, et al., (1991) Mol. Cell. Biol., 2887-2895; Potter et al., (1984) Proc. Nat'l Acad. Sci. USA, 81, 7161-7165; Tur-Kaspa et al., (1986) Mol. Cell. Biol., 6, 716-718; Graham and van der Eb, (1973) Virology, 52, 456-467; Fechheimer et al., (1987) Proc. Nat'l Acad. Sci. USA, 84, 8463-8467; Ghosh and Bachhawat, (1991) In: Liver Diseases, Targeted Diagnosis and Therapy Using Specific Receptors and Ligands. pp. 87-104; Wu and Wu, (1987) J. Biol. Chem., 262, 4429-4432; Nicolau et al., (1987) Methods Enzymol., 149, 157-176; Klein et al., (1987) Nature, 327, 70-73; Yang et al., (1990) Proc. Nat'l Acad. Sci. USA, 87, 9568-9572; Renan, M. J. (1990) Radiother Oncol., 19, 197-218; Hearing et al., J. (1987) Virol., 67, 2555-2558; Tibbetts et. al. (1977) Cell, 12, 243-249; Hearing and Shenk, (1983) J. Mol. Biol. 167, 809-822; Coffin, (1990) In: Virology, ed., New York: Raven Press, pp. 1437-1500; Mann et al., (1983) Cell, 33, 153-159; Nicolas and Rubenstein, (1988) In: Vectors: A survey of molecular cloning vectors and their uses, pp. 493-513; Temin et al., (1986) In: Gene Transfer, Kucherlapati (ed.), New York: Plenum Press, pp. 149-188; Paskind et al., (1975) Virology, 67, 242-248; Roux et al., (1989) Proc. Nat'l Acad. Sci. USA, 86, 9079-9083; Samulski et al., J. Virol., 61:3096-3101 (1987); Carter and Flotte, (1995) Ann. N.Y. Acad. Sci., 770; 79-90; Chatteijee, et al., (1995) Ann. N.Y. Acad. Sci., 770, 79-90; Ferrari et al., (1996) J. Virol., 70, 3227-3234; Fisher et al., (1996) J. Virol., 70, 520-532; Flotte et al., Proc. Nat'l Acad. Sci. USA, 90, 10613-10617, (1993); Goodman et al. (1994), Blood, 84, 1492-1500; Kaplitt et al., (1994) Nat'l Genet., 8, 148-153; Kessler et al., (1996) Proc. Nat'l Acad. Sci. USA, 93, 14082-14087; Koeberl et al., (1997) Proc. Nat'l Acad. Sci. USA, 94, 1426-1431; Mizukami et al., (1996) Virology, 217, 124-130; McCown et al., (1996) Brain Res., 713, 99-107; Ping et al., (1996) Microcirculation, 3, 225-228; Xiao et al., (1996) J. Virol., 70, 8098-8108; Ridgeway, (1988) In: Vectors: A survey of molecular cloning vectors and their uses, pp. 467-492; Baichwal and Sugden, (1986) In, Gene Transfer, pp. 117-148; Zechner et al., Mol. Cell. Biol., 2394-2401, 1988; Nabel et al., Science, 244(4910):1342-1344, 1989; Wilson et al., Science, 244: 1344-1346, 1989; Chen and Okayama, Mol. Cell. Biol., 7(8): 2745-2752, 1987; Rippe et al., Mol. Cell. Biol., 10:689-695, 1990; Perales et al., Proc. Natl. Acad. Sci. USA, 91:4086-4090, 1994; Wagner et al., Proc. Natl. Acad. Sci. USA, 87(9): 3410-3414, 1990; Wu and Wu, Adv. Drug Delivery Rev., 12:159-167, 1993; Levrero et al., Gene, 101:195-202, 1991; Coupar et al., Gene, 68:1-10, 1988; Bennett, S. R., et al., Nature, 1998 Jun. 4. 393: p. 478-80; Ridge, J. P., D. R. F, and P. Nature, 1998 Jun. 4. 393: p. 474-8; Schoenberger, S. P., et al., Nature, 1998 Jun. 4. 393: p. 480-3; Tone, M., et al., Proc Natl Acad Sci USA, 2001. 98(4): p. 1751-1756; Spencer, D. M., et al., Science, 1993. 262: p. 1019-1024; Korber et al, eds HIV Molecular Immunology Database, Los Alamos National Laboratory, Los Alamos, N. Mex. 1977; Kawakami et al, J. Exp. Med. 180:347-352, 1994; Kawakami et al Proc. Nat'l Acad. Sci. USA 91:6458-6462, 1992; Hollstein et al Nucleic Acids Res. 22:3551-3555, 1994; Israeli et al Cancer Res. 53:227-230, 1993; Kwon et al PNAS 84:7473-7477, 1987; Cohen et al Nucleic Acid Res. 18:2807-2808, 1990; Chen et al PNAS 94: 1914-1918, 1997; Jackson et al EMBO J, 11:527-535, 1992; Zitvogel L, et al., J Exp Med 1996. 183: 87-97; Nociari et al., J. Immunol. Methods, 213(2): 157-167, 1998; Simpson et al., Gastroenterology, 115(4):849-855, 1998; Bernard et al., AIDS, 12(16):2125-2139, 1998; Spencer D. M. et al., Curr Biol 1996, 6:839-847; Blau, C. A. et al., Proc Natl Acad. Sci. USA 1997, 94:3076-3081; Luo, Z. et al., Nature 1996, 383:181-185; MacCorkle, R. A. et al., Proc Natl Acad Sci USA 1998, 95:3655-3660; Ho, S. N. et al., Nature 1996, 382:822-826; Rivera, V. M. et al., Nat. Med. 1996, 2:1028-1032; Spencer D. M. et al., Proc. Natl. Acad. Sci. USA 1995, 92:9805-9809; Holsinger, L. J. et al., Proc. Natl. Acad. Sci. USA 1995, 95:9810-9814; Kohler & Milstein, Nature, 256:495-497, 1975; Kohler & Milstein, Eur. J. Immunol., 6:511-519, 1976; Campbell, in: Monoclonal Antibody Technology, Laboratory Techniques in Biochemistry and Molecular Biology, Vol. 13, Burden & Von Knippenberg, Amsterdam, Elseview, pp. 75-83, 1984; Gefter et al., Somatic Cell Genet., 3:231-236, 1977; Medzhitov et al., Nature, 388: 394-397, 1997; Banchereau, J., & Steinman, R. M. Dendritic cells and the control of immunity. Nature 392, 245-252 (1998); Adema, G. J., et al., Nature, 1997 Jun. 12. 387: p. 713-7; Termeer, C. C., et al., J Immunol, 2000, Aug. 15. 165: p. 1863-70; Lanzavecchia, A. and F. Sallusto, Science, 2000. 290: p. 92-96; Fearon et al. (1996) Science 272: 50-3; Banchereau, J., et al., Annu Rev Immunol, 2000, 18: p. 767-811; Anderson, D. M., et al., Nature, 1997 Nov. 13. 390: p. 175-9; Ohshima, Y., et al., J Immunol, 1997 Oct. 15. 159: p. 3838-48; Sallusto, F., et al., Eur J Immunol, 1998 Sep. 28: p. 2760-9; Bennett, S. R., et al., Nature, 1998 Jun. 4. 393: p. 478-80; Clarke, S. R., J Leukoc Biol, 2000, May. 67: p. 607-14; Fernandez, N. C., et al., Nat Med, 1999 Apr. 5: p. 405-11; Ridge, J. P., D. R. F, and P. Nature, 1998 Jun. 4. 393: p. 474-8; Schoenberger, S. P., et al., Nature, 1998 Jun. 4. 393: p. 480-3; McWhirter, S. M., et al., Proc Natl Acad Sci USA, 1999 Jul. 20. 96: p. 8408-13; Ni, C., et al., PNAS, 2000, 97(19): 10395-10399; Pullen, S. S., et al., J Biol Chem, 1999, May 14.274: p. 14246-54; Janeway et al. (1989) Cold Spring Harb. Symp. Quant. Biol., 54: 1-13; Kuby, 2000, Immunology, 4.sup.th edition, W.H. Freeman and company.

VI. Formulations and Routes for Administration to Patients

Where clinical applications are contemplated, it will be necessary to prepare pharmaceutical compositions-expression constructs, expression vectors, fused proteins, transduced cells, activated DCs, transduced and loaded DCs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. A pharmaceutically acceptable carrier includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For oral administration, the compositions of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient also may be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media, which can be employed, will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

VII. Methods for Treating a Disease

The present invention also encompasses methods of treatment or prevention of a disease caused by pathogenic microorganisms and/or a hyperproliferative disease.

Diseases may be treated or prevented by use of the present invention include diseases caused by viruses, bacteria, yeast, parasites, protozoa, cancer cells and the like. The pharmaceutical composition of the present invention (transduced DCs, expression vector, expression construct, etc.) of the present invention may be used as a generalized immune enhancer (DC activating composition or system) and as such has utility in treating diseases. Exemplary disease that can be treated and/or prevented utilizing the pharmaceutical composition of the present invention include, but are not limited to infections of viral etiology such as HIV, influenza, Herpes, viral hepatitis, Epstein Bar, polio, viral encephalitis, measles, chicken pox, Papilloma virus etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc.

Preneoplastic or hyperplastic states which may be treated or prevented using the pharmaceutical composition of the present invention (transduced DCs, expression vector, expression construct, etc.) of the present invention include but are not limited to preneoplastic or hyperplastic states such as colon polyps, Crohn's disease, ulcerative colitis, breast lesions and the like.

Cancers which may be treated using the pharmaceutical composition of the present invention of the present invention include, but are not limited to primary or metastatic melanoma, adenocarcinoma, squamous cell carcinoma, adenosquamous cell carcinoma, thymoma, lymphoma, sarcoma, lung cancer, liver cancer, non-Hodgkin's lymphoma, Hodgkin's lymphoma, leukemias, uterine cancer, breast cancer, prostate cancer, ovarian cancer, pancreatic cancer, colon cancer, multiple myeloma, neuroblastoma, NPC, bladder cancer, cervical cancer and the like.

Other hyperproliferative diseases that may be treated using DC activation system of the present invention include, but are not limited to rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis.

In the method of treatment, the administration of the pharmaceutical composition (expression construct, expression vector, fused protein, transduced cells, activated DCs, transduced and loaded DCs) of the invention may be for either "prophylactic" or "therapeutic" purpose. When provided prophylactically, the pharmaceutical composition of the present invention is provided in advance of any symptom. The prophylactic administration of pharmaceutical composition serves to prevent or ameliorate any subsequent infection or disease. When provided therapeutically, the pharmaceutical composition is provided at or after the onset of a symptom of infection or disease. Thus the present invention may be provided either prior to the anticipated exposure to a disease-causing agent or disease state or after the initiation of the infection or disease.

The term "unit dose" as it pertains to the inoculum refers to physically discrete units suitable as unitary dosages for mammals, each unit containing a predetermined quantity of pharmaceutical composition calculated to produce the desired immunogenic effect in association with the required diluent. The specifications for the novel unit dose of an inoculum of this invention are dictated by and are dependent upon the unique characteristics of the pharmaceutical composition and the particular immunologic effect to be achieved.

An effective amount of the pharmaceutical composition would be the amount that achieves this selected result of enhancing the immune response, and such an amount could be determined as a matter of routine by a person skilled in the art. For example, an effective amount of for treating an immune system deficiency could be that amount necessary to cause activation of the immune system, resulting in the development of an antigen specific immune response upon exposure to antigen. The term is also synonymous with "sufficient amount."

The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

A. Genetic Based Therapies

Specifically, the present inventors intend to provide, to a cell, an expression construct capable of providing a co-stimulatory polypeptide, such as CD40 to the cell, such as an antigen-presenting cell and activating CD40. The lengthy discussion of expression vectors and the genetic elements employed therein is incorporated into this section by reference. Particularly preferred expression vectors are viral vectors such as adenovirus, adeno-associated virus, herpes virus, vaccinia virus and retrovirus. Also preferred is lysosomal-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver $1 \times 10e4$, $1 \times 10e5$, $1 \times 10e6$, $1 \times 10e7$, $1 \times 10e8$, $1 \times 10e9$, $1 \times 10e10$, $1 \times 10e11$ or $1 \times 10e12$ infectious particles to the patient. Similar figures may be extrapolated for liposomal or other non-viral formulations by comparing relative uptake efficiencies. Formulation as a pharmaceutically acceptable composition is discussed below.

B. Cell Based Therapy

Another therapy that is contemplated is the administration of transduced antigen-presenting cells. The antigen-presenting cells may be transduced in vitro. Formulation as a pharmaceutically acceptable composition is discussed above.

In cell based therapies, the transduced antigen-presenting cells may be transfected with target antigen nucleic acids, such as mRNA or DNA or proteins; pulsed with cell lysates, proteins or nucleic acids; or electrofused with cells. The cells, proteins, cell lysates, or nucleic acid may derive from cells, such as tumor cells or other pathogenic microorganism, for example, viruses, bacteria, protozoa, etc.

C. Combination Therapies

In order to increase the effectiveness of the expression vector of the present invention, it may be desirable to combine these compositions and methods of the invention with an agent effective in the treatment of the disease.

In certain embodiments, anti-cancer agents may be used in combination with the present invention. An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents include, for example, chemotherapy agents (chemotherapy), radiotherapy agents (radiotherapy), a surgical procedure (surgery), immune therapy agents (immunotherapy), genetic therapy agents (gene therapy), hormonal therapy, other biological agents (biotherapy) and/or alternative therapies.

In further embodiments antibiotics can be used in combination with the pharmaceutical composition of the present invention to treat and/or prevent an infectious disease. Such antibiotics include, but are not limited to, amikacin, aminoglycosides (e.g., gentamycin), amoxicillin, amphotericin B, ampicillin, antimonials, atovaquone sodium stibogluconate, azithromycin, capreomycin, cefotaxime, cefoxitin, ceftriaxone, chloramphenicol, clarithromycin, clindamycin, clofazimine, cycloserine, dapsone, doxycycline, ethambutol, ethionamide, fluconazole, fluoroquinolones, isoniazid, itraconazole, kanamycin, ketoconazole, minocycline, ofloxacin), para-aminosalicylic acid, pentamidine, polymixin definsins, prothionamide, pyrazinamide, pyrimethamine sulfadiazine, quinolones (e.g., ciprofloxacin), rifabutin, rifampin, sparfloxacin, streptomycin, sulfonamides, tetracyclines, thiacetazone, trimethaprim-sulfamethoxazole, viomycin or combinations thereof.

More generally, such an agent would be provided in a combined amount with the expression vector effective to kill or inhibit proliferation of a cancer cell and/or microorganism. This process may involve contacting the cell(s) with an agent(s) and the pharmaceutical composition of the present invention at the same time or within a period of time wherein separate administration of the pharmaceutical composition of the present invention and an agent to a cell, tissue or organism produces a desired therapeutic benefit. This may be achieved by contacting the cell, tissue or organism with a single composition or pharmacological formulation that includes both the pharmaceutical composition of the present invention and one or more agents, or by contacting the cell with two or more distinct compositions or formulations, wherein one composition includes the pharmaceutical composition of the present invention and the other includes one or more agents.

The terms "contacted" and "exposed," when applied to a cell, tissue or organism, are used herein to describe the process by which the pharmaceutical composition and/or another agent, such as for example a chemotherapeutic or radiotherapeutic agent, are delivered to a target cell, tissue or organism or are placed in direct juxtaposition with the target cell, tissue or organism. To achieve cell killing or stasis, the pharmaceutical composition and/or additional agent(s) are delivered to one or more cells in a combined amount effective to kill the cell(s) or prevent them from dividing.

The administration of the pharmaceutical composition may precede, be co-current with and/or follow the other agent(s) by intervals ranging from minutes to weeks. In embodiments where the pharmaceutical composition of the present invention, and other agent(s) are applied separately to a cell, tissue or organism, one would generally ensure that a significant period of time did not expire between the times of each delivery, such that the pharmaceutical composition of the present invention and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the pharmaceutical composition of the present invention. In other aspects, one or more agents may be administered within of from substantially simultaneously, about 1 minute, to about 24 hours to about 7 days to about 1 to about 8 weeks or more, and any range derivable therein, prior to and/or after administering the expression vector. Yet further, various combination regimens of the pharmaceutical composition of the present invention and one or more agents may be employed.

EXAMPLES

The following examples are provided to illustrate aspects of the invention and are not limiting.

Example 1

Materials and Methods

Described hereafter are materials and methods utilized in studies described in subsequent Examples.

Tumor Cell Lines and Peptides

NA-6-Mel, T2, SK-Mel-37 and LNCaP cell lines were purchased from ATCC (Manassas, Va.). HLA-A2-restricted peptides MAGE-3 p271-279 (FLWGPRALV) (SEQ ID NO: 8), influenza matrix (IM) p58-66 (GILGFVFTL) (SEQ ID NO: 9), and HIV-1 gag p77-85 (SLYNTVATL) (SEQ ID NO: 10) were used to analyze CD8+ T cell responses. In T helper cell polarization experiments, tetanus toxoid peptide TTp30 FNNFTVSFWLRVPKVSASHLE (SEQ ID NO: 5) was used. All peptides were synthesized by Genemed Synthesis Inc (San Francisco, Calif.), with an HPLC-determined purity of >95%.

Recombinant Adenovirus Encoding Human Inducible CD40

The human CD40 cytoplasmic domain was Pfu I polymerase (Stratagene, La Jolla, Calif.) amplified from human monocyte-derived DC cDNA using an Xho I-flanked 5' primer (5hCD40X), 5'-atatactcgagaaaaaggtggccaa-gaagccaacc-3' (SEQ ID NO: 11), and a Sal I-flanked 3' primer (3hCD40S), 5'-atatagtcgactcactgtctctcctgcactgagatg-3' (SEQ ID NO: 12). The PCR fragment was subcloned into Sal I-digested pSH1/M-FvFvls-E15 and sequenced to create pSH1/M-FvFvls-CD40-E. Inducible CD40 was subsequently subcloned into a non-replicating E1, E3-deleted Ad5/f35-based vector expressing the transgene under a cytomegalovirus early/immediate promoter. The iCD40-encoding sequence was confirmed by restriction digest and sequencing. Amplification, purification, and titration of all adenoviruses were carried out in the Viral Vector Core Facility of Baylor College of Medicine.

Western Blot

Total cellular extracts were prepared with RIPA buffer containing a protease inhibitor cocktail (Sigma-Aldrich, St. Louis, Mo.) and quantitated using a detergent-compatible protein concentration assay (Bio-Rad, Hercules, Calif.). 10-15 micrograms of total protein were routinely separated on 12% SDS-PAGE gels, and proteins were transferred to nitrocellulose membranes (Bio-Rad). Blots were hybridized with goat anti-CD40 (T-20, Santa Cruz Biotechnology, Santa Cruz, Calif.) and mouse anti-alpha-tubulin (Santa Cruz Biotechnology) Abs followed by donkey anti-goat and goat anti-mouse IgG-HRP (Santa Cruz Biotechnology), respectively. Blots were developed using the SuperSignal West Dura Stable substrate system (Pierce, Rockford, Ill.).

Generation and Stimulation of Human DCs

Peripheral blood mononuclear cells (PBMCs) from healthy donors were isolated by density centrifugation of heparinized blood on Lymphoprep (Nycomed, Oslo, Norway). PBMCs were washed with PBS, resuspended in CellGenix DC medium (Freiburg, Germany) and allowed to adhere in culture plates for 2 h at 37° C. and 5% $CO_2$. Non-adherent cells were removed by extensive washings, and adherent monocytes were cultured for 5 days in the presence of 500 U/ml hIL-4 and 800 U/ml hGM-CSF (R&D Systems, Minneapolis, Minn.). As assessed by morphology and FACS analysis, the resulting immature DCs (imDCs) were MHC-class I, IIhi, and expressed CD40lo, CD80lo, CD83lo, CD86lo. The imDCs were CD14neg and contained<3% of contaminating CD3+T, CD19+B, and CD16+NK cells.

Approximately $2\times10^6$ cells/ml were cultured in a 24-well dish and transduced with adenoviruses at 10,000 viral particle (vp)/cell (~160 MOI) for 90 min at 37° C. and 5% $CO_2$. Immediately after transduction DCs were stimulated with MPL, FSL-1, Pam3CSK4 (InvivoGen, San Diego, Calif.), LPS (Sigma-Aldrich, St. Louis, Mo.), AP20187 (kind gift from ARIAD Pharmaceuticals, Cambridge, Mass.) or maturation cocktail (MC), containing 10 ng/ml TNF-alpha, 10 ng/ml IL-1beta, 150 ng/ml IL-6 (R&D Systems, Minneapolis, Minn.) and 1 micrograms/ml of $PGE_2$ (Cayman Chemicals, Ann Arbor, Mich.). In T cell assays DCs were pulsed with 50 micrograms/ml of PSMA or MAGE 3 peptide 24 hours before and after adenoviral transduction.

Surface Markers and Cytokine Production

Cell surface staining was done with fluorochrome-conjugated monoclonal antibodies (BD Biosciences, San Diego, Calif.). Cells were analyzed on a FACSCalibur cytometer (BD Biosciences, San Jose, Calif.). Cytokines were measured in culture supernatants using enzyme-linked immunosorbent assay kits for human IL-6 and IL-12p70 (BD Biosciences).

Real Time Q-PCR Assay for Human SOCS1

Total RNA was purified and reverse transcribed with random hexamers using SuperScript II RTase (Invitrogen, Carlsbad, Calif.). mRNA levels were quantified in DCs by subjecting cDNA to TaqMan PCR analysis using the GeneAmp 5700 Sequence Detection System (Applied Biosystems, Foster City, Calif.). Pre-developed sequence detection reagents (Applied Biosystems) specific for human SOCS1 and 18S rRNA, including forward and reverse primers as well as a fluorogenic TaqMan FAM-labeled hybridization probe, were supplied as mixtures and were used at 1 microliter/20 microliter PCR. Samples were run in duplicates. The level of SOCS1 expression in each sample was normalized to the level of 18S rRNA from the same sample using the comparative 2-ΔΔCT method[21].

DC Migration Assay

Chemotaxis of DCs was measured by migration through a polycarbonate filter with 8 micrometer pore size in 96-Multiwell HTS Fluoroblok plates (BD Biosciences). Assay medium (250 μL) containing 100 ng/ml CCL19 (R&D Systems) or assay medium alone (as a control for spontaneous migration) were loaded into the lower chamber. DCs (50,000) were labeled with Green-CMFDA cell tracker (Invitrogen), unstimulated or stimulated for 48 h with the indicated reagents, and were added to the upper chamber in a total volume of 500_, for 1 hour at 37° C. and 5% $CO_2$. Fluorescence of cells, which had migrated through the microporous membrane, was measured using the FLUOstar OPTIMA reader (BMG Labtech Inc., Durham, N.C.). The mean fluorescence of spontaneously migrated cells was subtracted from the total number of migrated cells for each condition.

IFN-Gamma ELISPOT Assay

DCs from HLA-A2-positive healthy volunteers were pulsed with MAGE-3 A2.1 peptide (residues 271-279; FLWGPRALV) (SEQ ID NO: 8) on day 4 of culture, followed by transduction with Ad-iCD40 and stimulation with various stimuli on day 5. Autologous T cells were purified from PBMCs by negative selection (Miltenyi Biotec, Auburn, Calif.) and mixed with DCs at DC:T cell ratio 1:3. Cells were incubated in complete RPMI with 20 U/ml hIL-2 (R&D Systems) and 25 micrograms/ml of MAGE 3 A2.1 peptide. T cells were restimulated at day 7 and assayed at day 14 of culture.

ELISPOT Quantitation

Flat-bottom, 96-well nitrocellulose plates (MultiScreen-HA; Millipore, Bedford, Mass.) were coated with IFN-gamma mAb (2 μg/ml, 1-D1K; Mabtech, Stockholm, Sweden) and incubated overnight at 4° C. After washings with PBS containing 0.05% TWEEN 20, plates were blocked with complete RPMI for 2 h at 37° C. A total of $1\times10^5$ presensitized CD8+T effector cells were added to each well and incubated for 20 h with 25 micrograms/ml peptides. Plates were then washed thoroughly with PBS containing 0.05% Tween 20, and anti-IFN-mAb (0.2 μg/ml, 7-B6-1-biotin; Mabtech) was added to each well. After incubation for 2 h at 37° C., plates were washed and developed with streptavidin-alkaline phosphatase (1 μg/ml; Mabtech) for 1 h at room temperature. After washing, substrate (3-amino-9-ethyl-carbazole; Sigma-Aldrich) was added and incubated for 5 min. Plate membranes displayed dark-pink spots that were scanned and analyzed by ZellNet Consulting Inc. (Fort Lee, N.J.).

Chromium Release Assay

Antigen recognition was assessed using target cells labeled with $^{51}$Chromium (Amersham) for 1 h at 37° C. and washed three times. Labeled target cells (5000 cells in 50 μl) were then added to effector cells (1000 at the indicated effector:target cell ratios in V-bottom microwell plates at the indicated concentrations. Supernatants were harvested after 6-h incubation at 37° C., and chromium release was measured using MicroBeta Trilux counter (Perkin-Elmer Inc, Torrance Calif.). Assays involving LNCaP cells were run for 18 hours.

The percentage of specific lysis was calculated as: 100*[(experimental−spontaneous release)/(maximum−spontaneous release)].

Tetramer Staining

HLA-A2 tetramers assembled with MAGE-3.A2 peptide (FLWGPRALV) (SEQ ID NO: 8) were obtained from Baylor College of Medicine Tetramer Core Facility (Houston, Tex.). Presensitized CD8+ T cells in 50 μl of PBS containing 0.5% FCS were stained with PE-labeled tetramer for 15 min on ice before addition of FITC-CD8 mAb (BD Biosciences). After washing, results were analyzed by flow cytometry.

Polarization of naïve T Helper Cells

Naïve CD4+CD45RA+ T-cells from HLA-DR11.5-positive donors (genotyped using FASTYPE HLA-DNA SSP typing kit; BioSynthesis, Lewisville, Tex.) were isolated by negative selection using naïve CD4+ T cell isolation kit (Miltenyi Biotec, Auburn, Calif.). T cells were stimulated with autologous DCs pulsed with tetanus toxoid (5 FU/ml) and stimulated with various stimuli at a stimulator to responder ratio of 1:10. After 7 days, T cells were restimulated with autologous DCs pulsed with the HLA-DR11.5-restricted helper peptide TTp30 and transduced with adenovector Ad-iCD40. Cells were stained with PE-anti-CD4 Ab (BD Biosciences), fixed and permeabilized using BD Cytofix/Cytoperm kit (BD Biosciences), then stained with hIFN-gamma mAb (eBioscience, San Diego, Calif.) and analyzed by flow cytometry. Supernatants were analyzed using human TH1/TH2 BD Cytometric Bead Array Flex Set on BD FACSArray Bioanalyzer (BD Biosciences).

PSMA Protein Purification

The baculovirus transfer vector, pAcGP67A (BD Biosciences) containing the cDNA of extracellular portion of PSMA (residues 44-750) was kindly provided by Dr Pamela J. Bjorkman (Howard Hughes Medical Institute, California Institute of Technology, Pasadena, Calif.). PSMA was fused with a hydrophobic secretion signal, Factor Xa cleavage site, and N-terminal 6x-His (SEQ ID NO: 37) affinity tag. High titer baculovirus was produced by the Baculovirus/Monoclonal antibody core facility of Baylor College of Medicine. PSMA protein was produced in High 5 cells infected with recombinant virus, and protein was purified from cell supernatants using Ni-NTA affinity columns (Qiagen, Chatsworth, Calif.) as previously described 24. After purification the ~100 kDa solitary band of PSMA protein was detected by silver staining of acrylamide gels.

Migration of Human DCs in Mouse Host

In order to assess the migration of human DCs in vivo, adenovector, Ad5-CBR, which expresses red-shifted (emission peak=613 nM) luciferase from Pyrophorus plagiophalamus click beetles (Promega, Madison, Wis.) was developed. Human DCs were transduced with ~50 MOI of Ad5-CBR, and 160 MOI of Ad5f354CD40. DCs were then matured with MC or 1 micrograms/ml LPS (Sigma-Aldrich, St. Louis, Mo.). Mouse bone-marrow derived DCs were obtained as described before[13] and were matured with 1 micrograms/ml LPS. Approximately 2×10$^6$ DCs were injected into the left and right hind footpads of irradiated (250 rads) Balb/c mice (both hind legs of three mice per group, n=6). Mice were i.p. injected with D-Luciferin (~1 mg/25 g animal) and imaged over several days using an IVIS™ 100 imaging system (Xenogen Corp., Alameda, Calif.). Luminescent signal was measured in 3 mice per group, and popliteal and inguinal lymph nodes (LN) were removed at day 2 post-DC inoculation. The LNs' signal was measured and the background was subtracted for each group (n=6).

Data Analysis

Results are expressed as the mean±standard error. Sample size was determined with a power of 0.8, with a one-sided alpha-level of 0.05. Differences between experimental groups were determined by the Student t test.

Example 2

Expression of iCD40 and Induction of DC Maturation

To investigate whether iCD40 signaling can enhance the immunogenic functions of human DCs, adenovirus, Ad5/f35-ihCD40 (simplified to Ad-iCD40) was generated, expressing inducible human CD40 receptor, based on the previously described mouse iCD40 vector13 (FIG. 1A). The human CD40 cytoplasmic signaling domain was cloned downstream of a myristoylation-targeting domain and two tandem domains (from human FKBP12(V36), designated as "Fv"), which bind dimerizing drug AP2018722. As shown in FIG. 1B, immature DCs expressed endogenous CD40, which was induced by LPS and CD40L. Transduction of Ad-iCD40 led to expression of the distinctly sized iCD40, which did not interfere with endogenous CD40 expression. Interestingly, the expression of iCD40 was also significantly enhanced by LPS stimulation, likely due to inducibility of ubiquitous transcription factors binding the "constitutive" CMV promoter.

Figure 2:
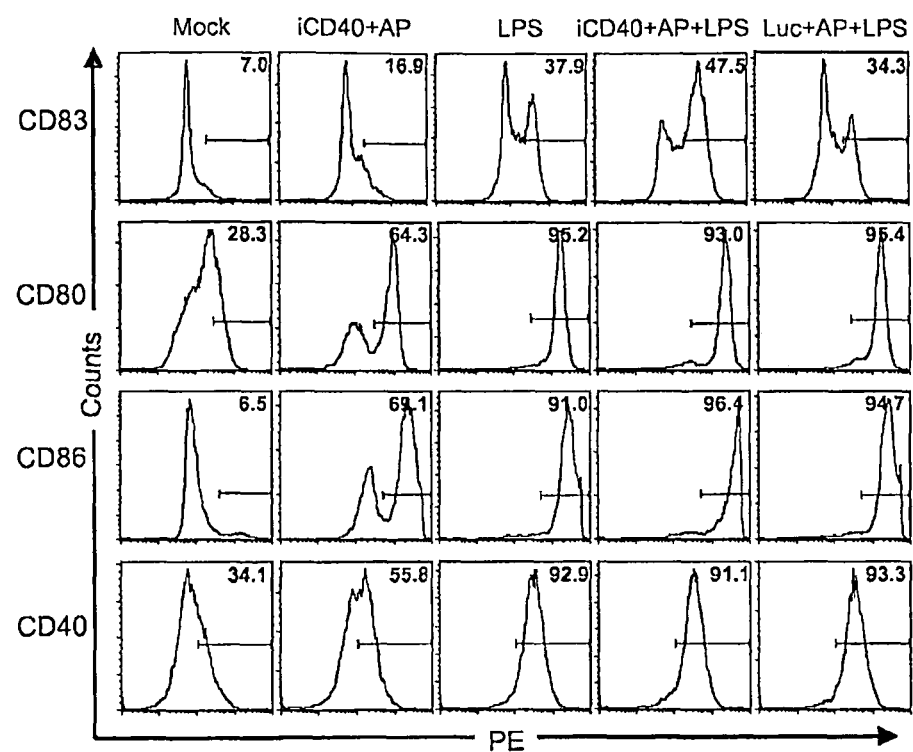
FIG. 2. Enhanced maturation status of iCD40 DCs stimulated with LPS Immature DCs were transduced with Ad5/f35- iCD40 or Ad5/f35-Luciferase (Luc) and stimulated with LPS (1 microgram/ml) for 48 hours in presence of 100 nM AP20187 (AP). Alternatively, DCs were matured in the presence of LPS alone. Percentage of DCs expressing CD40, CD80, CD83 and CD86 was determined using PE-conjugated anti-human mAbs (BD Biosciences) by flow cytometric analysis. FACS histograms from one donor (out of at least five) experiment are shown.

One of the issues for the design of DC-based vaccines is to obtain fully matured and activated DCs, as maturation status is linked to the transition from a tolerogenic to an activating, immunogenic State[4,13,23]. It has been shown that expression of mouse variant Ad-iCD40 can induce murine bone marrow-derived DC maturation[13]. To determine whether humanized iCD40 affects the expression of maturation markers in DCs, DCs were transduced with Ad-iCD40 and the expression of maturation markers CD40, CD80, CD83, and CD86 were evaluated. TLR-4 signaling mediated by LPS or its derivative MPL is a potent inducer of DC maturation[18,24-26]. It was also previously reported that endogenous CD40 signaling specifically up-regulates CD83 expression in human DCs27. Consistent with previous reports[27], the expression levels of CD83 were upregulated upon Ad-iCD40 transduction, and CD83 expression was further upregulated following LPS or MPL addition (FIG. 2 and data not shown). As shown in FIG. 2 the expression of CD40, CD80, and CD86 maturation markers were also highly induced by iCD40 with the addition of the dimerizer, AP20187, and further induced by the addition of LPS or MPL. In contrast, control adenovirus expressing renilla luciferase, Ad-Luc, only provided incidental activation. These results show that the combination of inducible CD40 and TLR-4 ligands provides sufficient stimulation for full DC maturation. This up-regulation of CD40, CD80, CD83 and CD86 expression was similar to that achieved by standard maturation cocktail (MC) and CD40L (data not shown).

Example 3

Inducible CD40 Signaling and TLR4 Ligation Synergize for IL-12p70 and L-6 Production in Human DCs Interleukin-12 (IL-12) activates T and NK cell responses, and induces IFN-gamma production. It also favors the differentiation of TH1 cells and is a vital link between innate and adaptive immunity[1,28]. Therefore, induction of biologically active IL-12p70 heterodimer is likely critical for optimum DC-based vaccines. Nonetheless, current DC vaccination protocols that include PGE$_2$ produce only limited IL-12[29]. IL-12 is a heterodimeric cytokine consisting of p40 and p35 chains. Previously, it was reported that inducible CD40 signaling promotes the expression of the p35 subunit of IL-12p70 in mouse bone marrow-derived DCs[13]. It was also reported that TLR-4 ligation can promote p40 expression[30]. Therefore, iCD40-DCs was cultured in the presence of LPS or MPL and assayed supernatants by ELISA for production of IL-12p70.

Predictably, similar to DCs treated with standard MC, iCD40-DCs did not produce detectable IL-12p70 heterodimer (FIG. 3A). If PGE$_2$ was withheld from the MC, DCs produced detectable but low levels of IL-12p70 (FIG. 3B), consistent with a potentially deleterious role for PGE$_2$. Furthermore, DCs cultured for 12 h in the presence of LPS or MPL alone also failed to produce IL-12 (<30 pg/ml). However, when Ad-iCD40-transduced DCs were cultured in the presence of either MPL or LPS they produced very high levels of IL-12p70 (16.4±7.8 ng/ml for MPL). This level of IL-12 was about 25-fold higher than levels induced by standard MC lacking PGE$_2$. Interestingly, this synergism of iCD40 and TLR4 was partially independent of AP20187 addition, implying that basal iCD40 signaling can also synergize with TLR4 ligation. IL-12p70 production in iCD40-DCs was also dose-dependent as IL-12 levels correlated with viral particles dose (Supplementary FIG. 1).

To determine whether other TLRs could also synergize with iCD40, ligands for TLR 1, 2, 4, and 6 were tested for IL12 production. As shown in FIG. 3B, FSL-1 (ligand for TLR2/TLR6) and Pam3 CSK4 (ligand for TLR1/TLR2) induced only low levels of IL12-p70 in iCD40-DCs. As before, TLR4 ligation with MPL or LPS synergized with CD40 signaling.

Since CD40 signaling is normally tightly restricted to a relatively short time period[31,32], potentially limiting adaptive immunity, it was determined whether iCD40 could induce not only enhanced, but also prolonged, expression of IL-12p70 in TLR-4-stimulated DCs. To evaluate the kinetics of IL-12 expression, LPS-treated iCD40-DCs with LPS and CD40L-stimulated DCs were compared. It was observed that iCD40-DCs were able to produce IL-12p70 for over 72 hours post stimulation compared to CD40L or control vector-transduced DCs (FIG. 3C) in which IL-12p70 expression ceased when LPS stimulation was removed. These results indicate that inducible CD40 signaling allows DCs to produce increased levels of IL-12p70 continuously in response to TLR-4 stimulation.

Finally, the induction of the suppressor of cytokine signaling (SOCS1) was evaluated. SOCS1 is negative feedback inhibitor of DC activation, that can attenuate[33] responsiveness to LPS and cytokine stimulation[34]. FIG. 3D shows that LPS stimulation up-regulated SOCS1 expression in DCs, as previously reported[33]. Strikingly, however, in the presence of LPS, iCD40-DCs expressed 3-fold lower levels of SOCS1 than CD40L-stimulated DCs. Moreover, iCD40 did not induce SOCS1 by itself, unlike CD40L. These data indicate that iCD40 can partially bypass SOCS1 induction in human DCs and may partly explain the observed sustained elevation of IL-12 levels and DC maturation markers.

In addition to IL-12, IL-6 plays an important role in cell survival and resistance to T regulatory cells[19,35]. It was observed that upon transfection with Ad-iCD40, IL-6 expression was significantly enhanced and further upregulated when iCD40-DCs were stimulated with dimerizer drug and TLR-4 ligands (FIG. 3E). Thus, iCD40 signaling is sufficient for production of some pro-inflammatory cytokines, but requires additional TLR signaling for production of the key TH1 cytokine, IL-12.

Example 4 iCD40 and TLR-4-Stimulated DCs Enhance Antigen-Specific TH1 Polarization

To further investigate whether iCD40-DCs matured with TLR-4 ligands can effectively prime CD4+ T helper (TH) cells, it was determined whether they can augment CD4+ epitope-specific T-cell responses in vitro. Naïve CD4+ CD45RA+ T cells were stimulated for 7 days in the presence of autologous Ad-iCD40 DCs pulsed with the model antigen, tetanus toxoid. At day 7, T cells were stimulated with the MHC class II-restricted tetanus toxoid epitope, TTp30. FIG. 4A shows that the production of IFN-gamma was significantly increased in the CD4+ T cells co-cultured with iCD40-DCs and iCD40-DCs stimulated with either MPL or MC. IFN-gamma production was iCD40-specific, as it was not induced by control virus Ad-GFP-transduced DCs or by MPL or MC stimulation alone (FIG. 4A and data not shown). In addition, T cell polarization was analyzed by assessing TH1/TH2 cytokine levels in the supernatants of T cells using a cytometric bead array (FIG. 4B). The levels of IFN-gamma, TNF-alpha, IL-4, and IL-5 secreted cytokines were increased in helper T cells stimulated by iCD40-DCs, indicating the expansion of both TH1 and TH2-polarized T cells. However, the levels of TH1 cytokines were significantly higher than TH2-associated cytokines, indicating a predominant expansion of TH1 cells. In contrast, induction of TT-specific CD4+ T-helper cells from naive CD4+CD45RA+ cells, using MC-matured DCs, led to only a modest bias in TT epitope-specific TH1 differentiation. These results suggest that iCD40 signaling in DCs enables them to effectively induce antigen-specific TH1 differentiation, possibly due to higher IL-12 production.

Example 5

MPL-Stimulated iCD40-DCs Induce Strong Tumor Antigen-Specific CTL Responses

It was determined whether iCD40 and MPL could enhance cytotoxic T lymphocyte (CTL) responses to poorly immunogenic melanoma self-antigen MAGE-3. iCD40-DCs from HLA-A2-positive donors were pulsed with class-1HLA-A2.1-restricted MAGE3-derived immunodominant peptide, FLWGPRALV (SEQ ID NO: 8), and co-cultured with autologous T cells. After a series of stimulations, the frequency of antigen-specific T cells was assessed by IFN-gamma-specific ELISPOT assay (FIG. 5A). iCD40-DCs stimulated with MPL led to a 50% increase in MAGE-3-specific T cells relative to iCD40-DCs stimulated with MC and about a five-fold increase in antigen-specific T cells compared to control non-transduced (WT) DCs.

It also was determined whether iCD40-DCs were capable of enhancing CTL-mediated killing of tumor cells in an antigen-specific fashion. Immature DCs from HLA-A2-positive volunteers were transfected with Ad-iCD40, pulsed with MAGE-3 protein, and used as stimulators to generate CTLs in vitro. SK-MEL-37 cells (HLA-A2+, MAGE-3+) and T2 cells pulsed with MAGE-3 A2.1 peptide (HLA-A2+, MAGE-3+) were utilized as targets. NA-6-MEL cells (HLA A2-, MAGE-3+) and T2 cells (HLA-A2+) pulsed with an irrelevant A2.1-restricted influenza matrix peptide served as negative controls. As shown in FIG. 5B, the CTLs induced by iCD40-DCs were capable of efficiently recognizing and lysing their cognate targets (SK-MEL-37, left top panel), and also T2 cells pulsed with MAGE-3 A2.1 peptide (lower left panel), indicating the presence of MAGE-3-specific CTLs. In contrast, control targets were lysed at significantly lower levels (right panels). Improved lytic activity was consistently observed when iCD40-DCs treated with MPL or MC were used as stimulators compared with non-transduced DCs treated with MPL or MC alone. In addition, a significant expansion of MAGE-3/HLA-A2-specific tetramer positive CD8+CTLs by iCD40-DCs that were treated with MPL (FIG. 5C) was observed.

Similarly, to test whether LPS and iCD40-stimulated DCs could enhance CTL lytic activity, their ability to break tolerance to prostate-specific membrane antigen (PSMA) was examined. DCs generated from healthy HLA-A2+ volunteers were pulsed with PSMA protein[36] or MAGE-3, transduced with AD-iCD40 or Ad-Luc, and were co-cultured with autologous T cells. After three rounds of stimulation, antigen-specific CTL activity was measured by chromium-release assay using LNCaP cells (HLA-A2+PSMA$^+$) as targets and SK-MeI-37 (HLA-A2+PSMA-) as control cells for PSMA-pulsed DCs (FIG. 6A). SK-MeI-37 cells (MAGE-3+) were used as targets when DCs of the same donor were pulsed with MAGE-3, and LNCaP cells (MAGE-3-) were used here as negative controls (FIG. 6B). Collectively, these data indicate that iCD40-transduced DCs are capable of inducing significantly more potent antigen-specific CTL responses in vitro than MC-treated DCs.

Example 6

Inducible CD40 Enhances CCR7 Expression and Migratory Abilities of DCs Without PGE$_2$ In addition to other maturation markers, CCR7 is up-regulated on DCs upon maturation and is responsible for directing their migration to draining lymph nodes[37]. Recently, several reports have indicated that, apart from chemotaxis, CCR7 also affects DC "cytoarchitecture", the rate of endocytosis, survival, migratory speed, and maturation[38]. Along with costimulatory molecules and TH1 cytokines, iCD40 specifically up-regulates CCR7 expression in human DCs (FIG. 7A). Moreover, CCR7 expression correlated with Ad-iCD40 viral dose-escalation (Supplementary FIG. 2).

Because CCR7 expression levels correlate with enhanced migration towards MIP-3 beta CCL19), it was determined whether human iCD40-DCs could migrate in vitro towards MIP-3 beta in transwell assays. FIG. 7B shows that iCD40-DCs treated with AP20187 dimerizer has migration levels comparable to those induced by MC. Moreover, iCD40-DC migration was further increased by MPL or MC stimulation, even when PGE$_2$ was not present. These data were highly reproducible and indicate that iCD40 is sufficient to induce CCR7 expression and DC migration in vitro in contrast to the widely held belief that PGE$_2$ is essential for lymph node homing of human DC.

Chemokines and chemokine receptors share a high degree of sequence identity within a species and between species[39]. On the basis of this knowledge, a novel xenograft model was developed for monitoring the migration of human DCs in vivo. Human DCs were transduced with iCD40 and matured with LPS or MC, and mouse DCs were matured with LPS. Since DCs were co-transduced with Ad5-CBR, bioluminescence was immediately visible (FIG. 7C and not shown). As expected, immature DCs did not migrate to the draining popliteal lymph nodes. However, iCD40-DCs matured with LPS or MC were detectable in the xenogeneic popliteal lymph nodes within 2 days post-inoculation (FIG. 7C). The migration of iCD40-DCs stimulated with LPS was significantly (p=0.036) higher than non-stimulated DCs and was comparable to mouse DC migration (FIG. 7D). Moreover, at day 2 the iCD40-DCs were detected in inguinal LNs while MC-stimulated DCs were undetectable, suggesting higher migratory abilities of iCD40-DCs than stimulated with MC. Collectively, these results indicate that iCD40 signaling in DCs plays a critical role in controlling CCR7 expression and is sufficient for DC migration to lymph nodes. The migration of iCD40-DCs is further enhanced when the cells are stimulated with LPS, correlating with enhanced CCR7 expression.

Example 7

Analysis of Results Presented in Example 2 to Example 6 and Documents Cited in Specification Through Example 7

Dendritic cell efficacy depends on many variables, especially maturation status and efficient migration to lymph nodes. Several clinical trials in cancer patients showed the potency of DCs to induce adaptive immunity to tumor-specific antigens[40,41,42]. However, clinical responses were transient, and warrant further improvement in DC vaccine design[43,44]. Limitation of current DC-based vaccines are the transient activation state within lymphoid tissues, low induction of CD4+ T cell immunity, and impaired ability to migrate to the draining lymph nodes[45]. Less than 24 hours following exposure to LPS, DCs terminate synthesis of the TH1-polarizing cytokine, IL-12, and become refractory to further stimuli[46], limiting their ability to activate T helper cells and CTLs. Other studies indicate that less than 5% of intradermally administered mature DCs reach the lymph nodes, showing inefficient homing[39]. These findings underscore the need for either prolonging the activation state and migratory capacities of the DCs and/or temporally coordinating the DC activation "window" with engagement of cognate T cells within lymph nodes.

A method for promoting mouse DC function in vivo was developed by manipulation of a chimeric inducible CD40 receptor[13]. It has been observed that the inducible CD40 approach is also effective in enhancing the immunostimulatory function of human DCs. Consistent with previous reports of the synergistic activity of combining TLR and CD40 signaling for IL-12p70 secretion, iCD40 plus TLR4 signaling induced high level IL-12 secretion, DC maturation, T cell stimulatory functions, and extensive migratory capacities[29,47].

It was also demonstrated that increased and prolonged secretion of IL-12p70 in DCs could break self tolerance, which likely is attributable in part to over-riding the production of SOCS1, which inhibits IL-12 signaling[34]. It has been determined that although endogenous CD40 signaling stimulated by soluble CD40L leads to SOCS1 upregulation, iCD40 activates DCs without significant SOCS1 induction. Additionally, iCD40 signaling unleashes high and prolonged expression of IL-12p70 in DCs, which exhibit enhanced potency in stimulating CD4+ T cells and CTLs.

IL-6 is implicated in the survival of many different cell types by activation of anti-apoptotic pathways, such as p38 MAPK, ERK1, 2 47 and PI3-kinase[48]. The induction of IL-6 expression by iCD40 and TLR-4 signalings in DCs also was identified. This finding could partly explain the prolonged survival of DCs described previously[3]. Furthermore, IL-6 expression is critical in the ability of DCs to inhibit the generation of CD4+CD25+T regulatory cells[35]. In this context, an iCD40-DCs-based vaccine could potentially suppress negative regulators in vivo, inhibiting peripheral tolerance to targeting antigens.

One major focus of cancer immunotherapy has been the design of vaccines to promote strong tumor antigen-specific CTL responses in cancer patients3. However, accumulating evidence suggests that CD4+ T cells also play a critical role in antitumor immunity, as they contribute to the induction, persistence and expansion of CD8+ T cells[49]. Our study showed that iCD40-DCs could effectively prime naïve T cells and effectively expand antigen-specific cells representing both arms of the immune response (i.e. MAGE-3 and PSMA specific CTLs and TT-specific CD4+ T cells). It was demonstrated that TH1 (IFN-gamma and TNF-alpha) cytokines were produced predominantly in the milieu of iCD40-DC-stimulated CD4+ T cells, indicating expansion of TH1 cells. As expected, these cytokines were not detected when T cells were stimulated with MC-treated DCs, because $PGE_2$ (a key MC component) is a powerful suppressor of TH1 responses[50,51,52].

Recent mouse studies have shown that DC migration directly correlates with T cell proliferation[53]. Therefore, the increase in migration should enhance efficacy of DC-based vaccines[45]. Current DC vaccine protocols include pre-conditioning the vaccine injection site with inflammatory cytokines or ex vivo stimulation of DCs with TLR ligands and pro-inflammatory cytokines, consisting primarily of MC constituents53,54. Despite its numerous immunosuppressive functions[8-12], $PGE_2$ has been used for the past few years as an indispensible component of the DC maturation cocktail because it stimulates the migratory capacity of DCs by up-regulating CCR7 and sensitization to its ligands. Alternative approaches enhancing DCs migration without $PGE_2$, should be beneficial for DC-based vaccine improvement.

The results of our study show that iCD40 signaling not only up-regulates CCR7 expression on DCs but also stimulates their chemotaxis to CCL19 in vitro. Additionally, immature DCs transduced with iCD40 were able to migrate as efficiently as MC-stimulated DCs both in vitro and in vivo. Moreover, migration of iCD40-DCs was further induced when cells were stimulated with TLR-4 ligands. It was recently shown that stimulation of CCR7 increases the migratory rate of DCs, indicating that this receptor can regulate DC locomotion and motility[55-57]. It has been shown that stimulation of CCR7 enhances the mature phenotype of DCs58. Thus, by transduction of DCs with iCD40, CCR7 expression, DC migration and maturation status have been enhanced, obviating the need for $PGE_2$. Further studies are underway to identify the specific mechanisms of iCD40 on DC migration.

Finally, iCD40 stimulation of DCs was capable of inducing a potent cytotoxic T cell response to the prostate-specific antigen, PSMA, which was capable of significantly increased killing of target LNCaP cells. Based on these observations, a clinical vaccine trial is planned using iCD40-transduced, PSMA protein-loaded DCs, in combination with AP20187, in patients with advanced, hormone refractory prostate cancer. Ultimately, by expanding antigen-specific T cells, the DC-based vaccine approach could compliment recently described techniques that are based on the expansion of tumor-derived T cells or the genetic modification of polyclonal endogenous T cells to antigen-specificity[59,60].

DOCUMENTS CITED

1. Banchereau J, Paczesny S, Blanco P, et al. Dendritic cells: controllers of the immune system and a new promise for immunotherapy. Ann N Y Acad. Sci. 2003; 987:180-187.
2. O'Neill D W, Adams S, Bhardwaj N. Manipulating dendritic cell biology for the active immunotherapy of cancer. Blood. 2004; 104:2235-2246.
3. Rosenberg S A. A new era for cancer immunotherapy based on the genes that encode cancer antigens. Immunity. 1999; 10:281-287.
4. Steinman R M, Hawiger D, Nussenzweig M C. Tolerogenic dendritic cells. Annu Rev Immunol. 2003; 21:685-711.
5. Vieweg J, Jackson A. Modulation of antitumor responses by dendritic cells. Springer Semin Immunopathol. 2005; 26:329-341.
6. Scandella E, Men Y, Gillessen S, Forster R, Groettrup M. Prostaglandin E2 is a key factor for CCR7 surface expression and migration of monocyte-derived dendritic cells. Blood. 2002; 100:1354-1361.
7. Luft T, Jefford M, Luetjens P, et al. Functionally distinct dendritic cell (DC) populations induced by physiologic stimuli: prostaglandin E(2) regulates the migratory capacity of specific DC subsets. Blood. 2002; 100:1362-1372.
8. Goodwin J S, Bankhurst A D, Messner R P. Suppression of human T-cell mitogenesis by prostaglandin. Existence of a prostaglandin-producing suppressor cell. J Exp Med. 1977; 146:1719-1734.
9. Goodwin J S. Immunomodulation by eicosanoids and anti-inflammatory drugs. Curr Opin Immunol. 1989; 2:264-268.
10. Kalinski P, Vieira P L, Schuitemaker J H, de Jong E C, Kapsenberg M L. Prostaglandin E(2) is a selective inducer of interleukin-12 p40 (IL-12p40) production and an inhibitor of bioactive IL-12p70 heterodimer. Blood. 2001; 97:3466-3469.
11. van der Pouw Kraan T C, Boeije L C, Smeenk R J, Wijdenes J, Aarden L A. Prostaglandin-E2 is a potent inhibitor of human interleukin 12 production. J Exp Med. 1995; 181:775-779.
12. Snyder D S, Beller D I, Unanue E R. Prostaglandins modulate macrophage Ia expression. Nature. 1982; 299:163-165.
13. Hanks B A, Jiang J, Singh R A, et al. Re-engineered CD40 receptor enables potent pharmacological activation of dendritic-cell cancer vaccines in vivo. Nat. Med. 2005; 11:130-137.
14. Spencer D M, Wandless T J, Schreiber S L, Crabtree G R. Controlling signal transduction with synthetic ligands. Science. 1993; 262:1019-1024.
15. Kadowaki N, Ho S, Antonenko S, et al. Subsets of human dendritic cell precursors express different toll-like receptors and respond to different microbial antigens. J Exp Med. 2001; 194:863-869.
16. Re F, Strominger J L. Toll-like receptor 2 (TLR2) and TLR4 differentially activate human dendritic cells. J Biol. Chem. 2001; 276:37692-37699.
17. Ardeshna K M, Pizzey A R, Devereux S, Khwaja A. The PI3 kinase, p38 SAP kinase, and NF-kappaB signal transduction pathways are involved in the survival and maturation of lipopolysaccharide-stimulated human monocyte-derived dendritic cells. Blood. 2000; 96:1039-1046.
18. Ismaili J, Rennesson J, Aksoy E, et al. Monophosphoryl lipid A activates both human dendritic cells and T cells. J. Immunol. 2002; 168:926-932.
19. Rescigno M, Martino M, Sutherland C L, Gold M R, Ricciardi-Castagnoli P. Dendritic cell survival and maturation are regulated by different signaling pathways. J Exp Med. 1998; 188:2175-2180.
20. Lapointe R, Toso J F, Butts C, Young H A, Hwu P. Human dendritic cells require multiple activation signals for the efficient generation of tumor antigen-specific T lymphocytes. Eur J. Immunol. 2000; 30:3291-3298.
21. Livak K J, Schmittgen T D. Analysis of relative gene expression data using real-time quantitative PCR and the 2(-Delta Delta C(T)) Method. Methods. 2001; 25:402-408.
22. Clackson T, Yang W, Rozamus L W, et al. Redesigning an FKBP-ligand interface to generate chemical dimerizers with novel specificity. Proc Natl Acad Sci USA. 1998; 95:10437-10442.
23. Banchereau J, Steinman R M. Dendritic cells and the control of immunity. Nature. 1998; 392:245-252.
24. Cisco R M, Abdel-Wahab Z, Dannull J, et al. Induction of human dendritic cell maturation using transfection with RNA encoding a dominant positive toll-like receptor 4. J. Immunol. 2004; 172:7162-7168.
25. De Becker G, Moulin V, Pajak B, et al. The adjuvant monophosphoryl lipid A increases the function of antigen-presenting cells. Int Immunol. 2000; 12:807-815.
26. Granucci F, Ferrero E, Foti M, Aggujaro D, Vettoretto K, Ricciardi-Castagnoli P. Early events in dendritic cell maturation induced by LPS. Microbes Infect. 1999; 1:1079-1084.
27. Megiovanni A M, Sanchez F, Gluckman J C, Rosenzwajg M. Double-stranded RNA stimulation or CD40 ligation of monocyte-derived dendritic cells as models to study their activation and maturation process. Eur Cytokine Netw. 2004; 15:126-134.
28. Puccetti P, Belladonna M L, Grohmann U. Effects of IL-12 and IL-23 on antigen-presenting cells at the interface between innate and adaptive immunity. Crit. Rev Immunol. 2002; 22:373-390.
29. Lee A W, Truong T, Bickham K, et al. A clinical grade cocktail of cytokines and $PGE_2$ results in uniform maturation of human monocyte-derived dendritic cells: implications for immunotherapy. Vaccine. 2002; 20 Suppl 4:A8-A22.
30. Liu J, Cao S, Herman L M, Ma X. Differential regulation of interleukin (IL)-12 p35 and p40 gene expression and interferon (IFN)-gamma-primed IL-12 production by IFN regulatory factor 1. J Exp Med. 2003; 198:1265-1276.
31. Contin C, Pitard V, Itai T, Nagata S, Moreau J F, Dechanet-Merville J. Membrane-anchored CD40 is processed by the tumor necrosis factor-alpha-converting enzyme. Implications for CD40 signaling. J Biol. Chem. 2003; 278:32801-32809.
32. Tone M, Tone Y, Fairchild P J, Wykes M, Waldmann H. Regulation of CD40 function by its isoforms generated through alternative splicing. Proc Natl Acad Sci USA. 2001; 98:1751-1756.
33. Wesemann D R, Dong Y, O'Keefe G M, Nguyen V T, Benveniste E N. Suppressor of cytokine signaling 1 inhibits cytokine induction of CD40 expression in macrophages. J. Immunol. 2002; 169:2354-2360.
34. Evel-Kabler K, Song X T, Aldrich M, Huang X F, Chen S Y. SOCS1 restricts dendritic cells' ability to break self tolerance and induce antitumor immunity by regulating IL-12 production and signaling. J Clin Invest. 2006; 116:90-100.
35. Pasare C, Medzhitov R. Toll pathway-dependent blockade of CD4+CD25+ T cell-mediated suppression by dendritic cells. Science. 2003; 299:1033-1036.
36. Davis M I, Bennett M J, Thomas L M, Bjorkman P J. Crystal structure of prostate-specific membrane antigen, a tumor marker and peptidase. Proc Natl Acad Sci USA. 2005; 102:5981-5986.
37. Cyster J G. Chemokines and cell migration in secondary lymphoid organs. Science. 1999; 286:2098-2102.
38. Sanchez-Sanchez N, Riol-Blanco L, Rodriguez-Fernandez J L. The Multiple Personalities of the Chemokine Receptor CCR7 in Dendritic Cells. J. Immunol. 2006; 176: 5153-5159.
39. De Vries I J, Krooshoop D J, Scharenborg N M, et al. Effective migration of antigen-pulsed dendritic cells to lymph nodes in melanoma patients is determined by their maturation state. Cancer Res. 2003; 63:12-17.
40. Nestle F O, Banchereau J, Hart D. Dendritic cells: On the move from bench to bedside. Nat. Med. 2001; 7:761-765.
41. Schuler G, Schuler-Thurner B, Steinman R M. The use of dendritic cells in cancer immunotherapy. Curr Opin Immunol. 2003; 15:138-147.
42. Cranmer L D, Trevor K T, Hersh E M. Clinical applications of dendritic cell vaccination in the treatment of cancer. Cancer Immunol Immunother. 2004; 53:275-306.
43. Ridgway D. The first 1000 dendritic cell vaccinees. Cancer Invest. 2003; 21:873-886.
44. Dallal R M, Lotze M T. The dendritic cell and human cancer vaccines. Cuff Opin Immunol. 2000; 12:583-588.
45. Adema G J, de Vries I J, Punt C J, Figdor C G. Migration of dendritic cell based cancer vaccines: in vivo veritas? Cuff Opin Immunol. 2005; 17:170-174.
46. Langenkamp A, Messi M, Lanzavecchia A, Sallusto F. Kinetics of dendritic cell activation: impact on priming of TH1, TH2 and nonpolarized T cells. Nat. Immunol. 2000; 1:311-316.
47. Napolitani G, Rinaldi A, Bertoni F, Sallusto F, Lanzavecchia A. Selected Toll-like receptor agonist combinations synergistically trigger a T helper type 1-polarizing program in dendritic cells. Nat. Immunol. 2005; 6:769-776.
48. Bisping G, Kropff M, Wenning D, et al. Targeting receptor kinases by a novel indolinone derivative in multiple myeloma: abrogation of stroma-derived interleukin-6 secretion and induction of apoptosis in cytogenetically defined subgroups. Blood. 2006; 107:2079-2089.
49. Kalams S A, Walker B D. The critical need for CD4 help in maintaining effective cytotoxic T lymphocyte responses. J Exp Med. 1998; 188:2199-2204.
50. Kalinski P, Hilkens C M, Snijders A, Snijdewint F G, Kapsenberg M L. Dendritic cells, obtained from peripheral blood precursors in the presence of $PGE_2$, promote Th2 responses. Adv Exp Med. Biol. 1997; 417:363-367.
51. Mcllroy A, Caron G, Blanchard S, et al. Histamine and prostaglandin E up-regulate the production of Th2-attracting chemokines (CCL17 and CCL22) and down-regulate IFN-gamma-induced CXCL10 production by immature human dendritic cells. Immunology. 2006; 117:507-516.
52. Meyer F, Ramanujam K S, Gobert A P, James S P, Wilson K T. Cutting edge: cyclooxygenase-2 activation suppresses Th1 polarization in response to *Helicobacter pylori*. J Immunol. 2003; 171:3913-3917.
53. Martln-Fontecha A, Sebastiani S, Hopken U E, et al. Regulation of dendritic cell migration to the draining lymph node: impact on T lymphocyte traffic and priming. J Exp Med. 2003; 198:615-621.
54. Prins R M, Craft N, Bruhn K W, et al. The TLR-7 agonist, imiquimod, enhances dendritic cell survival and promotes tumor antigen-specific T cell priming: relation to central nervous system antitumor immunity. J. Immunol. 2006; 176:157-164.
55. Riol-Blanco L, Sanchez-Sanchez N, Torres A, et al. The chemokine receptor CCR7 activates in dendritic cells two signaling modules that independently regulate chemotaxis and migratory speed. J. Immunol. 2005; 174:4070-4080.
56. Palecek S P, Loftus J C, Ginsberg M H, Lauffenburger D A, Horwitz A F. Integrin-ligand binding properties govern 57. Yanagawa Y, Onoe K. CCL19 induces rapid dendritic extension of murine dendritic cells. Blood. 2002; 100: 1948-1956.
58. Marsland B J, Battig P, Bauer M, et al. CCL19 and CCL21 induce a potent proinflammatory differentiation program in licensed dendritic cells. Immunity. 2005; 22:493-505.
59. Dudley M E, Wunderlich J R, Yang J C, et al. Adoptive cell transfer therapy following non-myeloablative but lymphodepleting chemotherapy for the treatment of patients with refractory metastatic melanoma. J Clin Oncol. 2005; 23:2346-2357.
60. Morgan R A, Dudley M E, Wunderlich J R, et al. Cancer Regression in Patients After Transfer of Genetically Engineered Lymphocytes. Science. 2006.

Other documents cited herein are referenced in U.S. patent application Ser. No. 10/781,384, filed Feb. 18, 2004, entitled "Induced Activation In Dendritic Cells," and naming Spencer et al. as inventors.

Example 8

Inducible Pattern Recognition Receptors

The innate immune system uses several families of pattern recognition receptors PRRs to sense pathological infection or injury. One family of PRRs is the Toll-like receptors (TLRs) that now include about 11 members in mammals. These typically bind to multi-valent ligands through a leucine-rich motif (LRM). The ligands can come from bacteria, viruses, fungi, or host cells and can bind to TLRs either on the cell surface or within endocytic vesicles (especially TLR 3, 7, 8 and 9). Within their cytoplasmic signaling domains, they share a conserved TIR (Toll/IL-1R) domain that binds to downstream TIR-containing adapter molecules, such as MyD88 and TRIF/TICAM-1, and adapters TIRAM/TICAM-2 and MAL/TIRAP. Additional PRRs include the NOD-like receptors (e.g. NOD1 and NOD2) and the RIG-like helicases, RIG-I and Mda-5. Many PRRs bind to ligands through flexible LRMs and couple to downstream signaling molecules through protein-protein binding motifs, such as TIR or CARD (caspase recruitment domain) domains.

Stimulation through TLR-4 in conjunction with signaling through the costimulatory molecule CD40 can promote high-level maturation and migratory properties in human monocyte-derived dendritic cells (MoDCs). Based on both published and unpublished data[2-7], this prolonged and enhanced activation state of human MoDCs in vitro and/or in vivo may both promote the activation and expansion of autologous tumor-specific T cells for adoptive immunotherapy and overcome the problems of self-limiting ex vivo-matured DCs for vaccination.

Currently, there is a limited array of TLR agonists available in clinical studies. So far, the only clinically approved TLR-4 ligand is monophosphoryl lipid A (MPL). To develop a simplified, unified vector for optimal MoDC activation in vitro and in vivo in the absence of added TLR or costimulatory ligands, a chemical inducer of dimerization (CID)-inducible TLRs (iTLRs) fused to costimulatory receptors, such as CD40, may be developed. Thus, rather than modifying MoDCs with several activation reagents, a unified chimeric receptor may be developed containing all components necessary for potent, inducible activation of MoDCs in vitro and in vivo within the context of an immunological synapse. Toward this goal, several iTLRs representing multiple TLR subfamilies are developed and their efficacy alone and when fused to iCD40 compared. Second, the most potent iCD40-TLR is compared with previously identified most potent methods for enhancing DC activation. Lastly synergistic effects are appraised in a spectrum of in vitro assays on human DCs.

Development of Synthetic Drug-Inducible Toll-Like Receptors and Composite Costimulatory Receptors within a Single Vector for Unified Broadly Applicable Immunotherapy.

To replace complex, poorly understood MoDC maturation cocktails or combinations of adjuvants and CD40 signaling, CID-inducible versions of toll-like receptor 4 (called iTLR4) and other iTLRs (i.e. TLR3, 7, 8, and 9) are developed and iTLRs are assayed for synergy with iCD40 either in trans or in cis within the same polypeptide chain. Efficacy is based on induction of transcription factors NF-kB and IRF3/7s, and phosphorylation of p38 and INK in the DC line, 2DSC/1. The most potent inducible receptor is subcloned into an adenovector for efficient transduction of MoDCs.

Comparison of Optimum iTLR-CD40 with Previously Developed Approaches (i.e. iCD40, $Myr_F$-ΔAkt, SOCS-1 shRNA) to Enhance MoDC Activation, Survival, and Function In Vitro and In Vivo.

The murine DC-vaccine models are extended to a preclinical human model for optimizing DC maturation and activation. Following MoDC modification with the recently developed "humanized" vectors, DC maturation (e.g. upregulated CD83, CCR7), and survival is compared in the absence of growth factors (i.e. GM-CSF), chemotactic response to CCL19/21 in a 2-chamber assay and in vivo in non-myoablatively irradiated scid mice using optical imaging. In addition to determining the capacity of enhanced DCs (eDCs) to trigger Th1 polarization (determined via multiplex cytokine assays (e.g. IL-4, IFN-gamma, IL-12, IL-23), and delta-4 mRNA), the activation of autologous T cells in healthy donors by various eDCs presenting two distinct cocktails of HLA-A2-restricted antigens, one strong and one weak is compared. Finally, SOCS-1 depletion is assayed for synergy with iTLR-CD40, iCD40 or $Myr_F$-ΔAkt signaling to produce a further optimized eDC. If synergy is found, a bicistronic adenovector containing both genetic elements will be developed and characterized. These 2 aims should lead to development of an extremely potent DC vaccine platform.

Significance

Dendritic cells Dendritic cells (DCs) play a critical role in initiating and regulating adaptive immunity[7,8]. Upon detection of "danger signals", DCs physiologically adapt to their microenvironment by undergoing a genetic maturation program[6]. Using a broad repertoire of antigen presentation and costimulatory molecules, DCs are capable of potently activating naïve antigen-specific T lymphocytes and regulating their subsequent phenotype and function[9]. In most cases, the development of robust cytotoxic T lymphocyte (CTL) immunity by DCs requires a "helper" signal from CD4+ T cells[10]. This signal is comprised of both soluble cytokines, such as IL-2, as well as CD40L-mediated stimulation of the surface CD40 receptor on the DC[11-13]. A member of the tumor necrosis factor receptor (TNFR) superfamily, CD40 triggers various pathways within the DC resulting in the upregulation of several antigen presentation, costimulatory, cytokine, and pro-survival genes, which collectively enable the DC to induce CTL activation[14,15].

Use of DCs in Immunotherapy

Given the pre-eminent role of DCs as antigen-presenting cells (APCs), their exploitation as natural adjuvants in vaccination protocols for the treatment of various malignancies is not surprising[16,17]. Typical applications include harvesting peripheral blood monocytes via leukapheresis, differentiation in culture in GM-CSF and IL-4, and loading immature monocyte (or CD34+ precursor cell)-derived DCs (MoDC) with tumor antigens by one of several methods, such as pulsing immature DCs with unfractionated tumor lysates, MHC-eluted peptides, tumor-derived heat shock proteins (HSPs), tumor associated antigens (TAAs (peptides or proteins)), or transfecting DCs with bulk tumor mRNA, or mRNA coding for TAAs (reviewed in 18,19). Antigen-loaded DCs are then typically matured ex vivo with inflammatory cytokines (e.g. TNFalpha, IL1beta, IL6, and PGE$_2$) or other adjuvants (e.g. LPS, CpG oligonucleotides) and injected into patients. In each case, the immuno-stimulatory properties of the DCs depend on many variables, especially the ability to migrate to lymph nodes and full maturation status. However, the limited success in recent clinical trials with DC immunotherapy has suggested that current protocols need to be refined if DC-based immunotherapy is to be included in the treatment arsenal alongside more conventional modalities of anti-cancer therapy[20,21].

Two key limitations of DC-based vaccines are the short lifespan of matured DCs and their transient activation state within lymphoid tissues. Less than 24 hours following exposure to lipopolysaccharide (LPS), DCs terminate synthesis of the $T_H1$-polarizing cytokine, IL-12, and become refractory to further stimuli[22], limiting their ability to activate cytotoxic T lymphocytes (CTLs). Other studies indicate that the survival of antigen-pulsed DCs within the draining lymph node (LN) is limited to only 48 hours following their delivery, due primarily to elimination by antigen-specific CTLs[23]. These findings underscore the need for improved methods of either prolonging the activation state and life span of the DCs and/or temporally coordinating the DC activation "window" with engagement of cognate T cells within LNs. Thus, enhancing the activation and survival of DCs may be critical to promoting immunity against tumors.

DC Survival

DC survival is regulated, at least partly, by pathogen-derived molecules acting through one or more conserved Toll-like receptors (TLRs) and T cell-expressed costimulatory molecules (e.g. CD40L and TRANCE), which are partly dependent on Bcl-2 and Bcl-x$_L$ for anti-apoptotic activity[3,24-27]. Although the importance of TLR-, CD40-, or Bcl-2-mediated DC longevity has been well documented, homeostatic feedback mechanisms are also likely to limit the utility of TLR-ligands or Bcl-2 family members to extend DC longevity in tumor vaccine protocols. These include receptor desensitization or downregulation[4,28,29], expression of negative regulators for TLR/IL-1Rs, like IRAK-M[30] and SOCS-1[5], and induction of pro-apoptotic molecules, like Bim[31], resulting in the neutralization of anti-apoptotic molecules by TLR signals.

Role of Akt in DC survival Akt/PKB family proteins, major downstream effectors of PI3 Kinases (PI3K), have been reported as critical components in the regulation of various biological processes, including growth, survival, transformation, and others (reviewed in 32). In DCs, it has been shown that inhibition of PI3K antagonizes LPS, TRANCE, CD40 or PGE$_2$-mediated dendritic cell survival[33,34]. In addition, recent studies reveal that some tumors escape from immune surveillance by the induction of inhibitory molecules, such as ceramide and TGF-beta, resulting in DC apoptosis through the suppression of Akt, NF-kappaB, and Bcl-X$_L$[35,36]. Taken together, these studies suggest that the PI3K/Akt pathway plays an important role in maintaining DC survival; however, the detailed molecular mechanisms have not been fully addressed.

Role of CD40 in DC Survival and Activation

Another particularly attractive target for manipulation is the TNF family receptor, CD40. Unlike pro-inflammatory cytokines or pathogen-associated molecules that DCs encounter throughout the periphery, the DC-expressed CD40 receptor is engaged by CD4+ T helper cells within the LN paracortex via its cognate ligand, CD40L[12,13,37]. Recent studies have further shown that CD40 stimulation enables DCs to "cross-present" antigen[38] and overcome peripheral T cell tolerance[39], prompting therapeutic studies based on CD40 stimulation. Strategies included systemic delivery of CD40-specific monoclonal antibodies (mAbs) or of trimerized CD40L[40], the utilization of CD40-stimulated, antigen-loaded DC-based vaccines[41], and administration of genetically modified CD40 ligand (CD40L)-expressing DCs[42]. Despite great potential, several properties of CD40 limit its therapeutic development, including ubiquitous expression of CD40 by a variety of other cell types, including B cells, macrophages, and endothelial cells[14], increasing the likelihood for side effects due to systemic administration of CD40 stimuli. Moreover, several mechanisms regulate the surface expression of CD40 by targeting its extracellular domain, including CD40L-induced cleavage by matrix metalloproteinase enzymes[29], negative feedback degradation by an alternatively spliced CD40 isoform[28], and CD40L-mediated endocytosis of CD40.

Therefore, novel DC activation system was developed based on the CD40 signaling pathway to extend the pro-stimulatory state of DCs within lymphoid tissues by providing DC-targeted functionality, temporal control, and resistance to CD40 regulatory mechanisms. This engineered recombinant receptor was comprised of the cytoplasmic domain of CD40 fused to ligand binding domains and a membrane-targeting sequence (FIG. 10). Administration of a lipid-permeable, dimerizing drug intraperitoneally led to the potent induction of CD40-dependent signaling cascades and greatly improved immunogenicity against both defined antigens and tumors in vivo relative to other activation modalities[4]. Hence the chimeric CD40 was named inducible CD40 (iCD40). The high utility of iCD40-activated DCs in mice, suggested that methods to stabilize endogenous CD40 signaling might also enhance the potency of DC vaccines.

Role of TLRs in DC Survival and Activation

TLRs binds to a variety of viral and bacterial-derived molecules, which trigger activation of target cells, such as T cells, macrophages and dendritic cells. Although the majority of the 10 or so mammalian TLRs utilize a signaling pathway initiated by the adapter protein, MyD88, leading to NF-kappaB activation, TLR3 relies instead on the adapter TRIF, leading to IRF3 and Type I interferon induction. Together, these signaling pathways can synergize to produce high levels of the Th1 cytokine, IL-12[43]. Interestingly, TLR-4 can utilize both pathways following binding of the potent mitogen, LPS, or derivatives. Stimulation through TLR-4 in conjunction with signaling through the costimulatory molecule CD40 can promote high-level maturation and migratory properties in human MoDCs (preliminary data). Currently, there is a limited array of TLR agonists available in clinical studies. So far, the only clinically approved TLR-4 ligand is monophosphoryl lipid A (MPL).

Like many cell-surface receptors that make a single pass through the plasma membrane, TLRs are likely to all be activated by homo or heterodimerization or oligomerization. Over the past few years there have been several citations showing homodimerization-mediated activation of TLR-4 and heterodimerization-mediated activation of TLR2 with TLR1 and TLR6[44-48]. Moreover, in a recent article, Ian Wilson and colleagues crystallized TLR-3 and identified dimerization regions within the extracellular domain, suggesting that it signals as a homodimer followed dsRNA binding[49]. Therefore, it is extremely likely that chemically induced dimerization of TLRs, especially TLR-4, will lead to their induction.

Considerations for the Development of Ex Vivo-Matured, Monocyte-Derived "Enhanced" Human DCs.

Our recent published and unpublished (see Preliminary Data) studies have suggested two potent methods to enhance DC function in vivo, ectopic expression of an optimized, constitutive Akt (Myr$_F$-ΔAkt) and manipulation of a chimeric inducible CD40 in vivo. Complementing this work, Si-Yi Chen (Baylor College of Medicine, Houston, Tex.) has shown that lowering SOCS-1 levels in DCs can also enhance efficacy[5]. With the addition of inducible TLRs, there would be at least 4 potent methods to activate DCs in vivo. Significant supporting data in mice for iCD40, Myr$_F$-ΔAkt, and SOCS-1 approaches, and human MoDCs are not identical to murine bone marrow-derived DCs. In particular, the most commonly used human DC vaccine protocol involves differentiation of MoDCs from monocytes, prior to treatment with the "gold standard" pro-inflammatory maturation cocktail, containing TNF-alpha, IL-1-beta, IL-6, and PGE$_2$. Although PGE$_2$ is considered necessary to upregulate CCR7 and gain chemotactic responsiveness to lymph node-derived chemokines, CCL19 and CCL21[50,51], PGE$_2$ can also impair DC signaling by suppressing bioactive IL12p70 production[52]. While it is unlikely that IL12 suppression is permanent in vivo, given the slowly building success rate of DC vaccines', it will be important to determine prior to clinical applications which of the methods outlined above can best overcome PGE$_2$-mediated IL12 suppression in human MoDCs without interfering with migratory capacity.

Although clinical success in DC-based vaccines has been modest[7,20], extremely low side effects and potentially exquisite specificity and sensitivity make this modality attractive. Multiple, potentially complementary approaches to enhance maturation, activity and survival of antigen-expressing DCs in vivo have been developed. Because interaction with antigen-specific T cells is likely to be prolonged, these enhanced DCs are likely to improve the clinical outcome of DC vaccines. The development of enhanced antigen-expressing DCs not only has potential applicability to treating malignancy, but also should be applicable to the treatment of numerous pathogens, as well. Moreover, this high impact approach should complement prior efforts by numerous labs, which have identified tumor antigens.

Preliminary Studies

The validation for the approach described herein for enhancing DC function has been recently described[4,5]. Preliminary data for the effects of iCD40, MyrF-ΔAkt, and siRNA SOCS-1 follow along with data on the development of iTLRs.

Characterization of iCD40 Functionality in Primary DCs and Development of an iCD40-Expressing DC-Based Prostate Cancer Vaccine.

After demonstrating functionality of iCD40 in murine D2SC/1 cells ([4] and not shown), which possess many characteristics of freshly isolated DCs, iCD40 functionality in primary bone marrow-derived DCs (BMDCs) by utilizing an iCD40-expressing adenovirus was examined. A helper-dependent, AE1, AE3-type 5 adenoviral vector, named Ad-iCD40-GFP, was engineered to express both iCD40 and EGFP under the control of the CMV early/immediate promoter/enhancer. Ad-iCD40-GFP successfully transduced and expressed the iCD40 transgene, as well as the EGFP marker, in purified BMDCs (FIG. 11A,B). Titrating Ad-iCD40-GFP while measuring iCD40-induced upregulation of B7.2 (CD86) showed that maximum drug-mediated iCD40 activation occurred at around 100 moi and proceeded asymptotically to plateau at higher viral titers (data not shown). Although the effects were modest, AP20187 induced the surface expression of MHC class I K$^b$, B7.2, as well as endogenous CD40 on iCD40-expressing BMDCs at 100 moi but not on non-transduced DCs (FIG. 11C and not shown). The effects of Ad-iCD40-GFP on BMDCs using intracellular cytokine staining to evaluate DC expression of the T$_H$1-polarizing cytokine, IL-12 was then investigated. These findings confirmed numerous previous reports that an empty adenoviral vector can contribute to background fluorescence readings by stimulating the production of low levels of this cytokine. (FIG. 11D)[53]. These experiments also revealed that the iCD40 transgene could generate a significant level of basal signaling at these titers even in the absence of CID. However, AP20187 exposure of these iCD40-expressing DCs managed to reproducibly overcome these cumulative effects to further increase the percentage of IL-12' DCs. Interestingly, the stimulation of IL-12p70/p40 synthesis with LPS and CD40L peaked at 8 hrs and decreased thereafter, while the percentage of IL-12' DCs continued to increase until at least 24 hrs following Ad-iCD40-GFP transduction. Previous work by Langenkamp et al. has demonstrated that prolonged treatment of DCs with LPS exhausts their capacity for cytokine production[54]. These results imply that the Ad-iCD40-GFP vector, as opposed to the LPS danger signal, is capable of promoting and maintaining a more durable IL-12 response by BMDCs.

In addition to DC activation state, DC longevity is another critical variable that influences the generation of T cell-dependent immunity. In fact, CTL-mediated killing of DCs is considered to be a significant mechanism for modulating immune responses while protecting the host from autoimmune pathologies[55,56]. Other work has established that CD40 stimulation of DCs prolongs their survival by a variety of mechanisms, including upregulation of the anti-apoptotic protein bcl-X$_L$ and the granzyme B inhibitor, Spi-6[57,58]. The effects of iCD40 relative to CD40L on DC survival were compared in an in vitro serum-starvation culture assay (FIG. 11E). By analyzing the vital dye (propidium iodide (PI))-positive cell population by flow cytometry, iCD40 expressing-BMDCs were found to exhibit greater longevity under these conditions relative to non-transduced DCs treated with CD40L. This effect was iCD40-dependent since Ad-GFP-transduced DCs failed to reflect improved survival under these conditions. This work also showed that exposure of iCD40 BMDCs to the AP20187 dimerizer drug even further enhanced this survival effect relative to untreated BMDCs. Moreover, when Ad-iCD40 transduced DCs were CFSE-stained and injected into footpads, significantly increased numbers of DCs were found in popliteal lymph nodes following i.p. injections of AP20187 versus in vitro stimulated iCD40 DCs or LPS/CD40L-treated DCs (FIG. 11F).

Despite well-known Ad-dependent maturation signals and basal signaling effects of iCD40 in primary BMDCs, enhanced DC activation was detected in the presence of AP20187. Overall, this data suggests that an inducible CD40 receptor designed to respond to a pharmacological agent is capable of maintaining primary DCs in a sustained state of activation compared to the more transient effects of CD40L stimulation and the potentially more complex effects of anti-CD40 antibodies. This data is consistent with earlier findings describing only short-term DC modulation for stimuli that target endogenous CD40.

The iCD40 Activation Switch Functions as a Potent Adjuvant for Anti-Tumor DNA Vaccines.

Previous studies have demonstrated that DCs play a critical role in the processing and presentation of DNA vaccines to responding T cells[59]. The in vivo anti-tumor efficacy of iCD40 DC-based vaccines as well as the in situ role of iCD40-expressing DCs in tumor immuno-surveillance was then studied. To establish a therapeutic tumor model, C57BL/6 mice were inoculated s.c. with the EG.7-OVA thymoma tumor line and allowed to progress until tumor volumes reached approximately 0.5 cm$^3$. These tumor-bearing mice were vaccinated with either SIINFEKL-pulsed (SEQ ID NO: 6) wt or iCD40 BMDCs. Vaccination with wt BMDCs, either untreated or stimulated in culture with LPS and CD40L or in vivo with anti-CD40 mAb, failed to slow the overall tumor growth rate (FIG. 12a). However, in vivo drug-mediated iCD40 activation of BMDC vaccines resulted in sustained decreases in tumor size (FIG. 12b). In addition, the response rate to in vivo activated iCD40-expressing BMDC vaccines was significantly higher than the response rates to wild type BMDCs under all other vaccination conditions (70% vs 30%). To confirm the elicitation of tumor antigen-specific T cell responses in tumor-bearing mice, H-2 K$^b$ OVA$_{257-264}$ tetramer analysis was performed on peripheral blood CD8 T cells. This analysis verified the presence of a expanded population of K$^b$OVA$_{257-264}$-specific CD8$^+$ T cells exclusively in mice vaccinated with in vivo activated iCD40 BMDCs (FIG. 12c, data not shown).

Enforced Expression of Akt-1 in DCs Extended their Survival and Potency.

Akt-1 is found to be essential for DC survival, especially following growth factor withdrawal. Moreover, overexpression of Akt-1 leads to enhanced DCs (eDCs) with greater apoptosis resistance, increased maturation, and improved immunogenicity against highly immunogenic tumors. Following is a summary of these results:

Rapid Down-Regulation of Akt Following Cytokine Withdrawal is Prevented by Innate and Acquired Immune Signals.

To investigate pathways involved in DC survival following inflammatory stimuli, the initial focus was on those signaling proteins that were known to be induced by the well-characterized TLR ligand, LPS, which was previously implicated in cell survival. Treatment with PI3 kinase (PI3K) and Src kinase inhibitors significantly antagonized LPS-mediated survival, whereas JAK and MAPK inhibitors had almost no effect even after 48 hr incubation (data not shown).

To further study the role of PI3K in DC survival, the kinetics of Akt expression, a key down-stream molecule of PI3K, during GM-CSF deprivation-mediated DC death[60] was determined Interestingly, within 24 hours of GM-CSF deprivation, total Akt protein levels were rapidly down-regulated prior to DC death, mirroring decreases in the protein level of Bcl-2, which has been suggested to be down-regulated upon induction of DC maturation[61] (not shown). Anti-CD40 mAb and LPS were then found to protect against GM-CSF deprivation-mediated DC death. Although GM-CSF deprivation consistently down-regulated Akt protein levels, LPS or anti-CD40 treatment prevented the down-regulation of Akt. Even though mild manipulation of DCs, such as replating, can contribute to Akt phosphorylation at day 2 following GM-CSF withdrawal, unlike untreated control cells, only LPS and CD40 signals maintained relatively high Akt phosphorylation and protein levels on day 4, suggesting that LPS and CD40 stimulation regulate not only the phosphorylation state but also the protein level of Akt, thereby promoting DC survival (not shown).

To further test the hypothesis that PI3K and Akt are common regulators for innate and acquired immune signal-mediated DC survival, various concentrations (0.05-5 µM) of PI3K inhibitor, wortmannin, in BMDCs treated with LPS or anti-CD40 were tested. Even low wortmannin concentration (0.05 µM), which has very little effect on other types of cells (data not shown), rapidly induced DC death in both LPS and anti-CD40 treatment, suggesting that PI3K is a common mediator of DC survival by inflammatory stimuli.

Functional Role of Akt in LPS Mediated-DC Survival.

To more directly investigate the role of Akt in PI3K-mediated DC survival, a previously described constitutively active Akt (M-Akt) allele, consisting of full length Akt, targeted to intracellular membranes with a myristoylation-targeting sequence from c-Src[62] was used. However, it has been suggested that c-Src, which is only myristoylated, is excluded from lipid rafts in fibroblasts because dual acylation, such as palmitoylation and myristoylation, is important for lipid raft localization of Src family kinases[63]. Therefore, to test the possibility that the efficient lipid raft localization of Akt improve its functions, this construct was compared with several distinct deregulated Akt alleles, containing myristoylation-targeting sequences from Src family kinases Src, Fyn and Lck fused to ΔAkt. The pleckstrin homology (PH) domain (residues 1-102) was removed to further improve Akt activity when PI3K is limiting[64]. Among the 3 membrane-targeting sequences, the Fyn myristoylation-targeting sequence ($M_F$) showed the most efficient lipid raft localization, 2-3-fold NF-κB induction, ~6-fold induced Akt-S473 and GSK3 phosphorylation, and enhanced viability of Jurkat cells following treatment with PI3K inhibitors (data not shown). Therefore, $M_F$-ΔAkt was used in subsequent experiments. Moreover, for improved expression in BMDCs, replication-defective adenovirus, Ad-$M_F$-ΔAkt, expressing functionally optimized Akt was generated. Consistently, Ad-$M_F$-ΔAkt led to higher GSK3α/β phosphorylation in BMDCs, compared with Ad-M-Akt[62]. In vitro DC survival assays indicated that both vectors could significantly inhibit wortmannin-mediated lethality in BMDCs relative to Ad-GFP (p<0.005). In addition, Ad-$M_F$-ΔAkt more efficiently protected DCs than Ad-M-Akt. Thus, functionally optimized Akt almost completely suppresses induction of DC death by PI3K (but not Src) inhibition.

Akt Transduced DCs Show Prolonged Longevity In Vitro and In Vivo.

Previous reports demonstrated a correlation between prolonging DC lifespan by overcoming various death signals in lymphoid tissues and the adjuvant potency of DC-based vaccines and T cell dependent immunity[4,25,26]. Therefore, induction of Akt activity promotes the survival of DCs under various conditions was assayed. First, the effects of Ad-M-Akt and LPS on DC survival following growth factor depravation was tested. As shown in FIGS. 13a and 13b, DCs pre-incubated with LPS (1 µg/ml) or infected with Ad-M-Akt maintained viability at least 5 days after GM-CSF withdrawal, whereas DCs untreated or transduced with Ad-GFP underwent significant cell death by day 4, suggesting that the induction of Akt inhibits cell death signals mediated by GM-CSF withdrawal in vitro.

To further investigate Akt-mediated survival of DCs in vivo, the viability of Ad-$M_F$-ΔAkt-transduced DCs with LPS— or Ad-GFP-transduced DCs in draining lymph nodes was compared. DCs were stained with the fluorescent dye CFSE followed by subcutaneous delivery into the hind legs of syngeneic mice (FIG. 13c). On day 5 after delivery, the quantity of CFSE $M_F$-ΔAkt-DCs residing in the draining popliteal lymph node was ~1% of total lymph node cells, which was a 2-3-fold higher percentage than control Ad-GFP-DC-treated mice. Consistent with previous findings[3], the percentage of CFSE$^+$ DCs from control mice injected with untreated or LPS-treated DCs rapidly decreased at later timepoints, whereas Akt-transduced DCs sustained their disproportionate representation for at least 10 days post-delivery (FIG. 13d). In addition, the average volume of draining lymph nodes exposed to $M_F$-ΔAkt-DCs was approximately 4-8-fold bigger than that from control mice, indicating that Ad-$M_F$-ΔAkt transduction strongly enhances the number of lymph node resident DCs compared to all negative control groups as well as LPS-treated DCs (FIG. 13e). Since the arrival of CFSE$^+$ DCs does not seem to differ significantly among the groups in the first 24 hr after injection, these data strongly suggest that ex vivo transduction of DCs with Ad-$M_F$-ΔAkt promotes prolonged lifespan, which would result in sustained immunity by overcoming various DC death signals in lymphoid tissues.

Akt Improves DC Ability to Induce T Cell Functions. In addition to promoting DC survival, optimal maturation and DC activation, accompanied by IL-12 production, is important for naïve T cell priming, leading to cell proliferation and IFN-γ production[65]. To directly test whether enhanced survival and activation of $M_F$-ΔAkt-DCs can promote T cell function, the proliferative response of allogeneic (BALB/c) and syngeneic OT-1 T cells (expressing transgenic TCRs specific for $K^b$-restricted OVA$_{257-264}$ peptide (SIINFEKL)) (SEQ ID NO: 6) to peptide-pulsed, Akt-transduced DCs was examined. After 24-hr incubation of DCs with syngeneic splenocytes from OT-1 mice, Ad-$M_F$-ΔAkt transduced DCs induced T cell proliferation comparable to LPS-treated DCs, but higher than Ad-GFP-transduced DCs. However, after ~72 hr incubation, $M_F$-ΔAkt-DCs induced about two-fold higher T cell proliferation than DCs activated with LPS. Moreover, Ad-M-Akt-transduced DCs also consistently revealed 5-7-fold higher allogeneic T cell proliferation responses than DCs pulsed with LPS or Ad-GFP at low DC:effector ratios after 72-hr incubations. Furthermore, $M_F$-ΔAkt-DCs produced at least 7-fold higher IFN-gamma$^+$ OVA peptide (SIINFEKL)-specific (SEQ ID NO: 6) splenocytes than DCs treated with LPS or Ad-GFP in our ELISpot assay. Taken together, these data strongly support the ability of Akt to induce DC maturation and survival, resulting in robust T cell proliferation and activation.

$M_F$-ΔAkt Enhances the DC Vaccine Ability to Eradicate a Pre-Established Tumor.

To more faithfully reflect clinical applications, antitumor efficacy of $M_F$-ΔAkt-DCs was measured. The induction of immunity by Ad-$M_F$-ΔAkt-transduced DC vaccines was monitored after immunization of C57BL/6 mice bearing large (~0.4 cm$^3$) s.c. EG.7-OVA tumors. While control SIINFEKL-pulsed (SEQ ID NO: 6) DC vaccines showed no significant inhibition of tumor growth or increased survival, a single i.p. dose of peptide-pulsed $M_F$-ΔAkt-DCs led to significant tumor growth inhibition (P<0.05) (FIG. 14a, b, and data not shown). At early timepoints, $M_F$-ΔAkt-DCs successfully suppressed all pre-established EG.7-ova tumors, although 2 of 5 tumors eventually relapsed at later timepoints (data not shown). To measure sustained antigen-specific T cell responses in tumor bearing mice, H-2 $K^b$ OVA$_{257-264}$ tetramer analysis was performed on peripheral blood CD8$^+$ T cell harvested 14 days after vaccination. This analysis clearly showed that the vaccination with Ad-$M_F$-Akt-transduced peptide-pulsed DCs led to an expanded population of OVA$_{257-264}$ antigen-specific CD8' T cells in mice (FIG. 14c, d). These findings indicate a crucial role for increased longevity of DCs in tumor immunosurveillance and clearly support the hypothesis that upregulation of Akt activity in DCs improves DC function, producing enhanced anti-tumor effects.

Development of CID-Inducible TLRs (iTLRs):

There are several subgroups of TLRs based on sublocalization and signaling pathways utilized. Development of both iTLR4, normally localized on the cell surface, and also iTLR3, 7, 8, and 9, normally localized intracellularly is assayed. Regardless of the normal subcellular localization of the ligand-binding extracellular domains, the signaling domains are cytoplasmic and should signal properly in all cases if homodimerization is the normal signaling mechanism. Analogous to iCD40, the TLR cytoplasmic signaling domains were PCR-amplified with flanking XhoI and SalI restriction sites for subcloning on the 5' or 3' side of two chemical inducers of dimerization (CID) binding domains (CBD), FKBP12$_{V36}$[1]. The chimeric CBD-TLRs were localized to the plasma membrane using myristoylation-targeting motifs (FIG. 15).

Initial testing of TLRs involved co-transfection of expression vectors into Jurkat-TAg or 293 cells along with an NF-kB-responsive SEAP (secreted alkaline phosphatase) reporter plasmid[66]. Interestingly, our preliminary data suggested that only iTLR7 and iTLR8 functioned in Jurkat-TAg cells, but not iTLR3, 4, and 9, regardless of the relative position of the CBDs and TLRs (FIG. 16 and not shown). Additional transfections in a panel of cells will be required to determine whether this reflects physiological tissue-specific signaling differences or other idiosyncrasies of these chimeric constructs.

Development of aggressive preclinical tumor model for in vivo imaging of vaccine efficacy. Although subcutaneous tumor models provide a convenient tool for approximating tumor size, their utility is typically limited to non-orthotopic tumors that are reasonably symmetrical. Also quantitation of metastasis necessitates euthanasia and is limited to a single measurement. As an improvement on this mainstay approach, tumor cells were developed that stably express a red-shifted luciferase from Caribbean click beetles (*Pyrophorus plagiophthalamus*). Imaging in mice following administration of substrate D-Luciferin (FIG. 17), confirms easy detection by either a cooled CCD camera (IVIS™ Imaging System, Xenogen Corp.) or standard calipers. Furthermore, the red-shifted (~613 nM emission) luciferase reporter should permit more linear quantitation of surface distant metastasis.

Research Design and Methods:

Specific Aim 1: Develop Synthetic Drug-Inducible Toll-Like Receptors and Composite Costimulatory Receptors within a Single Vector for Unified Broadly Applicable Immunotherapy.

A. Develop Most Potent icTLR.

This aim attempts to circumvent the requirement for pathogen-derived (or synthetic) adjuvant in DC activation by combining previous genetic manipulation of DCs with newly developed inducible TLRs. Initially, chimeric iTLR 3,4,7,8, and 9, were developed by cloning the cytoplasmic signaling domains of TLRs 5' (upstream) or 3' (downstream) of CID-binding domains (FIG. 15). Initial screening in Jurkat-TAG cells revealed that iTLR8 (and to a lesser extent iTLR7) triggered the largest induction of NF-kB (FIG. 16). However, the relative strength of various TLRs may be a tissue-specific parameter. To address this, these constructs will first be tested in the DC cell line, D2SC/1 initially with regards to NF-kB activation using an NF-kB SEAP reporter system based on transient transfection of multiple expression plasmids into target cells. 2DSC/1 cells represent a rare subset of immortalized DC lines that retain both the immature DC phenotype and the ability to mature following activation signals[67]. Since, NF-kB induction is not the only function of TLRs (FIG. 18), IRF3/7 induction may also be screened using an interferon (IFN)-stimulated response element (ISRE)-SEAP reporter plasmid that binds IRFs and induces reporter activity. To develop ISRE-SEAP, the ISRE-containing promoter from ISRE-luc (Stratagene) will replace the SRalpha promoter in our constitutive reporter plasmid pSH1/kSEAP. As a secondary induction of TLR signaling, INK and p38 phosphorylation are monitored by western blotting using phosphorylation-specific antibodies.

Since various distinct TLRs can differentially induce IRF and NF-kB and may synergize in DC activation and IL-12 production[43], initial testing of inducible TLRs, will be followed by combinatorial testing by cotransfection of iTLRs, two-at-a-time. Although both normal homodimerization and more unpredictable heterodimerization may occur, this approach should reveal synergism between different classes of TLRs. Activation of synergistic TLR pairs should confer enhanced immunostimulatory capacities to DCs. If synergism can be detected, a new series of constructs that are comprised of two tandem distinct (or identical) TLRs, called inducible composite TLRs (icTLRs) are tested (FIG. 19). In this case cytoplasmic XhoI-SalI-flanked TLR signaling domains from above are combined in various arrangements upstream and downstream of CBDs. Finally, the two most potent constructs are modified to contain the cytoplasmic domain of CD40, previously demonstrated to be activated by CID (FIG. 20).

Transfection of DCs.

Although transfection of DCs can be problematic, an improved method of electroporation was recently described by Vieweg and colleagues[68]. In their approach, survival following electroporation (300 V, 150 mF (Gene Pulser II: Bio-Rad)) is enhanced by resuspending DCs ($4 \times 10^7$/ml) in high potassium ion ViaSpan buffer (Barr Laboratories). Additionally, if transfection efficiency is still too low, expression vector pRSV-TAg, containing SV40 large T antigen for amplifying our pSH1 series expression vectors, which all contain the SV40 origin of replication will be cotransfected.

B. Develop Adenovector Expressing Unified Activation Gene icTLR/CD40.

Although D2SC/1 is a useful cell model for preclinical studies, the immunoregulatory genes will next be assayed in primary mouse and human DCs prior to clinical applications. To facilitate efficient gene transfer to primary cells, the most potent construct(s) is subcloned into adenovirus shuttle vector, pShuttle-X or pDNR-CMV and further transferred into Ad5 vector, pAdeno-X (BD) or AdXLP (BD), respectively. Preparation of high-titer virus is carried out. As has been achieved with previously developed Ad5/f35-iCD40, this vector is tested in both human and mouse DCs. Although Ad5/f35 pseudotyped adenovectors improve transduction efficiency a bit in human DCs, "pure" Ad5 enveloped adenovectors will be used to permit additional transduction of murine DCs.

For human studies, MoDCs are prepared by standard incubation of adherent peripheral blood DC precursors in GM-CSF and IL-4. Immature DCs are transduced with the developed icTLR/CD40 vector and control vectors (e.g. Ad5/f35-iCD40 and Ad5/f35-EGFP). Standard MoDC assays for maturation and activity are described herein and also include, for example, flow cytometry analysis of maturation markers (e.g. CD40, CD80, CD86, HLA class I and II, CCR7), IL-12 production, migration, and activation of antigen-specific T cells.

Expected Outcomes, Possible Pitfalls and Alternative Experiments:

Since MPL synergizes with iCD40, iTLR4 will likely synergize with iCD40; however, due to the vagaries of protein engineering, placing CD40 and TLR signaling domains in tandem may interfere with the signaling pathways activated by isolated domains. Therefore, if tandem domains have unanticipated signaling, the constructs will be coexpressed in viral vectors using alternative strategies, such as use of bicistronic expression cassettes or cloning into the E3 region of AE1AE3 adenovectors. Also, chimeric receptors may not signal identical to the endogenous proteins. Therefore, although TLR4 is thought to be the most potent TLR for activation of myeloid DCs, an alternative TLR(s) may function better when converted to a CID-activated receptor. Moreover, synergism between iTLRs and constitutive Akt, $M_F$-ΔAkt, or siRNA SOCS-1 may be found to be more potent than iCD40 and iTLR. In these cases, other combinations of immune regulatory genes may be combined in multicistronic adenovectors.

Specific Aim 2: Comparison of Optimum iTLR-Cd40 with Previously Developed Approaches (i.e. iCD40, $Myr_F$-ΔAkt, SOCS-1 shRNA) to Enhance MoDC Activation, Survival, and Function In Vitro and In Vivo.

Due to the pivotal role that DCs play in regulating adaptive immunity, there are many homeostatic mechanisms that downregulate DC activity. Nevertheless, heightened activation may be required for overcoming tumor- or viral-derived tolerogenic mechanisms. Several methods to circumvent these homeostatic mechanisms are discussed herein. Inducible CD40 can be activated in vivo within the context of an immunological synapse and lacks its extracellular domain, bypassing several negative feedback mechanisms that target this domain. "Optimized", constitutively active Akt, $M_F$-ΔAkt, is based on lipid-raft targeting of a truncated Akt1 allele. Reducing the inhibitor SOCS-1 with siRNA technology increases toll-receptor signaling and Type I interferon production. Thus, all three methods have the capacity to enhance MoDCs.

Preparation of MoDCs:

for Most Experiments Based on Optimization of Enhanced Dcs (eDCs), monocyte-derived DCs are differentiated and enriched from peripheral blood mononuclear cells obtained from the Blood Bank or healthy volunteers. Briefly, DC precursors are isolated by buoyant density techniques (Histopaque: Sigma-Aldrich) and then adherent (and semi-adherent) cells are cultured for 5 days in serum free X-VIVO 15 DC medium (Cambrex Bio Science) in the presence of cytokines GM-CSF (800 U/ml) and IL-4 (500 U/ml) (R&D Systems, Minneapolis, Minn.). Following 5 days in culture, immature DCs are incubated for an additional 24 hours in the presence of adenovectors expressing iCD40 (i.e. Ad5/f35-iCD40), constitutive Akt (Ad5/f35-MF-ΔAkt), shRNA SOCS1 (Ad5-shSOCS1), or Ad5-iTLR/CD40 at 10,000 viral particles (vp) per cell. (Note: Ad5 vectors may be added at 20,000 vp to compensate partly for somewhat reduced transduction efficiency). In a subset of samples, additional TLR4 ligand monophosphoryl lipid A (MPL; 1 mg/ml) or dimerizer AP20817 (100 nM; iCD40-DCs only) will be added for complete maturation.

Determination of Maturation State of MoDCs:

A number of surface proteins ("markers") are induced during MoDC activation, including CD25, CD40, CD80, CD83, CD86, HLA class I and class II, CCR7 and others. Preliminary studies demonstrated that iCD40 signaling alone is sufficient to upregulate CD83 and CCR7 on MoDCs (not shown). Additional TLR4 signaling (via MPL) leads to additive (or synergistic) activation of all maturation markers (FIG. 21 and not shown). Therefore, at a fixed vp number, induction of maturation markers (determined by flow cytometry) by all four viral vectors either alone or in combination with MPL is evaluated. Maturation by the previous "gold standard" maturation cocktail (MC), comprised of IL-1a, IL-6, TNFα, and PGE$_2$, acts as positive control and non-treated (mock) immature DCs serve as negative controls in these and the following experiments. In addition to phenotypic analysis of cell surface markers, production of IL-12 and other T$_H$1-polarizing cytokines (e.g. IL-23, TNFa), are also important for optimal anti-tumor immunity. While iCD40 is not sufficient for IL-12 production, combinations of MPL and iCD40 lead to potent synergistic production of IL-12 (FIG. 22). Therefore, DC culture supernatants, stimulated as above, are harvested 24 and 48 hours after transduction and maturation. IL-12 p70 levels, IL-12/IL-23 p40 dimers and TNFα concentrations are determined by colorimetric sandwich ELISA assays (BD Biosciences). Alternatively, multiplex beads developed by BD to simultaneously assay multiple additional cytokines (e.g. IL-1, IL-6, IFNa, etc.) may be used.

Determination of Migration Capacity:

Unlike murine bone marrow-derived DCs (BMDCs) that are competent for LN migration, immature MoDCs are deficient in this crucial function. While PGE$_2$ is typically used to upregulate CCR7 and migratory capacity, the utility of PGE$_2$ is tempered by potential deleterious effects, which include down regulation of CD40 signaling and IL-12 production and upregulation of IL-10[50,52,69]. Moreover, even in the presence of PGE$_2$, migration to LNs is modest and around 1-2% of injected cells[70]. Although CCR7 expression is likely a prerequisite for migration to lymph nodes, chemotactic responsiveness to the LN-derived CCR7 chemokines, CCL19 and CCL21, is a more direct measure of likely migration to lymph nodes. Therefore, migration to CCL19/MIP3b may be compared in a modified 2-chamber assay.

Preliminary experiments demonstrate the surprising result that iCD40 signaling is sufficient for migratory capacity even in the absence of PGE$_2$ (FIG. 23). In this assay MoDCs were transduced with Ad5/f35-ihCD40 and labeled with fluorescent dye, Green-CMFDA (Molecular Probes). Cells were placed in the top chamber of a 2-chamber 8-mm assay plate and total fluorescence in the bottom chamber was quantitated and compared with PGE$_2$-mediated stimulation. Similarly, the migratory capacity in vitro of iCD40-TLR-, iCD40-, and Akt-MoDCs, and SOCS1-deficient MoDCs individually and in combination with and without TLR4 ligands may be compared.

As a second more direct assay for migration capacity, migration in vivo may be compared by injecting eDCs into the lower leg of non-myeloablatively irradiated immunodeficient SCID mice. Minimal radiation (~250 rad) is needed to suppress natural killer (NK) cell activity against xenogeneic cells. Despite species differences, human MoDCs can respond to murine chemokines and migrate to draining LNs[71]. To visualize successfully migrated MoDCs, cells are labeled with the fluorescent dye, Green-CMFDA cell tracker, which is quantitated by flow cytometry. Second, in addition to adenovector-mediated "enhancement", MoDCs are transduced with adenovector, Ad5/f35-CBR, expressing red-shifted (510 nm excitation peak) click beetle (*Pyrophorus plagiophthalamus*) luciferase (Promega). Use of the CBR luciferase allele should more easily allow detection of bioluminescent DCs (using our IVIS® Imaging System (Xenogen Corp, Alameda, Calif.)) both within the draining popliteal LN and at more distant and membrane-distal sites.

Activation and Polarization of Autologous T Cells:

In addition to maturation and migration, ability to activate a T$_H$1-biased antigen-specific immune response in vivo is the sine qua non of DC vaccination against solid tumors. Therefore, the ability of eDCs to stimulate both T helper and cytotoxic function may be evaluated. Initially, stimulation of proliferation of allogeneic CD4' T cells may be assayed. Enhanced DCs are matured and activated using the conditions described above, irradiated (3000 rad) and cultured 1:10 with allogeneic magnetic bead-purified (Miltenyi Biotec, Auburn, Calif.) CD4' T cells. Proliferation is assessed 4 days later after 16-hour incubation with [$^3$H]-thymidine. To complement these studies, the T$_H$1 polarization (determined by ELISpot assays to IL-4 and IFNg) ability by various standard or eDCs may be determined To more specifically assay DC maturation state, ability to stimulate naïve CTL function is determined using HLA-A2-restricted tetramer analysis and CTL assays. (Note: several HLA-A2 carriers have recently been genotyped). Activation of autologous T cells in healthy donors by various eDCs presenting 2 distinct cocktails of HLA-A2-restricted antigens, one strong and one weak is compared. CTL assays will be based on antigen-specific lytic activity of T cells stimulated with standard or eDCs as above. These 4 T cell assays should provide a balanced preclinical analysis of enhanced DCs along with a functional analysis of the various approaches.

Finally, SOCS-1 depletion will be assessed for synergy with iCD40-TLR, iCD40 or Myr$_F$-ΔAkt signaling to produce a further optimized eDC, and if synergy is found, a bicistronic adenovector containing iCD40 (or Myr$_F$-ΔAkt) and SOCS-1 shRNA may be developed and characterized.

CITATIONS REFERRED TO IN THIS EXAMPLE

1. Clackson, T. et al. Redesigning an FKBP-ligand interface to generate chemical dimerizers with novel specificity. *Proc Nad Acad Sci USA* 95, 10437-10442 (1998).
2. Labeur, M. S. et al. Generation of tumor immunity by bone marrow-derived dendritic cells correlates with dendritic cell maturation stage. *J Immunol* 162, 168-75 (1999).
3. Nopora, A. & Brocker, T. Bcl-2 controls dendritic cell longevity in vivo. *J Immunol* 169, 3006-14 (2002).
4. Hanks, B. A. et al. Re-engineered CD40 receptor enables potent pharmacological activation of dendritic-cell cancer vaccines in vivo. *Nat Med* 11, 130-7 (2005).
5. Shen, L., Evel-Kabler, K., Strube, R. & Chen, S. Y. Silencing of SOCS1 enhances antigen presentation by dendritic cells and antigen-specific anti-tumor immunity. *Nat Biotechnol* 22, 1546-53 (2004).
6. Reis e Sousa, C. Dendritic cells as sensors of infection. *Immunity* 14, 495-8 (2001).
7. Banchereau, J. & Palucka, A. K. Dendritic cells as therapeutic vaccines against cancer. *Nat Rev Immunol* 5, 296-306 (2005).
8. Banchereau, J. et al. Immunobiology of dendritic cells. *Annu Rev Immunol* 18, 767-811 (2000).
9. Lanzavecchia, A. & Sallusto, F. Regulation of T cell immunity by dendritic cells. *Cell* 106, 263-6 (2001).
10. Smith, C. M. et al. Cognate CD4(+) T cell licensing of dendritic cells in CD8(+) T cell immunity. *Nat Immunol* 5, 1143-8 (2004).
11. Schoenberger, S. P., Toes, R. E., EI, v.d.V., Offringa, R. & Melief, C. J. T-cell help for cytotoxic T lymphocytes is mediated by CD40-CD40L interactions [see comments]. *Nature* 393, 480-3 (1998).
12. Bennett, S. R. et al. Help for cytotoxic-T-cell responses is mediated by CD40 signaling. *Nature* 393, 478-80 (1998).

13. Ridge, J. P., Di Rosa, F. & Matzinger, P. A conditioned dendritic cell can be a temporal bridge between a CD4+T-helper and a T-killer cell. *Nature* 393, 474-8 (1998).
14. Grewal, I. S. & Flavell, R. A. CD40 and CD154 in cell-mediated immunity. *Annu Rev Immunol* 16, 111-35 (1998).
15. O'Sullivan, B. & Thomas, R. CD40 and dendritic cell function. *Crit. Rev Immunol* 23, 83-107 (2003).
16. Nestle, F. O., Banchereau, J. & Hart, D. Dendritic cells: On the move from bench to bedside. *Nat Med* 7, 761-5 (2001).
17. Schuler, G., Schuler-Thurner, B. & Steinman, R. M. The use of dendritic cells in cancer immunotherapy. *Curr Opin Immunol* 15, 138-47 (2003).
18. Gilboa, E. & Vieweg, J. Cancer immunotherapy with mRNA-transfected dendritic cells. *Immunol Rev* 199, 251-63 (2004).
19. Gilboa, E. The promise of cancer vaccines. *Nat Rev Cancer* 4, 401-11 (2004).
20. Ridgway, D. The first 1000 dendritic cell vaccinees. *Cancer Invest* 21, 873-86 (2003).
21. Dallal, R. M. & Lotze, M. T. The dendritic cell and human cancer vaccines. *Curr Opin Immunol* 12, 583-8 (2000).
22. Langenkamp, A., Messi, M., Lanzavecchia, A. & Sallusto, F. Kinetics of dendritic cell activation: impact on priming of TH1, TH2 and nonpolarized T cells. *Nat Immunol* 1, 311-6 (2000).
23. Hermans, I. F., Ritchie, D. S., Yang, J., Roberts, J. M. & Ronchese, F. CD8+ T cell-dependent elimination of dendritic cells in vivo limits the induction of antitumor immunity. *J Immunol* 164, 3095-101 (2000).
24. Park, Y., Lee, S. W. & Sung, Y. C. Cutting Edge: CpG DNA inhibits dendritic cell apoptosis by up-regulating cellular inhibitor of apoptosis proteins through the phosphatidylinositide-3'-OH kinase pathway. *J Immunol* 168, 5-8 (2002).
25. Josien, R. et al. TRANCE, a tumor necrosis factor family member, enhances the longevity and adjuvant properties of dendritic cells in vivo. *J Exp Med* 191, 495-502 (2000).
26. Miga, A. J. et al. Dendritic cell longevity and T cell persistence is controlled by CD154-CD40 interactions. *Eur J Immunol* 31, 959-65 (2001).
27. Cremer, I. et al. Long-lived immature dendritic cells mediated by TRANCE-RANK interaction. *Blood* 100, 3646-55 (2002).
28. Tone, M., Tone, Y., Fairchild, P. J., Wykes, M. & Waldmann, H. Regulation of CD40 function by its isoforms generated through alternative splicing. *Proc Natl Acad Sci USA* 98, 1751-1756. (2001).
29. Contin, C. et al. Membrane-anchored CD40 is processed by the tumor necrosis factor-alpha-converting enzyme. Implications for CD40 signaling. *J Biol Chem* 278, 32801-9 (2003).
30. Kobayashi, K. et al. IRAK-M is a negative regulator of Toll-like receptor signaling. *Cell* 110, 191-202 (2002).
31. Hou, W. S. & Van Parijs, L. A Bcl-2-dependent molecular timer regulates the lifespan and immunogenicity of dendritic cells. *Nat Immunol* 5, 583-9 (2004).
32. Kandel, E. S. & Hay, N. The regulation and activities of the multifunctional serine/threonine kinase Akt/PKB. *Exp Cell Res* 253, 210-29 (1999).
33. Vassiliou, E., Sharma, V., Jing, H., Sheibanie, F. & Ganea, D. Prostaglandin E2 promotes the survival of bone marrow-derived dendritic cells. *J Immunol* 173, 6955-64 (2004).
34. Ardeshna, K. M., Pizzey, A. R., Devereux, S. & Khwaja, A. The PI3 kinase, p38 SAP kinase, and NF-kappaB signal transduction pathways are involved in the survival and maturation of lipopolysaccharide-stimulated human monocyte-derived dendritic cells. *Blood* 96, 1039-46 (2000).
35. Kanto, T., Kalinski, P., Hunter, O. C., Lotze, M. T. & Amoscato, A. A. Ceramide mediates tumor-induced dendritic cell apoptosis. *J Immunol* 167, 3773-84 (2001).
36. Mochizuki, T. et al. Akt protein kinase inhibits non-apoptotic programmed cell death induced by ceramide. *J Biol Chem* 277, 2790-7 (2002).
37. Bennett, M. R., Evan, G. I. & Schwartz, S. M. Apoptosis of rat vascular smooth muscle cells is regulated by p53-dependent and -independent pathways. *Circ. Res.* 77, 266-273 (1995).
38. Albert, M. L., Jegathesan, M. & Darnell, R. B. Dendritic cell maturation is required for the cross-tolerization of CD8+ T cells. *Nat Immunol* 2, 1010-7 (2001).
39. Diehl, L. et al. CD40 activation in vivo overcomes peptide-induced peripheral cytotoxic T-lymphocyte tolerance and augments anti-tumor vaccine efficacy. *Nat Med* 5, 774-9 (1999).
40. Vonderheide, R. H. et al. CD40 activation of carcinoma cells increases expression of adhesion and major histocompatibility molecules but fails to induce either CD80/CD86 expression or T cell alloreactivity. *Int J Oncol* 19, 791-8 (2001).
41. Mazouz, N. et al. CD40 triggering increases the efficiency of dendritic cells for antitumoral immunization. *Cancer Immun* 2, 2 (2002).
42. Kikuchi, T., Worgall, S., Singh, R., Moore, M. A. & Crystal, R. G. Dendritic cells genetically modified to express CD40 ligand and pulsed with antigen can initiate antigen-specific humoral immunity independent of CD4+ T cells. *Nat Med* 6, 1154-9 (2000).
43. Napolitani, G., Rinaldi, A., Bertoni, F., Sallusto, F. & Lanzavecchia, A. Selected Toll-like receptor agonist combinations synergistically trigger a T helper type 1-polarizing program in dendritic cells. *Nat Immunol* 6, 769-76 (2005).
44. Medzhitov, R., Preston-Hurlburt, P. & Janeway, C. A., Jr. A human homologue of the *Drosophila* Toll protein signals activation of adaptive immunity. *Nature* 388, 394-7 (1997).
45. Hoshino, K. et al. Cutting edge: Toll-like receptor 4 (TLR4)-deficient mice are hyporesponsive to lipopolysaccharide: evidence for TLR4 as the Lps gene product. *J Immunol* 162, 3749-52 (1999).
46. Ozinsky, A. et al. The repertoire for pattern recognition of pathogens by the innate immune system is defined by cooperation between toll-like receptors. *Proc Natl Acad Sci USA* 97, 13766-71 (2000).
47. Zhang, H., Tay, P. N., Cao, W., Lu, W. & Lu, J. Integrin-nucleated Toll-like receptor (TLR) dimerization reveals subcellular targeting of TLRs and distinct mechanisms of TLR4 activation and signaling. *FEBS Lett* 532, 171-6 (2002).
48. Lee, H. K., Dunzendorfer, S. & Tobias, P. S. Cytoplasmic domain-mediated dimerizations of toll-like receptor 4 observed by beta-lactamase enzyme fragment complementation. *J Biol Chem* 279, 10564-74 (2004).
49. Choe, J., Kelker, M. S. & Wilson, I. A. Crystal structure of human toll-like receptor 3 (TLR3) ectodomain. *Science* 309, 581-5 (2005).
50. Luft, T. et al. Functionally distinct dendritic cell (DC) populations induced by physiologic stimuli: prostaglandin E(2) regulates the migratory capacity of specific DC subsets. *Blood* 100, 1362-72 (2002).

51. Scandella, E. et al. CCL19/CCL21-triggered signal transduction and migration of dendritic cells requires prostaglandin E2. *Blood* 103, 1595-601 (2004).
52. Kalinski, P., Vieira, P. L., Schuitemaker, J. H., de Jong, E. C. & Kapsenberg, M. L. Prostaglandin E(2) is a selective inducer of interleukin-12 p40 (IL-12p40) production and an inhibitor of bioactive IL-12p70 heterodimer. *Blood* 97, 3466-9 (2001).
53. Korst, R., Mahtabifard, A., Yamada, R., and Crystal, R. Effect of Adenovirus Gene Transfer Vectors on the Immunologic Functions of Mouse Dendritic Cells. *Molecular Therapy* 5, 307-315 (2002).
54. Langenkamp, A., Messi, M., Lanzavecchia, A., and Sallusto, F. Kinetics of dendritic cell activation: impact on priming of Th1, Th2, and nonpolarized T cells. *Nature Immunology* 1, 311-316 (2000).
55. Hermans, I., Ritchie, D., Yang, J., Roberts, J., and Ronchese, F. CD8 T cell-dependent elimination of dendritic cells in vivo limits the induction of antitumor immunity. *Journal of Immunology* 164, 3095-3101 (2000).
56. Wong, P.a.P., E. Feedback Regulation of Pathogen-Specific T Cell Priming *Immunity* 188, 499-511 (2003).
57. Miga, A., Masters, S., Durell, B., Gonzalez, M., Jenkins, M., Maliszewski, C., Kikutani, H., Wade, W., and Noelle, R. Dendritic cell longevity and T cell persistence is controlled by CD154-CD40 interactions. *European Journal of Immunology* 31, 959-965 (2001).
58. Medema, J., Schuurhuis, D., Rea, D., van Tongeren, J., de Jong, J., Bres, S., Laban, S., Toes, R., Toebes, M., Schumacher, T., Bladergroen, B., Ossendorp, F., Kummer, J., Melief, C., and Offringa, R. Expression of the serpin serine protease inhibitor 6 protects dendritic cells from cytotoxic T lymphocyte-induced apoptosis: differential modulation by T helper type 1 and type 2 cells. *Journal of Experimental Medicine* 194, 657-667 (2001).
59. Steinman, R.a.P., M. Exploiting dendritic cells to improve vaccine efficacy. *Journal of Clinical Investigation* 109, 1519-1526 (2002).
60. Woltman, A. M. et al. Rapamycin specifically interferes with GM-CSF signaling in human dendritic cells, leading to apoptosis via increased p27KIP1 expression. *Blood* 101, 1439-45 (2003).
61. Granucci, F. et al. Inducible IL-2 production by dendritic cells revealed by global gene expression analysis. *Nat Immunol* 2, 882-8 (2001).
62. Fujio, Y. & Walsh, K. Akt mediates cytoprotection of endothelial cells by vascular endothelial growth factor in an anchorage-dependent manner. *J Biol Chem* 274, 16349-54 (1999).
63. Mukherjee, A., Arnaud, L. & Cooper, J. A. Lipid-dependent recruitment of neuronal Src to lipid rafts in the brain. *J Biol Chem* 278, 40806-14 (2003).
64. Li, B., Desai, S. A., MacCorkle-Chosnek, R. A., Fan, L. & Spencer, D. M. A novel conditional Akt 'survival switch' reversibly protects cells from apoptosis. *Gene Ther* 9, 233-44. (2002).
65. Sporri, R. & Reis e Sousa, C. Inflammatory mediators are insufficient for full dendritic cell activation and promote expansion of CD4+ T cell populations lacking helper function. *Nat Immunol* 6, 163-70 (2005).
66. Spencer, D. M., Wandless, T. J., Schreiber, S. L. & Crabtree, G. R. Controlling signal transduction with synthetic ligands. *Science* 262, 1019-1024 (1993).
67. Granucci, F. et al. Modulation of cytokine expression in mouse dendritic cell clones. *Eur J Immunol* 24, 2522-6 (1994).
68. Su, Z. et al. Telomerase mRNA-transfected dendritic cells stimulate antigen-specific CD8+ and CD4+ T cell responses in patients with metastatic prostate cancer. *J Immunol* 174, 3798-807 (2005).
69. Scandella, E., Men, Y., Gillessen, S., Forster, R. & Groettrup, M. Prostaglandin E2 is a key factor for CCR7 surface expression and migration of monocyte-derived dendritic cells. *Blood* 100, 1354-61 (2002).
70. Morse, M. A. et al. Migration of human dendritic cells after injection in patients with metastatic malignancies. *Cancer Res* 59, 56-8 (1999).
71. Hammad, H. et al. Monocyte-derived dendritic cells induce a house dust mite-specific Th2 allergic inflammation in the lung of humanized SCID mice: involvement of CCR7. *J Immunol* 169, 1524-34 (2002).

Example 9

Expression Constructs and Testing

TLRs 3, 4, 7, 8 and 9 were initially selected to construct inducible chimeric proteins as they represent TLRs from the different subfamilies that are know to trigger the Th1 cytokine, IL-12, in monocyte-derived DCs. Further, TLR4 has been shown to trigger signaling following cross linking of chimeric TLR4 alleles via heterologous extracellular domains. The cytoplasmic domains of each (including TIRs) were PCR-amplified and placed adjacent (5' and 3') to two (2) FKBP12 (V36) ($F_v$ and $F_{v'}$ (wobbled)) genes, which were attached to the plasma membrane using a myristoylation-targeting sequence from c-Src. Chimeric proteins having a third FKBP gene have been developed to improve oligomerization.

Additionally, chimeric versions of adapters MyD88 and TRIF have been generated by fusing these cytoplasmic proteins to two (2) FKBPs. Finally, the tandem CARD domains from cytoplasmic PRRs, NOD2 and RIG-I, have been fused to tandem FKBPs. These constructs and reporter assays are described below.

Constructs:

(i) Inducible iTLRs:

TLR3, 4, 7, 8 and 9 were PCR-amplified from cDNA derived from MoDCs. PCR primers were flanked by XhoI and SalI restriction sites to permit cloning 5' and 3' of tandem FKBPs in the XhoI and SalI sites, respectively, of pSH1/M-$F_v$-$F_{vls}$-$E^{1,2}$. The primers used were (a) 5TLR3cX (5'-cgatcactcgagggctggaggatatcttttattgg-3') (SEQ ID NO: 13) and 3TLR3cS (5'-tgatcggtcgacatgtacagagttttggatccaagtg-3') (SEQ ID NO: 14) to give pSH1/M-TLR3-$F_v$-$F_{vls}$-E and pSH1/M-$F_v$-$F_{vls}$-TLR3-E; (b) 5TLR4cX (5'-cgatcactcgag-tataagttctattttcacctgatgcttc-3') (SEQ ID NO: 15) and 3TLR4cS (5'-tgatcggtcgacgatagatgttgcttcctgccaattg-3') (SEQ ID NO: 16) to give pSH1/M-TLR4-$F_v$-$F_{vls}$-E and pSH1/M-$F_v$-$F_{vls}$-TLR4-E; (c) 5TLR7cS (5'-cgatcagtcgac-gatgtgtggtatatttaccatttctg-3') (SEQ ID NO: 17) and 3TLR7cS (5'-tgatcggtcgacgaccgtttccttgaacacctgac-3') (SEQ ID NO: 18) to give pSH1/M-TLR7-$F_v$-$F_{vls}$-E and pSH1/M-$F_v$-$F_{vls}$-TLR7-E; (d) 5TLR8cX (5'-cgatcactcgaggatgtttggtt-tatatataatgtgtg-3') (SEQ ID NO: 19) and 3TLR8cS (5'-tcggtc-gacgtattgcttaatggaatcgacatac-3') (SEQ ID NO: 20) to give pSH1/M-TLR8-$F_v$-$F_{vls}$-E and pSH1/M-$F_v$-$F_{vls}$-TLR8-E; (e) 5TLR9cX (5'-cgatcactcgaggacctctggtactgcttccacc-3') (SEQ ID NO: 21) and 3TLR9cS (5'-tgatctgtcgacttcggccgtgggtc-cctggc-3') (SEQ ID NO: 22) to give pSH1/M-TLR9-$F_v$-$F_{vls}$-E and pSH1/M-$F_v$-$F_{vls}$-TLR9-E. All inserts were confirmed by sequencing and for appropriate size by western blot to the 3' hemagluttinin (HA) epitope (E). M, myristoylation-targeting sequence from c-Src (residues 1-14). pSH1, expression vector. Additionally, a third XhoI/SalI-linkered $F_{v'}$ domain was added to the XhoI sites of pSH1/M-$F_{v}$-$F_{vls}$-TLR4-E and pSH1/M-$F_{v}$-$F_{vls}$-TLR8-E to get pSH1/M-$F_{v}$2-$F_{vls}$-TLR4-E and pSH1/M-$F_{v}$2-$F_{vls}$-TLR8-E, respectively, to improve oligomerization.

To faithfully reflect physiological TLR4 signaling, full-length 2.5-kb TLR4 was PCR-amplified from TLR4 cDNA (from the Medzhitov lab) using SacII and XhoI-linkered primers 5hTLR4 (5'-aatctaccgcggccaccatgatgtctgc-ctcgcgcctg-3') (SEQ ID NO: 23) and 3hTLR4 (5'-tcagttctc-gaggatagatgttgcttcctgccaattg-3') (SEQ ID NO: 24), respectively. The 2546-bp PCR product was subcloned into pCR-Blunt-TOPO and sequenced. The sequence-verified insert was SacII/XhoI-digested and subcloned into SacIIIXhoI digested (and "CIPped") pSH1/M-$F_{v}$-$F_{vls}$-E to give pSH1/hTLR4-$F_{v}$-$F_{vls}$-E. An additional $F_{v'}$ was added to XhoI site to give pSH1/hTLR4-$F_{v}$2-$F_{vls}$-E.

(ii) Inducible Composite iTLR4-CD40:

The 191-bp XhoI-SalI-linkered human CD40 cytoplasmic domain was PCR-amplified with primers hCD405X (5'-atatactcgagaaaaaggtggccaagaagccaacc-3') (SEQ ID NO: 25) and hCD403Sns (5'-acatagtcgacctgtctctcctgcactgagatg-3') (SEQ ID NO: 26) and subcloned into the SalI site of pSH1/hTLR4-$F_{v}$-$F_{vls}$-E and pSH1/hTLR4-$F_{v}$2-$F_{vls}$-E to get pSH1/hTLR4-$F_{v}$-$F_{vls}$-CD40-E and pSH1/hTLR4-$F_{v}$2-$F_{vls}$-CD40-E.

(iii) Inducible iNOD2:

The ~800-bp amino terminus of the PRR NOD2 (containing tandem CARD domains) was PCR-amplified with XhoI/SalI-linkered primers 5NOD2X (5'-atagcactcgagatgggggaa-gagggtggttcag-3') (SEQ ID NO: 27) and 3NOD2Sb (5'-cttcatgtcgacgacctccaggacattctctgtg-3') (SEQ ID NO: 28) and subcloned into the XhoI and SalI sites of pSH1/S-$F_{v}$-$F_{vls}$-E to give pSH1/S-NOD2-$F_{v}$-$F_{vls}$-E and pSH1/S-$F_{v}$-$F_{vls}$-NOD2-E=Fv' NOD2.

(iv) Inducible iRIG-I:

The ~650 bp amino terminus of the RNA helicase RIG-I (containing tandem CARD domains) was PCR-amplified with XhoI/SalI-linkered primers 5RIGX (5'-atagcactcgagac-caccgagcagcgacgcag-3') (SEQ ID NO: 29) and 3RIGS (5'-cttcatgtcgacaatctgtatgtcagaagtttccatc-3') (SEQ ID NO: 30) and subcloned into the XhoI and SalI sites of pSH1/S-$F_{v}$-$F_{vls}$-E to give pSH1/S-RIGI-$F_{v}$-$F_{vls}$-E and pSH1/S-$F_{v}$-$F_{vls}$-RIGI-E=Fv'RIG-I.

(v) Inducible iMyD88:

Human TIR-containing adapter MyD88 (~900-bp) was PCR-amplified from 293 cDNA using XhoI/SalI-linkered primers 5MyD88S (5'-acatcaactcgagatggctgcaggaggtcccgg-3') (SEQ ID NO: 31) and 3MyD88S (5'-actcatagtcgaccagg-gacaaggccttggcaag-3') (SEQ ID NO: 32) and subcloned into the XhoI and SalI sites of pSH1/M-$F_{v}$-$F_{vls}$-E to give pSH1/M-MyD88-$F_{v}$-$F_{vls}$-E and pSH1/M-$F_{v}$-$F_{vls}$-MyD88-E, respectively.

(vi) Inducible iTRIF:

Human TIR-containing adapter TRIF2 (~2150-bp) was PCR-amplified from 293 cDNA using XhoI/SalI-linkered primers 5TRIFX (5'-acatcaactcgagatggcctgcacaggccatcac-3') (SEQ ID NO: 33) and 3TRIFS (5'-actcatagtcgacttctgcctc-ctgcgtcttgtcc-3') (SEQ ID NO: 34) and subcloned into SalI-digested pSH1/M-$F_{v}$-$F_{vls}$-E to give pSH1/M-$F_{v}$-$F_{vls}$-TRIF-E.

(vii) IFN-beta-SEAP:

The minimal IFNbi promoter was PCR-amplified from human genomic DNA using primers 5IFNbM1 (5'-aacta-gacgcgtactactaaaatgtaaatgacataggaaaac-3') (SEQ ID NO: 35) and 31FNbH (5'-gacttgaagcttaacacgaacagtgtcgcctactac-3') (SEQ ID NO: 36). The MluI-HindIII—digested fragment was subcloned into a promoter-less SEAP reporter plasmid.

Certain constructs were specifically targeted to plasma membrane lipid rafts using myristoylation sequences from Fyn as well as the PIP2 membrane targeting domain of TIRAP. (5)

Secreted Alkaline Phosphatase (SEAP) Assays:

Reporters assays were conducted in human Jurkat-TAg (T cells) or 293 (kidney embryonic epithelial) cells or murine RAW264.7 (macrophage) cells. Jurkat-TAg cells ($10^7$) in log-phase growth were electroporated (950 mF, 250V) with 2 mg expression plasmid and 2 mg of reporter plasmid NF-kB-SEAP[3] or IFNbeta-TA-SEAP (see above). 293 or RAW264.7 cells (~2×$10^5$ cells per 35-mm dish) in log phase were transfected with 6 ml of FuGENE-6 in growth media. After 24 hr, transformed cells were stimulated with CID. After an additional 20 h, supernatants were assayed for SEAP activity as described previously[3].

Tissue Culture:

Jurkat-TAg and RAW264.7 cells were grown in RPMI 1640 medium, 10% fetal bovine serum (FBS), 10 mM HEPES (pH 7.14), penicillin (100 U/ml) and streptomycin (100 mg/ml). 293 cells were grown in Dulbecco's modified Eagle's medium, 10% FBS, and pen-strep.

Western Blots Analysis:

Protein expression was determined by western blot using antibodies to the common hemagluttinin (HA) epitope (E) tag.

Results

Chimeric iTLR4 with the PIP2 membrane targeting motif is activated 2-fold. The construct encoded two ligand binding domains. However, the rest of the iTLRs are not induced at robust levels by CID in 293, RAW or D2SC1 cells, as observed in reporter assays (FIGS. 25A and 25B). This might be attributed to the varied membrane targeting requirements of the iTLRs. Therefore, inducible Nod2 and RIG-1 were developed, which are cytoplasmic PRRs that do not need targeting to the plasma membrane. While iNod2 was activated 2 fold by the dimerizer drug in 293 cells, no such effect is observed in RAW 264.7 cells. With the addition of increasing concentrations of CID, iNod2 activity decreases in RAW cells. Also the effect of iNod2 and iCD40 together, on NFkappaB activation, is additive in 293 cells (FIG. 26). iRIG-1 is activated by 2.5 fold (FIG. 27). Inducible versions of the full-length adaptor molecules MyD88 and TRIF that are the primary mediators of signaling downstream of TLRs are in the screening process.

CITATIONS REFERRED TO IN THIS EXAMPLE

1. Xie, X. et al. Adenovirus-mediated tissue-targeted expression of a caspase-9-based artificial death switch for the treatment of prostate cancer. Cancer Res 61, 6795-804. (2001).
2. Fan, L., Freeman, K. W., Khan, T., Pham, E. & Spencer, D. M. in Human Gene Therapy 2273-2285 (1999).
3. Spencer, D. M., Wandless, T. J., Schreiber, S. L. & Crabtree, G. R. Controlling signal transduction with synthetic ligands. Science 262, 1019-1024 (1993).
4. Thompson, B. S., P. M. Chilton, J. R. Ward, J. T. Evans, And T. C. Mitchell. 2005. The Low-Toxicity Versions Of Lps, Mpl Adjuvant And Rc529, Are Efficient Adjuvants For Cd4+ T Cells. J Leukoc Biol 78:1273-1280.
5. Salkowski, C. A., G. R. Detore, And S, N. Vogel. 1997. Lipopolysaccharide And Monophosphoryl Lipid A Differentially Regulate Interleukin-12, Gamma Interferon, And Interleukin-10 Mrna Production In Murine Macrophages. Infect Immun 65:3239-3247.
6. Beutler, B. 2004. Inferences, Questions And Possibilities In Toll-Like Receptor Signalling. Nature 430:257-263.
7. Wefts, C., S. E. Girardin, And D. J. Philpott. 2006. Tir, Card And Pyrin: Three Domains For An Antimicrobial Triad. Cell Death Differ 13:798-815.
8. Kagan, J. C., And R. Medzhitov. 2006. Phosphoinositide-Mediated Adaptor Recruitment Controls Toll-Like Receptor Signaling. Cell 125:943-955.

Example 10

Drug-Dependent Induction of NF-Kappa B Activityin Cells Transfected with iRIG-I, iCD40, and iNOD2

293 cells were transfected with 1 microgram NF-KappaB-SEAP reporter construct+1 microgram inducible PRR construct using Fugene 6 transfection reagent. The transfections were performed in a 6-well plate at $1*10^6$ cells/well or transfection.

Jurkat TAg cells were transfected with 2 micrograms NF-kappa B-SEAP reporter construct and 3 micrograms inducible PRR construct using electroporation at 950 microF and 0.25 kV. The cells were transfected at $10*10^6$ cells/transfection.

24 hours later, the cells were plated in a 96-well plate with 2 different concentrations of AP20187 (100 nM and 1000 nM). After a further 24 hour incubation at 37° C., 5% $CO_2$, supernatants were collected and analyzed for SEAP activity by incubation with SEAP substrate, 4-methylumbilliferyl phosphate (MUP). Fluorescence was determined at excitation 355 nm and emission 460 nm using a FLUOstar Optima plate reader (BMG Labtech).

For iNOD2 and combination experiments, transfections were normalized for total DNA using an "empty" expression vector, pSH1/S-Fv'-Fvls-E.

FIGS. 31-34 are graphs that show drug-dependent induction of NF-kappaB activity and SEAP reporter counts. Each graph is representative of a separate individual experiment.

For purposes of clarity in the graphs, some of the vectors were renamed for the figures.
Fv'RIG-I=pSH1-Fv'Fvls-RIG-I=pSH1/S-Fv'-Fvls-RIG-I
Fv'NOD2=pSH1-Fv'Fvls-NOD2=pSH1/S-Fv'-Fvls-NOD2-E
Fv'2NOD2=pSH1-Fv'2Fvls-NOD2
Fv'NOD2+=pSH1-Fv'Fvls-NOD2 (SFpk3-NOD2 sequence (Ogura, Y., et al. J. Biol. Chem. 276:4812-18 (2001))
Fv'CD40=pSH1-Fv'Fvls-CD40

Example 11

Examples of Particular Embodiments

Examples of certain non-limiting embodiments of the invention are listed hereafter.

A1. A method for activating an antigen-presenting cell, which comprises:
(a) transducing an antigen-presenting cell with a nucleic acid having a nucleotide sequence that encodes a chimeric protein, wherein the chimeric protein comprises a membrane targeting region, a ligand-binding region and a CD40 cytoplasmic polypeptide region lacking the CD40 extracellular domain;
(b) contacting the antigen-presenting cell with a non-protein multimeric ligand that binds to the ligand-binding region; and
(c) contacting the antigen-presenting cell with a Pattern Recognition Receptor (PRR) ligand, whereby the antigen-presenting cell is activated.

A2. The method of embodiment A1, wherein the membrane targeting region is a myristoylation targeting region.

A3. The method of embodiment A1, wherein the CD40 cytoplasmic polypeptide region is encoded by a polynucleotide sequence in SEQ ID NO: 1.

A4. The method of embodiment A1, wherein the multimeric ligand is a small molecule.

A5. The method of embodiment A4, wherein the multimeric ligand is dimeric.

A6. The method of embodiment A5, wherein the multimeric ligand is a dimeric FK506 or a dimeric FK506 analog.

A7. The method of embodiment A6, wherein the multimeric ligand is AP1903.

A8. The method of any of embodiments A1-A7, A15-A22, wherein the PRR ligand is selected from the group consisting of RIG1 ligand, Mac-1 ligand, LRP ligand, peptidoglycan ligand, techoic acid ligand, CD11c/CR4 ligand, TLR ligand, PGRP ligand, NOD1 ligand, and NOD2 ligand.

A9. The method of any of embodiments A1-A7, A15-A22, wherein the PRR ligand is a Toll like receptor (TLR) ligand.

A10. The method of any of embodiments A1-A7, A15-A22, wherein the PRR ligand is RIG1 ligand or NOD2 ligand.

A11. The method of embodiment A9, wherein the TLR ligand is selected from the group consisting of lipopolysaccharide (LPS), MPL, FSL-1, Pam3, CSK4, poly(I:C), synthetic imidazoquinoline resiquimod (R848) and CpG.

A12. The method of embodiment A9, wherein the TLR ligand is a TLR4 ligand.

A13. The method of embodiment A12, wherein the TLR ligand is lipopolysaccharide (LPS).

A14. The method of embodiment A12 wherein the TLR ligand is monophosphoryl lipid A (MPL).

A15. The method of embodiment A1, wherein the nucleic acid is contained within a viral vector.

A16. The method of embodiment A15, wherein the viral vector is an adenoviral vector.

A17. The method of embodiment A1, wherein the antigen-presenting cell is transduced with the nucleic acid ex vivo.

A18. The method of embodiment A1, wherein the antigen-presenting cell is transduced with the nucleic acid in vivo.

A19. The method of embodiment A1, wherein the antigen-presenting cell is a dendritic cell.

A20. The method of embodiment A19, wherein the dendritic cell is a human dendritic cell.

A21. The method of embodiment A1, wherein the antigen-presenting cell is not contacted with prostaglandin $E_2$ ($PGE_2$) when contacted with the multimeric ligand.

A22. The method of embodiment A1, wherein the antigen-presenting cell is not contacted with a composition comprising prostaglandin $E_2$ ($PGE_2$) and one or more components selected from the group consisting of IL-1beta, IL-6 and TNF alpha.

B1. A method for activating an antigen-presenting cell, which comprises:
(a) transducing an antigen-presenting cell with a nucleic acid having a nucleotide sequence that encodes a chimeric protein, wherein the chimeric protein comprises a membrane targeting region, a ligand-binding region and a CD40 cytoplasmic polypeptide region lacking the CD40 extracellular domain; and (b) contacting the antigen-presenting cell with a non-protein multimeric ligand that binds to the ligand-binding region, wherein the antigen-presenting cell is not contacted with prostaglandin $E_2$ ($PGE_2$) when contacted with the multimeric ligand, whereby the antigen-presenting cell is activated.

B2. The method of embodiment B1, wherein the membrane targeting region is a myristoylation targeting region.

B3. The method of embodiment B1, wherein the CD40 cytoplasmic polypeptide region is encoded by a polynucleotide sequence in SEQ ID NO: 1.

B4. The method of embodiment B1, wherein the multimeric ligand is a small molecule.

B5. The method of embodiment B4, wherein the multimeric ligand is dimeric.

B6. The method of embodiment B5, wherein the multimeric ligand is a dimeric FK506 or a dimeric FK506 analog.

B7. The method of embodiment B6, wherein the multimeric ligand is AP1903.

B8. The method of any of embodiments B1-B7, B13-B22, which further comprises contacting the antigen-presenting cell with a Pattern Recognition Receptor (PRR) ligand.

B9. The method of embodiment B8, wherein the PRR ligand is selected from the group consisting of RIG1 ligand, Mac-1 ligand, LRP ligand, peptidoglycan ligand, techoic acid ligand, CD11c/CR4 ligand, TLR ligand, PGRP ligand, NOD1 ligand, and NOD2 ligand.

B10. The method of embodiment B8, wherein the PRR ligand is RIG1 ligand or NOD2 ligand.

B11. The method of embodiment B8, wherein the PRR ligand is a TLR ligand.

B12. The method of embodiment B11, wherein the TLR ligand is selected from the group consisting of lipopolysaccharide (LPS), MPL, FSL-1, Pam3, CSK4, poly(I:C), synthetic imidazoquinoline resiquimod (R848) and CpG.

B13. The method of embodiment B11, wherein the TLR ligand is a TLR4 ligand.

B14. The method of embodiment B12, wherein the TLR ligand is lipopolysaccharide (LPS).

B15. The method of embodiment B13, wherein the TLR ligand is monophosphoryl lipid A (MPL).

B16. The method of embodiment B1, wherein the nucleic acid is contained within a viral vector.

B17. The method of embodiment B16, wherein the viral vector is an adenoviral vector.

B18. The method of embodiment B1, wherein the antigen-presenting cell is transduced ex vivo with the nucleic acid.

B19. The method of embodiment B1, wherein the antigen-presenting cell is transduced in vivo with the nucleic acid.

B20. The method of embodiment B1, wherein the antigen-presenting cell is a dendritic cell.

B21. The method of embodiment B20, wherein the dendritic cell is a human dendritic cell.

B22. The method of embodiment B1, wherein the antigen-presenting cell is not contacted with a composition comprising prostaglandin $E_2$ ($PGE_2$) and one or more components selected from the group consisting of IL-1beta, IL-6 and TNF alpha.

C1. A method for inducing a cytotoxic T lymphocyte (CTL) immune response against an antigen, which comprises: contacting an antigen-presenting cell sensitized with an antigen with:
  (a) a multimeric ligand that binds to a chimeric protein in the cell, wherein the chimeric protein comprises a membrane targeting region, a ligand-binding region and a CD40 cytoplasmic polypeptide region lacking the CD40 extracellular domain, and
  (b) a Pattern Recognition receptor (PRR) ligand; whereby a CTL immune response is induced against the antigen.

C2. The method of embodiment C1, wherein the membrane targeting region is a myristoylation targeting region.

C3. The method of embodiment C1, wherein the CD40 cytoplasmic polypeptide region is encoded by a polynucleotide sequence in SEQ ID NO: 1.

C4. The method of embodiment C1, wherein the multimeric ligand is a small molecule.

C5. The method of embodiment C4, wherein the multimeric ligand is dimeric.

C6. The method of embodiment C5, wherein the multimeric ligand is a dimeric FK506 or a dimeric FK506 analog.

C7. The method of embodiment C6, wherein the multimeric ligand is AP1903.

C8. The method of any of embodiments C1-C7, C15-C30, wherein the PRR ligand is selected from the group consisting of RIG1 ligand, Mac-1 ligand, LRP ligand, peptidoglycan ligand, techoic acid ligand, CD11c/CR4 ligand, TLR ligand, PGRP ligand, NOD1 ligand, and NOD2 ligand.

C9. The method of any of embodiments C1-C7, C15-C30, wherein the PRR ligand is a Toll like receptor (TLR) ligand.

C10. The method of any of embodiments C1-C7, C15-C30, wherein the PRR ligand is RIG1 ligand or NOD2 ligand.

C11. The method of embodiment C1, wherein the TLR ligand is selected from the group consisting of lipopolysaccharide (LPS), MPL, FSL-1, Pam3, CSK4, poly(I:C), synthetic imidazoquinoline resiquimod (R848) and CpG.

C12. The method of embodiment C9, wherein the TLR ligand is a TLR4 ligand.

C13. The method of embodiment C12, wherein the TLR ligand is lipopolysaccharide (LPS).

C14. The method of embodiment C12, wherein the TLR ligand is monophosphoryl lipid A (MPL).

C15. The method of embodiment C1, wherein the antigen-presenting cell is transduced ex vivo or in vivo with a nucleic acid that encodes the chimeric protein.

C16. The method of embodiment C15, wherein the antigen-presenting cell is transduced ex vivo with the nucleic acid.

C17. The method of embodiment C15, wherein the nucleic acid is contained within a viral vector.

C18. The method of embodiment C16, wherein the viral vector is an adenoviral vector.

C19. The method of embodiment C1, wherein the antigen-presenting cell is a dendritic cell.

C20. The method of embodiment C16, wherein the dendritic cell is a human dendritic cell.

C21. The method of embodiment C1, wherein the antigen-presenting cell is not contacted with prostaglandin $E_2$ ($PGE_2$) when contacted with the multimeric ligand.

C22. The method of embodiment C1, wherein the antigen-presenting cell is not contacted with a composition comprising prostaglandin $E_2$ ($PGE_2$) and one or more components selected from the group consisting of IL-1beta, IL-6 and TNF alpha.

C23. The method of embodiment C1, wherein the antigen-presenting cell is sensitized to the antigen at the same time the antigen-presenting cell is contacted with the multimeric ligand.

C24. The method of embodiment C1, wherein the antigen-presenting cell is pre-sensitized to the antigen before the antigen-presenting cell is contacted with the multimerization ligand.

C25. The method of embodiment C1, wherein the antigen-presenting cell is contacted with the antigen ex vivo.

C26. The method of embodiment C1, wherein the antigen is a tumor antigen.

C27. The method of embodiment C1, wherein the antigen-presenting cell is transduced with the nucleic acid ex vivo and administered to the subject by intradermal administration.

C28. The method of embodiment C1, wherein the antigen-presenting cell is transduced with the nucleic acid ex vivo and administered to the subject by subcutaneous administration.

C29. The method of embodiment C1, wherein the CTL immune response is induced by migration of the antigen-presenting cell to a draining lymph node.

C30. The method of any of embodiments C1-C29, wherein said antigen is a prostate specific membrane antigen.

D1. A method for inducing an immune response against an antigen, which comprises: contacting an antigen-presenting cell sensitized with an antigen with a multmeric ligand that binds to a chimeric protein in the cell, wherein:
  (a) the chimeric protein comprises a membrane targeting region, a ligand-binding region and a CD40 cytoplasmic polypeptide region lacking the CD40 extracellular domain, and
  (b) the antigen-presenting cell is not contacted with prostaglandin $E_2$ ($PGE_2$) when contacted with the multimeric ligand; whereby an immune response against the antigen is induced.

D2. The method of embodiment D1, wherein the membrane targeting region is a myristoylation targeting region.

D3. The method of embodiment D1, wherein the CD40 cytoplasmic polypeptide region is encoded by a polynucleotide sequence in SEQ ID NO: 1.

D4. The method of embodiment D1, wherein the multimeric ligand is a small molecule.

D5. The method of embodiment D4, wherein the multimeric ligand is dimeric.

D6. The method of embodiment D5, wherein the multimeric ligand is a dimeric FK506 or a dimeric FK506 analog.

D7. The method of embodiment D6, wherein the multimeric ligand is AP1903.

D8. The method of any of embodiments D1-D7, D13-D30, which further comprises contacting the antigen-presenting cell with a Pattern Recognition receptor (PRR) ligand.

D9. The method of embodiment D8, wherein the PRR ligand is selected from the group consisting of RIG1 ligand, Mac-1 ligand, LRP ligand, peptidoglycan ligand, techoic acid ligand, CD11c/CR4 ligand, TLR ligand, PGRP ligand, NOD1 ligand, and NOD2 ligand.

D10. The method of embodiment D8, wherein the PRR ligand is RIG1 ligand or NOD2 ligand.

D11. The method of embodiment D11, wherein the PRR ligand is a TLR ligand.

D12. The method of embodiment D8, wherein the TLR ligand is selected from the group consisting of lipopolysaccharide (LPS), MPL, FSL-1, Pam3, DSK4, poly(I:D), synthetic imidazoquinoline resiquimod (R848) and DpG.

D13. The method of embodiment D11, wherein the TLR ligand is a TLR4 ligand.

D14. The method of embodiment D13, wherein the TLR ligand is lipopolysaccharide (LPS).

D15. The method of embodiment D13, wherein the TLR ligand is monophosphoryl lipid A (MPL).

D16. The method of embodiment D1, wherein the antigen-presenting cell is transduced ex vivo or in vivo with a nucleic acid that encodes the chimeric protein.

D17. The method of embodiment D16, wherein the antigen-presenting cell is transduced ex vivo with the nucleic acid.

D18. The method of embodiment D16, wherein the nucleic acid is contained within a viral vector.

D19. The method of embodiment D18, wherein the viral vector is an adenoviral vector.

D20. The method of embodiment D1, wherein the antigen-presenting cell is a dendritic cell.

D21. The method of embodiment D20, wherein the dendritic cell is a human dendritic cell.

D22. The method of embodiment D1, wherein the antigen-presenting cell is not contacted with a composition comprising prostaglandin $E_2$ ($PGE_2$) and one or more components selected from the group consisting of IL-1beta, IL-6 and TNF alpha.

D23. The method of embodiment D1, wherein the antigen-presenting cell is sensitized to the antigen at the same time the antigen-presenting cell is contacted with the multimeric ligand.

D24. The method of embodiment D1, wherein the antigen-presenting cell is pre-sensitized to the antigen before the antigen-presenting cell is contacted with the multimerization ligand.

D25. The method of embodiment D1, wherein the antigen-presenting cell is contacted with the antigen ex vivo.

D26. The method of embodiment D1, wherein the antigen is a tumor antigen.

D27. The method of embodiment D1, wherein the antigen-presenting cell is transduced with the nucleic acid ex vivo and administered to the subject by intradermal administration.

D28. The method of embodiment D1, wherein the antigen-presenting cell is transduced with the nucleic acid ex vivo and administered to the subject by subcutaneous administration.

D29. The method of embodiment D1, wherein the immune response is a cytotoxic T-lymphocyte (DTL) immune response.

D30. The method of embodiment D29, wherein the DTL immune response is induced by migration of the antigen-presenting cell to a draining lymph node.

E1. A method for inducing a cytotoxic T lymphocyte (CTL) immune response against an antigen, which comprises: contacting a human antigen-presenting cell sensitized with an antigen with:
  (a) a multimeric molecule having two or more regions that bind to and multimerize native CD40, and
  (b) a Pattern Recognition Receptor (PRR ligand); whereby a CTL immune response is induced against the antigen.

E2. The method of embodiment E1, wherein the multimeric molecule is an antibody that binds to an epitope in the CD40 extracellular domain.

E3. The method of embodiment E1, wherein the multimeric molecule is a CD40 ligand.

E4. The method of embodiment E1, wherein the multimeric ligand is a small molecule.

E5. The method of embodiment E4, wherein the multimeric ligand is dimeric.

E6. The method of embodiment E5, wherein the multimeric ligand is a dimeric FK506 or a dimeric FK506 analog.

E7. The method of embodiment E6, wherein the multimeric ligand is AP1903.

E8. The method of any of embodiments E1-E7, E15-E22, wherein the PRR ligand is selected from the group consisting of RIG1 ligand, Mac-1 ligand, LRP ligand, peptidoglycan ligand, techoic acid ligand, CD11c/CR4 ligand, TLR ligand, PGRP ligand, NOD1 ligand, and NOD2 ligand.

E9. The method of any of embodiments E1-E7, E15-E22, wherein the PRR ligand is a Toll like receptor (TLR) ligand.

E10. The method of any of embodiments E1-E7, E15-E22, wherein the PRR ligand is RIG1 ligand or NOD2 ligand.

E11. The method of embodiment E9, wherein the TLR ligand is selected from the group consisting of lipopolysaccharide (LPS), MPL, FSL-1, Pam3, CSK4, poly(I:C), synthetic imidazoquinoline resiquimod (R848) and CpG.

E12. The method of embodiment E9, wherein the TLR ligand is a TLR4 ligand.

E13. The method of embodiment E12, wherein the TLR ligand is lipopolysaccharide (LPS).

E14. The method of embodiment E12 wherein the TLR ligand is monophosphoryl lipid A (MPL).

E15. The method of embodiment E1, wherein the nucleic acid is contained within a viral vector.

E16. The method of embodiment E15, wherein the viral vector is an adenoviral vector.

E17. The method of embodiment A1, wherein the antigen-presenting cell is transduced with the nucleic acid ex vivo.

E18. The method of embodiment A1, wherein the antigen-presenting cell is transduced with the nucleic acid in vivo.

E19. The method of embodiment A1, wherein the antigen-presenting cell is a dendritic cell.

E20. The method of embodiment A19, wherein the dendritic cell is a human dendritic cell.

E21. The method of embodiment A1, wherein the antigen-presenting cell is not contacted with prostaglandin $E_2$ ($PGE_2$) when contacted with the multimeric ligand.

E22. The method of embodiment A1, wherein the antigen-presenting cell is not contacted with a composition comprising prostaglandin $E_2$ ($PGE_2$) and one or more components selected from the group consisting of IL-1beta, IL-6 and TNF alpha.

E23. The method of embodiment E1, wherein the antigen-presenting cell is sensitized to the antigen at the same time the antigen-presenting cell is contacted with the multimeric ligand.

E24. The method of embodiment E1, wherein the antigen-presenting cell is pre-sensitized to the antigen before the antigen-presenting cell is contacted with the multimerization ligand.

E25. The method of embodiment E1, wherein the antigen-presenting cell is contacted with the antigen ex vivo.

E26. The method of embodiment E1, wherein the antigen is a tumor antigen.

E27. The method of embodiment E1, wherein the antigen-presenting cell is transduced with the nucleic acid ex vivo and administered to the subject by intradermal administration.

E28. The method of embodiment E1, wherein the antigen-presenting cell is transduced with the nucleic acid ex vivo and administered to the subject by subcutaneous administration.

E29. The method of embodiment E1, wherein the CTL immune response is induced by migration of the antigen-presenting cell to a draining lymph node.

E30. The method of any of embodiments E1-E29, wherein said antigen is a prostate specific membrane antigen.

F1. A composition comprising an antigen-presenting cell and a Pattern Recognition Receptor (PRR) ligand, wherein:
the antigen-presenting cell is transduced with a nucleic acid having a nucleotide sequence that encodes a chimeric protein, and
the chimeric protein comprises a membrane targeting region, a ligand-binding region and a CD40 cytoplasmic polypeptide region lacking the CD40 extracellular domain.

F2. The composition of embodiment F1, which further comprises a non-protein multimeric ligand that binds to the ligand-binding region.

F3. The method of embodiment F1, wherein the membrane targeting region is a myristoylation targeting region.

F4. The method of embodiment F1, wherein the CD40 cytoplasmic polypeptide region is encoded by a polynucleotide sequence in SEQ ID NO: 1.

F5. The method of embodiment F2, wherein the multimeric ligand is a small molecule.

F6. The method of embodiment F2, wherein the multimeric ligand is dimeric.

F7. The method of embodiment F6, wherein the multimeric ligand is a dimeric FK506 or a dimeric FK506 analog.

F8. The method of embodiment F2, wherein the multimeric ligand is AP1903.

F9. The method of any of embodiments F1-F8, F15-F27, wherein the PRR ligand is selected from the group consisting of RIG1 ligand, Mac-1 ligand, LRP ligand, peptidoglycan ligand, techoic acid ligand, CD11c/CR4 ligand, TLR ligand, PGRP ligand, NOD1 ligand, and NOD2 ligand.

F10. The method of any of embodiments F1-F8, F15-F27, wherein the PRR ligand is a Toll like receptor (TLR) ligand.

F11. The method of any of embodiments F1-F8, F15-F27, wherein the PRR ligand is RIG1 ligand or NOD2 ligand.

F12. The method of embodiment F10, wherein the TLR ligand is selected from the group consisting of lipopolysaccharide (LPS), MPL, FSL-1, Pam3, CSK4, poly(I:C), synthetic imidazoquinoline resiquimod (R848) and CpG.

F13. The method of embodiment F10, wherein the TLR ligand is a TLR4 ligand.

F14. The method of embodiment F13, wherein the TLR ligand is lipopolysaccharide (LPS).

F15. The method of embodiment F13 wherein the TLR ligand is monophosphoryl lipid A (MPL).

F16. The method of embodiment F1, wherein the nucleic acid is contained within a viral vector.

F17. The method of embodiment F16, wherein the viral vector is an adenoviral vector.

F18. The method of embodiment F1, wherein the antigen-presenting cell is transduced with the nucleic acid ex vivo.

F19. The method of embodiment F1, wherein the antigen-presenting cell is transduced with the nucleic acid in vivo.

F20. The method of embodiment F1, wherein the antigen-presenting cell is a dendritic cell.

F21. The method of embodiment F20, wherein the dendritic cell is a human dendritic cell.

F22. The method of embodiment F1, wherein the antigen-presenting cell is not contacted with prostaglandin $E_2$ ($PGE_2$) when contacted with the multimeric ligand.

F23. The method of embodiment F1, wherein the antigen-presenting cell is not contacted with a composition comprising prostaglandin $E_2$ ($PGE_2$) and one or more components selected from the group consisting of IL-1beta, IL-6 and TNF alpha.

F24. The method of embodiment F1, wherein the antigen is a tumor antigen.

F25. The method of embodiment F1, wherein the antigen-presenting cell is transduced with the nucleic acid ex vivo and administered to the subject by intradermal administration.

F26. The method of embodiment F1, wherein the antigen-presenting cell is transduced with the nucleic acid ex vivo and administered to the subject by subcutaneous administration.

F27. The method of any of embodiments F1-F26, wherein said antigen is a prostate specific membrane antigen.

G1. A method for assessing migration of an antigen-presenting cell to a lymph node, which comprises:
(a) injecting into a subject an antigen-presenting cell that produces a detectable protein, and
(b) determining the amount of the detectable protein in the lymph node of the animal, whereby migration of the antigen-presenting cell to the lymph node is assessed from the amount of the detectable protein in the lymph node.

G2. The method of embodiment G1, wherein the animal is a rodent.

G3. The method of embodiment G2, wherein the rodent is a mouse.

G4. The method of embodiment G3, wherein the mouse is an irradiated mouse.

G5. The method of embodiment G1, wherein the detectable protein is a luciferase protein.

G6. The method of embodiment G5, wherein the luciferase protein is from a chick beetle.

G7. The method of embodiment G6, wherein the chick beetle is Pyrophorus plagiophalamus.

G8. The method of embodiment G1, wherein the antigen-presenting cell has been transduced with a nucleic acid having a polynucleotide sequence that encodes the detectable protein.

G9. The method of embodiment G6, wherein the amount of the luciferase protein is determined by administering D-Luciferin to the animal and detecting the D-Luciferin product generated by the luciferase.

G10. The method of embodiment G1, wherein the lymph node is the popliteal lymph node.

G11. The method of embodiment G1, wherein the lymph node is the inguinal lymph node.

G12. The method of embodiment G1, wherein the antigen-presenting cell is a dendritic cell.

G13. The method of embodiment G12, wherein the dendritic cell is a human dendritic cell.

G14. The method of embodiment G1, wherein the lymph node is removed from the animal before the amount of detectable protein is determined G15. The method of embodiment G5, wherein the luciferase is a red-shifted luciferase protein.

H1. A method for activating an antigen-presenting cell, which comprises:
transducing an antigen-presenting cell with a nucleic acid having a nucleotide sequence that encodes a chimeric protein, wherein the chimeric protein comprises (i) a membrane targeting region, (ii) a ligand-binding region and (iii-a) a signaling region and/or cytoplasmic region of a pattern recognition receptor (PRR) or (iii-b) an adapter of a PRR; and
contacting the antigen-presenting cell with a non-protein multimeric ligand that binds to the ligand-binding region;
whereby the antigen-presenting cell is activated.

H2. The method of embodiment H1, wherein the chimeric protein comprises a CD40 cytoplasmic polypeptide region lacking the CD40 extracellular domain. H2.1. The method of embodiment H1 or H2, wherein the chimeric protein comprises a signaling region and/or cytoplasmic region of a PRR.

H3. The method of embodiment H2.1, wherein the PRR is a NOD-like PRR.

H4. The method of embodiment H3, wherein the NOD-like PRR is a NOD1 PRR.

H5. The method of embodiment H3, wherein the NOD-like PRR is a NOD2 PRR.

H6. The method of embodiment H1 or H2, wherein the PRR is not a NOD-like PRR.

H7. The method of embodiment H6, wherein the NOD-like PRR is not a NOD1 PRR.

H8. The method of embodiment H6, wherein the NOD-like PRR is not a NOD2 PRR.

H9. The method of any one of embodiments H1-H3 and H6-H8, wherein the PRR is a RIG-like helicase (RLH).

H10. The method of embodiment H9, wherein the RLH is a RIG-I PRR.

H11. The method of embodiment H9, wherein the RLH is a Mda-5 PRR.

H12. The method of any one of embodiments H1-H3 and H6-H8, wherein the PRR is a Toll-like receptor (TLR) PRR.

H13. The method of embodiment H12, wherein the TLR is selected from the group consisting of TLR3, TLR4, TLR7, TLR8 and TLR9.

H14. The method of embodiment H13, wherein the TLR is a TLR4.

H15. The method of embodiment H13, wherein the TLR is a TLR8.

H16. The method of embodiment H13, wherein the TLR is a TLR9.

H17. The method of any one of embodiments H12-H14, wherein the chimeric protein comprises a cytoplasmic region from a TLR PRR.

H18. The method of embodiment H17, wherein the chimeric protein comprises a TIR domain.

H19. The method of embodiment H18, wherein the chimeric protein consists essentially of a TIR domain.

H20. The method of embodiment H1 or H2, wherein the chimeric protein comprises an adapter that binds to a PRR of any one of embodiments H2-H14.

H21. The method of embodiment H20, wherein the adaptor is selected from the group consisting of MyD88, TRIF/TICAM-1, TIRAM/ICAM-2, MAL/TIRAP, TIR and CARD.

H22. The method of any one of embodiments H1-H21, wherein the membrane targeting region is a myristoylation targeting region.

H23. The method of embodiment H2, wherein the CD40 cytoplasmic polypeptide region is encoded by a polynucleotide sequence in SEQ ID NO: 1.

H24. The method of any one of embodiments H1-H23, wherein the ligand is a small molecule.

H25. The method of any one of embodiments H1-H24, wherein the ligand is dimeric.

H26. The method of embodiment H25, wherein the ligand is a dimeric FK506 or a dimeric FK506 analog.

H27. The method of embodiment H26, wherein the ligand is AP1903.

H28. The method of any one of embodiments H1-H27, wherein the nucleic acid is contained within a viral vector.

H29. The method of embodiment H28, wherein the viral vector is an adenoviral vector.

H30. The method of any one of embodiments H1-H29, wherein the antigen-presenting cell is contacted with an antigen.

H31. The method of embodiment H30, wherein the antigen-presenting cell is contacted with the antigen ex vivo.

H32. The method of embodiment H30 or H31, wherein the antigen-presenting cell is in a subject and an immune response is generated against the antigen.

H33. The method of embodiment H32, wherein the immune response is a cytotoxic T-lymphocyte (CTL) immune response.

H34. The method of embodiment H32 or H33, wherein the immune response is generated against a tumor antigen.

H35. The method of any one of embodiments H1-H34, wherein the antigen-presenting cell is transduced with the nucleic acid ex vivo and administered to the subject by intradermal administration.

H36. The method of any one of embodiments H1-H34, wherein the antigen-presenting cell is transduced with the nucleic acid ex vivo and administered to the subject by subcutaneous administration.

H37. The method of any one of embodiments H1-H34, wherein the antigen-presenting cell is transduced with the nucleic acid ex vivo.

H38. The method of any one of embodiments H1-H30, wherein the antigen-presenting cell is transduced with the nucleic acid in vivo.

H39. The method of any one of embodiments H1-H38, wherein the antigen-presenting cell is a dendritic cell.

H40. The method of any one of embodiments H1-H39, wherein the nucleic acid comprises a promoter sequence operably linked to the polynucleotide sequence.

I1. A composition which comprises a nucleic acid having a polynucleotide sequence that encodes a chimeric protein, wherein the chimeric protein comprises (i) a membrane targeting region, (ii) a ligand-binding region that binds to a multimeric non-protein ligand, and (iii-a) a signaling region and/or cytoplasmic region of a pattern recognition receptor (PRR) or (iii-b) an adapter of a PRR.

I2. The composition of embodiment I1, wherein the chimeric protein comprises a CD40 cytoplasmic polypeptide region lacking the CD40 extracellular domain.

I2.1. The method of embodiment I1 or I2, wherein the chimeric protein comprises a signaling region and/or cytoplasmic region of a PRR.

I3. The composition of embodiment I2.1, wherein the PRR is a NOD-like PRR.

I4. The composition of embodiment I3, wherein the NOD-like PRR is a NOD1 PRR.

I5. The composition of embodiment I3, wherein the NOD-like PRR is a NOD2 PRR.

I6. The composition of embodiment I1 or I2, wherein the PRR is not a NOD-like PRR.

I7. The composition of embodiment B6, wherein the NOD-like PRR is not a NOD1 PRR.

I8. The composition of embodiment B6, wherein the NOD-like PRR is not a NOD2 PRR.

I9. The composition of any one of embodiments I1-I3 and B6-B8, wherein the PRR is a RIG-like helicase (RLH).

I10. The composition of embodiment B9, wherein the RLH is a RIG-I PRR.

I11. The composition of embodiment B9, wherein the RLH is a Mda-5 PRR.

I12. The composition of any one of embodiments I1-I3 and B6-B8, wherein the PRR is a Toll-like receptor (TLR) PRR.

I13. The composition of embodiment I12, wherein the TLR is selected from the group consisting of TLR3, TLR4, TLR7, TLR8 and TLR9.

I14. The composition of embodiment I13, wherein the TLR is a TLR4.

I15. The composition of embodiment I13, wherein the TLR is a TLR3.

I16. The composition of embodiment I13, wherein the TLR is a TLR7.

I17. The composition of any one of embodiments I12-I14, wherein the chimeric protein comprises a cytoplasmic region from a TLR PRR.

I18. The composition of embodiment I17, wherein the chimeric protein comprises a TIR domain.

I19. The composition of embodiment I18, wherein the chimeric protein consists essentially of a TIR domain.

I20. The composition of embodiment I1 or I2, wherein the chimeric protein comprises an adapter binds to a PRR of any one of embodiments I2-I14.

I21. The composition of embodiment I20, wherein the adaptor is selected from the group consisting of MyD88, TRIF/TICAM-1, TIRAM/ICAM-2, MAL/TIRAP, TIR and CARD.

I22. The composition of any one of embodiments I1-I21, wherein the membrane targeting region is a myristoylation targeting region.

I23. The composition of embodiment I2, wherein the CD40 cytoplasmic polypeptide region is encoded by a polynucleotide sequence in SEQ ID NO: 1.

I24. The composition of embodiment I1, wherein the membrane targeting region is a myristoylation targeting region.

I25. The composition of embodiment I2, wherein the CD40 cytoplasmic polypeptide region is encoded by a polynucleotide sequence in SEQ ID NO: 1.

I26. The composition of any one of embodiments I1-I25, wherein the ligand is a small molecule.

I27. The composition of embodiment I26, wherein the ligand is dimeric.

I28. The composition of embodiment I27, wherein the ligand is a dimeric FK506 or a dimeric FK506 analog.

I29. The composition of embodiment I28, wherein the ligand is AP1903.

I30. The composition of any one of embodiments I1-I29, wherein the nucleic acid is contained within a viral vector.

I31. The composition of embodiment I30, wherein the viral vector is an adenoviral vector.

I32. The composition of any one of embodiments I1-I31, wherein the nucleic acid comprises a promoter sequence operably linked to the polynucleotide sequence.

Example 12

Examples of Particular Nucleic Acid and Amino Acid Sequences

```
(nucleic acid sequence encoding human CD40;
Genbank accession no. NM_001250)
                                      SEQ ID NO: 1
   1 gccaaggctg gggcagggga gtcagcagag gcctcgctcg ggcgcccagt ggtcctgccg 61 cctggtctca cctcgctatg gttcgtctgc ctctgcagtg cgtcctctgg ggctgcttgc 121 tgaccgctgt ccatccagaa ccacccactg catgcagaga aaaacagtac ctaataaaca 181 gtcagtgctg ttctttgtgc cagccaggac agaaactggt gagtgactgc acagagttca 241 ctgaaacgga atgccttcct tgcggtgaaa gcgaattcct agacacctgg aacagagaga 301 cacactgcca ccagcacaaa tactgcgacc ccaacctagg gcttcgggtc cagcagaagg 361 gcacctcaga aacagacacc atctgcacct gtgaagaagg ctggcactgt acgagtgagg 421 cctgtgagag ctgtgtcctg caccgctcat gctcgcccgg ctttggggtc aagcagatt g
```

```
  481 ctacaggggt tctgatacc atctgcgagc cctgcccagt
cggcttcttc tccaatgtgt 541 catctgcttt cgaaaaatgt caccccttgga caagctgtga
gaccaaagac ctggttgtgc 601 aacaggcagg cacaaacaag actgatgttg tctgtggtcc
ccaggatcgg ctgagagccc 661 tggtggtgat cccatcatc ttcgggatcc tgtttgccat
cctcttggtg ctggtctttta 721 tcaaaaaggt ggccaagaag ccaaccaata aggcccccca
ccccaagcag gaaccccagg 781 agatcaattt tcccgacgat cttcctggct ccaacactgc
tgctccagtg caggagactt 841 tacatggatg ccaaccggtc acccaggagg atggcaaaga
gagtcgcatc tcagtgcagg 901 agagacagta aggctgcacc cacccaggag tgtggccacg
tgggcaaaca ggcagttggc 961 cagagagcct ggtgctgctg ctgctgtggc gtgagggtga
ggggctggca ctgactgggc 1021 atagctcccc gcttctgcct gcacccctgc agtttgagac
aggagacctg gcactggatg 1081 cagaaacagt tcaccttgaa gaacctctca cttcaccctg
gagcccatcc agtctcccaa 1141 cttgtattaa agacagaggc agaagtttgg tggtggtggt
gttggggtat ggtttagtaa 1201 tatccaccag accttccgat ccagcagttt ggtgcccaga
gaggcatcat ggtggcttcc 1261 ctgcgcccag gaagccatat acacagatgc ccattgcagc
attgtttgtg atagtgaaca 1321 actggaagct gcttaactgt ccatcagcag gagactggct
aaataaaatt gaatatatt 1381 tatacaacag aatctcaaaa acactgttga gtaaggaaaa
aaaggcatgc tgctgaatga 1441 tgggtatgga acttttttaaa aaagtacatg cttttatgta
tgtatattgc ctatggatat 1501 atgtataaat acaatatgca tcatatattg atataacaag
ggttctggaa gggtacacag 1561 aaaacccaca gctcgaagag tggtgacgtc tggggtgggg
aagaagggtc tggggg (amino acid sequence encoding human CD40)
                                      SEQ ID NO: 2
MVRLPLQCVLWGCLLTAVHPEPPTACREKQYLINSQCCSLCQPGQKLV
SDCTEFTETECLPCGESEFLDTWNRETHCHQHKYCDPNLGLRVQQKGT
SETDTICTCEEGWHCTSEACESCVLHRSCSPGFGVKQIATGVSDTICE
PCPVGFFSNVSSAFEKCHPWTSCETKDLVVQQAGTNKTDVVCGPQDRL
RALVVIPIIFGILFAILLVLVFIKKVAKKPTNKAPHPKQEPQEINFPD
DLPGSNTAAPVQETLHGCQPVTQEDGKESRISVQERQ (nucleotide sequence encoding PSMA)
                                      SEQ ID NO: 3
gcggatccgc atcatcatca tcatcacagc tccggaatcg agggacgt ggtaaatcct ccaatgaagc tactaacatt actccaaagc ataatatg aaagcatttt tggatgaatt gaaagctgag aacatcaaga agttctta tataatttta cacagatacc acatttagca ggaacagaac aaaacttt cagcttgcaa agcaaattca atcccagtgg aaagaatttg gcctggat tctgttgagc tagcacatta tgatgtcctg ttgtcctacc caaataag actcatccaa ctacatctca ataattaatg aagatggaaa tgagatt ttcaacacat cattatttga accacctcct ccaggatatg aaaatgtt tcggatattg taccaccttt cagtgctttc tctcctcaag gaatgcca gagggcgatc tagtgtatgt taactatgca cgaactgaag acttctttt aaattggaac gggacatgaa aatcaattgc tctgggaaaa ttgtaatt gccagatatg ggaaagtttt cagaggaaat aaggttaaaa atgcccag ctggcagggg ccaaaggagt cattctctac tccgaccctg ctgactac tttgctcctg gggtgaagtc ctatccagat ggttggaatc ttcctgga ggtggtgtcc agcgtggaaa tatcctaaat ctgaatggtg caggagac cctctcacac caggttaccc agcaaatgaa tatgcttata ggcgtgga attgcagagg ctgttggtct tccaagtatt cctgttcatc caattgga tactatgatg cacagaagct cctagaaaaa atgggtggct cagcacca ccagatagca gctggagagg aagtctcaaa gtgccctaca atgttgga cctggctttac tggaaacttt tctacacaaa aagtcaagat gcacatc cactctacca atgaagtgac aagaattaca atgtgatagg tactctc agaggagcag tggaaccaga cagatatgtc attctgggag gtcaccgg gactcatggg tgtttggtgg tattgaccct cagagtggag cagctgtt gttcatgaaa ttgtgaggag ctttggaaca ctgaaaagga agggtgg agacctagaa gaacaatttt gtttgcaagc tgggatgcag aagaattt ggtcttcttg gttctactga gtgggcagag gagaattcaa gactcctt caagagcgtg gcgtggctta tattaatgct gactcatcta tagaagga aactacactc tgagagttga ttgtacaccg ctgatgtaca gcttggta cacaacctaa caaaagagct gaaaagccct gatgaaggct ttgaaggc aaatctcttt atgaaagttg gactaaaaaa gtcctttccc cagagttc agtggcatgc ccaggataag caaattggga tctggaaatg attttgag gtgttcttcc aacgacttgg aattgcttca ggcagagcac ggtatact aaaaattggg aaacaaacaa attcagcggc tatccactgt atcacagt gtctatgaaa catatgagtt ggtggaaaag ttttatgatc caatgtttt aaatatcacc tcactgtggc ccaggttcga ggagggatgg tgtttgag
```

```
ctagccaattccatagtgctcccttttgattgtcgagattatgctgta gttttaagaaagtatgctgacaaaatctacagtatttctatgaaacat ccacaggaaatgaagacatacagtgtatcatttgattcacttttttct gcagtaaagaattttacagaaattgcttccaagttcagtgagagactc caggactttgacaaaagcaagcatgtcatctatgctccaagcagccac aacaagtatgcaggggagtcattcccaggaatttatgatgctctgttt gatattgaaagcaaagtggaccct tccaaggcctggggagaagtgaag agacagatttatgttgcagccttcacagtgcaggcagctgcagagact ttgagtgaagtagcctaagcggccgcatagca (PSMA amino acid sequence encoded by SEQ ID NO: 3)
                                         SEQ ID NO: 4
MWNLLHETDSAVATARRPRWLCAGALVLAGGFFLLGFLFGWFIKSSNE

ATNITPKHNMKAFLDELKAENIKKFLYNFTQIPHLAGTEQNFQLAKQI

QSQWKEFGLDSVELAHYDVLLSYPNKTHPNYISIINEDGNEIFNTSLF

EPPPPGYENVSDIVPPFSAFSPQGMPEGDLVYVNYARTEDFFKLERDM

KINCSGKIVIARYGKVFRGNKVKNAQLAGAKGVILYSDPADYFAPGVK

SYPDGWNLPGGGVQRGNILNLNGAGDPLTPGYPANEYAYRRGIAEAVG

LPSIPVHPIGYYDAQKLLEKMGGSAPPDSSWRGSLKVPYNVGPGFTGN

FSTQKVKMHIHSTNEVTRINVIGTLRGAVEPDRYVILGGHRDSWVFGG

IDPQSGAAVVHEIVRSFGTLKKEGWRPRRTILFASWDAEEFGLLGSTE

WAEENSRLLQERGVAYINADSSIEGNYTLRVDCTPLMYSLVHNLTKEL

KSPDEGFEGKSLYESWTKKSPSPEFSGMPRISKLGSGNDFEVFFQRLG

IASGRARYTKNWETNKFSGYPLYHSVYETYELVEKFYDPMFKYHLTVA

QVRGGMVFELANSIVLPFDCRDYAVVLRKYADKIYSISMKHPQEMKTY

SVSFDSLFSAVKNFTEIASKFSERLQDFDKSKHVIYAPSSHNKYAGES

FPGIYDALFDIESKVDPSKAWGEVKRQIYVAAFTVQAAAETLSEVA
```

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Each of U.S. patent application Ser. No. 10/781,384 filed Feb. 18, 2004 and published as US2004/0209836 on Oct. 21, 2004, entitled "Induced Activation in Dendritic Cells," and U.S. Provisional Application No. 60/803,025 filed May 23, 2006, entitled "Modified Dendritic Cells having Enhanced Survival and Immunogenicity and Related Compositions and Methods" is incorporated by reference herein in its entirety.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following embodiments.

What is claimed is:

1. A method for activating an antigen-presenting cell, which comprises:
   a. transducing an antigen-presenting cell with a nucleic acid comprising a promoter operably linked to a nucleotide sequence that encodes a chimeric protein, wherein the chimeric protein comprises
      (i) a membrane targeting region,
      (ii) a multimeric FKBP ligand-binding region, and
      (iiia) a cytoplasmic region of a pattern recognition receptor (PRR) selected from the group consisting of NOD1 PRR, NOD2 PRR, and RIG-1 PRR or (iiib) MyD88, wherein the chimeric protein is expressed in the antigen-presenting cell; and
   b. contacting the antigen-presenting cell with a non-peptidic multimeric ligand that binds to the multimeric FKBP ligand-binding region;
   whereby the NF-κB pathway is activated and the antigen-presenting cell is activated.

2. The method of claim 1, wherein the chimeric protein comprises a CD40 cytoplasmic polypeptide region lacking the CD40 extracellular domain.

3. The method of claim 1, wherein the chimeric protein comprises a cytoplasmic region of a PRR.

4. The method of claim 1, wherein the PRR is RIG-1 PRR.

5. The method of claim 1, wherein the chimeric protein comprises a TIR domain.

6. The method of claim 1, wherein the antigen-presenting cell is contacted with an antigen.

7. The method of claim 6, wherein said antigen is a tumor antigen.

8. The method of claim 1, wherein the antigen-presenting cell is a dendritic cell.

9. The method of claim 1, wherein the multimeric FKBP ligand binding region is a multimeric FKBP12 ligand binding region.

10. The method of claim 1, wherein the non-peptidic multimeric ligand is an FK506 dimer or a dimeric FK506 analog ligand.

11. The method of claim 10, wherein the ligand is AP1903.

12. The method of claim 9, wherein the multimeric FKBP ligand binding region comprises FKBP12(V36).

13. The method of claim 1, wherein the chimeric protein comprises an additional FKBP ligand binding region.

14. The method of claim 12, wherein the chimeric protein comprises an additional FKBP12(V36) ligand binding region.

* * * * *

UNITED STATES PATENT AND TRADEMARK OFFICE
CERTIFICATE OF CORRECTION

PATENT NO.       : 8,691,210 B2  
APPLICATION NO. : 12/445939  
DATED            : April 8, 2014  
INVENTOR(S)      : Spencer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1291 days.

Signed and Sealed this

Twenty-ninth Day of September, 2015

Michelle K. Lee
*Director of the United States Patent and Trademark Office*

SEQUENCE LISTING

```
<160> NUMBER OF SEQ ID NOS: 37

<210> SEQ ID NO 1
<211> LENGTH: 1616
<212> TYPE: DNA
<213> ORGANISM: Homo sapiens

<400> SEQUENCE: 1
gccaaggctg gggcagggga gtcagcagag gcctcgctcg ggcgcccagt ggtcctgccg      60
cctggtctca cctcgctatg gttcgtctgc ctctgcagtg cgtcctctgg ggctgcttgc     120
tgaccgctgt ccatccagaa ccacccactg catgcagaga aaaacagtac ctaataaaca     180
gtcagtgctg ttctttgtgc cagccaggac agaaactggt gagtgactgc acagagttca     240
ctgaaacgga atgccttcct tgcggtgaaa gcgaattcct agacacctgg aacagagaga     300
cacactgcca ccagcacaaa tactgcgacc ccaacctagg gcttcgggtc cagcagaagg     360
gcacctcaga aacagacacc atctgcacct gtgaagaagg ctggcactgt acgagtgagg     420
cctgtgagag ctgtgtcctg caccgctcat gctcgcccgg ctttggggtc aagcagattg     480
ctacaggggt ttctgatacc atctgcgagc cctgcccagt cggcttcttc tccaatgtgt     540
catctgcttt cgaaaaatgt cacccttgga caagctgtga gaccaaagac ctggttgtgc     600
```

```
aacaggcagg cacaaacaag actgatgttg tctgtggtcc ccaggatcgg ctgagagccc    660
tggtggtgat ccccatcatc ttcgggatcc tgtttgccat cctcttggtg ctggtcttta    720
tcaaaaaggt ggccaagaag ccaaccaata aggccccccca ccccaagcag gaaccccagg   780
agatcaattt tcccgacgat cttcctggct ccaacactgc tgctccagtg caggagactt    840
tacatggatg ccaaccggtc acccaggagg atggcaaaga gagtcgcatc tcagtgcagg    900
agagacagtg aggctgcacc cacccaggag tgtggccacg tgggcaaaca ggcagttggc    960
cagagagcct ggtgctgctg ctgctgtggc gtgagggtga ggggctggca ctgactgggc    1020
atagctcccc gcttctgcct gcacccctgc agtttgagac aggagacctg gcactggatg    1080
cagaaacagt tcaccttgaa gaacctctca cttcaccctg gagcccatcc agtctcccaa    1140
cttgtattaa agacagaggc agaagtttgg tggtggtggt gttggggtat ggtttagtaa    1200
tatccaccag accttccgat ccagcagttt ggtgcccaga gaggcatcat ggtggcttcc    1260
ctgcgcccag gaagccatat acacagatgc ccattgcagc attgtttgtg atagtgaaca    1320
actggaagct gcttaactgt ccatcagcag gagactggct aaataaaatt agaatatatt    1380
tatacaacag aatctcaaaa acactgttga gtaaggaaaa aaaggcatgc tgctgaatga    1440
tgggtatgga acttttttaaa aaagtacatg cttttatgta tgtatattgc ctatggatat    1500
atgtataaat acaatatgca tcatatattg atataacaag ggttctggaa gggtacacag    1560
aaaacccaca gctcgaagag tggtgacgtc tggggtgggg aagaagggtc tggggg        1616

<210> SEQ ID NO 2
<211> LENGTH: 277
<212> TYPE: PRT
<213> ORGANISM: Homo sapiens

<400> SEQUENCE: 2

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
```

```
                195                 200                 205
Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
                260                 265                 270

Val Gln Glu Arg Gln
        275

<210> SEQ ID NO 3
<211> LENGTH: 2096
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gcggatccgc atcatcatca tcatcacagc tccggaatcg agggacgtgg taaatcctcc     60
aatgaagcta ctaacattac tccaaagcat aatatgaaag cattttttgga tgaattgaaa    120 gctgagaaca tcaagaagtt cttatataat tttacacaga taccacattt agcaggaaca    180
gaacaaaact ttcagcttgc aaagcaaatt caatcccagt ggaaagaatt tggcctggat    240
tctgttgagc tagcacatta tgatgtcctg ttgtcctacc caaataagac tcatcccaac    300
tacatctcaa taattaatga agatggaaat gagattttca acacatcatt atttgaacca    360
cctcctccag gatatgaaaa tgtttcggat attgtaccac ctttcagtgc tttctctcct    420
caaggaatgc cagagggcga tctagtgtat gttaactatg cacgaactga agacttcttt    480
aaattggaac gggacatgaa aatcaattgc tctgggaaaa ttgtaattgc cagatatggg    540
aaagttttca gaggaaataa ggttaaaaat gcccagctgg caggggccaa aggagtcatt    600
ctctactccg accctgctga ctactttgct cctggggtga gtccatatcc agatggttgg    660
aatcttcctg gaggtggtgt ccagcgtgga aatatcctaa atctgaatgg tgcaggagac    720
cctctcacac aggttacccc agcaaatgaa tatgcttata ggcgtggaat tgcagaggct    780
gttggtcttc caagtattcc tgttcatcca attggatact atgatgcaca gaagctccta    840
gaaaaaatgg gtggctcagc accaccagat agcagctgga gaggaagtct caaagtgccc    900
tacaatgttg gacctggctt tactggaaac ttttctacac aaaaagtcaa gatgcacatc    960
cactctacca atgaagtgac aagaatttac aatgtgatag tactctcag aggagcagtg   1020 gaaccagaca gatatgtcat tctgggaggt caccgggact catgggtgtt tggtggtatt   1080
gaccctcaga gtgagcagc tgttgttcat gaaattgtga ggagctttgg aacactgaaa    1140
aaggaagggt ggagacctag aagaacaatt tgtttgcaa gctgggatgc agaagaattt    1200
ggtcttcttg gttctactga gtgggcagag gagaattcaa gactccttca agagcgtggc   1260
gtggcttata ttaatgctga ctcatctata gaaggaaact acactctgag agttgattgt    1320
acaccgctga tgtacagctt ggtacacaac ctaacaaaag agctgaaaag ccctgatgaa    1380
ggctttgaag gcaaatctct ttatgaaagt tggactaaaa aaagtccttc cccagagttc    1440
agtggcatgc ccaggataag caaattggga tctggaaatg attttgaggt gttcttccaa    1500
cgacttggaa ttgcttcagg cagagcacgg tatactaaaa attgggaaac aaacaaattc    1560
```

```
agcggctatc cactgtatca cagtgtctat gaaacatatg agttggtgga aaagttttat    1620
gatccaatgt ttaaatatca cctcactgtg gcccaggttc gaggagggat ggtgtttgag    1680
ctagccaatt ccatagtgct ccctttgat tgtcgagatt atgctgtagt tttaagaaag    1740
tatgctgaca aaatctacag tatttctatg aaacatccac aggaaatgaa gacatacagt    1800
gtatcatttg attcactttt ttctgcagta aagaattta cagaaattgc ttccaagttc    1860
agtgagagac tccaggactt tgacaaaagc aagcatgtca tctatgctcc aagcagccac    1920
aacaagtatg caggggagtc attcccagga atttatgatg ctctgtttga tattgaaagc    1980
aaagtggacc cttccaaggc ctggggagaa gtgaagagac agatttatgt tgcagccttc    2040
acagtgcagg cagctgcaga gactttgagt gaagtagcct aagcggccgc atagca        2096
```

<210> SEQ ID NO 4
<211> LENGTH: 719
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270
```

```
Pro Ala Asn Glu Tyr Ala Tyr Arg Arg Gly Ile Ala Glu Ala Val Gly
            275                 280                 285

Leu Pro Ser Ile Pro Val His Pro Ile Gly Tyr Tyr Asp Ala Gln Lys
        290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
                340                 345                 350

Thr Arg Ile Tyr Asn Val Ile Gly Thr Leu Arg Gly Ala Val Glu Pro
            355                 360                 365

Asp Arg Tyr Val Ile Leu Gly Gly His Arg Asp Ser Trp Val Phe Gly
        370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Lys His Val Ile Tyr Ala Pro Ser Ser His Asn Lys Tyr Ala Gly Glu
            660                 665                 670

Ser Phe Pro Gly Ile Tyr Asp Ala Leu Phe Asp Ile Glu Ser Lys Val
        675                 680                 685

Asp Pro Ser Lys Ala Trp Gly Glu Val Lys Arg Gln Ile Tyr Val Ala
690                 695                 700
```

```
Ala Phe Thr Val Gln Ala Ala Ala Glu Thr Leu Ser Glu Val Ala
705                 710                 715

<210> SEQ ID NO 5
<211> LENGTH: 21
<212> TYPE: PRT
<213> ORGANISM: Clostridium tetani

<400> SEQUENCE: 5

Phe Asn Asn Phe Thr Val Ser Phe Trp Leu Arg Val Pro Lys Val Ser
1               5                   10                  15

Ala Ser His Leu Glu
            20

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ile Ile Asn Phe Glu Lys Leu
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-acylated Gly
<220> FEATURE:
<221> NAME/KEY: MOD_RES
<222> LOCATION: (3)..(3)
<223> OTHER INFORMATION: Cys or S-acylated Cys
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Cys or S-acylated Cys
<220> FEATURE:
<223> OTHER INFORMATION: see specification as filed for detailed
      description of substitutions and preferred embodiments

<400> SEQUENCE: 7

Met Gly Cys Xaa Cys
1               5

<210> SEQ ID NO 8
<211> LENGTH: 9
<212> TYPE: PRT
<213> ORGANISM: Homo sapiens

<400> SEQUENCE: 8

Phe Leu Trp Gly Pro Arg Ala Leu Val
1               5

<210> SEQ ID NO 9
<211> LENGTH: 9
<212> TYPE: PRT
```

<213> ORGANISM: Influenza A virus

<400> SEQUENCE: 9

Gly Ile Leu Gly Phe Val Phe Thr Leu
1 5

<210> SEQ ID NO 10
<211> LENGTH: 9
<212> TYPE: PRT
<213> ORGANISM: Human immunodeficiency virus type 1

<400> SEQUENCE: 10

Ser Leu Tyr Asn Thr Val Ala Thr Leu
1 5

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
atatactcga gaaaaaggtg gccaagaagc caacc 35

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
atatagtcga ctcactgtct ctcctgcact gagatg 36

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
cgatcactcg agggctggag gatatctttt tattgg 36

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
tgatcggtcg acatgtacag agtttttgga tccaagtg 38

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
cgatcactcg agtataagtt ctattttcac ctgatgcttc        40

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgatcggtcg acgatagatg ttgcttcctg ccaattg        37

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgatcagtcg acgatgtgtg gtatatttac catttctg        38

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tgatcggtcg acgaccgttt ccttgaacac ctgac        35

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgatcactcg aggatgtttg gtttatatat aatgtgtg        38

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tcggtcgacg tattgcttaa tggaatcgac atac        34

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgatcactcg aggacctctg gtactgcttc cacc        34

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgatctgtcg acttcggccg tgggtccctg gc                                    32

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aatctaccgc ggccaccatg atgtctgcct cgcgcctg                              38

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcagttctcg aggatagatg ttgcttcctg ccaattg                               37

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atatactcga gaaaaggtg gccaagaagc caacc                                  35

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acatagtcga cctgtctctc ctgcactgag atg                                   33

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atagcactcg agatgggggga agagggtggt tcag                                 34

-continued

```
<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cttcatgtcg acgacctcca ggacattctc tgtg                                  34

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atagcactcg agaccaccga gcagcgacgc ag                                    32

<210> SEQ ID NO 30
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cttcatgtcg acaatctgta tgtcagaagt ttccatc                               37

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acatcaactc gagatggctg caggaggtcc cgg                                   33

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
actcatagtc gaccagggac aaggccttgg caag                                  34

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acatcaactc gagatggcct gcacaggccc atcac                                 35

<210> SEQ ID NO 34
<211> LENGTH: 35
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
actcatagtc gacttctgcc tcctgcgtct tgtcc                                   35

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aactagacgc gtactactaa aatgtaaatg acataggaaa ac                           42

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gacttgaagc ttaacacgaa cagtgtcgcc tactac                                  36

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 37

His His His His His His
1               5
```